(12) United States Patent
Guessregen et al.

(10) Patent No.: US 12,195,510 B2
(45) Date of Patent: Jan. 14, 2025

(54) INSULIN CONJUGATES

(71) Applicant: SANOFI, Paris (FR)

(72) Inventors: Stefan Guessregen, Frankfurt am Main (DE); Martin Will, Frankfurt am Main (DE); Thomas Boehme, Frankfurt am Main (DE); Marcus Hermann Korn, Frankfurt am Main (DE)

( * ) Notice: Subject to any disclaimer, the term of this patent is extended or adjusted under 35 U.S.C. 154(b) by 152 days.

(21) Appl. No.: 17/329,558

(22) Filed: May 25, 2021

(65) Prior Publication Data

US 2022/0048968 A1 Feb. 17, 2022

Related U.S. Application Data

(62) Division of application No. 16/709,208, filed on Dec. 10, 2019, now Pat. No. 11,098,102.

(30) Foreign Application Priority Data

| Dec. 11, 2018 | (EP) | ................................. 18306657 |
| Dec. 11, 2018 | (EP) | ................................. 18306658 |
| Dec. 11, 2018 | (EP) | ................................. 18306659 |

(51) Int. Cl.
  *C07K 14/62* (2006.01)
  *A61K 31/18* (2006.01)
  *A61K 47/64* (2017.01)

(52) U.S. Cl.
  CPC .............. *C07K 14/62* (2013.01); *A61K 31/18* (2013.01); *A61K 47/64* (2017.08)

(58) Field of Classification Search
  CPC ........ C07K 14/62; A61K 47/64; A61K 31/18; A61K 47/542
  See application file for complete search history.

(56) References Cited

U.S. PATENT DOCUMENTS

| 8,691,759 | B2 | 4/2014 | Madsen et al. |
| 10,159,715 | B2 | 12/2018 | Kim et al. |
| 11,098,102 | B2 | 8/2021 | Mendez Perez et al. |
| 11,560,422 | B2 | 1/2023 | Winters et al. |
| 2017/0281709 | A1 | 10/2017 | Neerup et al. |
| 2020/0181223 | A1 | 6/2020 | Mendez Perez et al. |
| 2023/0265173 | A1 | 8/2023 | Winters et al. |
| 2023/0346949 | A1 | 11/2023 | Boehme et al. |

FOREIGN PATENT DOCUMENTS

| CN | 104114575 B | 10/2014 |
| EP | 2371853 A2 | 10/2011 |
| EP | 2963056 A1 | 1/2016 |
| EP | 3156066 A1 | 4/2017 |
| EP | 3495384 A1 | 6/2019 |
| EP | 3578204 A1 | 12/2019 |
| JP | 2011-515358 A | 5/2011 |
| JP | 2017-521377 A | 8/2017 |
| RU | 2571857 C2 | 12/2015 |
| RU | 2016130933 A | 2/2018 |
| WO | WO 1995/007931 A1 | 3/1995 |
| WO | WO 1996/029344 A1 | 9/1996 |
| WO | WO 1997/031022 A1 | 8/1997 |
| WO | WO 1999/021573 A1 | 5/1999 |
| WO | WO 2006/005667 A2 | 1/2006 |
| WO | WO 2006/082204 A1 | 8/2006 |
| WO | WO 2006/082205 A1 | 8/2006 |
| WO | WO 2007/020256 A1 | 2/2007 |
| WO | WO 2007/096431 A1 | 8/2007 |
| WO | WO 2007/104736 A2 | 9/2007 |
| WO | WO 2007/128815 A1 | 11/2007 |
| WO | WO 2007/128817 A2 | 11/2007 |
| WO | WO 2008/015099 A2 | 2/2008 |
| WO | WO 2008/034881 A1 | 3/2008 |
| WO | WO 2008/049711 A1 | 5/2008 |
| WO | WO 2008/049931 A1 | 5/2008 |
| WO | WO 2008/053360 A2 | 5/2008 |
| WO | WO 2009/010428 A1 | 1/2009 |
| WO | WO 2009/022006 A1 | 2/2009 |
| WO | WO 2009/022013 A1 | 2/2009 |
| WO | WO 2009/067636 A2 | 5/2009 |
| WO | WO 2009/112583 A2 | 9/2009 |
| WO | WO 2009/115469 A1 | 9/2009 |
| WO | WO 2009/121884 A1 | 10/2009 |
| WO | WO 2010/049488 A1 | 5/2010 |
| WO | WO 2010/066636 A1 | 6/2010 |
| WO | WO 2010/080606 A1 | 7/2010 |

(Continued)

OTHER PUBLICATIONS

Bowie et al (Science, 1990, 247:1306-1310) (Year: 1990).*
Burgess et al (J. Cell Biol. 111:2129-2138, 1990) (Year: 1990).*
Lazar et al (Mol. Cell. Biol., 8:1247-1252, 1988) (Year: 1988).*
European Search Report in related European Application No. EP18306657.0, dated May 10, 2019, 14 pages.
European Search Report in related European Application No. EP18306658.8, dated May 28, 2019, 9 pages.
European Search Report in related European Application No. EP18306659.6, dated May 20, 2019, 10 pages.
Frei, "Albumin binding ligands and albumin conjugate uptake by cancer cells", Diabetology & Metaboloc Syndrome, 2011, vol. 3, No. 11, 4 pages.
Glendorf et al., "Importance of the solvent-exposed residues of the insulin B chanin alpha-helix for receptor binding", Biochemistry, vol. 47, pp. 4743-4751, Apr. 22, 2008.

(Continued)

*Primary Examiner* — Sudhakar Katakam
(74) *Attorney, Agent, or Firm* — LATHROP GPM LLP; James H. Velema, Esq.; Laura A. Labeots, Esq.

(57) ABSTRACT

The present invention relates to a conjugate comprising a sulfonamide of formula (I) and an active pharmaceutical ingredient such as an insulin analog comprising at least one mutation relative to the parent insulin, wherein the insulin analog comprises a mutation at position B16 which is substituted with a hydrophobic amino acid and/or a mutation at position B25 which is substituted with a hydrophobic amino acid. The present invention further relates to a sulfonamide of formula (A). Moreover, the present invention relates to an insulin analog comprising at least one mutation relative to the parent insulin.

21 Claims, 8 Drawing Sheets

Specification includes a Sequence Listing.

(56) References Cited

FOREIGN PATENT DOCUMENTS

| WO | WO 2010/080609 A1 | 7/2010 |
|---|---|---|
| WO | WO 2010/130638 A1 | 11/2010 |
| WO | WO 2011/141407 A1 | 11/2011 |
| WO | WO 2011/163462 A2 | 12/2011 |
| WO | WO 2012/049307 A2 | 4/2012 |
| WO | WO 2012/171994 A1 | 12/2012 |
| WO | WO 2013/086927 A1 | 6/2013 |
| WO | WO 2013/093009 A1 | 6/2013 |
| WO | WO 2014/009316 A1 | 1/2014 |
| WO | WO 2014/071405 A2 | 5/2014 |
| WO | WO 2014/071405 A3 | 5/2014 |
| WO | WO 2014/133324 A1 | 9/2014 |
| WO | WO 2014/147141 A1 | 9/2014 |
| WO | WO 2014/158900 A1 | 10/2014 |
| WO | WO 2014/177623 A1 | 11/2014 |
| WO | WO 2014/195452 A1 | 12/2014 |
| WO | WO 2015/016293 A1 | 2/2015 |
| WO | WO 2015/108398 A1 | 7/2015 |
| WO | WO 2015/128403 A2 | 9/2015 |
| WO | WO 2015/199511 A1 | 12/2015 |
| WO | WO 2016/001185 A1 | 1/2016 |
| WO | WO 2016/006963 A1 | 1/2016 |
| WO | WO 2016/119854 A1 | 8/2016 |
| WO | WO 2016/172269 A2 | 10/2016 |
| WO | WO 2017/032599 A1 | 3/2017 |
| WO | WO 2017/032795 A1 | 3/2017 |
| WO | WO 2017/032797 A1 | 3/2017 |
| WO | WO 2017/126984 A1 | 7/2017 |
| WO | WO 2018/056764 A1 | 3/2018 |
| WO | WO 2018/094388 A1 | 5/2018 |
| WO | WO 2018/109162 A1 | 6/2018 |
| WO | WO 2018/174668 A2 | 9/2018 |
| WO | WO 2018/217573 A1 | 11/2018 |
| WO | WO 2019/066570 A1 | 4/2019 |
| WO | WO 2019/125879 A2 | 6/2019 |

OTHER PUBLICATIONS

Hartmann et al., "Effect of the long-acting insulin analogues glargine and degludec on cardiomyocyte cell signalling and function", Cardiovascular Diabetology, 2016, 15:96, 11 pages.

International Search Report and Written Opinion for PCT International Application No. PCT/EP2019/084400, dated Jan. 30, 2020, 14 pages.

International Search Report and Written Opinion for PCT International Application No. PCT/EP2019/084427, dated Jan. 30, 2020, 19 pages.

International Search Report and Written Opinion for PCT International Application No. PCT/EP2019/084433, dated Mar. 10, 2020, 11 pages.

International Search Report and Written Opinion for PCT International Application No. PCT/EP2020/085415, dated Feb. 8, 2020, 19 pages.

Koehler et al., "Albumin affinity tags increase peptide half-life in vivo", Bioorganic & Medicinal Chemistry Letters, vol. 12, No. 20, pp. 2883-2886, Jun. 11, 2017.

Kyte, et al., "A Simple Method for Displaying the Hydropathic Character of a Protein", Journal of Molecular Biology, vol. 157, No. 1, pp. 105-132, 1982.

Lin et al., "Comparative Pharmacokinetic and Pharmacodynamic Studies of Human Insulin and Analogues in Chronic Diabetic Yucatan Minipigs", The Journal of Pharmacology and Experimental Therapeutics, 1998, vol. 286, No. 2, pp. 959-966.

Mayer et al., "Insulin Structure and Function", Biopolymers (Peptide Science), 2007, vol. 88, No. 5, pp. 687-713.

Rajpal et al., "Single-Chain Insulins as Receptor Agonists", Molecular Endocrinology, May 2009, vol. 23, No. 5, pp. 679-688.

Scholtan, "Die Bindung der Sulfonamide an Eiweißkörper", 3. Mitt., 1. u. 2. T. Arzneimittelforsch.14, 348-356, 469-473 (1964), English abstract is included on p. 473.

Scholtan, "The binding of sulfonamides to proteins" (English translation of "Die Bindung der Sulfonamide an Eiweißkörper"), 3. Mitt., 1. u. 2. T. Arzneimittelforsch. 14, 348-356, 469-473 (1964).

Shoelson et al., "Mutations at the dimer, hexamer, and receptor-binding surfaces of insulin independently affect insulin-insulin and insulin-receptor interactions", Biochemistry, vol. 31, pp. 1757-1767, Feb. 18, 1992.

Sommerfeld et al., "In Vitro Metabolic and Mitogenic Signaling od Insulin Glargine and Its Metabolites", PLoS One, 2010, vol. 5, No. 3, e9540, 9 pages.

Xu et al., "Diabetes-associated mutations in insulin: Consecutive residues in the B chain contact distinct domains of the insulin receptor", American Chemical Society, vol. 43, No. 26, pp. 8356-8372, Jul. 6, 2004.

U.S. Appl. No. 16/709,208, 2020/0181223, now U.S. Pat. No. 11,098,102, filed Dec. 10, 2019, Jun. 11, 2020, Aug. 24, 2021, Maria Mendez Perez.

U.S. Appl. No. 17/329,558, filed May 25, 2021, Maria Mendez Perez.

Colombian Office Action regarding the opposition filed by Laboratorios Legrand S.A., in Colombian Patent Application No. NC2021/0012186, mailed Oct. 21, 2021, with English translation.

Chen et al., "Selective lysine modification of native peptides via aza-Michael addition", Org. Biomol. Chem., 2017, 15: 7339-7345.

Dyson and May, May's Chemistry of Synthetic Drugs, London: Longmans, Green and Co., 1959; in Russian language translation: G. Daison, P. Mey, Khimiya Sinteticheskikh Veshchestv, Moscow: Mir, 1964, pp. 12-19.

Pokrovsky, Editor-in-Chief, Populyarnaya Meditsinskaya Entsiklopediya, 4th Ed., Ulyanovsk: Knigochey, 1997, p. 317 (medicines).

U.S. Appl. No. 16/709,208, 2020/0181223, now U.S. Pat. No. 11,098,102, filed Dec. 10, 2019, Jun. 11, 2020, Aug. 24, 2021, Maria Mendez Perez, Insulin Conjugates.

U.S. Appl. No. 17/329,558, 2022/0048968, filed May 25, 2021, Feb. 17, 2022, Maria Mendez Perez, Insulin Conjugates.

U.S. Appl. No. 17/778,935, 2023/0346949, filed May 23, 2022, Nov. 2, 2023, Thomas Boehme, A Method of Forming a Conjugate of a Sulfonamide and a Polypeptide.

* cited by examiner

SEQUENCE LISTING

```
<160> NUMBER OF SEQ ID NOS: 105

<210> SEQ ID NO 1
<211> LENGTH: 21
<212> TYPE: PRT
<213> ORGANISM: Homo sapiens
<220> FEATURE:
<223> OTHER INFORMATION: Chain A

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens
<220> FEATURE:
<223> OTHER INFORMATION: Chain B

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 3
<211> LENGTH: 21
<212> TYPE: PRT
<213> ORGANISM: Artificial Sequence
<220> FEATURE:
<223> OTHER INFORMATION: Chain A

<400> SEQUENCE: 3

Gly Ile Val Glu Gln Cys Cys Thr Ser Ile Cys Ser Leu Glu Gln Leu
1               5                   10                  15

Glu Asn Tyr Cys Asn
            20
```

<210> SEQ ID NO 4
<211> LENGTH: 29
<212> TYPE: PRT
<213> ORGANISM: Artificial Sequence
<220> FEATURE:
<223> OTHER INFORMATION: Chain B

<400> SEQUENCE: 4

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25

<210> SEQ ID NO 5
<211> LENGTH: 21
<212> TYPE: PRT
<213> ORGANISM: Artificial Sequence
<220> FEATURE:
<223> OTHER INFORMATION: Chain A

<400> SEQUENCE: 5

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 6
<211> LENGTH: 29
<212> TYPE: PRT
<213> ORGANISM: Artificial Sequence
<220> FEATURE:
<223> OTHER INFORMATION: Chain B

<400> SEQUENCE: 6

Phe Val Asn Gln His Leu Cys Gly Ser His Leu Val Glu Ala Leu Leu
1               5                   10                  15

Leu Val Cys Gly Glu Arg Gly Phe Phe Tyr Thr Pro Lys
            20                  25

<210> SEQ ID NO 7
<211> LENGTH: 21
<212> TYPE: PRT
<213> ORGANISM: Artificial Sequence
<220> FEATURE:
<223> OTHER INFORMATION: Chain A

<400> SEQUENCE: 7

Gly Ile Val Glu Gln Cys Cys Thr Ser Ile Cys Ser Leu Tyr Gln Leu
1               5                   10                  15

Glu Asn Tyr Cys Gly
            20

<210> SEQ ID NO 8
<211> LENGTH: 29
<212> TYPE: PRT
<213> ORGANISM: Artificial Sequence
<220> FEATURE:
<223> OTHER INFORMATION: Chain B

<400> SEQUENCE: 8

Phe Val Asn Gln His Leu Cys Gly Ser His Leu Val Glu Ala Leu Trp
1               5                   10                  15

Leu Val Cys Gly Glu Arg Gly Phe Phe Tyr Thr Pro Lys
            20                  25

<210> SEQ ID NO 9
<211> LENGTH: 21
<212> TYPE: PRT
<213> ORGANISM: Artificial Sequence
<220> FEATURE:
<223> OTHER INFORMATION: Chain A

<400> SEQUENCE: 9

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 10
<211> LENGTH: 29
<212> TYPE: PRT
<213> ORGANISM: Artificial Sequence
<220> FEATURE:
<223> OTHER INFORMATION: Chain B

<400> SEQUENCE: 10

Phe Val Asn Gln His Leu Cys Gly Ser His Leu Val Glu Ala Leu His
1               5                   10                  15

Leu Val Cys Gly Glu Arg Gly Phe Phe Tyr Thr Pro Lys
            20                  25

<210> SEQ ID NO 11
<211> LENGTH: 21
<212> TYPE: PRT
<213> ORGANISM: Artificial Sequence
<220> FEATURE:
<223> OTHER INFORMATION: Chain A

<400> SEQUENCE: 11

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 12
<211> LENGTH: 29
<212> TYPE: PRT
<213> ORGANISM: Artificial Sequence
<220> FEATURE:
<223> OTHER INFORMATION: Chain B

<400> SEQUENCE: 12

Phe Val Asn Gln His Leu Cys Gly Ser His Leu Val Glu Ala Leu Val
1               5                   10                  15

Leu Val Cys Gly Glu Arg Gly Phe Phe Tyr Thr Pro Lys
            20                  25

<210> SEQ ID NO 13
<211> LENGTH: 21
<212> TYPE: PRT
<213> ORGANISM: Artificial Sequence
<220> FEATURE:
<223> OTHER INFORMATION: Chain A

```
<400> SEQUENCE: 13

Gly Ile Val Glu Gln Cys Cys Thr Ser Ile Cys Ser Leu Tyr Gln Leu
1               5                  10                  15

Glu Asn Tyr Cys Asn
            20

<210> SEQ ID NO 14
<211> LENGTH: 30
<212> TYPE: PRT
<213> ORGANISM: Artificial Sequence
<220> FEATURE:
<223> OTHER INFORMATION: Chain B

<400> SEQUENCE: 14

Phe Val Asn Gln His Leu Cys Gly Ser His Leu Val Glu Ala Leu Tyr
1               5                  10                  15

Leu Val Cys Gly Glu Arg Gly Phe Ala Tyr Thr Pro Lys Thr
            20                  25                  30

<210> SEQ ID NO 15
<211> LENGTH: 21
<212> TYPE: PRT
<213> ORGANISM: Artificial Sequence
<220> FEATURE:
<223> OTHER INFORMATION: Chain A

<400> SEQUENCE: 15

Gly Ile Val Glu Gln Cys Cys Thr Ser Ile Cys Ser Leu Tyr Gln Leu
1               5                  10                  15

Glu Asn Tyr Cys Asn
            20

<210> SEQ ID NO 16
<211> LENGTH: 29
<212> TYPE: PRT
<213> ORGANISM: Artificial Sequence
<220> FEATURE:
<223> OTHER INFORMATION: Chain B

<400> SEQUENCE: 16

Phe Val Asn Gln His Leu Cys Gly Ser His Leu Val Glu Ala Leu Tyr
1               5                  10                  15

Leu Val Cys Gly Glu Arg Gly Phe Ala Tyr Thr Pro Lys
            20                  25

<210> SEQ ID NO 17
<211> LENGTH: 21
<212> TYPE: PRT
<213> ORGANISM: Artificial Sequence
<220> FEATURE:
<223> OTHER INFORMATION: Chain A

<400> SEQUENCE: 17

Gly Ile Val Glu Gln Cys Cys Thr Ser Ile Cys Ser Leu Tyr Gln Leu
1               5                  10                  15

Glu Asn Tyr Cys Asn
            20

<210> SEQ ID NO 18
<211> LENGTH: 29
<212> TYPE: PRT
<213> ORGANISM: Artificial Sequence
<220> FEATURE:
```

```
<223> OTHER INFORMATION: Chain B

<400> SEQUENCE: 18

Phe Val Asn Gln His Leu Cys Gly Ser His Leu Val Glu Ala Leu Tyr
1               5                   10                  15

Leu Val Cys Gly Glu Arg Gly Phe Glu Tyr Thr Pro Lys
            20                  25

<210> SEQ ID NO 19
<211> LENGTH: 21
<212> TYPE: PRT
<213> ORGANISM: Artificial Sequence
<220> FEATURE:
<223> OTHER INFORMATION: Chain A

<400> SEQUENCE: 19

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 20
<211> LENGTH: 29
<212> TYPE: PRT
<213> ORGANISM: Artificial Sequence
<220> FEATURE:
<223> OTHER INFORMATION: Chain B

<400> SEQUENCE: 20

Phe Val Asn Gln His Leu Cys Gly Ser His Leu Val Glu Ala Leu Tyr
1               5                   10                  15

Leu Val Cys Gly Glu Arg Gly Phe His Tyr Thr Pro Lys
            20                  25

<210> SEQ ID NO 21
<211> LENGTH: 21
<212> TYPE: PRT
<213> ORGANISM: Artificial Sequence
<220> FEATURE:
<223> OTHER INFORMATION: Chain A

<400> SEQUENCE: 21

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 22
<211> LENGTH: 29
<212> TYPE: PRT
<213> ORGANISM: Artificial Sequence
<220> FEATURE:
<223> OTHER INFORMATION: Chain B

<400> SEQUENCE: 22

Phe Val Asn Gln His Leu Cys Gly Ser His Leu Val Glu Ala Leu Tyr
1               5                   10                  15

Leu Val Cys Gly Glu Arg Gly Phe Leu Tyr Thr Pro Lys
            20                  25

<210> SEQ ID NO 23
<211> LENGTH: 21
<212> TYPE: PRT
<213> ORGANISM: Artificial Sequence
```

```
<220> FEATURE:
<223> OTHER INFORMATION: Chain A

<400> SEQUENCE: 23

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 24
<211> LENGTH: 29
<212> TYPE: PRT
<213> ORGANISM: Artificial Sequence
<220> FEATURE:
<223> OTHER INFORMATION: Chain B

<400> SEQUENCE: 24

Phe Val Asn Gln His Leu Cys Gly Ser His Leu Val Glu Ala Leu Tyr
1               5                   10                  15

Leu Val Cys Gly Glu Arg Gly Phe Val Tyr Thr Pro Lys
            20                  25

<210> SEQ ID NO 25
<211> LENGTH: 21
<212> TYPE: PRT
<213> ORGANISM: Artificial Sequence
<220> FEATURE:
<223> OTHER INFORMATION: Chain A

<400> SEQUENCE: 25

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 26
<211> LENGTH: 29
<212> TYPE: PRT
<213> ORGANISM: Artificial Sequence
<220> FEATURE:
<223> OTHER INFORMATION: Chain B

<400> SEQUENCE: 26

Phe Val Asn Gln His Leu Cys Gly Ser His Leu Val Glu Ala Leu His
1               5                   10                  15

Leu Val Cys Gly Glu Arg Gly Phe His Tyr Thr Pro Lys
            20                  25

<210> SEQ ID NO 27
<211> LENGTH: 21
<212> TYPE: PRT
<213> ORGANISM: Artificial Sequence
<220> FEATURE:
<223> OTHER INFORMATION: Chain A

<400> SEQUENCE: 27

Gly Ile Val Glu Gln Cys Cys Thr Ser Ile Cys Ser Leu Tyr Gln Leu
1               5                   10                  15

Glu Asn Tyr Cys Gly
            20

<210> SEQ ID NO 28
<211> LENGTH: 29
<212> TYPE: PRT
```

```
<213> ORGANISM: Artificial Sequence
<220> FEATURE:
<223> OTHER INFORMATION: Chain B

<400> SEQUENCE: 28

Phe Val Asn Gln His Leu Cys Gly Ser His Leu Val Glu Ala Leu Trp
1               5                   10                  15

Leu Val Cys Gly Glu Arg Gly Phe His Tyr Thr Pro Lys
            20                  25

<210> SEQ ID NO 29
<211> LENGTH: 21
<212> TYPE: PRT
<213> ORGANISM: Artificial Sequence
<220> FEATURE:
<223> OTHER INFORMATION: Chain A

<400> SEQUENCE: 29

Gly Ile Val Glu Gln Cys Cys Thr Ser Ile Cys Ser Leu Tyr Gln Leu
1               5                   10                  15

Glu Asn Tyr Cys Gly
            20

<210> SEQ ID NO 30
<211> LENGTH: 29
<212> TYPE: PRT
<213> ORGANISM: Artificial Sequence
<220> FEATURE:
<223> OTHER INFORMATION: Chain B

<400> SEQUENCE: 30

Phe Val Asn Gln His Leu Cys Gly Ser His Leu Val Glu Ala Leu Trp
1               5                   10                  15

Leu Val Cys Gly Glu Arg Gly Phe Trp Tyr Thr Pro Lys
            20                  25

<210> SEQ ID NO 31
<211> LENGTH: 21
<212> TYPE: PRT
<213> ORGANISM: Artificial Sequence
<220> FEATURE:
<223> OTHER INFORMATION: Chain A

<400> SEQUENCE: 31

Gly Ile Val Glu Gln Cys Cys Thr Ser Ile Cys Ser Leu Glu Gln Leu
1               5                   10                  15

Glu Asn Tyr Cys Asn
            20

<210> SEQ ID NO 32
<211> LENGTH: 29
<212> TYPE: PRT
<213> ORGANISM: Artificial Sequence
<220> FEATURE:
<223> OTHER INFORMATION: Chain B

<400> SEQUENCE: 32

Phe Val Asn Gln His Leu Cys Gly Ser His Leu Val Glu Ala Leu His
1               5                   10                  15

Leu Val Cys Gly Glu Arg Gly Phe Phe Tyr Thr Pro Lys
            20                  25

<210> SEQ ID NO 33
<211> LENGTH: 21
```

```
<212> TYPE: PRT
<213> ORGANISM: Artificial Sequence
<220> FEATURE:
<223> OTHER INFORMATION: Chain A

<400> SEQUENCE: 33

Gly Ile Val Glu Gln Cys Cys Thr Ser Ile Cys Ser Leu Glu Gln Leu
1               5                   10                  15

Glu Asn Tyr Cys Gly
            20

<210> SEQ ID NO 34
<211> LENGTH: 29
<212> TYPE: PRT
<213> ORGANISM: Artificial Sequence
<220> FEATURE:
<223> OTHER INFORMATION: Chain B

<400> SEQUENCE: 34

Phe Val Asn Gln His Leu Cys Gly Ser His Leu Val Glu Ala Leu Trp
1               5                   10                  15

Leu Val Cys Gly Glu Arg Gly Phe Phe Tyr Thr Pro Lys
            20                  25

<210> SEQ ID NO 35
<211> LENGTH: 21
<212> TYPE: PRT
<213> ORGANISM: Artificial Sequence
<220> FEATURE:
<223> OTHER INFORMATION: Chain A

<400> SEQUENCE: 35

Gly Ile Val Glu Gln Cys Cys Thr Ser Ile Cys Ser Leu Glu Gln Leu
1               5                   10                  15

Glu Asn Tyr Cys Asn
            20

<210> SEQ ID NO 36
<211> LENGTH: 29
<212> TYPE: PRT
<213> ORGANISM: Artificial Sequence
<220> FEATURE:
<223> OTHER INFORMATION: Chain B

<400> SEQUENCE: 36

Phe Val Asn Gln His Leu Cys Gly Ser His Leu Val Glu Ala Leu Ile
1               5                   10                  15

Leu Val Cys Gly Glu Arg Gly Phe Phe Tyr Thr Pro Lys
            20                  25

<210> SEQ ID NO 37
<211> LENGTH: 21
<212> TYPE: PRT
<213> ORGANISM: Artificial Sequence
<220> FEATURE:
<223> OTHER INFORMATION: Chain A

<400> SEQUENCE: 37

Gly Ile Val Glu Gln Cys Cys Thr Ser Ile Cys Ser Leu Glu Gln Leu
1               5                   10                  15

Glu Asn Tyr Cys Asn
            20

<210> SEQ ID NO 38
```

```
<211> LENGTH: 29
<212> TYPE: PRT
<213> ORGANISM: Artificial Sequence
<220> FEATURE:
<223> OTHER INFORMATION: Chain B

<400> SEQUENCE: 38

Phe Val Asn Gln His Leu Cys Gly Ser His Leu Val Glu Ala Leu Val
1               5                   10                  15

Leu Val Cys Gly Glu Arg Gly Phe Phe Tyr Thr Pro Lys
            20                  25

<210> SEQ ID NO 39
<211> LENGTH: 21
<212> TYPE: PRT
<213> ORGANISM: Artificial Sequence
<220> FEATURE:
<223> OTHER INFORMATION: Chain A

<400> SEQUENCE: 39

Gly Ile Val Glu Gln Cys Cys Thr Ser Ile Cys Ser Leu Glu Gln Leu
1               5                   10                  15

Glu Asn Tyr Cys Asn
            20

<210> SEQ ID NO 40
<211> LENGTH: 29
<212> TYPE: PRT
<213> ORGANISM: Artificial Sequence
<220> FEATURE:
<223> OTHER INFORMATION: Chain B

<400> SEQUENCE: 40

Phe Val Glu Gln His Leu Cys Gly Ser His Leu Val Glu Ala Leu Val
1               5                   10                  15

Leu Val Cys Gly Glu Arg Gly Phe Phe Tyr Thr Pro Lys
            20                  25

<210> SEQ ID NO 41
<211> LENGTH: 21
<212> TYPE: PRT
<213> ORGANISM: Artificial Sequence
<220> FEATURE:
<223> OTHER INFORMATION: Chain A

<400> SEQUENCE: 41

Gly Ile Val Glu Gln Cys Cys Thr Ser Ile Cys Ser Leu Glu Gln Leu
1               5                   10                  15

Glu Asn Tyr Cys Asn
            20

<210> SEQ ID NO 42
<211> LENGTH: 29
<212> TYPE: PRT
<213> ORGANISM: Artificial Sequence
<220> FEATURE:
<223> OTHER INFORMATION: Chain B

<400> SEQUENCE: 42

Phe Val Asn Gln His Leu Cys Gly Ser His Leu Val Glu Ala Leu Tyr
1               5                   10                  15

Leu Val Cys Gly Glu Arg Gly Phe His Tyr Thr Pro Lys
            20                  25
```

```
<210> SEQ ID NO 43
<211> LENGTH: 21
<212> TYPE: PRT
<213> ORGANISM: Artificial Sequence
<220> FEATURE:
<223> OTHER INFORMATION: Chain A

<400> SEQUENCE: 43

Gly Ile Val Glu Gln Cys Cys Thr Ser Ile Cys Ser Leu Glu Gln Leu
1               5                   10                  15

Glu Asn Tyr Cys Asn
            20

<210> SEQ ID NO 44
<211> LENGTH: 29
<212> TYPE: PRT
<213> ORGANISM: Artificial Sequence
<220> FEATURE:
<223> OTHER INFORMATION: Chain B

<400> SEQUENCE: 44

Phe Val Asn Gln His Leu Cys Gly Ser His Leu Val Glu Ala Leu Tyr
1               5                   10                  15

Leu Val Cys Gly Glu Arg Gly Phe Ile Tyr Thr Pro Lys
            20                  25

<210> SEQ ID NO 45
<211> LENGTH: 21
<212> TYPE: PRT
<213> ORGANISM: Artificial Sequence
<220> FEATURE:
<223> OTHER INFORMATION: Chain A

<400> SEQUENCE: 45

Gly Ile Val Glu Gln Cys Cys Thr Ser Ile Cys Ser Leu Glu Gln Leu
1               5                   10                  15

Glu Asn Tyr Cys Gly
            20

<210> SEQ ID NO 46
<211> LENGTH: 29
<212> TYPE: PRT
<213> ORGANISM: Artificial Sequence
<220> FEATURE:
<223> OTHER INFORMATION: Chain B

<400> SEQUENCE: 46

Phe Val Asn Gln His Leu Cys Gly Ser His Leu Val Glu Ala Leu Tyr
1               5                   10                  15

Leu Val Cys Gly Glu Arg Gly Phe Trp Tyr Thr Pro Lys
            20                  25

<210> SEQ ID NO 47
<211> LENGTH: 21
<212> TYPE: PRT
<213> ORGANISM: Artificial Sequence
<220> FEATURE:
<223> OTHER INFORMATION: Chain A

<400> SEQUENCE: 47

Gly Ile Val Glu Gln Cys Cys Thr Ser Ile Cys Ser Leu Glu Gln Leu
1               5                   10                  15

Glu Asn Tyr Cys Asn
            20
```

```
<210> SEQ ID NO 48
<211> LENGTH: 29
<212> TYPE: PRT
<213> ORGANISM: Artificial Sequence
<220> FEATURE:
<223> OTHER INFORMATION: Chain B

<400> SEQUENCE: 48

Phe Val Asn Gln His Leu Cys Gly Ser His Leu Val Glu Ala Leu Tyr
1               5                   10                  15

Leu Val Cys Gly Glu Arg Gly Phe Val Tyr Thr Pro Lys
            20                  25

<210> SEQ ID NO 49
<211> LENGTH: 21
<212> TYPE: PRT
<213> ORGANISM: Artificial Sequence
<220> FEATURE:
<223> OTHER INFORMATION: Chain A

<400> SEQUENCE: 49

Gly Ile Val Glu Gln Cys Cys Thr Ser Ile Cys Ser Leu Glu Gln Leu
1               5                   10                  15

Glu Asn Tyr Cys Gly
            20

<210> SEQ ID NO 50
<211> LENGTH: 29
<212> TYPE: PRT
<213> ORGANISM: Artificial Sequence
<220> FEATURE:
<223> OTHER INFORMATION: Chain B

<400> SEQUENCE: 50

Phe Val Glu Gln His Leu Cys Gly Ser His Leu Val Glu Ala Leu Tyr
1               5                   10                  15

Leu Val Cys Gly Glu Arg Gly Phe Val Tyr Thr Pro Lys
            20                  25

<210> SEQ ID NO 51
<211> LENGTH: 21
<212> TYPE: PRT
<213> ORGANISM: Artificial Sequence
<220> FEATURE:
<223> OTHER INFORMATION: Chain A

<400> SEQUENCE: 51

Gly Ile Val Glu Gln Cys Cys Thr Ser Ile Cys Ser Leu Glu Gln Leu
1               5                   10                  15

Glu Asn Tyr Cys Asn
            20

<210> SEQ ID NO 52
<211> LENGTH: 29
<212> TYPE: PRT
<213> ORGANISM: Artificial Sequence
<220> FEATURE:
<223> OTHER INFORMATION: Chain B

<400> SEQUENCE: 52

Phe Val Asn Gln His Leu Cys Gly Ser His Leu Val Glu Ala Leu Glu
1               5                   10                  15

Leu Val Cys Gly Glu Arg Gly Phe His Tyr Thr Pro Lys
            20                  25
```

<210> SEQ ID NO 53
<211> LENGTH: 21
<212> TYPE: PRT
<213> ORGANISM: Artificial Sequence
<220> FEATURE:
<223> OTHER INFORMATION: Chain A

<400> SEQUENCE: 53

Gly Ile Val Glu Gln Cys Cys Thr Ser Ile Cys Ser Leu Glu Gln Leu
1               5                   10                  15

Glu Asn Tyr Cys Asn
            20

<210> SEQ ID NO 54
<211> LENGTH: 29
<212> TYPE: PRT
<213> ORGANISM: Artificial Sequence
<220> FEATURE:
<223> OTHER INFORMATION: Chain B

<400> SEQUENCE: 54

Phe Val Asn Gln His Leu Cys Gly Ser His Leu Val Glu Ala Leu His
1               5                   10                  15

Leu Val Cys Gly Glu Arg Gly Phe Ala Tyr Thr Pro Lys
            20                  25

<210> SEQ ID NO 55
<211> LENGTH: 21
<212> TYPE: PRT
<213> ORGANISM: Artificial Sequence
<220> FEATURE:
<223> OTHER INFORMATION: Chain A

<400> SEQUENCE: 55

Gly Ile Val Glu Gln Cys Cys Thr Ser Ile Cys Ser Leu Glu Gln Leu
1               5                   10                  15

Glu Asn Tyr Cys Asn
            20

<210> SEQ ID NO 56
<211> LENGTH: 29
<212> TYPE: PRT
<213> ORGANISM: Artificial Sequence
<220> FEATURE:
<223> OTHER INFORMATION: Chain B

<400> SEQUENCE: 56

Phe Val Asn Gln His Leu Cys Gly Ser His Leu Val Glu Ala Leu His
1               5                   10                  15

Leu Val Cys Gly Glu Arg Gly Phe His Tyr Thr Pro Lys
            20                  25

<210> SEQ ID NO 57
<211> LENGTH: 21
<212> TYPE: PRT
<213> ORGANISM: Artificial Sequence
<220> FEATURE:
<223> OTHER INFORMATION: Chain A

```
<400> SEQUENCE: 57

Gly Ile Val Glu Gln Cys Cys Thr Ser Ile Cys Ser Leu Glu Gln Leu
1               5                   10                  15

Glu Asn Tyr Cys Asn
            20

<210> SEQ ID NO 58
<211> LENGTH: 29
<212> TYPE: PRT
<213> ORGANISM: Artificial Sequence
<220> FEATURE:
<223> OTHER INFORMATION: Chain B

<400> SEQUENCE: 58

Phe Val Asn Gln His Leu Cys Gly Ser His Leu Val Glu Ala Leu Ile
1               5                   10                  15

Leu Val Cys Gly Glu Arg Gly Phe Ile Tyr Thr Pro Lys
            20                  25

<210> SEQ ID NO 59
<211> LENGTH: 21
<212> TYPE: PRT
<213> ORGANISM: Artificial Sequence
<220> FEATURE:
<223> OTHER INFORMATION: Chain A

<400> SEQUENCE: 59

Gly Ile Val Glu Gln Cys Cys Thr Ser Ile Cys Ser Leu Glu Gln Leu
1               5                   10                  15

Glu Asn Tyr Cys Asn
            20

<210> SEQ ID NO 60
<211> LENGTH: 29
<212> TYPE: PRT
<213> ORGANISM: Artificial Sequence
<220> FEATURE:
<223> OTHER INFORMATION: Chain B

<400> SEQUENCE: 60

Phe Val Glu Gln His Leu Cys Gly Ser His Leu Val Glu Ala Leu Ile
1               5                   10                  15

Leu Val Cys Gly Glu Arg Gly Phe Ile Tyr Thr Pro Lys
            20                  25

<210> SEQ ID NO 61
<211> LENGTH: 21
<212> TYPE: PRT
<213> ORGANISM: Artificial Sequence
<220> FEATURE:
<223> OTHER INFORMATION: Chain A

<400> SEQUENCE: 61

Gly Ile Val Glu Gln Cys Cys Thr Ser Ile Cys Ser Leu Glu Gln Leu
1               5                   10                  15

Glu Asn Tyr Cys Gly
            20

<210> SEQ ID NO 62
<211> LENGTH: 29
<212> TYPE: PRT
<213> ORGANISM: Artificial Sequence
<220> FEATURE:
```

```
<223> OTHER INFORMATION: Chain B

<400> SEQUENCE: 62

Phe Val Glu Gln His Leu Cys Gly Ser His Leu Val Glu Ala Leu Ile
1               5                   10                  15

Leu Val Cys Gly Glu Arg Gly Phe Trp Tyr Thr Pro Lys
            20                  25

<210> SEQ ID NO 63
<211> LENGTH: 21
<212> TYPE: PRT
<213> ORGANISM: Artificial Sequence
<220> FEATURE:
<223> OTHER INFORMATION: Chain A

<400> SEQUENCE: 63

Gly Ile Val Glu Gln Cys Cys Thr Ser Ile Cys Ser Leu Glu Gln Leu
1               5                   10                  15

Glu Asn Tyr Cys Asn
            20

<210> SEQ ID NO 64
<211> LENGTH: 29
<212> TYPE: PRT
<213> ORGANISM: Artificial Sequence
<220> FEATURE:
<223> OTHER INFORMATION: Chain B

<400> SEQUENCE: 64

Phe Val Asn Gln His Leu Cys Gly Ser His Leu Val Glu Ala Leu Ile
1               5                   10                  15

Leu Val Cys Gly Glu Arg Gly Phe Val Tyr Thr Pro Lys
            20                  25

<210> SEQ ID NO 65
<211> LENGTH: 21
<212> TYPE: PRT
<213> ORGANISM: Artificial Sequence
<220> FEATURE:
<223> OTHER INFORMATION: Chain A

<400> SEQUENCE: 65

Gly Ile Val Glu Gln Cys Cys Thr Ser Ile Cys Ser Leu Glu Gln Leu
1               5                   10                  15

Glu Asn Tyr Cys Gly
            20

<210> SEQ ID NO 66
<211> LENGTH: 29
<212> TYPE: PRT
<213> ORGANISM: Artificial Sequence
<220> FEATURE:
<223> OTHER INFORMATION: Chain B

<400> SEQUENCE: 66

Phe Val Glu Gln His Leu Cys Gly Ser His Leu Val Glu Ala Leu Ile
1               5                   10                  15

Leu Val Cys Gly Glu Arg Gly Phe Val Tyr Thr Pro Lys
            20                  25

<210> SEQ ID NO 67
<211> LENGTH: 21
<212> TYPE: PRT
<213> ORGANISM: Artificial Sequence
```

<220> FEATURE:
<223> OTHER INFORMATION: Chain A

<400> SEQUENCE: 67

Gly Ile Val Glu Gln Cys Cys Thr Ser Ile Cys Ser Leu Glu Gln Leu
1               5                   10                  15

Glu Asn Tyr Cys Asn
            20

<210> SEQ ID NO 68
<211> LENGTH: 29
<212> TYPE: PRT
<213> ORGANISM: Artificial Sequence
<220> FEATURE:
<223> OTHER INFORMATION: Chain B

<400> SEQUENCE: 68

Phe Val Asn Gln His Leu Cys Gly Ser His Leu Val Glu Ala Leu Leu
1               5                   10                  15

Leu Val Cys Gly Glu Arg Gly Phe Ala Tyr Thr Pro Lys
            20                  25

<210> SEQ ID NO 69
<211> LENGTH: 21
<212> TYPE: PRT
<213> ORGANISM: Artificial Sequence
<220> FEATURE:
<223> OTHER INFORMATION: Chain A

<400> SEQUENCE: 69

Gly Ile Val Glu Gln Cys Cys Thr Ser Ile Cys Ser Leu Glu Gln Leu
1               5                   10                  15

Glu Asn Tyr Cys Asn
            20

<210> SEQ ID NO 70
<211> LENGTH: 29
<212> TYPE: PRT
<213> ORGANISM: Artificial Sequence
<220> FEATURE:
<223> OTHER INFORMATION: Chain B

<400> SEQUENCE: 70

Phe Val Asn Gln His Leu Cys Gly Ser His Leu Val Glu Ala Leu Val
1               5                   10                  15

Leu Val Cys Gly Glu Arg Gly Phe Ile Tyr Thr Pro Lys
            20                  25

<210> SEQ ID NO 71
<211> LENGTH: 21
<212> TYPE: PRT
<213> ORGANISM: Artificial Sequence
<220> FEATURE:
<223> OTHER INFORMATION: Chain A

<400> SEQUENCE: 71

Gly Ile Val Glu Gln Cys Cys Thr Ser Ile Cys Ser Leu Glu Gln Leu
1               5                   10                  15

Glu Asn Tyr Cys Gly
            20

<210> SEQ ID NO 72
<211> LENGTH: 29
<212> TYPE: PRT

```
<213> ORGANISM: Artificial Sequence
<220> FEATURE:
<223> OTHER INFORMATION: Chain B

<400> SEQUENCE: 72

Phe Val Asn Gln His Leu Cys Gly Ser His Leu Val Glu Ala Leu Val
1               5                   10                  15

Leu Val Cys Gly Glu Arg Gly Phe Trp Tyr Thr Pro Lys
            20                  25

<210> SEQ ID NO 73
<211> LENGTH: 21
<212> TYPE: PRT
<213> ORGANISM: Artificial Sequence
<220> FEATURE:
<223> OTHER INFORMATION: Chain A

<400> SEQUENCE: 73

Gly Ile Val Glu Gln Cys Cys Thr Ser Ile Cys Ser Leu Glu Gln Leu
1               5                   10                  15

Glu Asn Tyr Cys Gly
            20

<210> SEQ ID NO 74
<211> LENGTH: 29
<212> TYPE: PRT
<213> ORGANISM: Artificial Sequence
<220> FEATURE:
<223> OTHER INFORMATION: Chain B

<400> SEQUENCE: 74

Phe Val Glu Gln His Leu Cys Gly Ser His Leu Val Glu Ala Leu Val
1               5                   10                  15

Leu Val Cys Gly Glu Arg Gly Phe Trp Tyr Thr Pro Lys
            20                  25

<210> SEQ ID NO 75
<211> LENGTH: 21
<212> TYPE: PRT
<213> ORGANISM: Artificial Sequence
<220> FEATURE:
<223> OTHER INFORMATION: Chain A

<400> SEQUENCE: 75

Gly Ile Val Glu Gln Cys Cys Thr Ser Ile Cys Ser Leu Glu Gln Leu
1               5                   10                  15

Glu Asn Tyr Cys Asn
            20

<210> SEQ ID NO 76
<211> LENGTH: 29
<212> TYPE: PRT
<213> ORGANISM: Artificial Sequence
<220> FEATURE:
<223> OTHER INFORMATION: Chain B

<400> SEQUENCE: 76

Phe Val Asn Gln His Leu Cys Gly Ser His Leu Val Glu Ala Leu Val
1               5                   10                  15

Leu Val Cys Gly Glu Arg Gly Phe Val Tyr Thr Pro Lys
            20                  25

<210> SEQ ID NO 77
<211> LENGTH: 21
```

```
<212> TYPE: PRT
<213> ORGANISM: Artificial Sequence
<220> FEATURE:
<223> OTHER INFORMATION: Chain A

<400> SEQUENCE: 77
```

Gly Ile Val Glu Gln Cys Cys Thr Ser Ile Cys Ser Leu Glu Gln Leu
1               5                   10                  15

Glu Asn Tyr Cys Asn
            20

```
<210> SEQ ID NO 78
<211> LENGTH: 29
<212> TYPE: PRT
<213> ORGANISM: Artificial Sequence
<220> FEATURE:
<223> OTHER INFORMATION: Chain B

<400> SEQUENCE: 78
```

Phe Val Glu Gln His Leu Cys Gly Ser His Leu Val Glu Ala Leu Val
1               5                   10                  15

Leu Val Cys Gly Glu Arg Gly Phe Val Tyr Thr Pro Lys
            20                  25

```
<210> SEQ ID NO 79
<211> LENGTH: 21
<212> TYPE: PRT
<213> ORGANISM: Artificial Sequence
<220> FEATURE:
<223> OTHER INFORMATION: Chain A

<400> SEQUENCE: 79
```

Gly Ile Val Glu Gln Cys Cys Thr Ser Ile Cys Ser Leu Glu Gln Leu
1               5                   10                  15

Glu Asn Tyr Cys Gly
            20

```
<210> SEQ ID NO 80
<211> LENGTH: 29
<212> TYPE: PRT
<213> ORGANISM: Artificial Sequence
<220> FEATURE:
<223> OTHER INFORMATION: Chain B

<400> SEQUENCE: 80
```

Phe Val Glu Gln His Leu Cys Gly Ser His Leu Val Glu Ala Leu Val
1               5                   10                  15

Leu Val Cys Gly Glu Arg Gly Phe Val Tyr Thr Pro Lys
            20                  25

```
<210> SEQ ID NO 81
<211> LENGTH: 21
<212> TYPE: PRT
<213> ORGANISM: Bos
<220> FEATURE:
<223> OTHER INFORMATION: Chain A

<400> SEQUENCE: 81
```

Gly Ile Val Glu Gln Cys Cys Ala Ser Val Cys Ser Leu Tyr Gln Leu
1               5                   10                  15

Glu Asn Tyr Cys Asn
            20

```
<210> SEQ ID NO 82
```

```
<211> LENGTH: 30
<212> TYPE: PRT
<213> ORGANISM: Bos
<220> FEATURE:
<223> OTHER INFORMATION: Chain B

<400> SEQUENCE: 82

Phe Val Asn Gln His Leu Cys Gly Ser His Leu Val Glu Ala Leu Tyr
1               5                   10                  15
Leu Val Cys Gly Glu Arg Gly Phe Phe Tyr Thr Pro Lys Ala
            20                  25                  30

<210> SEQ ID NO 83
<211> LENGTH: 21
<212> TYPE: PRT
<213> ORGANISM: Sus
<220> FEATURE:
<223> OTHER INFORMATION: Chain A

<400> SEQUENCE: 83

Gly Ile Val Glu Gln Cys Cys Thr Ser Ile Cys Ser Leu Tyr Gln Leu
1               5                   10                  15
Glu Asn Tyr Cys Asn
            20

<210> SEQ ID NO 84
<211> LENGTH: 30
<212> TYPE: PRT
<213> ORGANISM: Sus
<220> FEATURE:
<223> OTHER INFORMATION: Chain B

<400> SEQUENCE: 84

Phe Val Asn Gln His Leu Cys Gly Ser His Leu Val Glu Ala Leu Tyr
1               5                   10                  15
Leu Val Cys Gly Glu Arg Gly Phe Phe Tyr Thr Pro Lys Ala
            20                  25                  30

<210> SEQ ID NO 85
<211> LENGTH: 29
<212> TYPE: PRT
<213> ORGANISM: Artificial Sequence
<220> FEATURE:
<223> OTHER INFORMATION: Chain B

<400> SEQUENCE: 85

Phe Val Asn Gln His Leu Cys Gly Ser His Leu Val Glu Ala Leu Tyr
1               5                   10                  15
Leu Val Cys Gly Glu Arg Gly Phe Leu Tyr Thr Pro Lys
            20                  25

<210> SEQ ID NO 86
<211> LENGTH: 29
<212> TYPE: PRT
<213> ORGANISM: Artificial Sequence
<220> FEATURE:
<223> OTHER INFORMATION: Chain B

<400> SEQUENCE: 86

Phe Val Asn Gln His Leu Cys Gly Ser His Leu Val Glu Ala Leu Tyr
1               5                   10                  15
Leu Val Cys Gly Glu Arg Gly Phe Val Tyr Thr Pro Lys
            20                  25
```

-continued

<210> SEQ ID NO 87
<211> LENGTH: 29
<212> TYPE: PRT
<213> ORGANISM: Artificial Sequence
<220> FEATURE:
<223> OTHER INFORMATION: Chain B

<400> SEQUENCE: 87

Phe Val Asn Gln His Leu Cys Gly Ser His Leu Val Glu Ala Leu Tyr
1               5                   10                  15

Leu Val Cys Gly Glu Arg Gly Phe Ile Tyr Thr Pro Lys
            20                  25

<210> SEQ ID NO 88
<211> LENGTH: 29
<212> TYPE: PRT
<213> ORGANISM: Artificial Sequence
<220> FEATURE:
<223> OTHER INFORMATION: Chain B

<400> SEQUENCE: 88

Phe Val Asn Gln His Leu Cys Gly Ser His Leu Val Glu Ala Leu Tyr
1               5                   10                  15

Leu Val Cys Gly Glu Arg Gly Phe Val Tyr Thr Pro Lys
            20                  25

<210> SEQ ID NO 89
<211> LENGTH: 29
<212> TYPE: PRT
<213> ORGANISM: Artificial Sequence
<220> FEATURE:
<223> OTHER INFORMATION: Chain B

<400> SEQUENCE: 89

Phe Val Glu Gln His Leu Cys Gly Ser His Leu Val Glu Ala Leu Tyr
1               5                   10                  15

Leu Val Cys Gly Glu Arg Gly Phe Val Tyr Thr Pro Lys
            20                  25

<210> SEQ ID NO 90
<211> LENGTH: 29
<212> TYPE: PRT
<213> ORGANISM: Artificial Sequence
<220> FEATURE:
<223> OTHER INFORMATION: Chain B

<400> SEQUENCE: 90

Phe Val Asn Gln His Leu Cys Gly Ser His Leu Val Glu Ala Leu Ile
1               5                   10                  15

Leu Val Cys Gly Glu Arg Gly Phe Ile Tyr Thr Pro Lys
            20                  25

<210> SEQ ID NO 91
<211> LENGTH: 29
<212> TYPE: PRT
<213> ORGANISM: Artificial Sequence
<220> FEATURE:
<223> OTHER INFORMATION: Chain B

<400> SEQUENCE: 91

Phe Val Glu Gln His Leu Cys Gly Ser His Leu Val Glu Ala Leu Ile
1               5                   10                  15

Leu Val Cys Gly Glu Arg Gly Phe Ile Tyr Thr Pro Lys
            20                  25

```
<210> SEQ ID NO 92
<211> LENGTH: 29
<212> TYPE: PRT
<213> ORGANISM: Artificial Sequence
<220> FEATURE:
<223> OTHER INFORMATION: Chain B

<400> SEQUENCE: 92

Phe Val Asn Gln His Leu Cys Gly Ser His Leu Val Glu Ala Leu Ile
1               5                   10                  15

Leu Val Cys Gly Glu Arg Gly Phe Val Tyr Thr Pro Lys
            20                  25

<210> SEQ ID NO 93
<211> LENGTH: 29
<212> TYPE: PRT
<213> ORGANISM: Artificial Sequence
<220> FEATURE:
<223> OTHER INFORMATION: Chain B

<400> SEQUENCE: 93

Phe Val Glu Gln His Leu Cys Gly Ser His Leu Val Glu Ala Leu Ile
1               5                   10                  15

Leu Val Cys Gly Glu Arg Gly Phe Val Tyr Thr Pro Lys
            20                  25

<210> SEQ ID NO 94
<211> LENGTH: 29
<212> TYPE: PRT
<213> ORGANISM: Artificial Sequence
<220> FEATURE:
<223> OTHER INFORMATION: Chain B

<400> SEQUENCE: 94

Phe Val Asn Gln His Leu Cys Gly Ser His Leu Val Glu Ala Leu Val
1               5                   10                  15

Leu Val Cys Gly Glu Arg Gly Phe Ile Tyr Thr Pro Lys
            20                  25

<210> SEQ ID NO 95
<211> LENGTH: 29
<212> TYPE: PRT
<213> ORGANISM: Artificial Sequence
<220> FEATURE:
<223> OTHER INFORMATION: Chain B

<400> SEQUENCE: 95

Phe Val Asn Gln His Leu Cys Gly Ser His Leu Val Glu Ala Leu Val
1               5                   10                  15

Leu Val Cys Gly Glu Arg Gly Phe Val Tyr Thr Pro Lys
            20                  25

<210> SEQ ID NO 96
<211> LENGTH: 29
<212> TYPE: PRT
<213> ORGANISM: Artificial Sequence
<220> FEATURE:
<223> OTHER INFORMATION: Chain B

<400> SEQUENCE: 96

Phe Val Glu Gln His Leu Cys Gly Ser His Leu Val Glu Ala Leu Val
1               5                   10                  15

Leu Val Cys Gly Glu Arg Gly Phe Val Tyr Thr Pro Lys
            20                  25
```

<210> SEQ ID NO 97
<211> LENGTH: 29
<212> TYPE: PRT
<213> ORGANISM: Artificial Sequence
<220> FEATURE:
<223> OTHER INFORMATION: Chain B

<400> SEQUENCE: 97

Phe Val Glu Gln His Leu Cys Gly Ser His Leu Val Glu Ala Leu Val
1               5                   10                  15

Leu Val Cys Gly Glu Arg Gly Phe Val Tyr Thr Pro Lys
            20                  25

<210> SEQ ID NO 98
<211> LENGTH: 44
<212> TYPE: PRT
<213> ORGANISM: Artificial Sequence
<220> FEATURE:
<223> OTHER INFORMATION: Lixisenatide

<400> SEQUENCE: 98

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 99
<211> LENGTH: 39
<212> TYPE: PRT
<213> ORGANISM: Artificial Sequence
<220> FEATURE:
<223> OTHER INFORMATION: Exenatide

<400> SEQUENCE: 99

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 100
<211> LENGTH: 31
<212> TYPE: PRT
<213> ORGANISM: Artificial Sequence
<220> FEATURE:
<223> OTHER INFORMATION: Semaglutide
<220> FEATURE:
<221> NAME/KEY: MOD_RES
<222> LOCATION: 2
<223> OTHER INFORMATION: Aib

<400> SEQUENCE: 100

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 101
<211> LENGTH: 31
<212> TYPE: PRT

<213> ORGANISM: Artificial Sequence
<220> FEATURE:
<223> OTHER INFORMATION: Dulaglutide

<400> SEQUENCE: 101

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 102
<211> LENGTH: 21
<212> TYPE: PRT
<213> ORGANISM: Homo sapiens
<220> FEATURE:
<223> OTHER INFORMATION: human insulin , A chain

<400> SEQUENCE: 102

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 103
<211> LENGTH: 30
<212> TYPE: PRT
<213> ORGANISM: Homo sapiens
<220> FEATURE:
<223> OTHER INFORMATION: human insulin , B chain

<400> SEQUENCE: 103

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 104
<211> LENGTH: 21
<212> TYPE: PRT
<213> ORGANISM: Artificial Sequence
<220> FEATURE:
<223> OTHER INFORMATION: insulin analog 1 , A chain

<400> SEQUENCE: 104

Gly Ile Val Glu Gln Cys Cys Thr Ser Ile Cys Ser Leu Glu Gln Leu
1               5                   10                  15

Glu Asn Tyr Cys Asn
            20

<210> SEQ ID NO 105
<211> LENGTH: 29
<212> TYPE: PRT
<213> ORGANISM: Artificial Sequence
<220> FEATURE:
<223> OTHER INFORMATION: insulin analog 1 , B chain

<400> SEQUENCE: 105

Phe Val Asn Gln His Leu Cys Gly Ser His Leu Val Glu Ala Leu His
1               5                   10                  15

Leu Val Cys Gly Glu Arg Gly Phe His Tyr Thr Pro Lys
            20                  25

INSULIN CONJUGATES

RELATED APPLICATIONS

This application is a division of U.S. patent application Ser. No. 16/709,208, filed Dec. 10, 2019, which claims priority to European Patent Application Nos. 18306659.6, 18306658.8, and 18306657.0, all filed Dec. 11, 2018, each of which is incorporated herein by reference in its entirety.

BACKGROUND

Worldwide, more than 400 million people suffer from type 1 or type 2 diabetes mellitus. Type 1 diabetes is treated with insulin substitution. In contrast to type 1 diabetes, there is basically no deficiency of insulin in type 2 diabetes, but in a large number of cases, especially in the advanced stage, type 2 diabetes patients are treated with insulin.

In a healthy person, the release of insulin by the pancreas is strictly coupled to the concentration of the blood glucose. Elevated blood glucose levels, such as occur after meals, and are rapidly compensated by a corresponding increase in insulin secretion. In the fasting state, the plasma insulin level falls to a basal value which is adequate to guarantee a continuous supply of insulin-sensitive organs and tissue with glucose and to keep hepatic glucose production low in the night. Often, the replacement of the endogenous insulin secretion by exogenous, mostly subcutaneous administration of insulin does not achieve the quality of the physiological regulation of the blood glucose described above. Deviations of the blood glucose upward or downward can occur, which in their severest forms can be life-threatening. It is to be derived from this that an improved therapy of diabetes is primarily to be aimed at keeping the blood glucose as closely as possible in the physiological range.

Human insulin is a polypeptide of 51 amino acids, which are divided into 2 amino acid chains: the A chain having 21 amino acids and the B chain having 30 amino acids. The chains are connected to one another by means of 2 disulfide bridges. A third disulfide bridge exists between the cysteines at position 6 and 11 of the A chain. Some products in current use for the treatment of diabetes mellitus are insulin analogs, i.e. insulin variants whose sequence differs from that of human insulin by one or more amino acid substitutions in the A chain and/or in the B chain.

Like many other peptide hormones, human insulin has a short half-life in vivo. Thus, it is administered frequently which is associated with discomfort for the patient. Therefore, insulin analogs are desired which have an increased half-life in vivo and, thus, a prolonged duration of action.

SUMMARY

The present disclosure provides insulin analogs, binding moieties, and conjugates of the insulin analogs and binding moieties which result in an increased half-life in vivo of the insulin analogs and, thus, a prolonged duration of action, which allow for sufficiently lowering the blood glucose level in vivo.

Provided herein are long-acting insulin analogs. The provided long-acting insulin analogs have a very low binding affinity (hence a lower clearance rate) whilst still maintaining high signal transduction. The insulin analogs are described in section A below.

Provided herein are serum albumin binding moieties (herein also referred to as "albumin binders" or "binders"), which when coupled to a peptide such as an insulin analog provided above lead to improved pharmacodynamics and/or pharmacokinetic properties of the peptide for example, an extended pharmacokinetic half life in blood and/or blood plasma and/or a prolonged profile of action, i.e. a prolonged reduction of blood glucose level. The provided albumin binders are sulfonamides of formula (A)

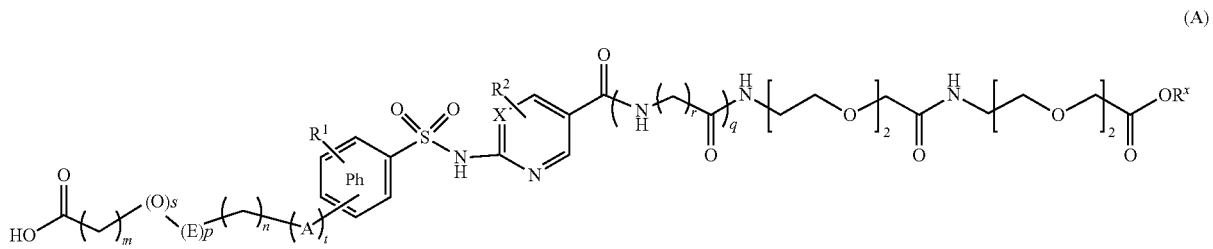

(A)

The serum albumin binding moieties are described in section B below.

Also provided herein are conjugates comprising an active pharmaceutical ingredient, such as an insulin analog defined in section A, and an insulin binder, such as a sulfonamide of formula (A) defined in section B. The conjugates are described in section C below.

DETAILED DESCRIPTION

Figure 1:
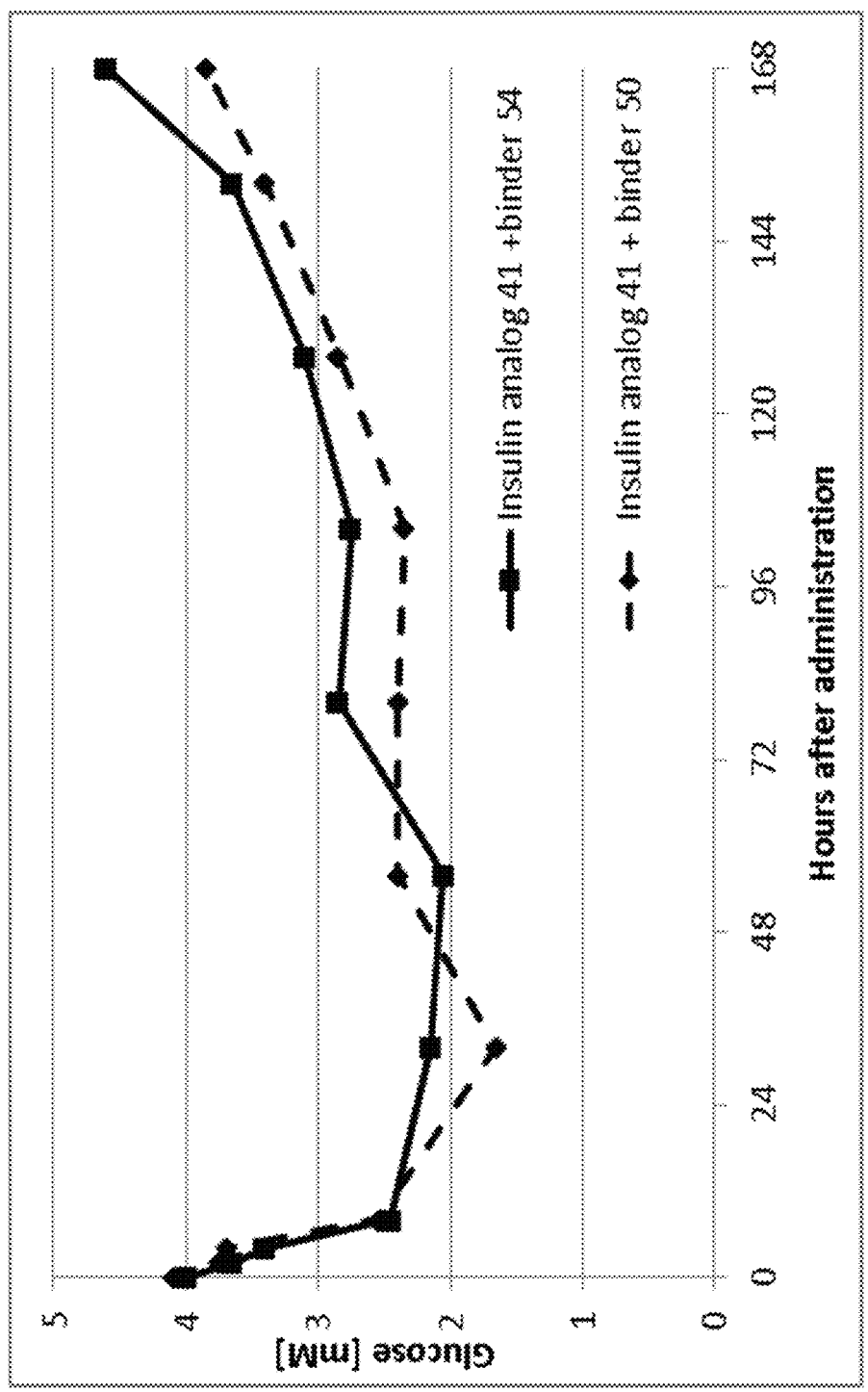
FIG. 1 shows the blood glucose lowering effect after s.c. application of the conjugates of insulin analog 41 with binder no. 50 and binder no. 54 respectively in (Göttingen) minipigs (12-18 kg, n=3). Both compounds were tested at a dose of (18 nmol/kg).

There is a need for insulin analogs which have a reduced insulin receptor-binding activity, and thus a reduced receptor-mediated clearance rate, but which have a signal transduction activity which allow for sufficiently lowering the blood glucose level in vivo. There is also a need for binding moieties which, when coupled to a peptide such as an insulin analog, lead to improved pharmacodynamics and/or pharmacokinetic properties of the peptide for example, an extended pharmacokinetic half life in blood and/or blood plasma and/or a prolonged profile of action, i.e. a prolonged reduction of blood glucose level. Further, there is a need for conjugates of the insulin analogs and binding moeities.

Provided herein are conjugates comprising a sulfonamide of formula (I) and an active pharmaceutical ingredient, such as an insulin analog, comprising at least one mutation relative to the parent insulin, wherein the insulin analog comprises a mutation at position B16 which is substituted with a hydrophobic amino acid and/or a mutation at position B25 which is substituted with a hydrophobic amino acid. Further provided herein are sulfonamides of formula (A) and insulin analogs comprising at least one mutation relative to the parent insulin, wherein the insulin analogs comprise a mutation at position B16 which is substituted with a hydrophobic amino acid and/or a mutation at position B25 which is substituted with a hydrophobic amino acid.

Section A: Insulin Analogs

In order to increase the duration of action of a drug, half-life plays a major role. Half-life ($t_{1/2}$) is proportional to the volume of distribution divided by clearance. In the case of human insulin, clearance is mainly driven by binding to the insulin receptor, internalization and subsequent degradation.

Surprisingly, it was shown in the context of the studies underlying the present invention that a substitution at position B16 and/or B25 of human insulin with a hydrophobic amino acid (such as leucine, isoleucine, valine, alanine and tryptophan) resulted in a decrease of insulin receptor binding activity (as compared to the insulin receptor binding activity of the parent insulin, see Examples). The strongest effects on insulin receptor binding activity were observed for substitutions with branched-chain amino acids (leucine, isoleucine and valine). Interestingly, insulin analogs with such substitutions at these positions (such as at position B25) showed up to 6-fold enhancement in signal transduction than expected based on their insulin receptor isoform B (IR-B) binding affinities (see Examples). Further, some tested insulin analogs showed improved proteolytic stability against α-chymotrypsin, cathepsin D and insulin degrading enzyme (see Examples).

Accordingly, provided herein are insulin analogs comprising at least one mutation relative to the parent insulin, wherein the insulin analogs comprise a mutation at position B16 which is substituted with a hydrophobic amino acid, and/or a mutation at position B25 which is substituted with a hydrophobic amino acid.

The expression "insulin analog" as used herein refers to a peptide which has a molecular structure which formally can be derived from the structure of a naturally occurring insulin (herein also referred to as "parent insulin", e.g. human insulin) by deleting and/or substituting at least one amino acid residue occurring in the naturally occurring insulin and/or adding at least one amino acid residue. The added and/or exchanged amino acid residue can either be codable amino acid residues or other naturally occurring residues or purely synthetic amino acid residues. The analog as referred to herein is capable of lowering blood glucose levels in vivo, such as in a human subject.

In some embodiments, the insulin analog provided herein comprises two peptide chains, an A-chain and a B-chain. Typically, the two chains are connected by disulfide bridges between cysteine residues. For example, in some embodiments, insulin analogs provided herein comprise three disulfide bridges: one disulfide bridge between the cysteines at position A6 and A11, one disulfide bridge between the cysteine at position A7 of the A-chain and the cysteine at position B7 of the B-chain, and one between the cysteine at position A20 of the A-chain and the cysteine at position B19 of the B-chain. Accordingly, insulin analogs provided herein may comprise cysteine residues at positions A6, A7, A11, A20, B7 and B19.

In some embodiments provided herein, the insulin analog is a single-chain insulin. A single-chain insulin is a single polypeptide chains in which the insulin B-chain is linked contiguously with the insulin A-chain via an uncleaved connecting peptide.

Mutations of insulin, i.e. mutations of a parent insulin, are indicated herein by referring to the chain, i.e. either the A-chain or the B-chain of the analog, the position of the mutated amino acid residue in the A- or B-chain (such as A14, B16 and B25), and the three letter code for the amino acid substituting the native amino acid in the parent insulin. The term "desB30" refers to an analog lacking the B30 amino acid from the parent insulin (i.e. the amino acid at position B30 is absent). For example, Glu(A14)Ile(B16) desB30 human insulin, is an analog of human insulin in which the amino acid residue at position 14 of the A-chain (A14) of human insulin is substituted with glutamic acid, the amino acid residue at position 16 of the B-chain (B16) is substituted with isoleucine, and the amino acid at position 30 of the B chain is deleted (i.e. is absent).

Insulin analogs provided herein comprise at least one mutation (substitution, deletion, or addition of an amino acid) relative to parent insulin. The term "at least one", as used herein means one, or more than one, such as "at least two", "at least three", "at least four", "at least five", etc. In some embodiments, the insulin analogs provided herein comprise at least one mutation in the B-chain and at least one mutation in the A-chain. In a further embodiment, the insulin analogs provided herein comprise at least two mutations in the B-chain and at least one mutation in the A-chain.

For example, the insulin analog may comprise a substitution at position B16, a deletion at position B30 and a substitution at position A14. Alternatively, the insulin analog may comprise a substitution at position B25, a deletion at position B30 and a substitution at position A14. Further, the insulin analog may comprise a substitution at position B16, a substitution at position B25, a deletion at position B30 and a substitution at position A14.

The insulin analogs provided herein may comprise mutations in addition to the mutations above. In some embodiments, the number of mutations does not exceed a certain number. In some embodiments, the insulin analogs comprise less than twelve mutations (i.e. deletions, substitution, additions) relative to the parent insulin. In another embodiment, the analog comprises less than ten mutations relative to the parent insulin. In another embodiment, the analog comprises less than eight mutations relative to the parent insulin. In another embodiment, the analog comprises less than seven mutations relative to the parent insulin. In another embodiment, the analog comprises less than six mutations relative to the parent insulin. In another embodiment, the analog comprises less than five mutations relative to the parent insulin. In another embodiment, the analog comprises less than four mutations relative to the parent insulin. In another embodiment, the analog comprises less than three mutations relative to the parent insulin.

The expression "parent insulin" as used herein refers to naturally occurring insulin, i.e. to an unmutated, wild-type insulin. In some embodiments, the parent insulin is animal insulin, such as mammalian insulin. For example, the parent insulin may be human insulin, porcine insulin, or bovine insulin.

In some embodiments, the parent insulin is human insulin. The sequence of human insulin is well known in the art and shown in Table 4 in the Example section. Human insulin comprises an A chain having an amino acid sequence as shown in SEQ ID NO: 1 (GIVEQCCTSICSLYQLENYCN) and a B chain having an amino acid sequence as shown in SEQ ID NO: 2 (FVNQHLCGSHLVEALYL-VCGERGFFYTPKT).

In another embodiment, the parent insulin is bovine insulin. The sequence of bovine insulin is well known in the art. Bovine insulin comprises an A chain having an amino acid sequence as shown in SEQ ID NO: 81 (GIVEQC-CASVCSLYQLENYCN) and a B chain having an amino acid sequence as shown in SEQ ID NO: 82 (FVNQHLCGSHLVEALYLVC-GERGFFYTPKA).

In another embodiment, the parent insulin is porcine insulin. The sequence of porcine insulin is well known in the art. Porcine insulin comprises an A chain having an amino acid sequence as shown in SEQ ID NO: 83 (GIVEQCCTSICSLYQLENYCN) and a B chain having an amino acid sequence as shown in SEQ ID NO: 84 (FVNQHLCGSHLVEALYLVC GERGFFYTPKA).

Human, bovine, and porcine insulin comprises three disulfide bridges: one disulfide bridge between the cysteines at position A6 and A11, one disulfide bridge between the cysteine at position A7 of the A-chain and the cysteine at position B7 of the B-chain, and one between the cysteine at position A20 of the A-chain and the cysteine at position B19 of the B-chain.

The insulin analogs provided herein have an insulin receptor binding affinity which is reduced as compared to the insulin receptor binding affinity of the corresponding parent insulin, e.g. of human insulin.

The insulin receptor can be any mammalian insulin receptor, such as a bovine, porcine or human insulin receptor. In some embodiments, the insulin receptor is a human insulin receptor, e.g. human insulin receptor isoform A or human insulin receptor isoform B (which was used in the Examples section).

Advantageously, the human insulin analogs provided herein have a significantly reduced binding affinity to the human insulin receptor as compared to the binding affinity of human insulin to the human insulin receptor (see Examples). Thus, the insulin analogs have a very low clearance rate, i.e. a very low insulin-receptor-mediated clearance rate.

In some embodiments, the insulin analogs have, i.e. exhibit, less than 20% of the binding affinity to the corresponding insulin receptor compared to its parent insulin. In another embodiment, the insulin analogs provided herein have less than 10% of the binding affinity to the corresponding insulin receptor compared to its parent insulin. In another embodiment, the insulin analogs provided herein have less than 5% of the binding affinity to the corresponding insulin receptor compared to its parent insulin, such as less than 3% of the binding affinity compared to its parent insulin. For example, the insulin analogs provided herein may have between 0.1% to 10%, such as between 0.3% to 5% of the of the binding affinity to the corresponding insulin receptor compared to its parent insulin. Also, the insulin analogs provided herein may have between 0.5% to 3%, such as between 0.5% to 2% of the of the binding affinity to the corresponding insulin receptor compared to its parent insulin.

Methods for determining the binding affinity of an insulin analog to an insulin receptor are well known in the art. For example, the insulin receptor binding affinity can be determined by a scintillation proximity assay which is based on the assessment of competitive binding between [125I]-labelled parent insulin, such as [125I]-labelled human insulin, and the (unlabeled) insulin analog to the insulin receptor. The insulin receptor can be present in a membrane of a cell, e.g. of CHO (Chinese Hamster Ovary) cell, which overexpresses a recombinant insulin receptor. In an embodiment, the insulin receptor binding affinity is determined as described in the Examples section.

Binding of a naturally occurring insulin or an insulin analog to the insulin receptor activates the insulin signaling pathway. The insulin receptor has tyrosine kinase activity. Binding of insulin to its receptor induces a conformational change that stimulates the autophosphorylation of the receptor on tyrosine residues. The autophosphorylation of the insulin receptor stimulates the receptor's tyrosine kinase activity toward intracellular substrates involved in the transduction of the signal. The autophosphorylation of the insulin receptor by an insulin analog is therefore considered as a measure for signal transduction caused by said analog.

The insulin analogs in Table 4 of the Examples section were subjected to autophosphorylation assays. Interestingly, insulin analogs with aliphatic substitutions at positions B16 and B25 caused higher than expected insulin receptor autophosphorylation based on their insulin receptor binding affinities. Thus, the insulin analogs provided herein have a low binding activity, and consequently a lower receptor-mediated clearance rate, but are nevertheless capable of causing a relatively high signal transduction. Therefore, the insulin analogs provided herein could be used as long-acting insulins. In some embodiments, the insulin analog provided herein are capable of inducing 1 to 10%, such as 2 to 8%, insulin receptor autophosphorylation relative to the parent insulin (such as human insulin). Further, in some embodiments, the insulin analogs provided herein are capable of inducing 3 to 7%, such as 5 to 7% insulin receptor autophosphorylation relative to the parent insulin (such as human insulin). The insulin receptor autophosphorylation relative to a parent insulin can be determined as described in the Examples section.

Insulin analogs provided herein were subjected to protease stability assays. As shown in Table 6, insulin analogs provided herein had higher stability towards at least some of the tested proteases as compared to human insulin. Improved proteolytic stability was observed against α-chymotrypsin, cathepsin D and insulin degrading enzyme (IDE). Accordingly, insulin analogs provided herein are, typically, proteolytically stable insulin analogs. Thus, they are slower degraded by proteases relative to the parent insulin. In some embodiments, the insulin analog provided herein are stabilized against degradation by α-chymotrypsin, cathepsin D and insulin degrading enzyme (IDE) compared to parent insulin.

As set forth above, the insulin analog comprises at least one mutation as compared to the parent insulin.

In some embodiments insulin analogs provided herein comprise a mutation at position B16 which is substituted with a hydrophobic amino acid. Thus, the amino acid at position B16 (tyrosine in human, bovine and porcine insulin) is replaced with a hydrophobic amino acid.

In another embodiment, insulin analogs provided herein comprise a mutation at position B25 which is substituted with a hydrophobic amino acid. Thus, the amino acid at position B25 (phenylalanine in human, bovine and porcine insulin) is replaced with a hydrophobic amino acid.

In another embodiment, insulin analogs provided herein comprise a mutation at position B16 which is substituted with a hydrophobic amino acid and a mutation at position B25 which is substituted with a hydrophobic amino acid.

The hydrophobic amino acid may be any hydrophobic amino acid. For example, the hydrophobic amino acid may be an aliphatic amino acid such as a branched-chain amino acid.

In some embodiments of the insulin analogs provided herein, the hydrophobic amino acid used for the substitution at position B16 and/or B25 is isoleucine, valine, leucine, alanine, tryptophan, methionine, proline, glycine, phenylalanine or tyrosine (or with a derivative of the aforementioned amino acids).

Several parent insulins such as human, bovine and porcine insulin comprise tyrosine at position B16 and phenylalanine at position B25. Thus, the amino acid at position B16 of the parent insulin may be substituted with isoleucine, valine, leucine, alanine, tryptophan, methionine, proline, glycine or phenylalanine (or with a derivative of the aforementioned amino acids). Further, the amino acid at position B25 of the parent insulin may be substituted with isoleucine, valine, leucine, alanine, tryptophan, methionine, proline, glycine, or tyrosine (or with a derivative of the aforementioned amino acids).

Derivatives of the aforementioned amino acids are known in the art.

Derivatives of leucine include, but are not limited to, homo-leucine and tert-leucine. Thus, the amino acid at position B16 and/or B25 may be substituted with homo-leucine or tert-leucine.

A derivative of valine is, e.g., 3-ethyl norvaline. Thus, the amino acid at position B16 and/or B25 may be substituted with 3-ethyl norvaline.

Derivatives of glycine include, but are not limited to cyclohexyl-glycine cyclopropylglycine, and trifluorethylglycine.

Derivatives of alanine include, but are not limited to, beta-t-butylalanine, cyclobutyl-alanine, cyclopropyl-alanine and homo-cyclohexylalanine.

In some embodiments, the hydrophobic amino acid used for the substitution at position B16 and/or B25 is isoleucine, valine, leucine, alanine, or tryptophan.

In some embodiments, the aliphatic amino acid is not alanine. Accordingly, the hydrophobic amino acid used for the substitution at position B16 and/or B25 may be isoleucine, valine, leucine, or tryptophan.

In some embodiments, the hydrophobic amino acid used for the substitution at position B16 and/or B25 is isoleucine, valine, or leucine.

In some embodiments, the amino acids referred to herein are L-amino acids (such as L-isoleucine, L-valine, or L-leucine). Accordingly, the amino acids (or the derivatives thereof) used for e.g. the substitution at position B16, B25 and/or A14 are typically L-amino acids.

In some embodiments, the hydrophobic amino acid is an aliphatic amino acid. Accordingly, the insulin analogs provided herein comprise a mutation at position B16 which is substituted with an aliphatic amino acid and a mutation at position B25 which is substituted with an aliphatic amino acid (and optionally further mutations including but not limited to Des(B30) and Glu(A14)).

Aliphatic amino acids are non-polar and hydrophobic amino acids comprising an aliphatic side chain functional group. Hydrophobicity increases with the number of carbon atoms on the hydrocarbon chain increases. A measure for the hydrophobicity of an aliphatic is the hydropathy index according to the Kyte and Doolittle scale which e.g. can be determined as disclosed by Kyte J. et al. Journal of Molecular Biology. 1982 157 (1): 105-32. In some embodiments, the aliphatic amino acid is an aliphatic amino acid having a hydropathy index (according to the Kyte and Doolittle scale) of larger than 2.0, such as larger than 3.0 or larger than 3.5.

Aliphatic amino acids include, but are not limited to, isoleucine, valine, leucine, alanine and glycine. For example, the aliphatic amino acid may be an amino acid selected from isoleucine, valine, leucine, and glycine, such as an amino acid selected from isoleucine, valine and leucine.

Isoleucine, valine and leucine are branched-chain amino acids (abbreviated BCAA). Thus, the aliphatic amino acid may be a branched-chain amino acid. In some embodiments the insulin analogs provided herein comprise a mutation at position B16 which is substituted with a branched-chain amino acid and a mutation at position B25 which is substituted with a branched-chain amino acid (and optionally further mutations including but not limited to Des(B30) and Glu(A14)).

BCAAs are amino acids such as isoleucine, valine, and leucine are amino acids having aliphatic side chains that are non-linear, i.e. branched-chain amino acids are amino acid having an aliphatic side-chain with a branch (a central carbon atom bound to three or more carbon atoms).

The branched-chain amino acid may be a proteinogenic BCAA, i.e. an amino acid that is incorporated biosynthetically into proteins during translation, or a non-proteinogenic BCAA, i.e. an amino acid that is not naturally encoded or found in the genetic code of any organism. For example, proteinogenic BCAAs are leucine, isoleucine, and valine.

Thus, the hydrophobic/aliphatic amino acid branched-chain amino acid may be leucine, isoleucine or valine (or a derivative of the leucine, isoleucine or valine, such as a derivative of leucine or valine as set forth above).

In some embodiments, the branched-chain amino acid is isoleucine. In some embodiments, the branched-chain amino acid is valine. In some embodiments, the branched-chain amino acid is leucine.

In addition to the mutation at position B16 and/or the mutation at position B25 as described above, insulin analogs provided herein may comprise further mutations relative to the parent insulin.

For example, the insulin analog may further comprise a mutation at position A14. Such mutations are known to increase protease stability (see e.g. WO 2008/034881). In some embodiments, the amino acid at position A14 is substituted with glutamic acid (Glu). In some embodiments, the amino acid at position A14 is substituted with aspartic acid (Asp). In some embodiments, the amino acid at position A14 is substituted with histidine (His).

Further, the insulin analogs provided herein may comprise a mutation at position B30. In some embodiment, the mutation at position B30 is the deletion of threonine at position B30 of the parent insulin (also referred to as Des(B30)-mutation).

Further, the insulin analog of the present invention may further comprise a mutation at position B3 which is substituted with a glutamic acid (Glu), and/or a mutation at position A21 which is substituted with glycine (Gly).

In an embodiment, the B chain of the insulin analog of the present invention comprises or consists of the amino acid sequence shown in SEQ ID NO: 22 (FVNQHLCGSHLVEALYLVCGERGFLYTPK).

In another embodiment, the B chain of the insulin analog of the present invention comprises or consists of the amino acid sequence shown in SEQ ID NO: 24 (FVNQHLCGSHLVEALYLVCGERGFVYTPK).

In another embodiment, the B chain of the insulin analog of the present invention comprises or consists of the amino acid sequence shown in SEQ ID NO: 44 (FVNQHLCGSHLVEALYLVCGERGFIYTPK).

In another embodiment, the B chain of the insulin analog of the present invention comprises or consists of the amino acid sequence shown in SEQ ID NO: 48 (FVNQHLCGSHLVEALYLVCGERGFVYTPK).

In another embodiment, the B chain of the insulin analog of the present invention comprises or consists of the amino acid sequence shown in SEQ ID NO: 50 (FVEQHLCGSHLVEALYLVCGERGFVYTPK).

In another embodiment, the B chain of the insulin analog of the present invention comprises or consists of the amino acid sequence shown in SEQ ID NO: 58 (FVNQHLCGSHLVEALILVCGERGFIYTPK).

In another embodiment, the B chain of the insulin analog of the present invention comprises or consists of the amino acid sequence shown in SEQ ID NO: 60 (FVEQHLCGSHLVEALILVCGERGFIYTPK).

In another embodiment, the B chain of the insulin analog of the present invention comprises or consists of the amino acid sequence shown in SEQ ID NO: 64 (FVNQHLCGSHLVEALILVCGERGFVYTPK).

In another embodiment, the B chain of the insulin analog of the present invention comprises or consists of the amino acid sequence shown in SEQ ID NO: 66 (FVEQHLCGSHLVEALILVCGERGFVYTPK).

In another embodiment, the B chain of the insulin analog of the present invention comprises or consists of the amino acid sequence shown in SEQ ID NO: 70 (FVNQHLCGSHLVEALVLVCGERGFIYTPK).

In another embodiment, the B chain of the insulin analog of the present invention comprises or consists of the amino acid sequence shown in SEQ ID NO: 78 (FVEQHLCGSHLVEALVLVCGERGFVYTPK).

In another embodiment, the B chain of the insulin analog of the present invention comprises or consists of the amino acid sequence shown in SEQ ID NO: 80 (FVEQHLCGSHLVEALVLVCGERGFVYTPK).

The B chains summarized above comprise the Des(B30) mutation. Accordingly, the amino acid which is present at position B30 of the parent insulin (threonine in human insulin, and alanine in porcine and bovine insulin) is deleted, i.e. not present. However, it is also envisaged that the B chains of the analogs of the present invention do not comprise this mutation, i.e. comprise a threonine at position 30. Accordingly, the B chain of the insulin analog of the present invention may comprise or consist of an amino acid sequence selected from the group consisting of:

```
                                             (SEQ ID NO: 85)
     FVNQHLCGSHLVEALYLVCGERGFLYTPKT (SEQ ID NO: 86)
     FVNQHLCGSHLVEALYLVCGERGFVYTPKT (SEQ ID NO: 87)
     FVNQHLCGSHLVEALYLVCGERGFIYTPKT (SEQ ID NO: 88)
     FVNQHLCGSHLVEALYLVCGERGFVYTPKT (SEQ ID NO: 89)
     FVEQHLCGSHLVEALYLVCGERGFVYTPKT (SEQ ID NO: 90)
     FVNQHLCGSHLVEALILVCGERGFIYTPKT (SEQ ID NO: 91)
     FVEQHLCGSHLVEALILVCGERGFIYTPKT (SEQ ID NO: 92)
     FVNQHLCGSHLVEALILVCGERGFVYTPKT (SEQ ID NO: 93)
     FVEQHLCGSHLVEALILVCGERGFVYTPKT (SEQ ID NO: 94)
     FVNQHLCGSHLVEALVLVCGERGFIYTPKT (SEQ ID NO: 95)
     FVNQHLCGSHLVEALVLVCGERGFVYTPKT (SEQ ID NO: 96)
     FVEQHLCGSHLVEALVLVCGERGFVYTPKT (SEQ ID NO: 97)
     FVEQHLCGSHLVEALVLVCGERGFVYTPKT
```

In an embodiment, the A chain of the insulin analog of the present invention comprises or consists of the amino acid sequence shown in SEQ ID NO: 1 (GIVEQCCTSICSLYQLENYCN).

In another embodiment, the A chain of the insulin analog of the present invention comprises or consists of the amino acid sequence shown in SEQ ID NO: 43 (GIVEQCCTSICSLEQLENYCN).

In another embodiment, the A chain of the insulin analog of the present invention comprises or consists of the amino acid sequence shown in SEQ ID NO: 45 (GIVEQCCTSICSLEQLENYCG).

Typically, the insulin analog of the present invention comprises an A-chain and a B-chain as set forth above.

For example, the insulin analog of the present invention is selected from the group consisting of:
Leu(B16)-insulin (e.g. human insulin, i.e. Leu(B16)-human insulin), Val(B16)-insulin (e.g. human insulin, i.e. Val(B16)-human insulin),
Ile(B16)-insulin (e.g. human insulin),
Leu(B16)Des(B30)-insulin (e.g. human insulin),
Val(B16)Des(B30)-insulin (e.g. human insulin),
Ile(B16)Des(B30)-insulin (e.g. human insulin),
Leu(B25)-insulin (e.g. human insulin),
Val(B25)-insulin (e.g. human insulin),
Ile(B25)-insulin (e.g. human insulin),
Leu(B25)Des(B30)-insulin (e.g. human insulin),
Val(B25)Des(B30)-insulin (e.g. human insulin),
Ile(B25)Des(B30)-insulin (e.g. human insulin),
Glu(A14)Leu(B16)Des(B30)-insulin (e.g. human insulin),
Glu(A14)Ile(B16)Des(B30)-insulin (e.g. human insulin),
Glu(A14)Val(B16)Des(B30)-insulin (e.g. human insulin),
Glu(A14)Leu(B16)-insulin (e.g. human insulin),
Glu(A14)Ile(B16)-insulin (e.g. human insulin),
Glu(A14)Val(B16)-insulin (e.g. human insulin),
Glu(A14)Leu(B25)Des(B30)-insulin (e.g. human insulin),
Glu(A14)Ile(B25)Des(B30)-insulin (e.g. human insulin),
Glu(A14)Val(B25)Des(B30)-insulin (e.g. human insulin),
Glu(A14)Leu(B25)-insulin (e.g. human insulin),
Glu(A14)Ile(B25)-insulin (e.g. human insulin),
Glu(A14)Val(B25)-insulin (e.g. human insulin),
Glu(A14)Gly(A21)Glu(B3)Val(B25)Des(B30)-insulin (e.g. human insulin),
Glu(A14)Ile(B16)Ile(B25)Des(B30)-insulin (e.g. human insulin),
Glu(A14)Glu(B3)Ile(B16)Ile(B25)Des(B30)-insulin (e.g. human insulin),
Glu(A14)Ile(B16)Val(B25)Des(B30)-insulin (e.g. human insulin),
Glu(A14)Gly(A21)Glu(B3)Ile(B16)Val(B25)Des(B30)-insulin (e.g. human insulin),
Glu(A14)Val(B16)Ile(B25)Des(B30)-insulin (e.g. human insulin),
Glu(A14)Val(B16)Val(B25)Des(B30)-insulin (e.g. human insulin),
Glu(A14)Glu(B3)Val(B16)Val(B25)Des(B30)-insulin (e.g. human insulin),
Glu(A14)Gly(A21)Glu(B3)Val(B16)Val(B25)Des(B30)-insulin (e.g. human insulin),
Glu(A14)Gly(A21)Glu(B3)Val(B25)-insulin (e.g. human insulin),
Glu(A14)Ile(B16)Ile(B25)-insulin (e.g. human insulin),
Glu(A14)Glu(B3)Ile(B16)Ile(B25)-insulin (e.g. human insulin),
Glu(A14)Ile(B16)Val(B25)-insulin (e.g. human insulin),
Glu(A14)Gly(A21)Glu(B3)Ile(B16)Val(B25)-insulin (e.g. human insulin),
Glu(A14)Val(B16)Ile(B25)-insulin (e.g. human insulin),
Glu(A14)Val(B16)Val(B25)-insulin (e.g. human insulin),
Glu(A14)Glu(B3)Val(B16)Val(B25)-insulin (e.g. human insulin), and
Glu(A14)Gly(A21)Glu(B3)Val(B16)Val(B25)-insulin (e.g. human insulin).

In another embodiment, the insulin analogs provided herein are selected from the group consisting of:
Asp(A14)Leu(B16)Des(B30)-insulin (e.g. human insulin, i.e. Asp(A14)Leu(B16)Des(B30)-human insulin),
Asp(A14)Ile(B16)Des(B30)-insulin (e.g. human insulin),
Asp(A14)Val(B16)Des(B30)-insulin (e.g. human insulin),
Asp(A14)Leu(B16)-insulin (e.g. human insulin),
Asp(A14)Ile(B16)-insulin (e.g. human insulin),
Asp(A14)Val(B16)-insulin (e.g. human insulin),
Asp(A14)Leu(B25)Des(B30)-insulin (e.g. human insulin),
Asp(A14)Ile(B25)Des(B30)-insulin (e.g. human insulin),
Asp(A14)Val(B25)Des(B30)-insulin (e.g. human insulin),
Asp(A14)Leu(B25)-insulin (e.g. human insulin),
Asp(A14)Ile(B25)-insulin (e.g. human insulin),
Asp(A14)Val(B25)-insulin (e.g. human insulin),
Asp(A14)Gly(A21)Glu(B3)Val(B25)Des(B30)-insulin (e.g. human insulin),
Asp(A14)Ile(B16)Ile(B25)Des(B30)-insulin (e.g. human insulin),
Asp(A14)Glu(B3)Ile(B16)Ile(B25)Des(B30)-insulin (e.g. human insulin),
Asp(A14)Ile(B16)Val(B25)Des(B30)-insulin (e.g. human insulin),
Asp(A14)Gly(A21)Glu(B3)Ile(B16)Val(B25)Des(B30)-insulin (e.g. human insulin),
Asp(A14)Val(B16)Ile(B25)Des(B30)-insulin (e.g. human insulin),
Asp(A14)Val(B16)Val(B25)Des(B30)-insulin (e.g. human insulin),
Asp(A14)Glu(B3)Val(B16)Val(B25)Des(B30)-insulin (e.g. human insulin),
Asp(A14)Gly(A21)Glu(B3)Val(B16)Val(B25)Des(B30)-insulin (e.g. human insulin),
Asp(A14)Gly(A21)Glu(B3)Val(B25)-insulin (e.g. human insulin),
Asp(A14)Ile(B16)Ile(B25)-insulin (e.g. human insulin),
Asp(A14)Glu(B3)Ile(B16)Ile(B25)-insulin (e.g. human insulin),
Asp(A14)Ile(B16)Val(B25)-insulin (e.g. human insulin),
Asp(A14)Gly(A21)Glu(B3)Ile(B16)Val(B25)-insulin (e.g. human insulin),
Asp(A14)Val(B16)Ile(B25)-insulin (e.g. human insulin),
Asp(A14)Val(B16)Val(B25)-insulin (e.g. human insulin),
Asp(A14)Glu(B3)Val(B16)Val(B25)-insulin (e.g. human insulin), and
Asp(A14)Gly(A21)Glu(B3)Val(B16)Val(B25)-insulin (e.g. human insulin).

In another embodiment, the insulin analogs provided herein are selected from the group consisting of:
His(A14)Leu(B16)Des(B30)-insulin (e.g. human insulin),
His(A14)Ile(B16)Des(B30)-insulin (e.g. human insulin),
His(A14)Val(B16)Des(B30)-insulin (e.g. human insulin),
His(A14)Leu(B16)-insulin (e.g. human insulin),
His(A14)Ile(B16)-insulin (e.g. human insulin),
His(A14)Val(B16)-insulin (e.g. human insulin),
His(A14)Leu(B25)Des(B30)-insulin (e.g. human insulin),
His(A14)Ile(B25)Des(B30)-insulin (e.g. human insulin),
His(A14)Val(B25)Des(B30)-insulin (e.g. human insulin),
His(A14)Leu(B25)-insulin (e.g. human insulin),
His(A14)Ile(B25)-insulin (e.g. human insulin),
His(A14)Val(B25)-insulin (e.g. human insulin),
His(A14)Gly(A21)Glu(B3)Val(B25)Des(B30)-insulin (e.g. human insulin),
His(A14)Ile(B16)Ile(B25)Des(B30)-insulin (e.g. human insulin),
His(A14)Glu(B3)Ile(B16)Ile(B25)Des(B30)-insulin (e.g. human insulin),
His(A14)Ile(B16)Val(B25)Des(B30)-insulin (e.g. human insulin), His(A14)Gly(A21)Glu(B3)Ile(B16)Val(B25)Des(B30)-insulin (e.g. human insulin),
His(A14)Val(B16)Ile(B25)Des(B30)-insulin (e.g. human insulin),
His(A14)Val(B16)Val(B25)Des(B30)-insulin (e.g. human insulin),
His(A14)Glu(B3)Val(B16)Val(B25)Des(B30)-insulin (e.g. human insulin),
His(A14)Gly(A21)Glu(B3)Val(B16)Val(B25)Des(B30)-insulin (e.g. human insulin),
His(A14)Gly(A21)Glu(B3)Val(B25)Des(B30)-insulin (e.g. human insulin),
His(A14)Ile(B16)Ile(B25)-insulin (e.g. human insulin),
His(A14)Glu(B3)Ile(B16)Ile(B25)-insulin (e.g. human insulin),
His(A14)Ile(B16)Val(B25)-insulin (e.g. human insulin),
His(A14)Gly(A21)Glu(B3)Ile(B16)Val(B25)-insulin (e.g. human insulin),
His(A14)Val(B16)Ile(B25)-insulin (e.g. human insulin),
His(A14)Val(B16)Val(B25)-insulin (e.g. human insulin),
His(A14)Glu(B3)Val(B16)Val(B25)-insulin (e.g. human insulin), and
His(A14)Gly(A21)Glu(B3)Val(B16)Val(B25)-insulin (e.g. human insulin).

In another embodiment, the insulin analog is Leu(B25)Des(B30)-Insulin (such as Leu(B25)Des(B30)-human insulin). The sequence of this analog is, e.g., shown in Table 4 of the Examples section (see Analog 11). For example, Leu(B25)Des(B30)-Insulin comprises an A chain having an amino acid sequence as shown in SEQ ID NO: 21 (GIVEQCCTSICSLYQLENYCN) and a B chain having an amino acid sequence as shown in SEQ ID NO: 22 (FVNQHLCGSHLVEALYLVCGERGFLYTPK).

In another embodiment, the insulin analog is Val(B25)Des(B30)-Insulin (such as Val(B25)Des(B30)-human insulin). The sequence of this analog is, e.g., shown in Table 4 of the Examples section (see Analog 12). For example, Val(B25)Des(B30)-Insulin comprises an A chain having an amino acid sequence as shown in SEQ ID NO: 23 (GIVEQCCTSICSLYQLENYCN) and a B chain having an amino acid sequence as shown in SEQ ID NO: 24 (FVNQHLCGSHLVEALYLVCGERGFVYTPK).

In another embodiment, the insulin analog is Glu(A14)Ile(B25)Des(B30)-Insulin (such as Glu(A14)Ile(B25)Des(B30)-human insulin). The sequence of this analog is, e.g., shown in Table 4 of the Examples section (see Analog 22). For example, Glu(A14)Ile(B25)Des(B30)-Insulin comprises an A chain having an amino acid sequence as shown in SEQ ID NO: 43 (GIVEQCCTSICSLEQLENYCN) and a B chain having an amino acid sequence as shown in SEQ ID NO: 44 (FVNQHLCGSHLVEALYLVCGERGFIYTPK).

In another embodiment, the insulin analog is Glu(A14)Val(B25)Des(B30)-Insulin (such as Glu(A14)Val(B25)Des(B30)-human insulin). The sequence of this analog is, e.g., shown in Table 4 of the Examples section (see Analog 24). For example, Glu(A14)Val(B25)Des(B30)-Insulin comprises an A chain having an amino acid sequence as shown in SEQ ID NO: 47 (GIVEQCCTSICSLEQLENYCN) and a B chain having an amino acid sequence as shown in SEQ ID NO: 48 (FVNQHLCGSHLVEALYLVCGERGFVYTPK).

In another embodiment, the insulin analog is Glu(A14)Gly(A21)Glu(B3)Val(B25)Des(B30)-Insulin (such as Glu(A14)Gly(A21)Glu(B3) Val(B25)Des(B30)-human insulin). The sequence of this analog is, e.g., shown in Table 4 of the Examples section (see Analog 25). For example, Glu(A14)Gly(A21)Glu(B3) Val(B25)Des(B30)-Insulin comprises an A chain having an amino acid sequence as shown in SEQ ID NO: 49 (GIVEQCCTSICSLEQLENYCG) and a B chain having an amino acid sequence as shown in SEQ ID NO: 50 (FVEQHLCGSHLVEALYLVCGERGFVYTPK).

In another embodiment, the insulin analog is Glu(A14)Ile(B16)Ile(B25)Des(B30)-Insulin(such as Glu(A14)Ile(B16)Ile(B25)Des(B30)-human insulin). The sequence of this analog is, e.g., shown in Table 4 of the Examples section (see Analog 29). For example, Glu(A14)Ile(B16)Ile(B25)Des(B30)-Insulin comprises an A chain having an amino acid sequence as shown in SEQ ID NO: 57 (GIVEQCCTSICSLEQLENYCN) and a B chain having an amino acid sequence as shown in SEQ ID NO: 58 (FVNQHLCGSHLVEALILVCGERGFIYTPK).

In another embodiment, the insulin analog is Glu(A14)Glu(B3)Ile(B16)Ile(B25)Des(B30)-Insulin(such as Glu(A14)Glu(B3)Ile(B16) Ile(B25)Des(B30)-human insulin). The sequence of this analog is, e.g., shown in Table 4 of the Examples section (see Analog 30). For example, Glu(A14)Glu(B3) Ile(B16)Ile(B25)Des(B30)-Insulin comprises an A chain having an amino acid sequence as shown in SEQ ID NO: 56 (GIVEQCCTSICSLEQLENYCN) and a B chain having an amino acid sequence as shown in SEQ ID NO: 60 (FVEQHLCGSHLVEALILVCGERGFIYTPK).

In another embodiment, the insulin analog is Glu(A14)Ile(B16)Val(B25)Des(B30)-Insulin (such as Glu(A14)Ile(B16)Val(B25)Des(B30)-human insulin) The sequence of this analog is, e.g., shown in Table 4 of the Examples section (see Analog 32). For example, Glu(A14)Ile(B16)Val(B25)Des(B30)-Insulin comprises an A chain having an amino acid sequence as shown in SEQ ID NO: 63 (GIVEQCCTSICSLEQLENYCN) and a B chain having an amino acid sequence as shown in SEQ ID NO: 64 (FVNQHLCGSHLVEALILVCGERGFVYTPK).

In another embodiment, the insulin analog is Glu(A14)Gly(A21)Glu(B3) Ile(B16)Val(B25)Des(B30)-Insulin (such as Glu(A14)Gly(A21)Glu(B3)Ile(B16)Val(B25) Des(B30)-human insulin). The sequence of this analog is, e.g., shown in Table 4 of the Examples section (see Analog 33). For example, Glu(A14)Gly(A21)Glu(B3)Ile(B16)Val(B25)Des (B30)-Insulin comprises an A chain having an amino acid sequence as shown in SEQ ID NO: 65 (GIVEQCCTSICSLEQLENYCG) and a B chain having an amino acid sequence as shown in SEQ ID NO: 66 (FVEQHLCGSHLVEALILVCGERGFVYTPK).

In another embodiment, the insulin analog is Glu(A14)Val(B16)Ile(B25)Des(B30)-Insulin (such as Glu(A14)Val(B16)Ile(B25)Des(B30)-human insulin). The sequence of this analog is, e.g., shown in Table 4 of the Examples section (see Analog 35). For example, Glu(A14)Val(B16)Ile(B25)Des(B30)-Insulin comprises an A chain having an amino acid sequence as shown in SEQ ID NO: 69 (GIVEQCCTSICSLEQLENYCN) and a B chain having an amino acid sequence as shown in SEQ ID NO: 70 (FVNQHLCGSHLVEALVLVCGERGFIYTPK).

In another embodiment, the insulin analog is Glu(A14)Val(B16)Val(B25)Des(B30)-Insulin (such as Glu(A14)Val(B16)Val(B25) Des(B30)-human insulin). The sequence of this analog is, e.g., shown in Table 4 of the Examples section (see Analog 38). For example, Glu(A14)Val(B16)Val(B25)Des(B30)-Insulin comprises an A chain having an amino acid sequence as shown in SEQ ID NO: 75

(GIVEQCCTSICSLEQLENYCN) and a B chain having an amino acid sequence as shown in SEQ ID NO: 76 (FVNQHLCGSHLVEALVLVCGERGFVYTPK).

In another embodiment, the insulin analog is Glu(A14) Glu(B3)Val(B16)Val(B25)Des(B30)-Insulin (such as Glu (A14)Glu(B3)Val(B16) Val(B25)Des(B30)-human insulin). The sequence of this analog is, e.g., shown in Table 4 of the Examples section (see Analog 39). For example, Glu(A14) Glu(B3)Val(B16) Val(B25)Des(B30)-Insulin comprises an A chain having an amino acid sequence as shown in SEQ ID NO: 77 (GIVEQCCTSICSLEQLENYCN) and a B chain having an amino acid sequence as shown in SEQ ID NO: 78 (FVEQHLCGSHLVEALVLVCGERGFVYTPK).

In another embodiment, the insulin analog is Glu(A14) Gly(A21)Glu(B3)Val(B16)Val(B25)Des(B30)-Insulin (such as Glu(A14)Gly(A21) Glu(B3)Val(B16)Val(B25)Des(B30)-human insulin). The sequence of this analog is, e.g., shown in Table 4 of the Examples section (see Analog 40). For example, Glu(A14)Gly(A21)Glu(B3)Val(B16)Val(B25)Des (B30)-Insulin comprises an A chain having an amino acid sequence as shown in SEQ ID NO: 79 (GIVEQCCTSICSLEQLENYCG) and a B chain having an amino acid sequence as shown in SEQ ID NO: 80 (FVEQHLCGSHLVEALVLVCGERGFVYTPK).

The insulin analog can be prepared by any method deemed appropriate. For example, the insulin analog can be prepared by recombinant methods or by solid-phase synthesis.

The definitions and explanations given herein above apply mutatis mutandis to the following.

Provided herein are insulin B chains, i.e. insulin B chain peptides, as defined herein above in connection with the B chain of the insulin analog provided herein. Accordingly, provided herein are insulin B chains which comprise at least one mutation relative to the insulin B chain of the parent insulin, wherein the B chains comprise a mutation at position B16 which is substituted with a hydrophobic amino acid, and/or a mutation at position B25 which is substituted with a hydrophobic amino acid. The insulin B chain may comprise further mutations as described herein above such as the des(B30) deletion.

Also provided herein are proinsulins comprising an insulin A chain and/or an insulin B chain of the insulin analogs provided herein. The B chain may be any B chain as defined herein above for the insulin analogs provided herein. For example, provided herein are proinsulins comprising an insulin A chain and an insulin B chain, wherein said B chain comprises at least one mutation relative to B chain of a parent insulin, wherein the mutation is in position B16 which is substituted with a hydrophobic amino acid and/or wherein the mutation is in position B25 which is substituted with a hydrophobic amino acid. The insulin B chain may comprise further mutations as described herein above for the B chain.

The A chain comprised by the proinsulin provided herein may be any A chain as defined herein above for the insulin analogs provided herein. In some embodiments, the A chain of said proinsulin comprises a mutation at position A14 which is substituted with an amino acid selected from glutamic acid (Glu), aspartic Acid (Asp) and histidine (His).

In addition to the insulin A chain and/or the insulin B chain, the proinsulins provided herein may comprise further elements such as leader sequences or a C-peptide. In some embodiments, the proinsulin may further comprise a C-peptide which is located between the insulin B chain and the insulin A chain. The C-peptide may have a length of 4-10 amino acids, such as a length of 4 to 9 amino acids. The orientation may be as follows (from N-terminus to C-terminus): B chain, C-peptide, A chain.

Provided herein are polynucleotides encoding the insulin analogs, insulin B chains, and the proinsulins provided herein. Said polynucleotide may be operably linked to a promoter which allows for the expression of said polynucleotide. In some embodiments, the promoter is heterologous with respect to said polynucleotide. In some embodiments, the promoter is a constitutive promoter. In another embodiment, the promoter is an inducible promoter.

Further, provided herein are vectors comprising the polynucleotide encoding the insulin analogs provided herein. In some embodiments, said vector is an expression vector.

Provided herein are host cells comprising nucleic acids encoding the insulin analogs, insulin B chains, and proinsulins, the polynucleotides, and/or the vectors provided herein. In some embodiments, the host cell is a bacterial cell such as a cell of belonging to the genus *Escherichia*, e.g. an *E. coli* cell. In another embodiment, the host cell is a yeast cell, such as a *Pichia pastoris* cell or *Klyveromyces lactis* cell.

Provided herein are pharmaceutical compositions comprising a pharmaceutically effective amount of an insulin analog provided herein and a pharmaceutically acceptable excipient.

Provided herein are methods for treating a disease comprising administering a pharmaceutically effective amount of one or more insulin analogs provided herein or the pharmaceutical composition thereof to a subject.

In some embodiments, the disease is diabetes mellitus such as diabetes type II mellitus.

Provided herein are insulin analogs or the pharmaceutical composition thereof for use in medicine.

Provided herein are insulin analogs or the pharmaceutical composition thereof for use in the treatment of diabetes mellitus, such as of diabetes type II mellitus.

Finally, provided herein are uses of the insulin analogs provided herein or the pharmaceutical compositions thereof for the preparation of a medicament or drug for the treatment of diabetes mellitus, such as of diabetes type II mellitus.

The insulin analogs, insulin B chains, proinsulins, and uses as described in section A are further illustrated by the following embodiments and combinations of embodiments as indicated by the respective dependencies and back-references. The definitions and explanations given herein above apply mutatis mutandis to the following embodiments.

1. An insulin analog comprising at least one mutation relative to the parent insulin, wherein the insulin analog comprises a mutation at position B16 which is substituted with a hydrophobic amino acid and/or a mutation at position B25 which is substituted with a hydrophobic amino acid.
2. The insulin analog of embodiment 1, wherein the parent insulin is human insulin, porcine insulin, or bovine insulin.
3. The insulin analog of embodiments 1 and 2, wherein the hydrophobic amino acid at position B16 and/or position B25 is an aliphatic amino acid.
4. The insulin analog of any one of embodiments 1 to 3, wherein said aliphatic amino acid at position B16 and/or position B25 is a branched-chain amino acid, such as a branched-chain amino acid selected from the group consisting of valine (Val), isoleucine (Ile), and leucine (Leu).

5. The insulin analog of any one of embodiments 1 to 3, wherein said insulin analog further comprises a mutation at position A14 which is substituted with an amino acid selected from the group consisting of glutamic acid (Glu), aspartic Acid (Asp) and histidine (His).

6. The insulin analog of any one of embodiments 1 to 5, wherein said insulin analog further comprises a mutation at position B30, e.g. wherein the mutation at position B30 is the deletion of the amino acid at position B30 of the parent insulin (Des(B30)-mutation).

7. The insulin analog of any one of embodiments 1 to 6, wherein said insulin analog further comprises a mutation at position B3 which is substituted with a glutamic acid (Glu).

8. The insulin analog of any one of embodiments 1 to 7, wherein said insulin further comprises a mutation at position A21 which is substituted with glycine (Gly).

9. The insulin analog of any one of embodiments 1 to 8, wherein the B chain of the insulin analog comprises or consists of an amino acid sequence selected from the group consisting of

```
                                         (SEQ ID NO: 22)
FVNQHLCGSHLVEALYLVCGERGFLYTPK (SEQ ID NO: 44)
FVNQHLCGSHLVEALYLVCGERGFIYTPK (SEQ ID NO: 48)
FVNQHLCGSHLVEALYLVCGERGFVYTPK (SEQ ID NO: 50)
FVEQHLCGSHLVEALYLVCGERGFVYTPK (SEQ ID NO: 58)
FVNQHLCGSHLVEALILVCGERGFIYTPK (SEQ ID NO: 60)
FVEQHLCGSHLVEALILVCGERGFIYTPK (SEQ ID NO: 64)
FVNQHLCGSHLVEALILVCGERGFVYTPK (SEQ ID NO: 66)
FVEQHLCGSHLVEALILVCGERGFVYTPK (SEQ ID NO: 70)
FVNQHLCGSHLVEALVLVCGERGFIYTPK (SEQ ID NO: 76)
FVNQHLCGSHLVEALVLVCGERGFVYTPK (SEQ ID NO: 78)
FVEQHLCGSHLVEALVLVCGERGFVYTPK (SEQ ID NO: 80)
FVEQHLCGSHLVEALVLVCGERGFVYTPK (SEQ ID NO: 85)
FVNQHLCGSHLVEALYLVCGERGFLYTPKT (SEQ ID NO: 86)
FVNQHLCGSHLVEALYLVCGERGFVYTPKT (SEQ ID NO: 87)
FVNQHLCGSHLVEALYLVCGERGFIYTPKT (SEQ ID NO: 88)
FVNQHLCGSHLVEALYLVCGERGFVYTPKT (SEQ ID NO: 89)
FVEQHLCGSHLVEALYLVCGERGFVYTPKT (SEQ ID NO: 90)
FVNQHLCGSHLVEALILVCGERGFIYTPKT (SEQ ID NO: 91)
FVEQHLCGSHLVEALILVCGERGFIYTPKT (SEQ ID NO: 92)
FVNQHLCGSHLVEALILVCGERGFVYTPKT (SEQ ID NO: 93)
FVEQHLCGSHLVEALILVCGERGFVYTPKT (SEQ ID NO: 94)
FVNQHLCGSHLVEALVLVCGERGFIYTPKT (SEQ ID NO: 95)
FVNQHLCGSHLVEALVLVCGERGFVYTPKT (SEQ ID NO: 96)
FVEQHLCGSHLVEALVLVCGERGFVYTPKT,
and (SEQ ID NO: 97)
FVEQHLCGSHLVEALVLVCGERGFVYTPKT.
```

10. The insulin analog of any one of embodiments 1 to 9, comprising
    (a) an A chain having an amino acid sequence as shown in SEQ ID NO: 43 (GIVEQCCTSICSLEQLENYCN) and a B chain having an amino acid sequence as shown in SEQ ID NO: 44 (FVNQHLCGSHLVEALYL-VCGERGFIYTPK),
    (b) an A chain having an amino acid sequence as shown in SEQ ID NO: 47 (GIVEQCCTSICSLEQLENYCN) and a B chain having an amino acid sequence as shown in SEQ ID NO: 48 (FVNQHLCGSHLVEALYL-VCGERGFVYTPK), or
    (c) an A chain having an amino acid sequence as shown in SEQ ID NO: 77 (GIVEQCCTSICSLEQLENYCN) and a B chain having an amino acid sequence as shown in SEQ ID NO: 78 (FVEQHLCGSHLVEALVLVCGERGFVYTPK).

11. An insulin analog selected from the group consisting of
    Leu(B16)-human insulin,
    Val(B16)-human insulin,
    Ile(B16)-human insulin,
    Leu(B16)Des(B30)-human insulin,
    Val(B16)Des(B30)-human insulin,
    Ile(B16)Des(B30)-human insulin,
    Leu(B25)-human insulin,
    Val(B25)-human insulin,
    Ile(B25)-human insulin,
    Leu(B25)Des(B30)-human insulin,
    Val(B25)Des(B30)-human insulin,
    Ile(B25)Des(B30)-human insulin,
    Glu(A14)Leu(B16)Des(B30)-human insulin,
    Glu(A14)Ile(B16)Des(B30)-human insulin,
    Glu(A14)Val(B16)Des(B30)-human insulin,
    Glu(A14)Leu(B16)-human insulin,
    Glu(A14)Ile(B16)-human insulin,
    Glu(A14)Val(B16)-human insulin,
    Glu(A14)Leu(B25)Des(B30)-human insulin,
    Glu(A14)Ile(B25)Des(B30)-human insulin,
    Glu(A14)Val(B25)Des(B30)-human insulin,
    Glu(A14)Leu(B25)-human insulin,
    Glu(A14)Ile(B25)-human insulin,
    Glu(A14)Val(B25)-human insulin,
    Glu(A14)Gly(A21)Glu(B3)Val(B25)Des(B30)-human insulin,
    Glu(A14)Ile(B16)Ile(B25)Des(B30)-human insulin, Glu(A14)Glu(B3)Ile(B16)Ile(B25)Des(B30)-human insulin,
Glu(A14)Ile(B16)Val(B25)Des(B30)-human insulin,
Glu(A14)Gly(A21)Glu(B3)Ile(B16)Val(B25)Des(B30)-human insulin,
Glu(A14)Val(B16)Ile(B25)Des(B30)-human insulin,
Glu(A14)Val(B16)Val(B25)Des(B30)-human insulin,
Glu(A14)Glu(B3)Val(B16)Val(B25)Des(B30)-human insulin,
Glu(A14)Gly(A21)Glu(B3)Val(B16)Val(B25)Des(B30)-human insulin,
Glu(A14)Gly(A21)Glu(B3)Val(B25)-human insulin,
Glu(A14)Ile(B16)Ile(B25)-human insulin,
Glu(A14)Glu(B3)Ile(B16)Ile(B25)-human insulin,
Glu(A14)Ile(B16)Val(B25)-human insulin,
Glu(A14)Gly(A21)Glu(B3)Ile(B16)Val(B25)-human insulin,
Glu(A14)Val(B16)Ile(B25)-human insulin,
Glu(A14)Val(B16)Val(B25)-human insulin,
Glu(A14)Glu(B3)Val(B16)Val(B25)-human insulin, and
Glu(A14)Gly(A21)Glu(B3)Val(B16)Val(B25)-human insulin.

12. An insulin B chain comprising at least one mutation relative to the B chain of the parent insulin, wherein the B chain comprises a mutation at position B16 which is substituted with a hydrophobic amino acid, and/or a mutation at position B25 which is substituted with a hydrophobic amino acid.

13. The insulin B chain according to embodiment 12, wherein the parent insulin is human insulin, porcine insulin, or bovine insulin.

14. The insulin B chain according to embodiments 12 and 13, wherein the hydrophobic amino acid at position B16 and/or position B25 is an aliphatic amino acid.

15. The insulin B chain according to any one of embodiments 12 to 14, wherein said aliphatic amino acid in a branched-chain amino acid, such as a branched-chain amino acid selected from the group consisting of valine (Val), isoleucine (Ile), and leucine (Leu).

16. The insulin B chain according to any one of embodiments 12 to 15, wherein said insulin B chain further comprises a mutation at position B3 which is substituted with a glutamic acid (Glu).

17. The insulin B chain according to any one of embodiments 12 to 16, wherein said insulin B chain further comprises a mutation at position B30, wherein the mutation at position B30 is the deletion of the amino acid at position B30 of the parent insulin (Des(B30)-mutation).

18. A proinsulin comprising an insulin A chain and an insulin B chain, wherein the insulin B chain comprises at least one mutation relative to B chain of a parent insulin, wherein the B chain comprises a mutation at position B16 which is substituted with a hydrophobic amino acid and/or a mutation at position B25 which is substituted with a hydrophobic amino acid.

19. The proinsulin of embodiment 18, wherein the insulin A chain of said proinsulin comprises a mutation at position A14 which is substituted with an amino acid selected from glutamic acid (Glu), aspartic acid (Asp) and histidine (His).

20. The proinsulin according to embodiments 18 and 19, wherein the parent insulin is human insulin, porcine insulin, or bovine insulin.

21. The proinsulin according to any one of embodiments 18 to 20, wherein the hydrophobic amino acid at position B16 and/or position B25 is an aliphatic amino acid.

22. The proinsulin according to any one of embodiments 18 to 21, wherein said aliphatic amino acid in a branched-chain amino acid, such as a branched-chain amino acid selected from the group consisting of valine (Val), isoleucine (Ile), and leucine (Leu).

23. The proinsulin according to any one of embodiments 18 to 22, wherein said proinsulin further comprises a mutation at position B3 which is substituted with a glutamic acid (Glu).

24. The proinsulin according to any one of embodiments 18 to 23, wherein said proinsulin further comprises a mutation at position B30, wherein the mutation at position B30 is the deletion of the amino acid at position B30 of the parent insulin (Des(B30)-mutation).

25. A polynucleotide encoding the insulin analog of any one of embodiments 1 to 11, the insulin B chain of any one of embodiments 12 to 17, and/or the proinsulin of any one of embodiment 18 to 24.

26. An expression vector comprising the polynucleotide of embodiment 25.

27. A host cell comprising insulin analog of any one of embodiments 1 to 11, the insulin B chain of any one of embodiments 12 to 17, the proinsulin of any one of embodiments 18 to 24, the polynucleotide of embodiment 25, and/or the expression vector of embodiment 26.

28. A method for treating a patient having diabetes mellitus comprising administering to the patient one or more insulin analog as defined in any one of embodiments 1 to 11.

29. The insulin analog as defined in any one of embodiments 1 to 11 for use in treating diabetes mellitus.

Section B: Serum Albumin Binding Moieties

Provided herein are serum albumin binding moieties (herein also referred to as "albumin binders" or "binders"), which when coupled to a peptide such as an insulin analog provided above lead to improved pharmacodynamics and/or pharmacokinetic properties of the peptide for example, an extended pharmacokinetic half life in blood and/or blood plasma and/or a prolonged profile of action, i.e. a prolonged reduction of blood glucose level. The provided serum albumin binding moieties are sulfonamides as described herein below.

Surprisingly, it was found that such peptide conjugates can be provided using specific sulfonamides, which can be used for peptide conjugates. The resulting peptide conjugates exhibit favorable half-life in blood and/or blood plasma and a prolonged profile of action. It could be shown that the resulting peptide conjugates have an increased pharmacokinetic half-life ($t_{1/2}$) and also an increased Mean Residence Time (MRT) compared to the unconjugated peptides. Moreover, the peptide conjugates have a significant prolongation of the duration of action in vivo in relation to the unconjugated peptides.

Thus, provided herein are sulfonamides of formula (A)

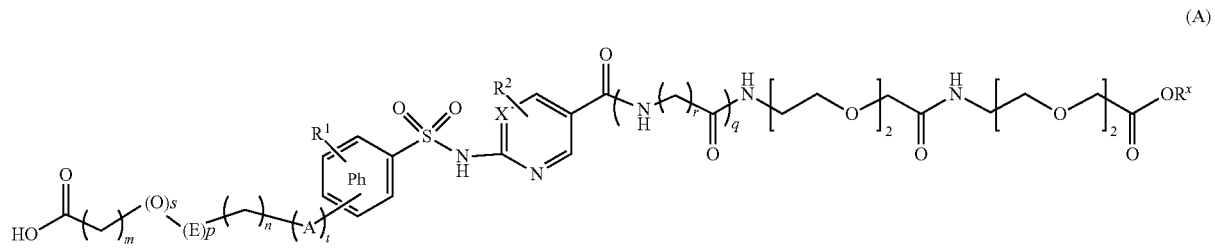

wherein:
A is selected from the group consisting of oxygen atom, —CH$_2$CH$_2$— group, —OCH$_2$— group and —CH$_2$O— group;
E represents a —O$_6$H$_3$R— group with R being a hydrogen atom or a halogen atom, wherein the halogen atom is selected from the group consisting of fluorine, chlorine, bromine and iodine atom;
X represents a nitrogen atom or a —CH— group;
m is an integer in the range from 5 to 17;
n is zero or an integer in the range from 1 to 3;
p is zero or 1;
q is zero or 1;
r is an integer in the range from 1 to 6;
is zero or 1;
t is zero or 1;
R$^1$ represents at least one residue selected from the group of hydrogen atom, halogen atom, C1 to C3 alkyl group and halogenated C1 to C3 alkyl group;
R$^2$ represents at least one residue selected from the group of hydrogen atom, halogen atom, C1 to C3 alkyl group and halogenated C1 to C3 alkyl group;
R$^x$ represents a hydrogen atom or an activation group, optionally an activation group selected from the group consisting of 7-azabenzotriazole (optionally derived from HATU [1-[bis(dimethylamino)methylene]-1H-1,2,3-triazolo[4,5-b]pyridinium 3-oxide hexafluorophosphate] or HBTU [3-[bis(dimethyl-amino)methyliumyl]-3H-benzotriazol-1-oxide hexafluorophosphate]), 4-nitro benzene and N-succinimidyl-group, wherein R$^x$ is optionally a N-succinimidyl-group.

In some embodiments, the combination of s being 1, p being zero, n being zero, A being an oxygen atom and t being 1 is excluded. In some embodiments, s is zero, wherein the remaining residues and indices have the meaning as indicated above for formula (A).

For example, the halogenated C1 to C3 alkyl group of R$^1$ and/or the halogenated C1 to C3 alkyl group of R$^2$ is/are partially halogenated or per halogenated. In some embodiments, the halogenated C1 to C3 alkyl group of R$^1$ and/or the halogenated C1 to C3 alkyl group of R$^2$ is/are per halogenated.

As used herein, the term "sulfonamides of formula (A)" comprises the sulfonamides of formula (A), pharmaceutically acceptable salts thereof and all pharmaceutically acceptable isotopically-labeled sulfonamides of formula (A), wherein one or more atoms are replaced by atoms having the same atomic number, but an atomic mass or mass number different from the atomic mass or mass number which predominates in nature. The same applies to all subtypes of the sulfonamides of formula (A), i.e. to the sulfonamides of formula (A-1) to (A-5) as detailed below and also to their substructures respectively, for example, the sulfonamides of formula (A-1-1). That is, the term "sulfonamides of formula (A- . . . )", wherein (A- . . . ) represents the number of the sulfonamides of formula (A-1) to (A-5) as detailed below and also to their substructures, comprises the compounds themselves, pharmaceutically acceptable salts and all pharmaceutically acceptable isotopically-labeled compounds thereof.

Pharmaceutically acceptable salts of the sulfonamides of formula (A) include base salts. Suitable base salts are formed from bases which form non-toxic salts. Examples include the aluminium, arginine, benzathine, calcium, choline, diethylamine, bis(2-hydroxyethyl)amine (diolamine), glycine, lysine, magnesium, meglumine, 2-aminoethanol (olamine), potassium, sodium, 2-amino-2-(hydroxymethyl) propane-1,3-diol (tris or tromethamine) and zinc salts. For a review on suitable salts, see Handbook of Pharmaceutical Salts: Properties, Selection, and Use by Stahl and Wermuth (Wiley-VCH, 2002).

The sulfonamides of formula (A), and pharmaceutically acceptable salts thereof, may exist in unsolvated and solvated forms. The term 'solvate' is used herein to describe a molecular complex comprising the sulfonamides of formula (A), or a pharmaceutically acceptable salt thereof, and one or more pharmaceutically acceptable solvent molecules, for example, ethanol. The term 'hydrate' is employed when said solvent is water.

Examples of isotopes suitable for inclusion in the sulfonamides of formula (A) include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, and sulfur, such as $^{35}$S.

Certain isotopically-labelled sulfonamides of formula (A), for example those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled sulfonamides of formula (A) can generally be prepared by conventional techniques known to those skilled in the art.

Pharmaceutically acceptable solvates in accordance with the invention include those wherein the solvent of crystallization may be isotopically substituted, e.g. D$_2$O, d$_6$-acetone, d$_6$-DMSO.

In order to identify suitable binder molecules, which when bound to a peptide, such as an insulin, are able to improve the half-life in plasma and to prolong the profile of action, a system was established based on affinity chromatography with serum albumin columns, i.e. columns with immobilized serum albumin.

The net retention time of the binders (samples) was calculated according to the following formula:

Net retention time=RetTime$_{Sample}$−RetTime$_{t0\ marker}$

Sulfonamides of formula (A) have a net retention in the range of from 9 to 19, for example in the range of from 9.5 to 18, and were consequently considered to be useful binders for peptide conjugates, such as insulin conjugates.

According to one embodiment, the sulfonamide has the formula (A-1)

from HATU or HBTU), 4-nitro benzene and N-succinimidyl-group, wherein $R^x$ is optionally a N-succinimidyl-group; with m being an integer in the range from 5 to 15 if p is zero, or m being an integer in the range from 7 to 15 if p is 1.

In one embodiment of the sulfonamide, $R^1$ and $R^2$ are hydrogen atoms.

In one embodiment of the sulfonamide, X represents a nitrogen atom.

According to another embodiment of the sulfonamide, the HOOC—$(CH_2)_m$—$(O)_s$-$(E)_p$-$(CH_2)_n$-$(A)_t$- group of formula (A) or the HOOC—$(CH_2)_m$-$(E)_p$-O— group of formula (A-1) is situated in meta or para position on phenyl ring Ph with respect to the —$S(O)_2$— group.

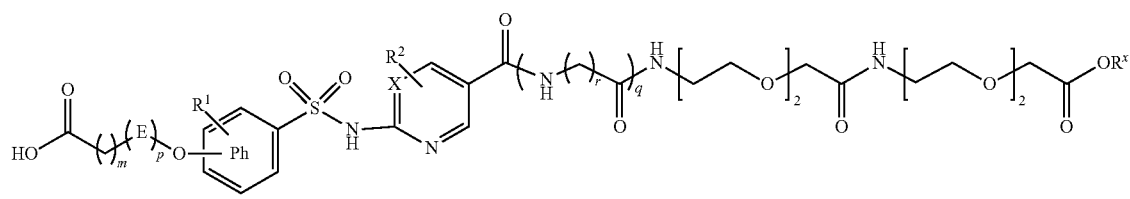

(A-1)

wherein:
E represents a —$C_6H_3R$— group with R being a hydrogen atom or a halogen atom, wherein the halogen atom is selected from the group consisting of fluorine, chlorine, bromine and iodine atom and is for example a fluorine atom;
X represents a nitrogen atom or a —CH— group;
p is zero or 1;
q is zero or 1;
r is an integer in the range from 1 to 6;

According to another embodiment of the sulfonamide, if p is 1, the HOOC—$(CH_2)_m$—$(O)_s$— group and the —$(CH_2)_n$-$(A)_t$- group are situated in meta or para position on $(E)p$ of formula (A) or the HOOC—$(CH_2)_m$— group and the —O— are situated in meta or para position on $(E)_p$ of formula (A-1).

According to another embodiment of the sulfonamide, q is zero.

According to another embodiment, the sulfonamide has the formula (A-1-1)

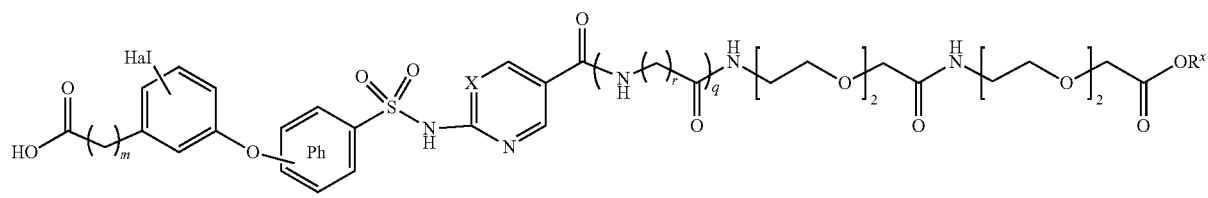

(A-1-1)

$R^1$ represents at least one residue selected from the group of hydrogen atom and halogen atom, wherein the halogen atom is for example a fluorine or chlorine atom;

$R^2$ represents at least one residue selected from the group of hydrogen atom, C1 to C3 alkyl group and halogenated C1 to C3 alkyl group, wherein the C1 to C3 alkyl group is for example a methyl group and the halogenated C1 to C3 alkyl group is for example perhalogenated such as a trifluoromethyl group;

$R^x$ represents a hydrogen atom or an activation group, optionally an activation group selected from the group consisting of 7-azabenzotriazole (optionally derived wherein X is a nitrogen atom or a —CH— group, for example a nitrogen atom; m is an integer in the range from 7 to 15; r is an integer in the range from 1 to 6; q is zero or 1, for example zero; Hal is a halogen atom selected from the group consisting of fluorine, chlorine, bromine and iodine atom, for example a fluorine atom; $R^x$ is a hydrogen atom or an activation group, optionally an activation group selected from the group consisting of 7-azabenzotriazole (optionally derived from HATU or HBTU), 4-nitro benzene and N-succinimidyl-group, wherein $R^x$ is optionally a N-succinimidyl-group; and the HOOC—$(CH_2)_m$—$C_6H_3Hal$-O— group is situated in meta or para position on phenyl ring Ph with respect to the —$S(O)_2$— group.

According to one embodiment, the sulfonamide has the formula (A-1-1a)

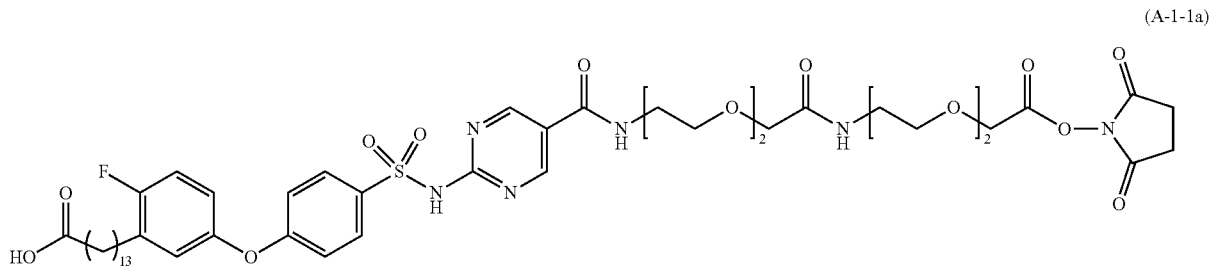

(A-1-1a)

According to another embodiment, the sulfonamide has the formula (A-1-2)

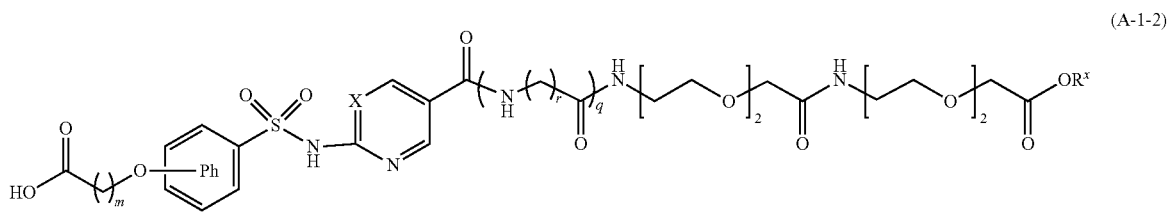

(A-1-2)

wherein X is a nitrogen atom or a —CH— group, for example a nitrogen atom; m is an integer in the range from 5 to 15; r is an integer in the range from 1 to 6; q is zero or 1, for example zero; $R^x$ is a hydrogen atom or an activation group, optionally an activation group selected from the group consisting of 7-azabenzotriazole (optionally derived from HATU or HBTU), 4-nitro benzene and N-succinimidyl-group, wherein $R^x$ is optionally a N-succinimidyl-group; and the HOOC—$(CH_2)_m$—O— group is situated in meta or para position on phenyl ring Ph with respect to the —S(O)$_2$— group.

According to one embodiment, the sulfonamide has the formula (A-1-2a)

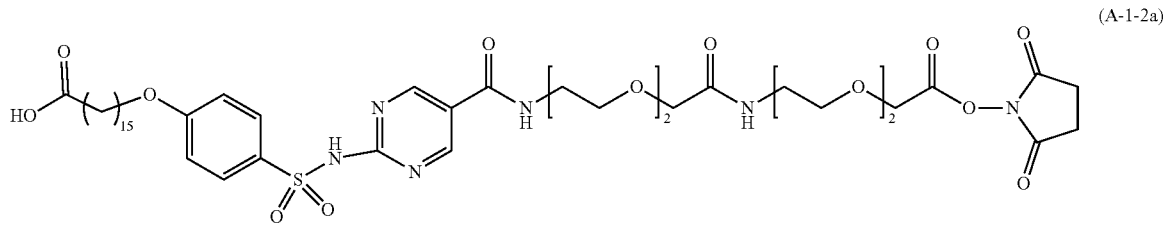

(A-1-2a)

or the formula (A-1-2b)

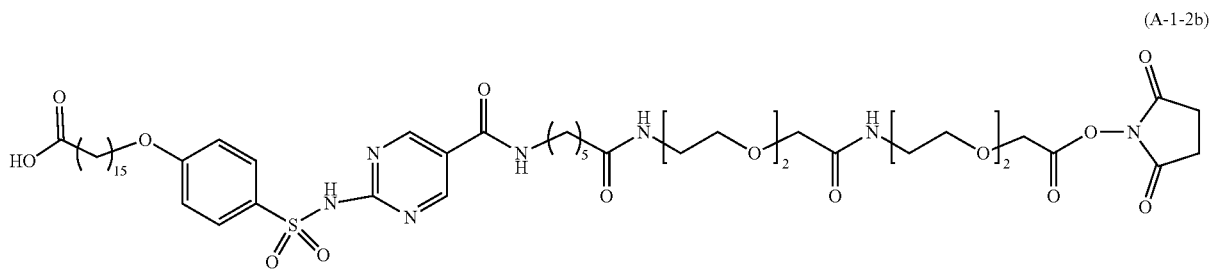

(A-1-2b)

or the formula (A-1-2c)

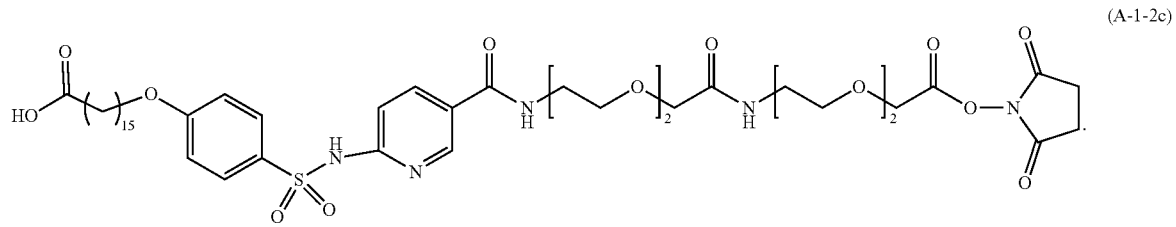

According to another embodiment, the sulfonamide has the formula (A-2)

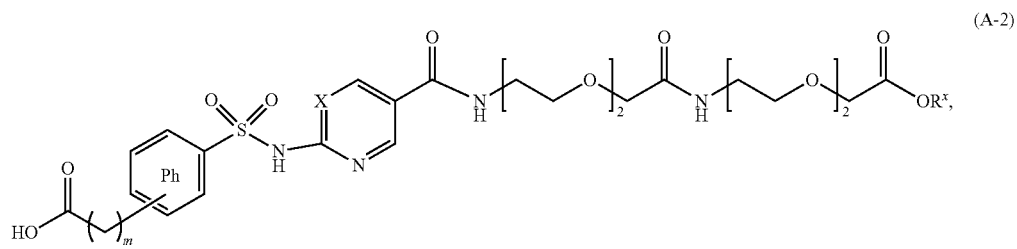

wherein
X represents a nitrogen atom or a —CH— group;
$R^x$ represents a hydrogen atom or an activation group, optionally an activation group selected from the group consisting of 7-azabenzotriazole (optionally derived from HATU or HBTU), 4-nitro benzene and N-succinimidyl-group, wherein $R^x$ is optionally a N-succinimidyl-group; and
m is an integer in the range from 5 to 17, for example in the range from 11 to 17.

According to one embodiment of the sulfonamide of formula (A-2), the HOOC—$(CH_2)_m$— group is s situated in meta or para position on phenyl ring Ph with respect to the —$S(O)_2$— group.

According to another embodiment, the sulfonamide has the formula (A-3)

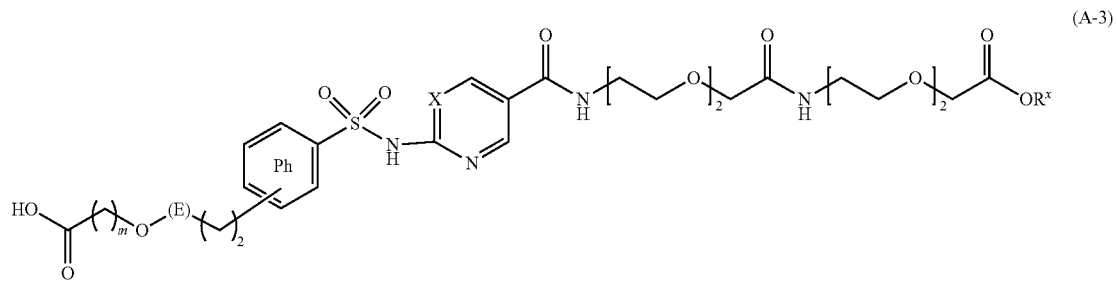

wherein
E represents a —$CH_3R$— group with R being a hydrogen atom or a halogen atom, wherein the halogen atom is selected from the group consisting of fluorine, chlorine, bromine and iodine atom;
X represents a nitrogen atom or a —CH— group;
$R^x$ represents a hydrogen atom or an activation group, optionally an activation group selected from the group consisting of 7-azabenzotriazole (optionally derived from HATU or HBTU), 4-nitro benzene and N-succinimidyl-group, wherein $R^x$ is optionally a N-succinimidyl-group; and
m is an integer in the range from 5 to 17, for example 11.

According to one embodiment of the sulfonamide of formula (A-3), the HOOC—$(CH_2)_m$—O— group and the —$(CH_2)_2$— group are situated in para position on (E) of formula (A-3) and the HOOC—$(CH_2)_m$—O-(E)-$(CH_2)_2$— group is situated in para position on phenyl ring Ph with respect to the —$S(O)_2$— group.

According to another embodiment, the sulfonamide has the formula (A-4)

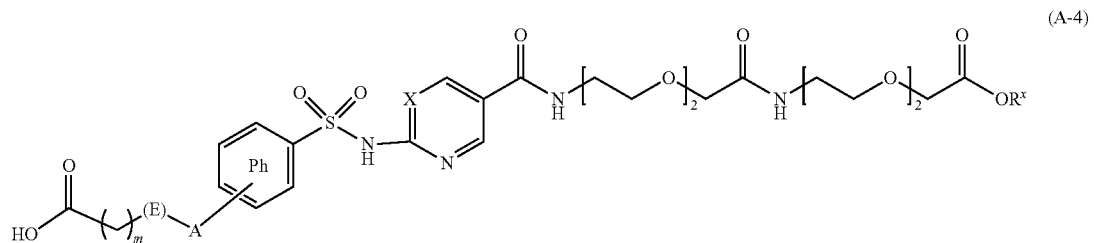

(A-4)

wherein
A is a —OCH$_2$— group or a —CH$_2$O— group;
E represents a —CH$_3$R— group with R being a hydrogen atom or a halogen atom, wherein the halogen atom is selected from the group consisting of fluorine, chlorine, bromine and iodine atom;
X represents a nitrogen atom or a —CH— group;
R$^x$ represents a hydrogen atom or an activation group, optionally an activation group selected from the group consisting of 7-azabenzotriazole (optionally derived from HATU or HBTU), 4-nitro benzene and N-succinimidyl-group, wherein R$^x$ is optionally a N-succinimidyl-group; and
m is an integer in the range of from 5 to 17, for example in the range of from 9 to 13.

According to one embodiment of the sulfonamide of formula (A-4), the HOOC—(CH$_2$)$_m$— group and the -A- group are situated in para position on (E) of formula (A-4) and the -A- group is situated in para position on phenyl ring Ph with respect to the —S(O)$_2$— group.

According to another embodiment, the sulfonamide has the formula (A-5)

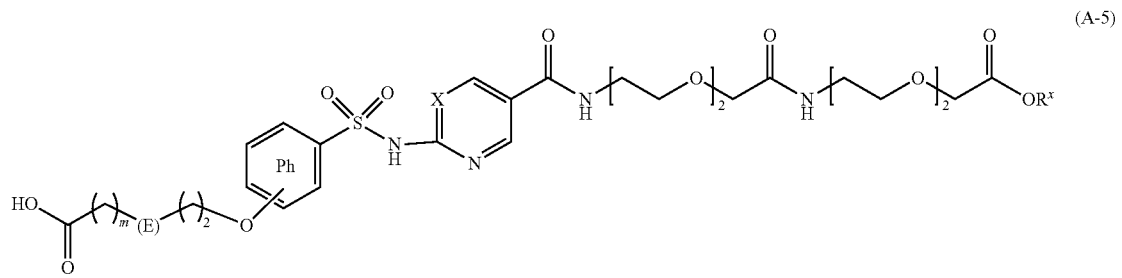

(A-5)

wherein
E represents a —CH$_3$R— group with R being a hydrogen atom or a halogen atom, wherein the halogen atom is selected from the group consisting of fluorine, chlorine, bromine and iodine atom;
X represents a nitrogen atom or a —CH— group;
R$^x$ represents a hydrogen atom or an activation group, optionally an activation group selected from the group consisting of 7-azabenzotriazole (optionally derived from HATU or HBTU), 4-nitro benzene and N-succinimidyl-group, wherein R$^x$ is optionally a N-succinimidyl-group; and
m is an integer in the range of from 5 to 17, for example in the range of from 7 to 9.

According to one embodiment of the sulfonamide of formula (A-5), the HOOC—(CH$_2$)$_m$— group and the —(CH$_2$)$_2$— group are situated in para position on (E) of formula (A-5) and the HOOC—(CH$_2$)$_m$E)-(CH$_2$)$_2$—O— group is situated in para position on phenyl ring Ph with respect to the —S(O)$_2$— group.

The albumin binders described in section B are further illustrated by the following embodiments and combinations of embodiments as indicated by the respective dependencies and back-references. In particular, it is noted that in each instance where a range of embodiments is mentioned, for example in the context of a term such as "The . . . of any of embodiments 1 to 4", every embodiment in this range is meant to be explicitly disclosed for the skilled person, i.e. the wording of this term is to be understood by the skilled person as being synonymous to "The . . . of any of embodiments 1, 2, 3, and 4".

1. A sulfonamide of formula (A)

$$\text{HO-C(O)-(CH}_2)_m\text{-(O)}_s\text{-(E)}_p\text{-(CH}_2)_n\text{-(A)}_t\text{-Ph(R}^1\text{)-S(O)}_2\text{-NH-[pyrimidine(X, R}^2\text{)]-C(O)-[NH-(CH}_2)_r\text{-C(O)]}_q\text{-NH-(CH}_2\text{CH}_2\text{O)}_2\text{-CH}_2\text{-C(O)-NH-(CH}_2\text{CH}_2\text{O)}_2\text{-CH}_2\text{-C(O)-OR}^x$$ (A)

wherein:
A is selected from the group consisting of oxygen atom, —CH$_2$CH$_2$— group, —OCH$_2$— group and —CH$_2$O— group;
E represents a —C$_6$H$_3$R— group with R being a hydrogen atom or a halogen atom, wherein the halogen atom is selected from the group consisting of fluorine, chlorine, bromine and iodine atom;
X represents a nitrogen atom or a —CH— group;
m is an integer in the range from 5 to 17;
n is zero or an integer in the range from 1 to 3;
p is zero or 1;
q is zero or 1;
r is an integer in the range from 1 to 6;
s is zero or 1;
t is zero or 1;
R$^1$ represents at least one residue selected from the group of hydrogen atom, halogen atom, C1 to C3 alkyl group and halogenated C1 to C3 alkyl group;
R$^2$ represents at least one residue selected from the group of hydrogen atom, halogen atom, C1 to C3 alkyl group and halogenated C1 to C3 alkyl group;
R$^x$ represents a hydrogen atom or an activation group, optionally an activation group selected from the group consisting of 7-azabenzotriazole (optionally derived from HATU or HBTU), 4-nitro benzene and N-succinimidyl-group, wherein R$^x$ is optionally a N-succinimidyl-group.

2. The sulfonamide according to embodiment 1 having the formula (A-1)

$$\text{HO-C(O)-(CH}_2)_m\text{-(E)}_p\text{-O-Ph(R}^1\text{)-S(O)}_2\text{-NH-[pyrimidine(X, R}^2\text{)]-C(O)-[NH-(CH}_2)_r\text{-C(O)]}_q\text{-NH-(CH}_2\text{CH}_2\text{O)}_2\text{-CH}_2\text{-C(O)-NH-(CH}_2\text{CH}_2\text{O)}_2\text{-CH}_2\text{-C(O)-OR}^x$$ (A-1)

wherein:
E represents a —C$_6$H$_3$R— group with R being a hydrogen atom or a halogen atom, wherein the halogen atom is selected from the group consisting of fluorine, chlorine, bromine and iodine atom;
X represents a nitrogen atom or a —CH— group;
p is zero or 1;
q is zero or 1;
r is an integer in the range from 1 to 6;
R$^1$ represents at least one residue selected from the group of hydrogen atom and halogen atom;
R$^2$ represents at least one residue selected from the group of hydrogen atom, C1 to C3 alkyl group and halogenated C1 to C3 alkyl group;
R$^x$ represents a hydrogen atom or an activation group, optionally an activation group selected from the group consisting of 7-azabenzotriazole (optionally derived from HATU or HBTU), 4-nitro benzene and N-succinimidyl-group, wherein R$^x$ is optionally a N-succinimidyl-group; and with m being an integer in the range from 5 to 15 if p is zero, or m being an integer in the range from 7 to 15 if p is 1.

3. The sulfonamide according to embodiment 1 or 2, wherein R$^1$ and R$^2$ are hydrogen atoms.

4. The sulfonamide according to any of embodiments 1 to 3, wherein X represents a nitrogen atom.

5. The sulfonamide according to any of embodiments 1 to 4, wherein the HOOC—(CH$_2$)$_m$—(O)$_s$-(E)$_p$-(CH$_2$)$_n$-(A)$_t$- group of formula (A) or the HOOC—(CH$_2$)$_m$-(E)$_p$-O— group of formula (A-1) is situated in meta or para position on phenyl ring Ph with respect to the —S(O)$_2$— group.

6. The sulfonamide according to any of embodiments 1 to 5, wherein, if p is 1, the HOOC—(CH$_2$)$_m$—(O)$_s$— group and the —(CH$_2$)$_n$-(A)$_t$- group are situated in meta or para position on (E)$_p$ of formula (A) or the HOOC—(CH$_2$)$_m$— group and the —O— are situated in meta or para position on (E)$_p$ of formula (A-1).

7. The sulfonamide according to any of embodiments 1 to 6, wherein q is zero.

8. The sulfonamide according to any of embodiments 1 to 7, wherein the sulfonamide has the formula (A-1-1)

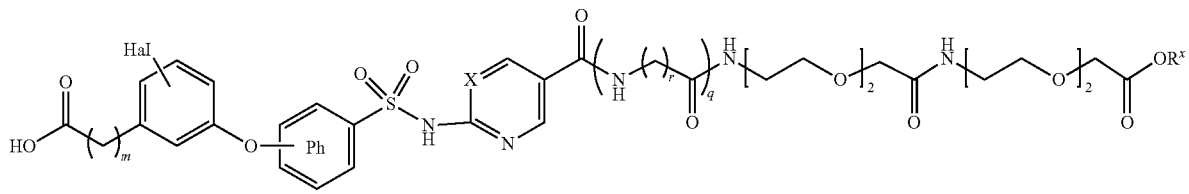

(A-1-1)

wherein X is a nitrogen atom or a —CH— group; m is an integer in the range from 7 to 15; r is an integer in the range from 1 to 6; q is zero or 1; Hal is a halogen atom selected from the group consisting of fluorine, chlorine, bromine and iodine atom; $R^x$ represents a hydrogen atom or an activation group, optionally an activation group selected from the group consisting of 7-azabenzotriazole (optionally derived from HATU or HBTU), 4-nitro benzene and N-succinimidyl-group, wherein $R^x$ is optionally a N-succinimidyl-group;

and the HOOC—$(CH_2)_m$—$C_6H_3$Hal-O— group is situated in meta or para position on phenyl ring Ph with respect to the —$S(O)_2$— group.

9. The sulfonamide according to any of embodiments 1 to 8, wherein the sulfonamide has the formula (A-1-1a)

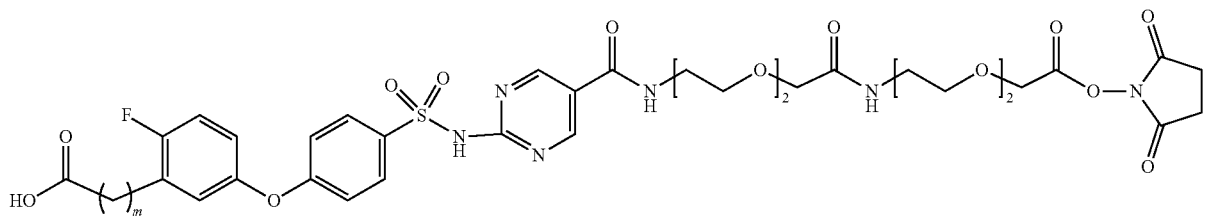

(A-1-1a)

10. The sulfonamide according to any of embodiments 1 to 7, wherein the sulfonamide has the formula (A-1-2)

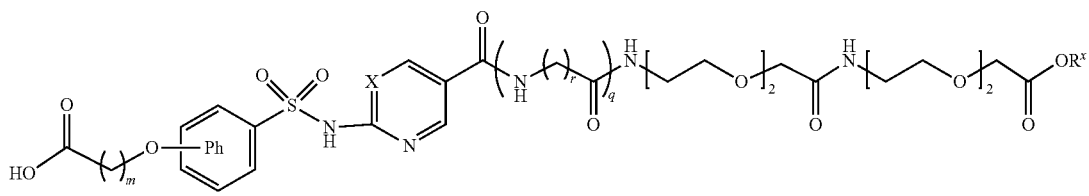

(A-1-2)

wherein X is a nitrogen atom or a —CH— group; m is an integer in the range from 5 to 15; r is an integer in the range from 1 to 6; q is zero or 1; and the HOOC—$(CH_2)_m$—O— group is situated in meta or para position on phenyl ring Ph with respect to the —$S(O)_2$— group.

11. The sulfonamide according to any of embodiments 1 to 7 or 10, wherein the sulfonamide has the formula (A-1-2a)

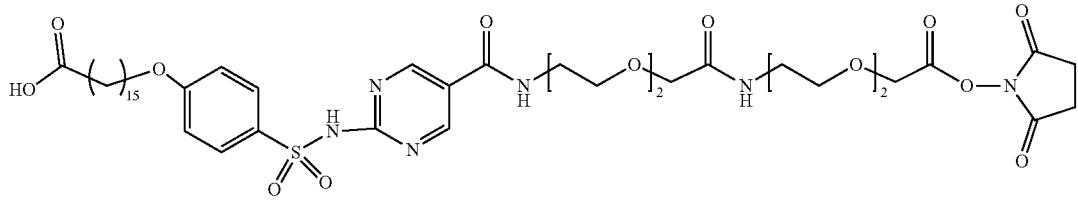

(A-1-2a)

or the formula (A-1-2b)

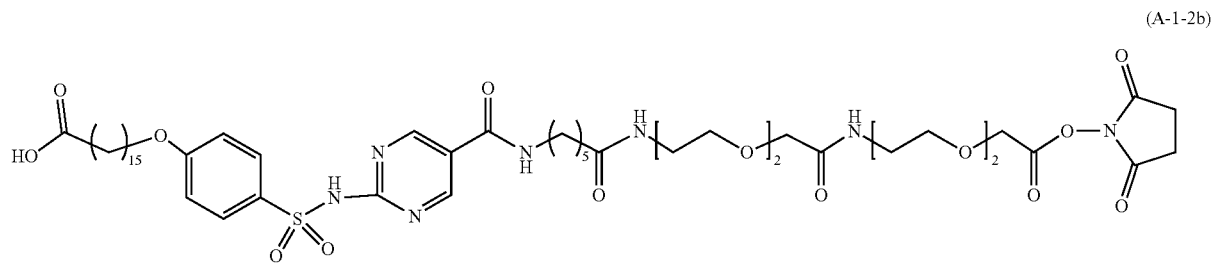

(A-1-2b)

or the formula (A-1-2c)

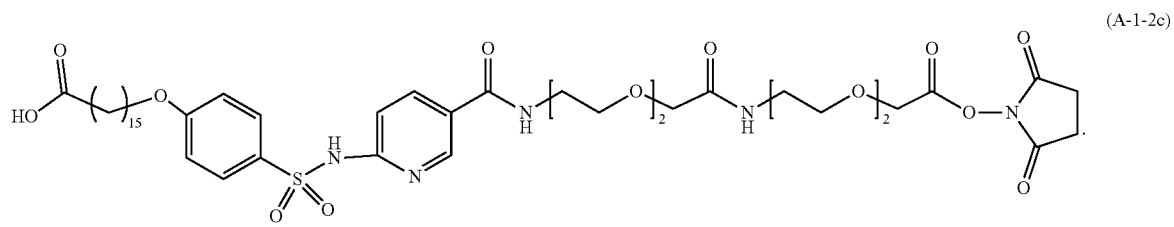

(A-1-2c)

Section C: Conjugate

Provided herein are conjugates comprising an albumin binder and an active pharmaceutical ingredient or a diagnostic compound. In an embodiment, the albumin binder is an albumin binder as defined in section B above and the active pharmaceutical ingredient is an insulin analog as defined in section A above.

Provided herein are conjugates comprising a sulfonamide of formula (I) and an active pharmaceutical ingredient or a diagnostic compound

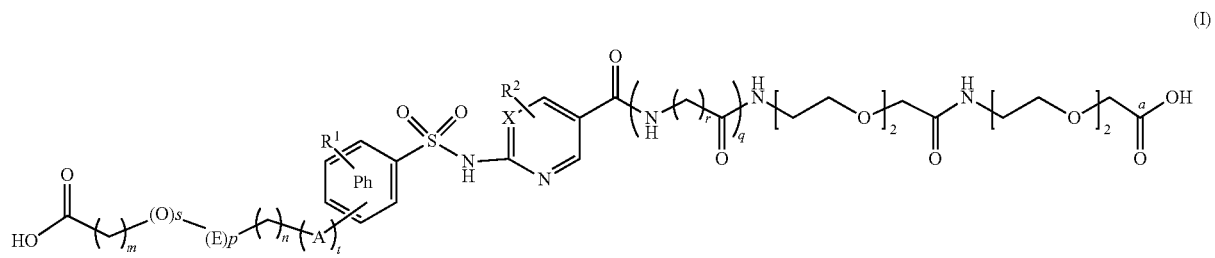

(I)

wherein in the sulfonamide of formula (I):

A is selected from the group consisting of oxygen atom, —CH$_2$CH$_2$— group, —OCH$_2$— group and —CH$_2$O— group;

E represents a —C$_6$H$_3$R— group with R being a hydrogen atom or a halogen atom, wherein the halogen atom is selected from the group consisting of fluorine, chlorine, bromine and iodine atom;

X represents a nitrogen atom or a —CH— group;

m is an integer in the range from 5 to 17;

n is zero or an integer in the range from 1 to 3;

p is zero or 1;

q is zero or 1;

r is an integer in the range from 1 to 6;

s is zero or 1;

t is zero or 1;

R$^1$ represents at least one residue selected from the group of hydrogen atom, halogen atom, C1 to C3 alkyl group and halogenated C1 to C3 alkyl group;

R$^2$ represents at least one residue selected from the group of hydrogen atom, halogen atom, C1 to C3 alkyl group and halogenated C1 to C3 alkyl group;

wherein the sulfonamide of formula (I) is covalently bound to the active pharmaceutical ingredient or the diagnostic compound.

In some embodiments, the combination of s being 1, p being zero, n being zero, A being an oxygen atom and t being 1 is excluded for the sulfonamide of formula (I). In some embodiments, s is zero, wherein the remaining residues and indices have the meaning as indicated above for formula (I).

In some embodiments, the sulfonamide of formula (I) is covalently bound to the active pharmaceutical ingredient or the diagnostic compound in that the terminal carboxy group "a" of the sulfonamide of formula (I) is covalently bound to a suitable functional group of the active pharmaceutical ingredient or of the diagnostic compound, for example to an amino group or a hydroxyl group of the active pharmaceutical ingredient or of the diagnostic compound. For example, the active pharmaceutical ingredient is a peptide, wherein the peptide and the sulfonamide of formula (I) are for example connected by an amide bond, for example formed between the terminal carboxy group "a" of the sulfonamide of formula (I) and an amino group of the peptide. It goes without saying that in case of an amide bond, the carboxyl group "a" is present in the conjugate as carbonyl group —C(=O)—, as shown below, wherein all residues E, A, $R^1$, $R^2$, X, as well as the indizes m, s, p, n, t, r and q habe the meaning as indicated above for formula (I) and the NH— group is already the part remaining from the peptide's amino group comprising a sulfonamide of formula (I- . . . )", wherein (I- . . . ) represents the number of the sulfonamides of formula (I-1) to (I-5) as detailed below and also their substructures, comprises the conjugates themselves, pharmaceutically acceptable salts and all pharmaceutically acceptable isotopically-labeled compounds thereof.

Pharmaceutically acceptable salts of the conjugates include acid addition and base salts. Suitable acid addition salts are formed from acids which form non-toxic salts. Examples include the acetate, adipate, aspartate, benzoate, besylate, bicarbonate/carbonate, bisulfate/sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihy-

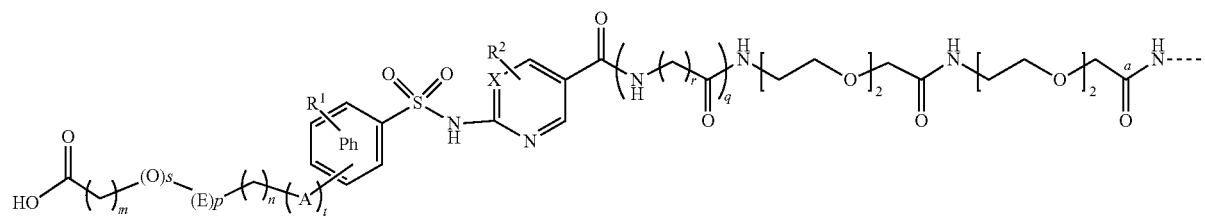

In some embodiments, the halogenated C1 to C3 alkyl group of $R^1$ and/or the halogenated C1 to C3 alkyl group of $R^2$ of the sulfonamide of formula (I) is/are partially halogenated or per halogenated. In some embodiments, the halogenated C1 to C3 alkyl group of $R^1$ and/or the halogenated C1 to C3 alkyl group of $R^2$ of the sulfonamide of formula (I) is/are per halogenated.

As already discussed above, it was surprisingly found that said conjugates exhibit favourable half life in blood and/or blood plasma and a prolonged profile of action, which has, for example, been proven in pre-clinical animal models.

As used herein, the term "active pharmaceutical ingredient" (API) includes any pharmaceutically active chemical or biological compound and any pharmaceutically acceptable salt thereof and any mixture thereof, that provides some pharmacologic effect and is used for treating or preventing a condition. As used herein, the terms "active pharmaceutical ingredient", "active agent", "active ingredient", "active substance" and "drug" are meant to be synonyms, i.e., have identical meaning.

As used herein, the term "conjugates comprising a sulfonamide of formula (I) and an active pharmaceutical ingredient or a diagnostic compound" comprises the conjugates themselves, pharmaceutically acceptable salts thereof and pharmaceutically acceptable isotopically-labeled conjugates, wherein one or more atoms are replaced by atoms having the same atomic number, but an atomic mass or mass number different from the atomic mass or mass number which predominates in nature. The same applies to all subtypes of the conjugates, i.e. to the conjugates comprising sulfonamides of formula (I-1) to (I-5) as detailed below and also to their substructures, for example, conjugates comprising the sulfonamides of formula (I-1-1). The same applies to all subtypes of the sulfonamides of formula (I), i.e. to the sulfonamides of formula (I-1) to (I-5) as detailed below and also to their substructures respectively, for example, the sulfonamides of formula (I-1-1). That is, the term "conjugate drogen phosphate, pyroglutamate, saccharate, stearate, succinate, tannate, tartrate, tosylate, trifluoroacetate, 1,5-naphathalenedisulfonic acid and xinafoate salts. Suitable base salts are formed from bases which form non-toxic salts. Examples include the aluminium, arginine, benzathine, calcium, choline, diethylamine, bis(2-hydroxyethyl)amine (diolamine), glycine, lysine, magnesium, meglumine, 2-aminoethanol (olamine), potassium, sodium, 2-amino-2-(hydroxymethyl)propane-1,3-diol (tris or tromethamine) and zinc salts. Hemisalts of acids and bases may also be formed, for example, hemisulfate and hemicalcium salts. For a review on suitable salts, see Handbook of Pharmaceutical Salts: Properties, Selection, and Use by Stahl and Wermuth (Wiley-VCH, 2002).

The conjugates, and pharmaceutically acceptable salts thereof, may exist in unsolvated and solvated forms. The term 'solvate' is used herein to describe a molecular complex comprising the compound of Formula I, or a pharmaceutically acceptable salt thereof, and one or more pharmaceutically acceptable solvent molecules, for example, ethanol. The term 'hydrate' is employed when said solvent is water.

Examples of isotopes suitable for inclusion in the conjugates include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, and sulfur, such as $^{35}$S.

Certain isotopically-labelled conjugates, for example those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled conjugates can generally be prepared by conventional techniques known to those skilled in the art.

Pharmaceutically acceptable solvates in accordance with the invention include those wherein the solvent of crystallization may be isotopically substituted, e.g. $D_2O$, $d_6$-acetone, $d_6$-DMSO.

In one embodiment, the active pharmaceutical ingredient is selected from the group comprising antidiabetic agent, anti-obesity agent, appetite regulating agent, antihypertensive agent, agent for the treatment and/or prevention of complications resulting from or associated with diabetes and agents for the treatment and/or prevention of complications and disorders resulting from or associated with obesity. Examples of these active pharmaceutical ingredient are: insulin, sulphonylureas, biguanides, meglitinides, glucosidase inhibitors, glucagon antagonists, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents as HMG CoA inhibitors (statins), Gastric Inhibitory Polypeptides (GIP analogs), compounds lowering food intake, RXR agonists and agents acting on the ATP-dependent potassium channel of the cells; cholestyramine, colestipol, clofibrate, gemfibrozil, lovastatin, pravastatin, simvastatin, probucol, dextrothyroxine, neteglinide, repaglinide; -blockers such as alprenolol, atenolol, timolol, pindolol, propranolol and metoprolol, ACE (angiotensin converting enzyme) inhibitors such as benazepril, captopril, enalapril, fosinopril, lisinopril, alatriopril, quinapril and ramipril, calcium channel blockers such as nifedipine, felodipine, nicardipine, isradipine, nimodipine, diltiazem and verapamil, and a-blockers such as doxazosin, urapidil, prazosin and terazosin; CART (cocaine amphetamine regulated transcript) agonists, NPY (neuropeptide Y) antagonists, PYY agonist, PYY2 agonists, PYY4 agonists, mixed PPY2/PYY4 agonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, 3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators, TR agonists; histamine H3 antagonists, Gastric Inhibitory Polypeptide to agonists or antagonists (GIP analogs), gastrin and gastrin analogs. In one embodiment, the active pharmaceutical ingredient is selected from the group consisting of antidiabetic agent, anti-obesity agent, appetite regulating agent, antihypertensive agent, agent for the treatment and/or prevention of complications resulting from or associated with diabetes and agents for the treatment and/or prevention of complications and disorders resulting from or associated with obesity. Examples of these active pharmaceutical ingredient are: Insulin, sulphonylureas, biguanides, meglitinides, glucosidase inhibitors, glucagon antagonists, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents as HMG CoA inhibitors (statins), Gastric Inhibitory Polypeptides (GIP analogs), compounds lowering food intake, RXR agonists and agents acting on the ATP-dependent potassium channel of the cells; cholestyramine, colestipol, clofibrate, gemfibrozil, lovastatin, pravastatin, simvastatin, probucol, dextrothyroxine, neteglinide, repaglinide; blockers such as alprenolol, atenolol, timolol, pindolol, propranolol and metoprolol, ACE (angiotensin converting enzyme) inhibitors such as benazepril, captopril, enalapril, fosinopril, lisinopril, alatriopril, quinapril and ramipril, calcium channel blockers such as nifedipine, felodipine, nicardipine, isradipine, nimodipine, diltiazem and verapamil, and a-blockers such as doxazosin, urapidil, prazosin and terazosin; CART (cocaine amphetamine regulated transcript) agonists, NPY (neuropeptide Y) antagonists, PYY agonist, PYY2 agonists, PYY4 agonists, mixed PPY2/PYY4 agonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, 3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators, TR agonists; histamine H3 antagonists, Gastric Inhibitory Polypeptide to agonists or antagonists (GIP analogs), gastrin and gastrin analogs.

In one embodiment, the active pharmaceutical ingredient is a therapeutically active peptide, wherein the peptide comprises at least 2 amino acids. In some embodiments, the peptide comprises at least 10 amino acids, or at least 20 amino acids. In some embodiments, the peptide comprises not more than 1000 amino acids, such as not more than 500 amino acids, for example not more than 100 amino acids.

In one embodiment of the conjugate, the active pharmaceutical ingredient is an antidiabetic agent, such as a peptide. In some embodiments, the peptide is GLP-1, GLP-1 analog, GLP-1 agonist; dual GLP-1 receptor/glucagon receptor agonist; human FGF21, FGF21 analog, FGF21 derivative; insulin (for example human insulin), insulin analog, or insulin derivative.

According to one embodiment of the conjugate, the active pharmaceutical ingredient is selected from the group comprising insulin, insulin analog, GLP-1, and GLP-1 analog (for example GLP(-1) agonist). In one embodiment of the conjugate, the active pharmaceutical ingredient is selected from the group consisting of insulin, insulin analog, GLP-1, and GLP-1 analog (for example GLP(-1) agonist).

As used herein, the term "GLP-1 analog" refers to a polypeptide which has a molecular structure which formally can be derived from the structure of a naturally occurring glucagon-like-peptide-1 (GLP-1), for example that of human GLP-1, by deleting and/or exchanging at least one amino acid residue occurring in the naturally occurring GLP-1 and/or adding at least one amino acid residue. The added and/or exchanged amino acid residue can either be codable amino acid residues or other naturally occurring residues or purely synthetic amino acid residues.

As used herein, the term "GLP(-1) agonist" refers to analogs of GLP(-1), which activate the glucagon-like-peptide-1-rezeptor (GLP-1-rezeptor). Examples of GLP(-1) agonists include, but are not limited to, the following: lixisenatide, exenatide/exendin-4, semaglutide, taspoglutide, albiglutide, dulaglutide.

Lixisenatide has the following amino acid sequence (SEQ ID NO: 98): His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser- Lys-Lys-Lys-Lys-Lys-Lys-$NH_2$ Exenatide has the following amino acid sequence (SEQ ID NO: 99): His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-$NH_2$ Semaglutide—Albumin binder coupled to Lys(20) has the following amino acid sequence (SEQ ID NO: 100):
His-Aib-Glu-Gly-Thr-Phe-Thr-Ser-Asp-Val-Ser-Ser-Tyr-Leu-Glu-Gly-Gln-Ala-Ala-Lys(AEEAc-AEEAc-γ-Glu-17-carboxyheptadecanoyl)-Glu-Phe-Ile-Ala-Trp-Leu-Val-Arg-Gly-Arg-Gly Dulaglutide (GLP1 (7-37) coupled via peptidic linker to an fc-fragment) has the following amino acid sequence (SEQ ID NO: 101):
His-Ala-Glu-Gly-Thr-Phe-Thr-Ser-Asp-Val-Ser-Ser-Tyr-Leu-Glu-Gy-Gln-Ala-Ala-Lys-Glu-Phe-Ile-Ala-Trp-Leu-Val-Lys-Gly-Arg-Gly As used herein, the term "FGF-21" means "fibroblast growth factor 21". FGF-21 compounds may be human FGF-21, an analog of FGF-21 (referred to "FGF-21 analog") or a derivative of FGF-21 (referred to "FGF-21 derivative").

In some embodiments, the active pharmaceutical ingredient is an insulin analog. Examples of analogs of insulin include, but are not limited to, the following:

(i). 'Insulin aspart' is human insulin where the amino acid B28 (i.e. the amino acid no. 28 in the B chain of human insulin), which is proline, is replaced by aspartic acid.

(ii). 'Insulin lispro' is human insulin where the penultimate lysine and proline residues on the C-terminal end of the B-chain of are reversed (human insulin: ProB28LysB29; insulin lispro: LysB28ProB29).

(iii). 'Insulin glulisine' differs from human insulin in that the amino acid asparagine at position B3 is replaced by lysine and the lysine in position B29 is replaced by glutamic acid.

(iv). "Insulin glargine" differs from human insulin in that the asparagine at position A21 is replaced by glycine and the B chain is extended at the carboxy terminal by two arginines.

Further, the insulin analog may be "Insulin detemir' which differs from human insulin in that amino acid threonine at position B30 is deleted and a fatty acid residue (myristic acid) is attached to the epsilon-amino function of the lysine in position B29. Alternatively, the insulin analog may be 'Insulin degludec' which differs from human insulin in that the amino acid threonine at position B30 is deleted and that a hexadecanedioic acid is conjugated to the amino acid lysine B29 via a gamma-L-glutamyl-linker. Insulin degludec is a long-acting insulin.

In some embodiments, the insulin analog is an insulin analog as described in section A above. The definitions and explanations provided above apply accordingly. In some embodiments, the insulin analog comprised by the conjugate is an insulin analog comprising at least one mutation relative to the parent insulin, wherein the insulin analog comprises a mutation at position B16 which is substituted with a hydrophobic amino acid, and/or a mutation at position B25 which is substituted with a hydrophobic amino acid. As described herein above in section A, the insulin analog may optionally comprise further mutations. For example, the amino acid residue at position 14 of the A-chain (A14) of the parent insulin (such as human insulin) may be substituted with glutamic acid, and the amino acid at position 30 of the B chain may be deleted, i.e. is absent (desB30 mutation).

In some embodiments, the insulin analog comprised by the conjugate is Glu(A14)Val(B25)Des(B30)-Insulin (such as Glu(A14)Val(B25)Des(B30)-human insulin). The sequence of this analog is, e.g., shown in Table 4 of the Examples section (see Analog 24). For example, Glu(A14) Val(B25)Des(B30)-Insulin comprises an A chain having an amino acid sequence as shown in SEQ ID NO: 47 (GIVEQCCTSICSLEQLENYCN) and a B chain having an amino acid sequence as shown in SEQ ID NO: 48 (FVNQHLCGSHLVEALYLVCGERGFVYTPK).

In some embodiments, the insulin analog comprised by the conjugate is Glu(A14)Ile(B25)Des(B30)-Insulin (such as Glu(A14)Ile(B25)Des(B30)-human insulin). The sequence of this analog is, e.g., shown in Table 4 of the Examples section (see Analog 22). For example, Glu(A14) Ile(B25)Des(B30)-Insulin comprises an A chain having an amino acid sequence as shown in SEQ ID NO: 43 (GIVEQCCTSICSLEQLENYCN) and a B chain having an amino acid sequence as shown in SEQ ID NO: 44 (FVNQHLCGSHLVEALYLVCGERGFIYTPK).

In some embodiments, the insulin analog comprised by the conjugate is Glu(A14)Glu(B3)Val(B16)Val(B25)Des (B30)-Insulin (such as Glu(A14)Glu(B3)Val(B16) Val(B25) Des(B30)-human insulin). The sequence of this analog is, e.g., shown in Table 1 of the Examples section (see Analog 39).

According to one embodiment of the conjugate, the active pharmaceutical ingredient is insulin or an insulin analog, for example an insulin analog as set forth above (such as Glu(A14)Val(B25)Des(B30)-human insulin, Glu(A14)Ile (B25)Des(B30)-human insulin), or Glu(A14)Glu(B3)Val (B16) Val(B25)Des(B30)-human insulin), wherein the amino group of the peptide, to which the sulfonamide of formula (I) is covalently bound, is an epsilon amino group of a lysine present in the insulin or insulin analog or is the N-terminal amino group of the B chain of the insulin or insulin analog. For example, the insulin or insulin analog has one lysine in the A chain and/or B chain. In some embodiments, the insulin or insulin analog has one lysine in the A and in the B chain.

According to one embodiment of the conjugate, the amino group of the peptide, to which the sulfonamide of formula (I) is covalently bound is an epsilon amino group of a lysine present at position B26 to B29, for example B29, of the B chain of human insulin or human insulin analog, for example of human insulin analog.

In some embodiments, the insulin analogs provided in section A above a single lysine residue is present. For example, Glu(A14)Val(B25)Des(B30)-human insulin, Glu (A14)Ile(B25)Des(B30)-human insulin), and Glu(A14)Glu (B3)Val(B16)Val(B25)Des(B30)-human insulin have a lysine residue at position B29. Said lysine residue is the terminal amino acid at the C-terminus of the B chain since the amino acid at position B30 is absent. In some embodiments of the conjugates provided herein, the sulfonamide of formula (I) is covalently bound to the epsilon amino group of said lysine residue, typically via an amide bond.

Exemplary conjugates are shown in FIG. 5 to FIG. 8 and described in the Examples section, e.g. in Example 10.

In some embodiments of the conjugate provided herein, the conjugate comprises Glu(A14)Val(B25)Des(B30)-human insulin (as insulin analog) and a sulfonamide of the following formula (as albumin binder):

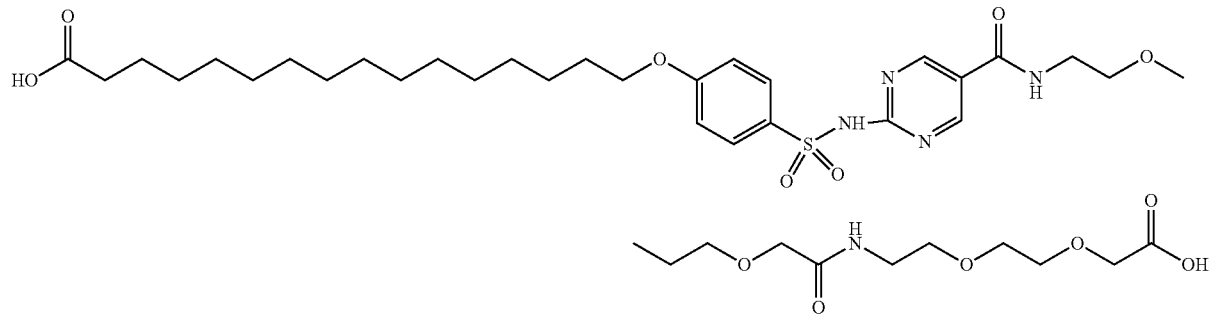

The above conjugate may have the following structure (see also FIG. 5, conjugate 1):

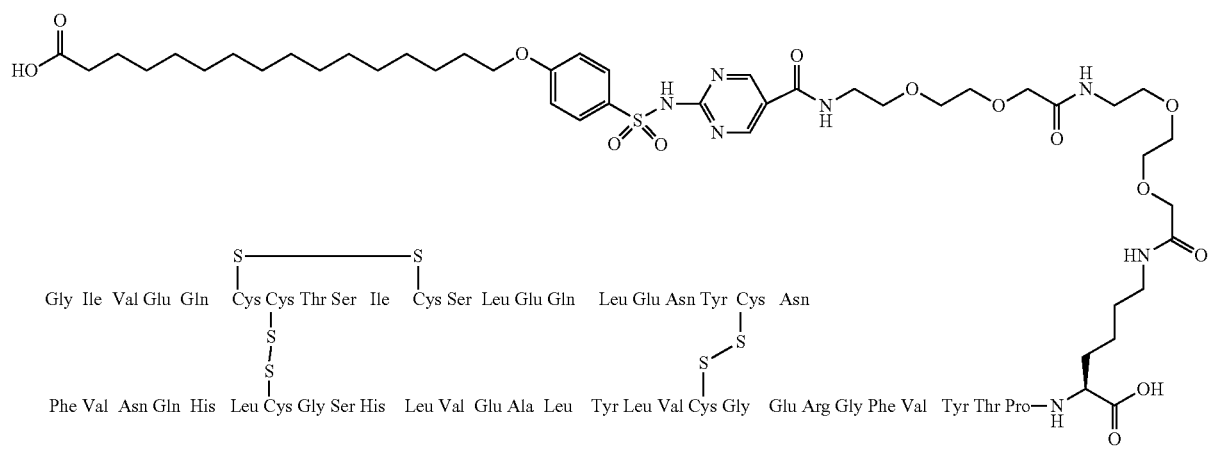

The sequences of the A chain (SEQ ID NO: 47) and the B chain (SEQ ID NO: 48) are indicated in three-letter-code, except for the last amino acid in the B chain (lysine at position B29). The structure of the lysine residue is shown. The lysine residue is covalently bound to the binder (via the epsilon amino acid of the lysine residue).

In some embodiments of the conjugate provided herein, the conjugate comprises Glu(A14)Val(B25)Des(B30)-human insulin (as insulin analog) and a sulfonamide of the following formula (as albumin binder):

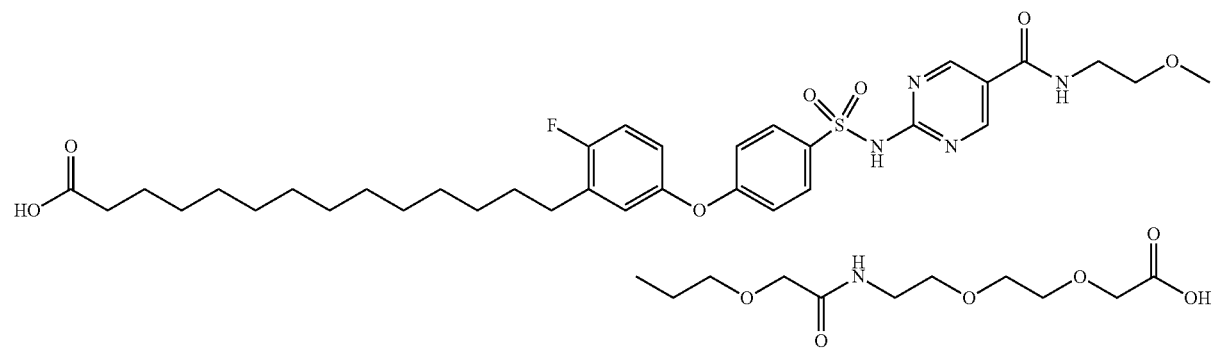

The above conjugate may have the following structure (see also FIG. 6, conjugate 2):

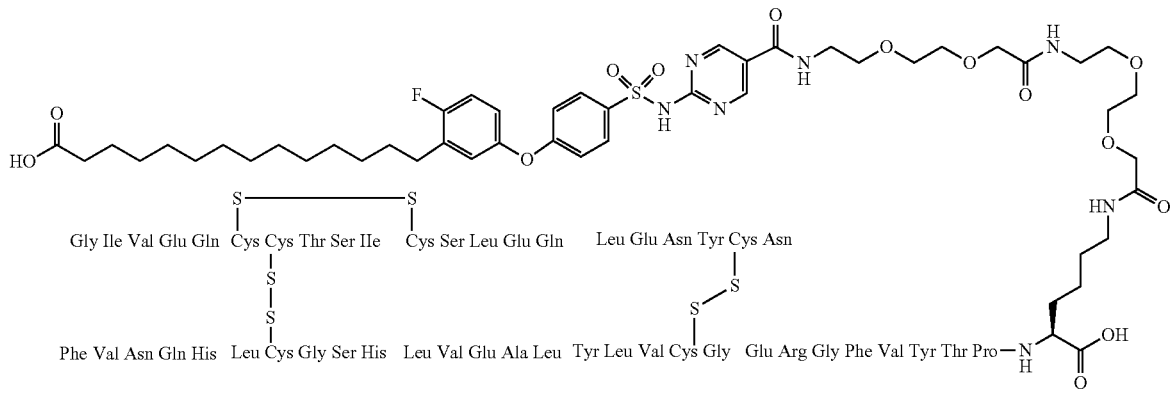

The sequences of the A chain (SEQ ID NO: 47) and the B chain (SEQ ID NO: 48) are indicated in three-letter-code, except for the last amino acid in the B chain (Lysine at position B29). The structure of the lysine residue is shown. The lysine residue is covalently bound to the binder (via the epsilon amino acid of the lysine residue).

In some embodiments of the conjugate provided herein, the conjugate comprises Glu(A14)Glu(B3)Val(B16)Val(B25)Des(B30)-human insulin (as insulin analog) and a sulfonamide of the following formula (as albumin binder):

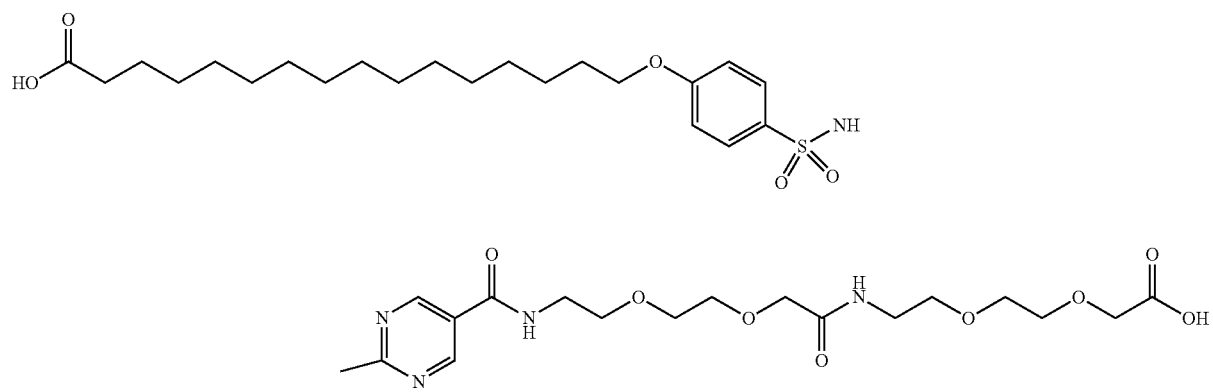

The above conjugate may have the following structure (see also FIG. 7, conjugate 3):

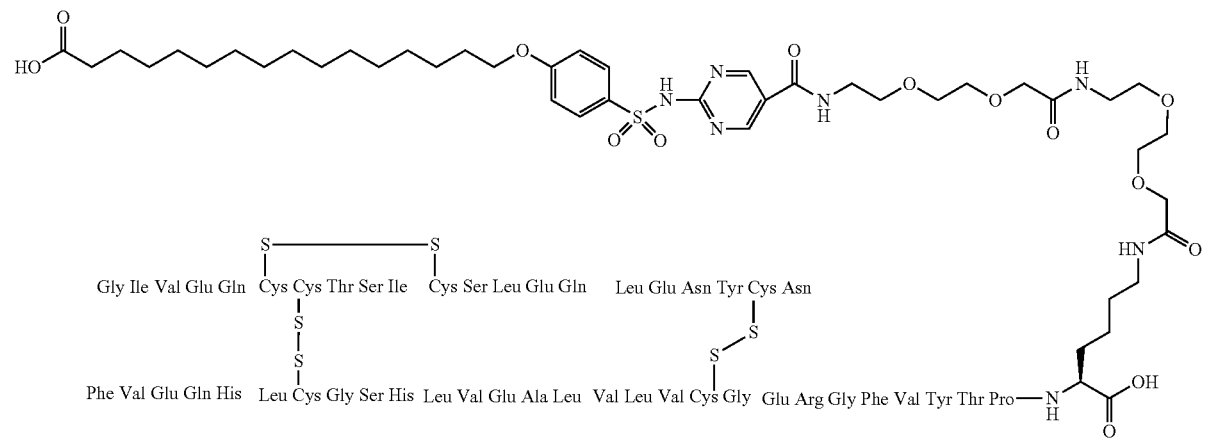

The sequences of the A chain (SEQ ID NO: 77) and the B chain (SEQ ID NO: 78) are indicated in three-letter-code, except for the last amino acid in the B chain (lysine at position B29). The structure of the lysine residue is shown. The lysine residue is covalently bound to the binder (via the epsilon amino acid of the lysine residue).

In some embodiments of the conjugates provided herein, the conjugate comprises Glu(A14)Ile(B25)Des(B30)-human insulin (as insulin analog) and a sulfonamide of the following formula (as albumin binder):

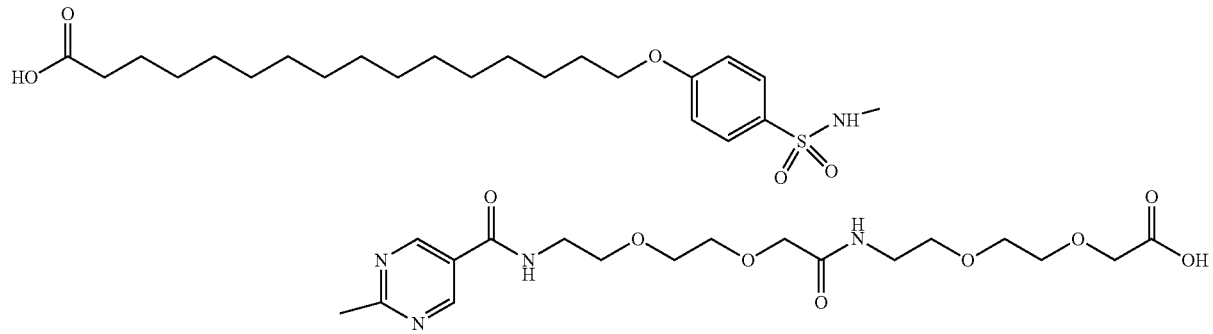

The above conjugate may have the following structure (see also FIG. 8, conjugate 4):

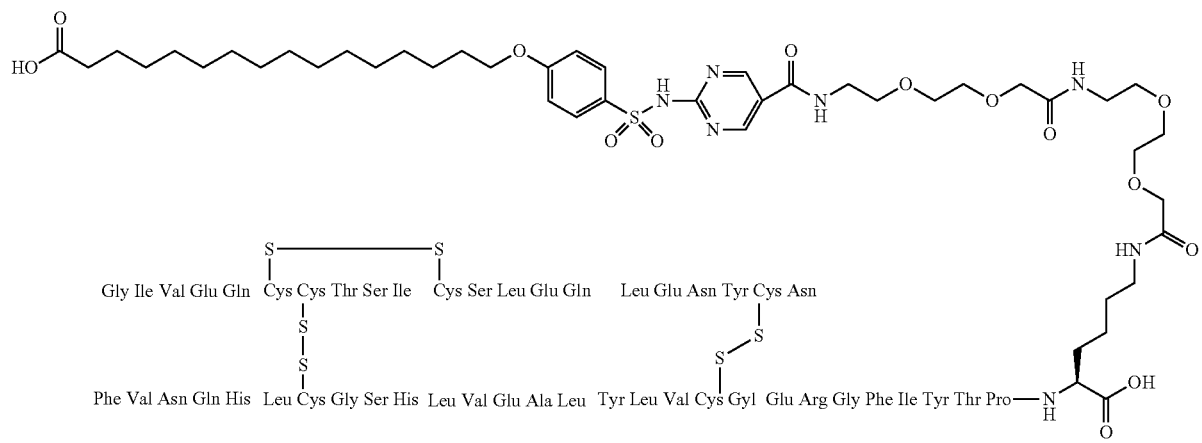

The sequences of the A chain (SEQ ID NO: 43) and the B chain (SEQ ID NO: 44) are indicated in three-letter-code, except for the last amino acid in the B chain (lysine at position B29). The structure of the lysine residue is shown. The lysine residue is covalently bound to the binder (via the epsilon amino group of the lysine residue).

Also provided herein are conjugates comprising a diagnostic compound. In some embodiments of the conjugate, the diagnostic compound is a contrast agent, such as a radio contrast agent. In some embodiments, the contrast agent is a gadolinium or iodine based magnetic resonance imaging (MRI) contrast agent. In some embodiments, the contrast agent is gadopentetate dimeglumine, gadoterate meglumine, gadobenate dimeglumine, gadoteridol, gadodiamide, gadoversetamide, gadoxetate disodium, amidotrizoate or a salt of amidotrizoate, for example a meglumine, sodium and/or lysine salt of amidotrizoate, iohexol (5-[acetyl(2,3-dihydroxypropyl)amino]-1-N,3-N-bis(2,3-dihydroxypropyl)-2,4,6-triiodobenzene-1,3-dicarboxamide), iopamidol (1-N,3-N-bis(1,3-dihydroxypropan-2-yl)-5-[[(2S)-2-hydroxypropanoyl]amino]-2,4,6-triiodobenzene-1,3-dicarboxamide), iopromide (1-N,3-N-bis(2,3-dihydroxypropyl)-2,4,6-triiodo-5-[(2-methoxyacetyl)amino]-3-N-methyl-benzene-1,3-dicarboxamide) or ioxidanol (5-[acetyl-[3-[acetyl-[3,5-bis(2,3-dihydroxypropylcarbamoyl)-2,4,6-triiodo-phenyl]amino]-2-hydroxy-propyl]amino]-N,N'-bis(2,3-dihydroxypropyl)-2,4,6-triiodo-benzene-1,3-dicarboxamide). In some embodiments, the contrast agent is selected from the group consisting of gadopentetate dimeglumine, gadoterate meglumine, gadobenate dimeglumine, gadoteridol, gadodiamide, gadoversetamide, gadoxetate disodium, amidotrizoate or a salt of amidotrizoate, for example a meglumine, sodium and/or lysine salt of amidotrizoate, iohexol (5-[acetyl(2,3-dihydroxypropyl)amino]-1-N,3-N-bis(2,3-dihydroxypropyl)-2,4,6-triiodobenzene-1,3-dicarboxamide), iopamidol (1-N,3-N-bis(1,3-dihydroxypropan-2-yl)-5-[[(2S)-2-hydroxypropanoyl]amino]-2,4,6-triiodobenzene-1,3- dicarboxamide), iopromide (1-N,3-N-bis(2,3-dihydroxypropyl)-2,4,6-triiodo-5-[(2-methoxyacetyl)amino]-3-N-methylbenzene-1,3-dicarboxamide) or ioxidanol (5-[acetyl-[3-[acetyl-[3,5-bis(2,3-dihydroxypropylcarbamoyl)-2,4,6-triiodo-phenyl]amino]-2-hydroxy-propyl]amino]-N,N'-bis(2,3-dihydroxypropyl)-2,4,6-triiodo-benzene-1,3-dicarboxamide).

As discussed above, the sulfonamide of formula (I) is covalently bound to the diagnostic compound in that the terminal carboxy group "a" of the sulfonamide of formula (I) is covalently bound to a suitable functional group of the diagnostic compound. The suitable functional group can be, for example, an amino group (primary or secondary) or a hydroxyl group of the diagnostic compound.

According to one embodiment of the conjugate, the sulfonamide has the formula (I-1)

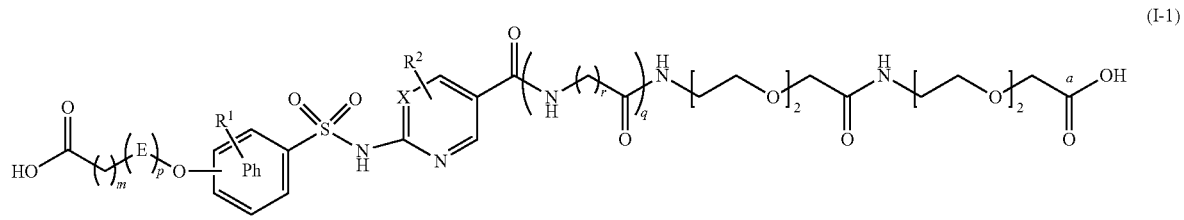

wherein:

E represents a —$C_6H_3R$— group with R being a hydrogen atom or a halogen atom, wherein the halogen atom is selected from the group consisting of fluorine, chlorine, bromine and iodine atom and is for example a fluorine atom;

X represents a nitrogen atom or a —CH— group;

p is zero or 1;

q is zero or 1;

r is an integer in the range from 1 to 6;

$R^1$ represents at least one residue selected from the group of hydrogen atom and halogen atom, wherein the halogen atom is for example a fluorine or chlorine atom;

$R^2$ represents at least one residue selected from the group of hydrogen atom, C1 to C3 alkyl group and halogenated C1 to C3 alkyl group, wherein the C1 to C3 alkyl group is for example a methyl group and the halogenated C1 to C3 alkyl group is for example perhalogenated such as a trifluoromethyl group;

with m being an integer in the range from 5 to 15 if p is zero, or m being an integer in the range from 7 to 15 if p is 1.

In one embodiment of the conjugate, the residues $R^1$ and $R^2$ of the sulfonamide are hydrogen atoms.

In one embodiment of the conjugate, the residue X of the sulfonamide represents a nitrogen atom.

According to another embodiment of the conjugate, the HOOC—$(CH_2)_m$—$(O)_s$-$(E)_p$-$(CH_2)_n$-$(A)_t$- group of formula (I) or the HOOC—$(CH_2)_m$-$(E)_p$-O— group of formula (I-1) of the sulfonamide is situated in meta or para position on phenyl ring Ph with respect to the —$S(O)_2$— group.

According to another embodiment of the conjugate, if p is 1, the HOOC—$(CH_2)_m$—$(O)_s$— group and the —$(CH_2)_n$-$(A)_t$- group are situated in meta or para position on $(E)_p$ of formula (I) of the sulfonamide or the HOOC—$(CH_2)_m$— group and the —O— are situated in meta or para position on $(E)_p$ of formula (I-1).

According to another embodiment of the conjugate, the index q of the sulfonamide is zero.

According to another embodiment of the conjugate, the sulfonamide has the formula (I-1-1)

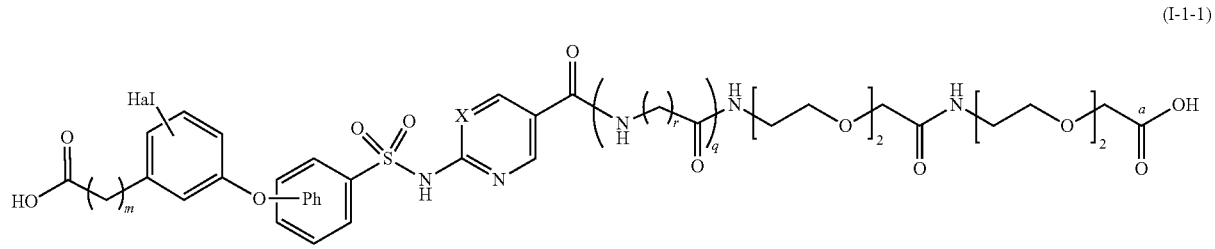

wherein X is a nitrogen atom or a —CH— group, for example a nitrogen atom; m is an integer in the range from 7 to 15; r is an integer in the range from 1 to 6; q is zero or 1, for example zero; Hal is a halogen atom selected from the group consisting of fluorine, chlorine, bromine and iodine atom, for example a fluorine atom; and the HOOC—$(CH_2)_m$—$C_6H_3$Hal-O— group is situated in meta or para position on phenyl ring Ph with respect to the —$S(O)_2$— group.

According to one embodiment of the conjugate, the sulfonamide has the formula (I-1-1a)

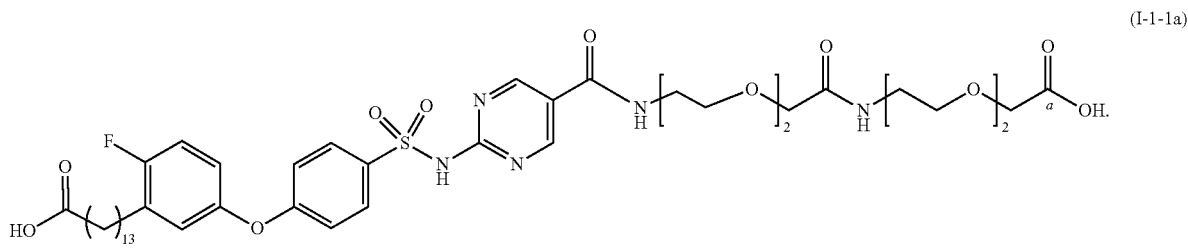

(I-1-1a)

According to another embodiment of the conjugate, the sulfonamide has the formula (I-1-2)

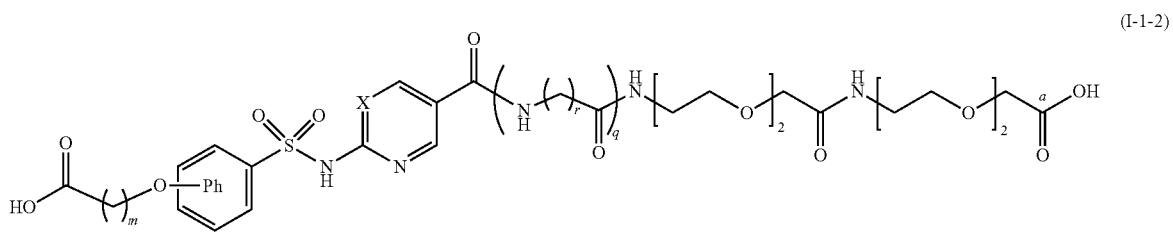

(I-1-2)

wherein X is a nitrogen atom or a —CH— group, for example a nitrogen atom; m is an integer in the range from 5 to 15; r is an integer in the range from 1 to 6; q is zero or 1, for example zero; and the HOOC—$(CH_2)_m$—O— group is situated in meta or para position on phenyl ring Ph with respect to the —$S(O)_2$— group.

According to one embodiment of the conjugate, the sulfonamide has the formula (I-1-2a)

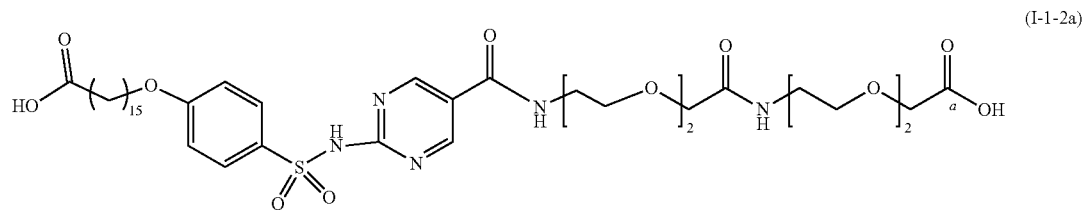

(I-1-2a)

or the formula (I-1-2b)

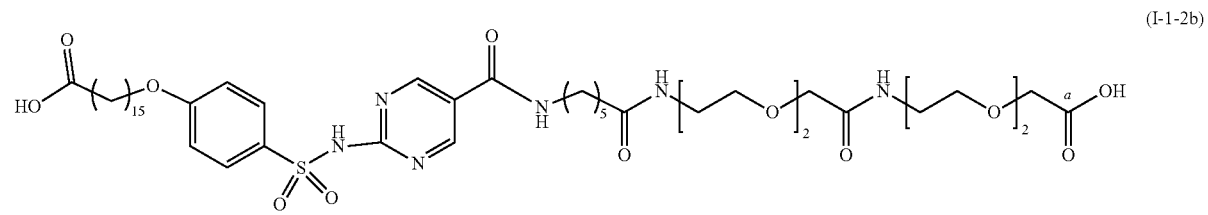

(I-1-2b)

or the formula (I-1-2c)

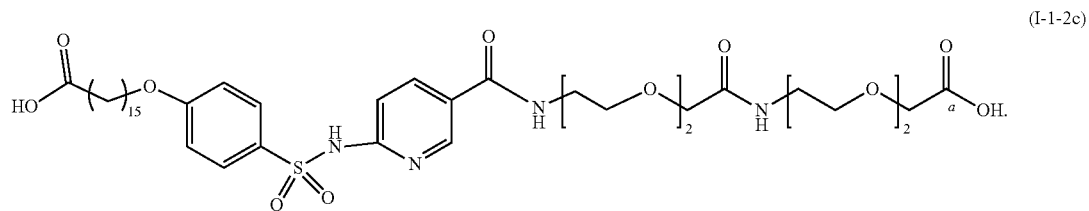

According to another embodiment of the conjugate, the sulfonamide has the formula (I-2)

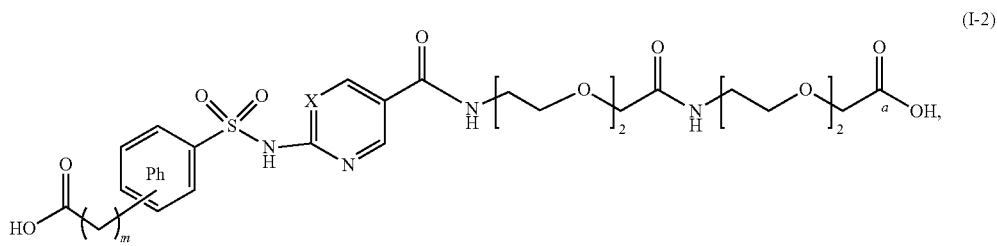

wherein
X represents a nitrogen atom or a —CH— group; and
m is an integer in the range from 5 to 17, for example in the range from 11 to 17.

According to one embodiment of the conjugate, the HOOC—$(CH_2)_m$— group of the sulfonamide of formula (I-2) is situated in meta or para position on phenyl ring Ph with respect to the —$S(O)_2$— group.

According to another embodiment of the conjugate, the sulfonamide has the formula (I-3)

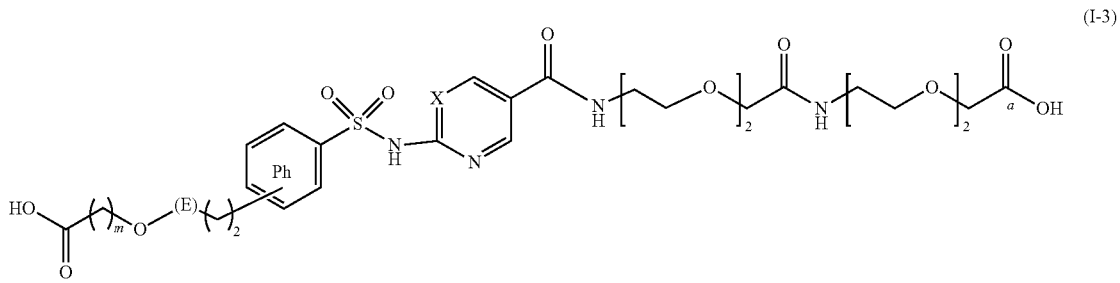

wherein
E represents a —$C_6H_3R$— group with R being a hydrogen atom or a halogen atom, wherein the halogen atom is selected from the group consisting of fluorine, chlorine, bromine and iodine atom;
X represents a nitrogen atom or a —CH— group;
m is an integer in the range from 5 to 17, for example 11.

According to one embodiment of the conjugate, the HOOC—$(CH_2)_m$—O— group and the —$(CH_2)_2$— group of the sulfonamide of formula (I-3) are situated in para position on (E) of formula (I-3) and the HOOC—$(CH_2)_m$—O-(E)-$(CH_2)_2$— group is situated in para position on phenyl ring Ph with respect to the —$S(O)_2$— group.

According to another embodiment of the conjugate, the sulfonamide has the formula (I-4)

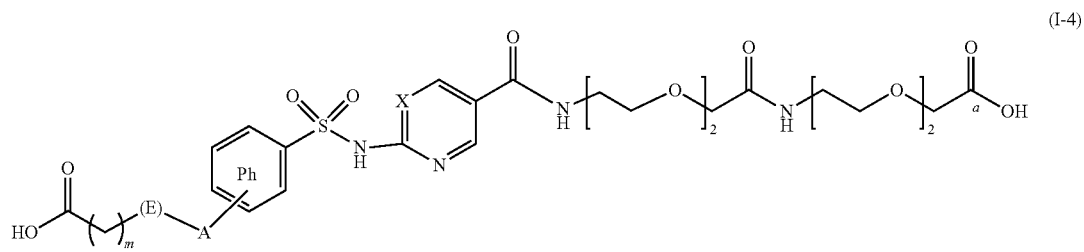

(I-4)

wherein
A is a OCH$_2$— group or a —CH$_2$O— group;
E represents a —C$_6$H$_3$R— group with R being a hydrogen atom or a halogen atom, wherein the halogen atom is selected from the group consisting of fluorine, chlorine, bromine and iodine atom;
X represents a nitrogen atom or a —CH— group;
m is an integer in the range of from 5 to 17, for example in the range of from 9 to 13.

According to one embodiment of the conjugate, the HOOC—(CH$_2$)$_m$— group and the -A- group of the sulfonamide of formula (I-4) are situated in para position on (E) of formula (I-4) and the -A- group is situated in para position on phenyl ring Ph with respect to the —S(O)$_2$— group.

According to another embodiment of the conjugate, the sulfonamide has the formula (I-5)

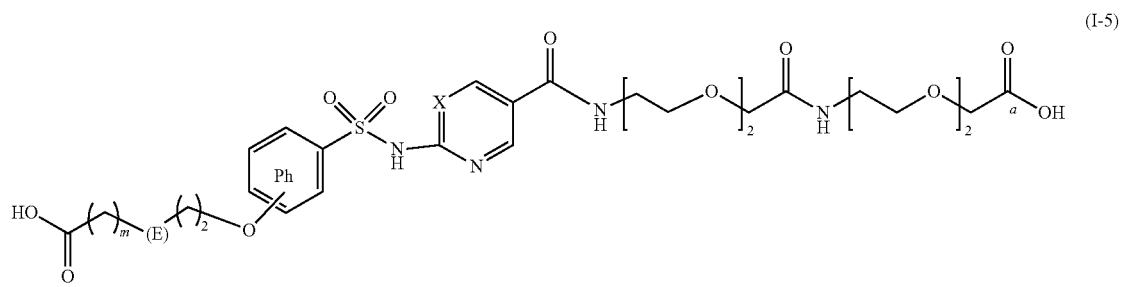

(I-5)

wherein
E represents a —C$_6$H$_3$R— group with R being a hydrogen atom or a halogen atom, wherein the halogen atom is selected from the group consisting of fluorine, chlorine, bromine and iodine atom;
X represents a nitrogen atom or a —CH— group;
m is an integer in the range of from 5 to 17, for example in the range of from 7 to 9.

According to one embodiment of the conjugate, the HOOC—(CH$_2$)$_m$ group and the —(CH$_2$)$_2$— group, of the sulfonamide of formula (I-5) are situated in para position on (E) of formula (I-5) and the HOOC—(CH$_2$)$_m$ (E)-(CH$_2$)$_2$—O— group is situated in para position on phenyl ring Ph with respect to the —S(O)$_2$— group.

Process for Preparing a Conjugate

Provided herein are processes for preparing a conjugate as described in section C above. Accordingly, provided herein are processes for preparing a conjugate comprising a sulfonamide of formula (I) and an active pharmaceutical ingredient

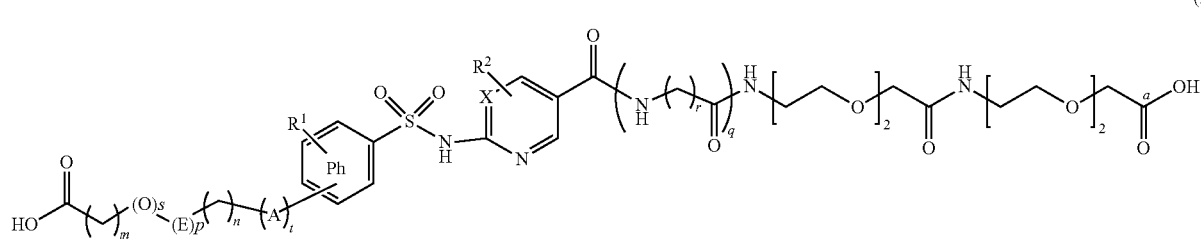

(I)

wherein in the sulfonamide of formula (I):
A is selected from the group consisting of oxygen atom, —CH$_2$CH$_2$— group, —OCH$_2$— group and —CH$_2$O— group;
E represents a —C$_6$H$_3$R— group with R being a hydrogen atom or a halogen atom, wherein the halogen atom is selected from the group consisting of fluorine, chlorine, bromine and iodine atom;
X represents a nitrogen atom or a —CH— group;
m is an integer in the range from 5 to 17;
n is zero or an integer in the range from 1 to 3;
p is zero or 1;
q is zero or 1;
r is an integer in the range from 1 to 6;
s is zero or 1;
t is zero or 1;
R$^1$ represents at least one residue selected from the group of hydrogen atom, halogen atom, C1 to C3 alkyl group and halogenated C1 to C3 alkyl group;
R$^2$ represents at least one residue selected from the group of hydrogen atom, halogen atom, C1 to C3 alkyl group and halogenated C1 to C3 alkyl group;
wherein the sulfonamide of formula (I) is covalently bound to the active pharmaceutical ingredient in that the terminal carboxy group "a" of the sulfonamide of formula (I) is covalently bound to an amino group of the active pharmaceutical ingredient;
(a) providing a sulfonamide of formula (Aa)

formula (I) as well as for the sulfonamide of formula (Aa). In some embodiments, s is zero for the sulfonamide of formula (I) as well as for the sulfonamide of formula (Aa), wherein the remaining residues and indices have the meaning as indicated above for formula (I) and (Aa) respectively.
It is also possible to prepare a conjugate as described here in section C above by a process comprising:
a) providing a sulfonamide of formula (Aa) wherein R$^x$ represents an activation group (R$^x$=activation group);
b) Providing an aqueous solution of an active pharmaceutical ingredient, wherein the aqueous solution optionally comprises an alcohol;
c) Contacting the aqueous solution of b) with the sulfonamide of formula (Aa) (R$^x$=activation group) of a); and
d) Reacting the sulfonamide of formula (Aa) with the active pharmaceutical ingredient, obtaining a solution comprising the conjugate of the sulfonamide and the active pharmaceutical ingredient, wherein the sulfonamide is covalently bound to the active pharmaceutical ingredient.
In this process, the active pharmaceutical ingredient is optionally an insulin polypeptide having a free amino group, optionally an insulin analog as in Section A above or a precursor thereof, each having a free amino group, wherein the precursor of the insulin analog comprises an additional linker peptide which has a length of at least two amino acids, or a length in the range from 2 to 30 amino acids, or a length

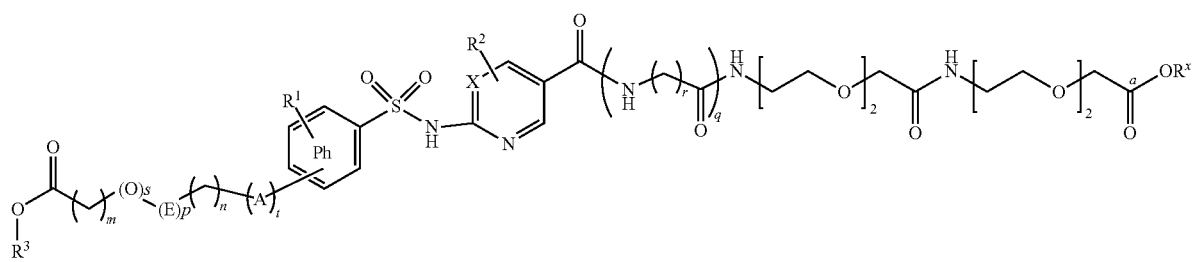

(Aa)

wherein X, Y, A, E, R$^1$, R$^2$ and the indices m, n, p, q, r, s, t have the meaning as defined above with respect to formula (I), R$^x$ is a hydrogen atom or an activation group, optionally an activation group selected from the group consisting of 7-azabenzotriazole (optionally derived from HATU or HBTU), 4-nitro benzene and N-succinimidyl-group, wherein R$^x$ is optionally a N-succinimidyl-group, and R$^3$ is a protective group or a hydrogen atom, optionally a hydrogen atom; and an active pharmaceutical ingredient having a protected or unprotected C terminus;
(b) reacting the sulfonamide of formula (Aa) and the active pharmaceutical ingredient having a protected or unprotected C terminus under conditions suitable to form an amide bond between the free or activated, optionally activated, carboxy group "a" of the sulfonamide of formula (Aa) and an amino group of the active pharmaceutical ingredient having a protected or unprotected C terminus;
(c) optionally removing one or both protection groups, for example removing both protective groups.
In some embodiments of the process, the combination of s being 1, p being zero, n being zero, A being an oxygen atom and t being 1 is excluded for the sulfonamide of in the range from 4 to 9 amino acids. In this process, the aqueous solution provided in a) has a pH value in the range of from 9 to 12, or in the range of from 9.5 to 11.5, or in the range of from 10 to 11, wherein the pH value is determined with a pH sensitive glass electrode according to ASTM E 70:2007; wherein the pH value is optionally adjusted in the respective range by addition of a base, or a base selected from the group consisting of alkali hydroxides (lithium hydroxide, sodium hydroxide, potassium hydroxide), alkyl amines and mixtures of two or more thereof; or selected from the group of tertiary alkyl amines N(C1-C5 alkyl)$_3$, primary alkyl amines H$_2$N—C(C1-C5 alkyl)$_3$ and mixtures of two or more thereof, wherein the C1-C5 alkyl groups of the tertiary amines and of the primary amines are each independently selected from branched or straight C1-C5 alkyl groups and wherein each C1-C5 alkyl group has at least one substituent selected from the group of hydrogen atom, hydroxyl group and carboxyl group; or selected from the group of tertiary alkyl amines N(C1-C3 alkyl)$_3$, primary alkyl amines H$_2$N—C(C1-C3 alkyl)$_3$ and mixtures of two or more thereof, wherein the C1-C3 alkyl groups of the tertiary amines and of the primary amines are each independently selected from branched or straight C1-C3 alkyl groups and wherein each C1-C3 alkyl group has at least one substituent selected from the group of hydrogen atom, hydroxyl group and carboxyl group; or selected from the group of bicine, trimethylamine, tris(hydroxymethyl)aminomethane and mixtures of two or more thereof; wherein the base optionally comprises at least triethylamine.

In one variant of this process, contacting the aqueous solution of b) with the sulfonamide of formula (Aa) ($R^x$=activation group) of a) according to step c) is done in that the sulfonamide of formula (Aa) ($R^x$=activation group) of a) is added as a solution of the sulfonamide of formula (Aa) ($R^x$=activation group) to the aqueous solution of b), wherein the solution of the sulfonamide of formula (Aa) ($R^x$=activation group) is optionally an organic solution, optionally a solution comprising the sulfonamide of formula (Aa) ($R^x$=activation group) and a polar aprotic organic solvent, optionally a polar aprotic organic solvent having an octanol-water-partition coefficient ($K_{OW}$) in the range of from 1 to 5, or in the range of from 2 to 4 at standard conditions (T: 20-25° C., p: 1013 mbar); or selected from the group consisting of tetrahydrofuran, acetonitrile, dimethylformamide, and mixtures of two or more thereof; or selected from the group of tetrahydrofuran, acetonitrile and mixtures of tetrahydrofuran and acetonitrile.

In one variant of this process, contacting the aqueous solution of b) with the sulfonamide of formula (Aa) ($R^x$=activation group) of a) according to step c) is done in that the sulfonamide of formula (Aa) ($R^x$=activation group) of a) is added in solid form to the aqueous solution of b), or at least partially in crystalline form, or at least 90 weight-% in crystalline form.

In this process, step d) optionally comprises: d.1) Reacting the sulfonamide of formula (Aa) ($R^x$=activation group) with a precursor of the insulin analog at a pH in the range from 9 to 12, or in the range from 9.5 to 11.5, or in the range from 10 to 11, obtaining a pre-conjugate comprising the the sulfonamide of formula (I) and the precursor of the insulin analog, wherein the sulfonamide of formula (I) is covalently bound to the precursor of the insulin analog by an amide bond C(=O)—NH— formed between the —C(=O)—O (R) of the sulfonamide of Formula (I) and the amino group of the precursor of the insulin analog; d.2) Enzymatic digestion, optionally at a pH in the range below 9, or at a pH in the range of 7 to 9, of the precursor of the insulin analog of the pre-conjugate obtained according to d.1), obtaining a solution comprising the conjugate of the sulfonamide of formula (I) and the insulin analog. The process further optionally comprises: e) Isolating the conjugate of the sulfonamide of formula (I) and the insulin analog from the solution obtained in d) or d.2).

In this process, the activation group $R^x$ of the sulfonamide of formula (Aa) is optionally selected from the group consisting of 7-azabenzotriazole (optionally derived from HATU or HBTU), 4-nitro benzene and N-succinimidyl-group, wherein $R^x$ is more optionally a N-succinimidyl-group.

In one variant of this process, the aqueous solution of the precursor of the insulin analog according to b) comprises an alcohol which is selected from the group consisting of C1-C4 monoalcohols and mixtures of two or more thereof, or from the group consisting of methanol, ethanol, propan-2-ol, propan-1-ol, butan-1-ol and mixtures of two or more thereof, or from the group consisting of ethanol, propan-2-ol, propan-1-ol, and mixtures of two or more thereof. Optionally, the alcohol is present in the aqueous solution in an amount in the range from 0.0001 to 35 volume-%, or in the range from 0.001 to 30 volume-%, or in the range from 0.01 to 25 volume-%, or in the range from 0.1 to 20 volume-%, each based on the total volume of water and alcohol. In this process, the enzymatic digestion according to d.2) comprises use of at least one enzyme selected from the group consisting of trypsin, a TEV protease (Tobacco Etch Virus protease) and mixtures of two or more thereof. In this process, the insulin analog is an insulin analog as described in section A above and/or here in Section C above. In this process, the sulfonamide of formula (I) is covalently bound to the insulin analog and the precursor thereof respectively by an amide bond C(=O)—NH— formed between the —C(=O)—O($R^3$) of the sulfonamide of formula (I) and the free amino group of the insulin analog and the precursor thereof respectively, wherein the free amino group of the insulin analog and the precursor thereof respectively is optionally the amino group of a lysine comprised in the insulin analog and the precursor thereof respectively, optionally a terminal lysine, optionally a lysine present at a C terminus of the insulin analog and the precursor thereof respectively, optionally a lysine present at the C terminus of the B-chain.

Provided herein are processes for preparing a conjugate comprising a sulfonamide of formula (I) and a diagnostic compound, wherein the diagnostic compound is covalently bound with a suitable functional group to a free or activated, optionally activated, carboxy group "a" of the sulfonamide of formula (Aa) in accordance with the method described above for the bonding with the active pharmaceutical ingredient.

Provided herein are conjugates comprising a sulfonamide of formula (I) and an active pharmaceutical ingredient or a diagnostic compound obtained or obtainable from the processes as described above.

Provided herein are pharmaceutical compositions comprising in a pharmaceutically or diagnostically effective amount, the conjugate comprising a sulfonamide of formula (I) and an active pharmaceutical ingredient or a diagnostic compound as described above.

Provided herein are conjugates comprising a sulfonamide of formula (I) and an active pharmaceutical ingredient as described above for use as a medicament.

One embodiment relates to the conjugate comprising a sulfonamide of formula (I) and an active pharmaceutical ingredient as described above for use as a medicament for treatment of a disease selected from the group consisting of gestational diabetes, diabetes mellitus type 1, diabetes mellitus type 2 and hyperglycemia and/or for lowering blood glucose levels. In some embodiments, the disease is diabetes mellitus type 2.

Provided herein are methods of treating a patient suffering from a disease selected from the group consisting of gestational diabetes, diabetes mellitus type 1, diabetes mellitus type 2, and hyperglycemia and/or being in need of lowering blood glucose levels, comprising administering a therapeutically effective amount of the conjugate comprising a sulfonamide of formula (I) and an active pharmaceutical ingredient as described above.

Provided herein are uses of the conjugate comprising a sulfonamide of formula (I) and an active pharmaceutical ingredient as described above for the manufacture of a medicament for treatment of a disease selected from the group consisting of gestational diabetes, diabetes mellitus type 1, diabetes mellitus type 2 and hyperglycemia and/or for lowering blood glucose levels.

Provided herein are conjugates comprising a sulfonamide of formula (I) and a diagnostic compound as described above for use as a diagnostic agent.

Provided herein are methods of diagnosing a disease, for example a disease selected from the group of cardiovascular diseases and cancers, in a patient or for determining the risk of a patient to develop a disease, for example a disease selected from the group of cardiovascular diseases and cancers, comprising administering a diagnostically effective amount of the conjugate comprising a sulfonamide of formula (I) and a diagnostic compound as described above.

Provided herein are uses of the conjugate comprising a sulfonamide of formula (I) and a diagnostic compound as described above for the manufacture of a diagnostic agent for diagnosis of a disease, for example a disease selected from the group of cardiovascular diseases and cancers.

The compositions, pharmaceutical compositions and uses as described in section C are further illustrated by the following embodiments and combinations of embodiments as indicated by the respective dependencies and back-references. The definitions and explanations given herein above in sections A, B and C apply mutatis mutandis to the following embodiments.

1. A conjugate comprising an insulin analog and a sulfonamide of formula (I)

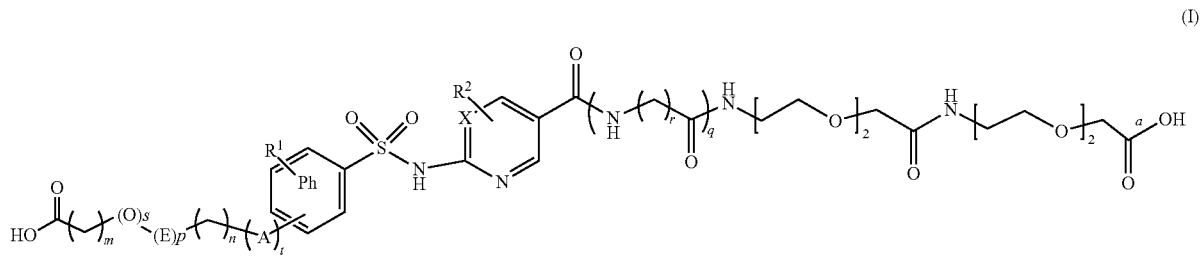

(I)

wherein:
A is selected from the group consisting of oxygen atom, —CH$_2$CH$_2$— group, —OCH$_2$— group and —CH$_2$O— group;
E represents a —C$_6$H$_3$R— group with R being a hydrogen atom or a halogen atom, wherein the halogen atom is selected from the group consisting of fluorine, chlorine, bromine and iodine atom;
X represents a nitrogen atom or a —CH— group;
m is an integer in the range from 5 to 17;
n is zero or an integer in the range from 1 to 3;
p is zero or 1;
q is zero or 1;
r is an integer in the range from 1 to 6;
s is zero or 1;
t is zero or 1;
$R^1$ represents at least one residue selected from the group of hydrogen atom, halogen atom, C1 to C3 alkyl group and halogenated C1 to C3 alkyl group;
$R^2$ represents at least one residue selected from the group of hydrogen atom, halogen atom, C1 to C3 alkyl group and halogenated C1 to C3 alkyl group
wherein the sulfonamide of formula (I) is covalently bound to the insulin analog in that terminal carboxy group "a" of the sulfonamide of formula (I) is covalently bound to an amino group of the insulin analog.

2. The conjugate according to embodiment 1, wherein the sulfonamide has the formula (I-1)

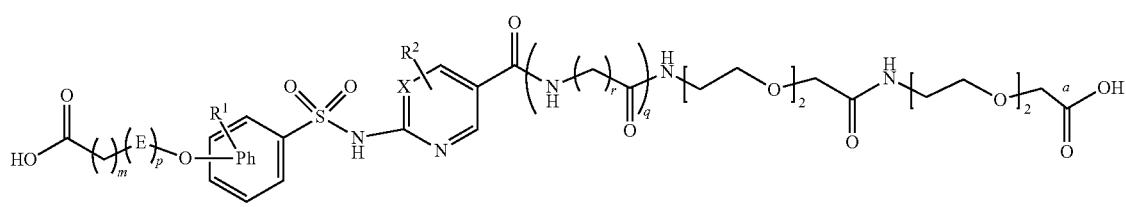

(I-1)

wherein:

E represents a —C$_6$H$_3$R— group with R being a hydrogen atom or a halogen atom, wherein the halogen atom is selected from the group consisting of fluorine, chlorine, bromine and iodine atom;

X represents a nitrogen atom or a —CH— group;

p is zero or 1;

q is zero or 1;

r is an integer in the range from 1 to 6;

R$^1$ represents at least one residue selected from the group of hydrogen atom and halogen atom;

R$^2$ represents at least one residue selected from the group of hydrogen atom, C1 to C3 alkyl group and halogenated C1 to C3 alkyl group;

with m being an integer in the range from 5 to 15 if p is zero, or m being an integer in the range from 7 to 15 if p is 1.

3. The conjugate according to embodiment 1 or 2, wherein the sulfonamide has the formula (I-1-1)

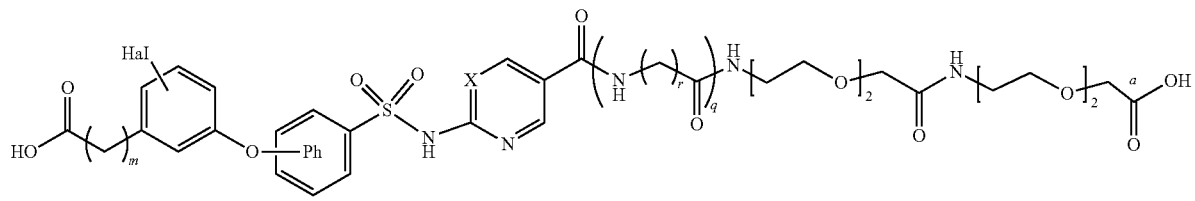

(I-1-1)

wherein X is a nitrogen atom or a —CH— group; m is an integer in the range from 7 to 15; r is an integer in the range from 1 to 6; q is zero or 1; Hal is a halogen atom selected from the group consisting of fluorine, chlorine, bromine and iodine atom; and the HOOC—(CH$_2$)$_m$—C$_6$H$_3$Hal-O— group is situated in meta or para position on phenyl ring Ph with respect to the —S(O)$_2$— group.

4. The conjugate according to any of embodiments 1 to 3, wherein the sulfonamide has the formula (I-1-1a)

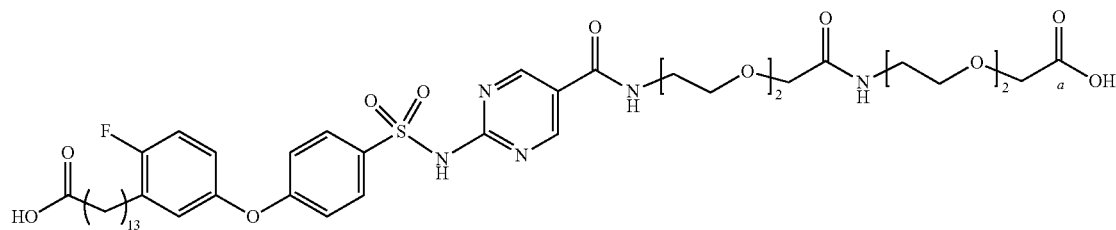

(I-1-1a)

5. The conjugate according to embodiment 1 or 2, wherein the sulfonamide has the formula (I-1-2)

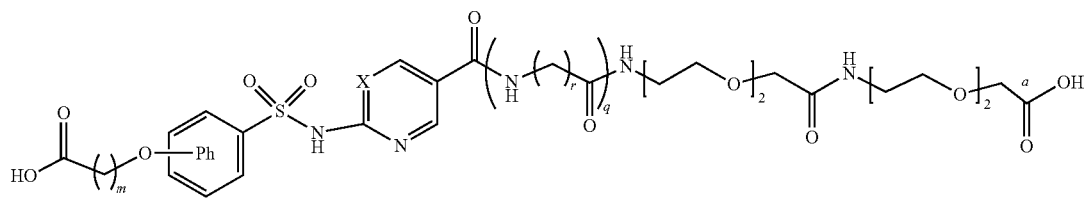

(I-1-2)

wherein X is a nitrogen atom or a —CH— group; m is an integer in the range from 5 to 15; r is an integer in the range from 1 to 6; q is zero or 1; and the HOOC—(CH$_2$)$_m$—O— group is situated in meta or para position on phenyl ring Ph with respect to the —S(O)$_2$— group.

6. The conjugate according to any of embodiments 1 to 2 or 5, wherein the sulfonamide has the formula (I-1-2a)

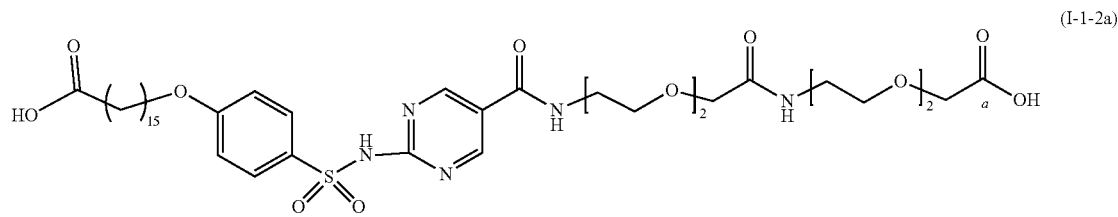

(I-1-2a)

or the formula (I-1-2b)

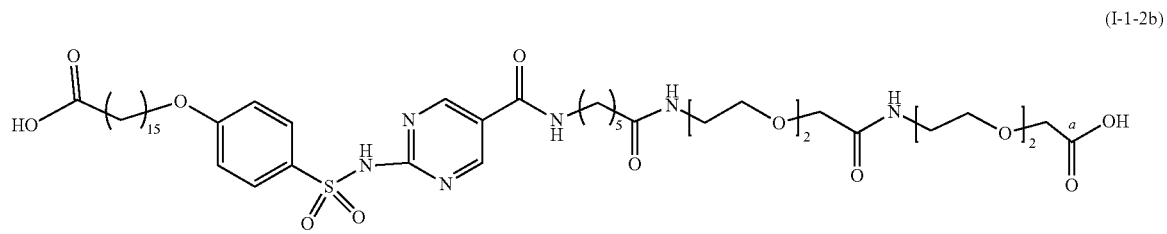

(I-1-2b)

or the formula (I-1-2c)

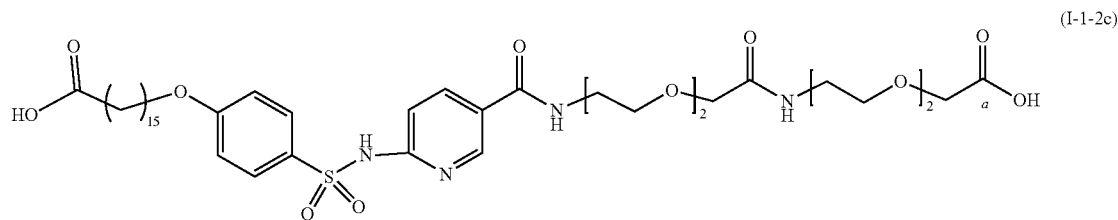

(I-1-2c)

7. The conjugate according to any one of embodiments 1 to 6, wherein the insulin analog comprises at least one mutation relative to the parent insulin, wherein the insulin analog comprises a mutation at position B16 which is substituted with a hydrophobic amino acid and/or a mutation at position B25 which is substituted with a hydrophobic amino acid, and optionally, wherein said insulin analog further comprises a mutation at position A14 which is substituted with an amino acid selected from the group consisting of glutamic acid (Glu), aspartic acid (Asp) and histidine (His) and/or a mutation at position B30.
8. The conjugate according to embodiment 7, wherein the parent insulin is human insulin, porcine insulin, or bovine insulin.
9. The conjugate according to embodiments 7 and 8, wherein the hydrophobic amino acid is a branched-chain amino acid, such as a branched-chain amino acid selected from the group consisting of valine (Val), isoleucine (Ile), and leucine (Leu).
10. The conjugate according to any one of embodiments 1 to 9, wherein the insulin analog is selected from
Leu(B16)-human insulin,
Val(B16)-human insulin,
Ile(B16)-human insulin,
Leu(B16)Des(B30)-human insulin,
Val(B16)Des(B30)-human insulin,
Ile(B16)Des(B30)-human insulin,
Leu(B25)-human insulin,
Val(B25)-human insulin,
Ile(B25)-human insulin,
Leu(B25)Des(B30)-human insulin,
Val(B25)Des(B30)-human insulin,
Ile(B25)Des(B30)-human insulin,
Glu(A14)Leu(B16)Des(B30)-human insulin,
Glu(A14)Ile(B16)Des(B30)-human insulin,
Glu(A14)Val(B16)Des(B30)-human insulin,
Glu(A14)Leu(B16)-human insulin,
Glu(A14)Ile(B16)-human insulin,
Glu(A14)Val(B16)-human insulin,
Glu(A14)Leu(B25)Des(B30)-human insulin,
Glu(A14)Ile(B25)Des(B30)-human insulin,
Glu(A14)Val(B25)Des(B30)-human insulin,
Glu(A14)Leu(B25)-human insulin,
Glu(A14)Ile(B25)-human insulin,
Glu(A14)Val(B25)-human insulin,
Glu(A14)Gly(A21)Glu(B3)Val(B25)Des(B30)-human insulin,
Glu(A14)Ile(B16)Ile(B25)Des(B30)-human insulin,
Glu(A14)Glu(B3)Ile(B16)Ile(B25)Des(B30)-human insulin,
Glu(A14)Ile(B16)Val(B25)Des(B30)-human insulin, Glu(A14)Gly(A21)Glu(B3)Ile(B16)Val(B25)Des(B30)-human insulin,
Glu(A14)Val(B16)Ile(B25)Des(B30)-human insulin,
Glu(A14)Val(B16)Val(B25)Des(B30)-human insulin,
Glu(A14)Glu(B3)Val(B16)Val(B25)Des(B30)-human insulin,
Glu(A14)Gly(A21)Glu(B3)Val(B16)Val(B25)Des(B30)-human insulin,
Glu(A14)Gly(A21)Glu(B3)Val(B25)-human insulin,
Glu(A14)Ile(B16)Ile(B25)-human insulin,
Glu(A14)Glu(B3)Ile(B16)Ile(B25)-human insulin,
Glu(A14)Ile(B16)Val(B25)-human insulin,
Glu(A14)Gly(A21)Glu(B3)Ile(B16)Val(B25)-human insulin,
Glu(A14)Val(B16)Ile(B25)-human insulin,
Glu(A14)Val(B16)Val(B25)-human insulin,
Glu(A14)Glu(B3)Val(B16)Val(B25)-human insulin, and
Glu(A14)Gly(A21)Glu(B3)Val(B16)Val(B25)-human insulin.

11. The conjugate according to any one of embodiments 1 to 10, wherein the insulin analog comprises
(a) an A chain having an amino acid sequence as shown in SEQ ID NO: 43 (GIVEQCCTSICSLEQLENYCN) and a B chain having an amino acid sequence as shown in SEQ ID NO: 44 (FVNQHLCGSHLVEALYL-VCGERGFIYTPK),
(b) an A chain having an amino acid sequence as shown in SEQ ID NO: 47 (GIVEQCCTSICSLEQLENYCN) and a B chain having an amino acid sequence as shown in SEQ ID NO: 48 (FVNQHLCGSHLVEALYL-VCGERGFVYTPK), or
(c) an A chain having an amino acid sequence as shown in SEQ ID NO: 77 (GIVEQCCTSICSLEQLENYCN) and a B chain having an amino acid sequence as shown in SEQ ID NO: 78 (FVEQHLCGSHLVEALVLVCGERGFVYTPK).

12. The conjugate of any one of embodiments 1 to 11, wherein the amino group of the insulin analog, to which the sulfonamide of formula (I) is covalently bound, is an epsilon amino group of a lysine present in the insulin analog or is the N-terminal amino group of the B chain of the insulin or insulin analog.

13. The conjugate according to embodiment 12, wherein the amino group is the epsilon amino group of lysine present at position B29 of the B chain.

14. The conjugate of any one of embodiments 1 to 13, wherein the conjugate is conjugate 1 (A chain sequence: SEQ ID NO: 47; B chain sequence: SEQ ID NO: 48):

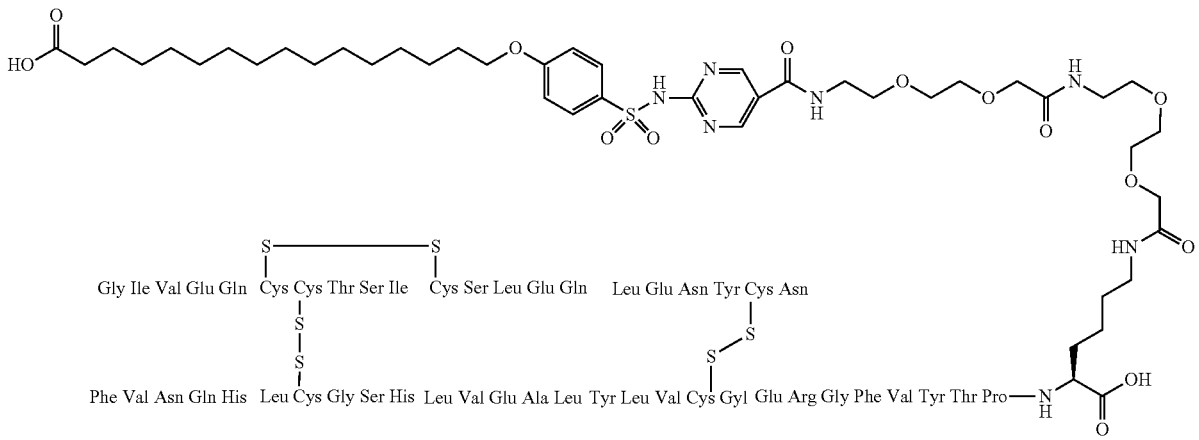

or
conjugate 3 (A chain sequence: SEQ ID NO: 77; B chain sequence: SEQ ID NO: 78):

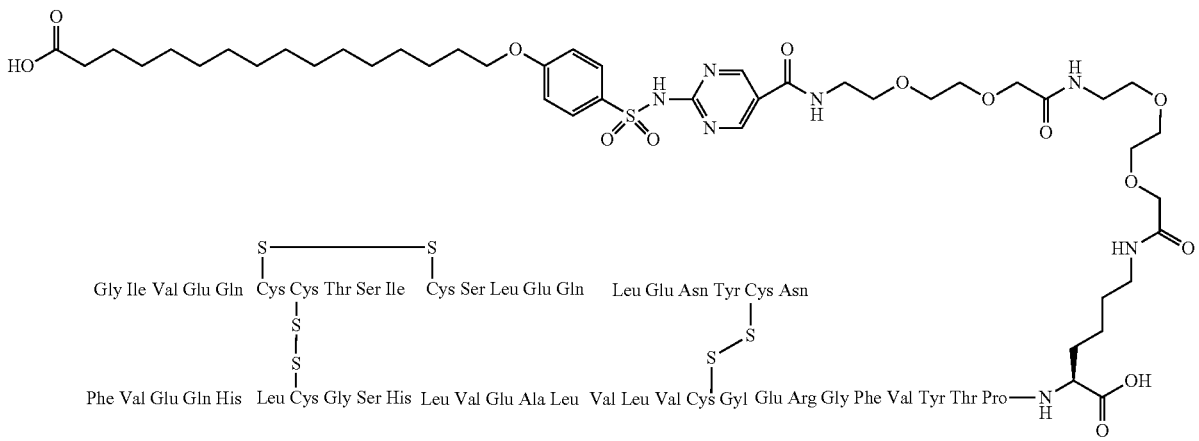

or conjugate 4 (A chain sequence: SEQ ID NO: 43; B chain sequence: SEQ ID NO: 44):

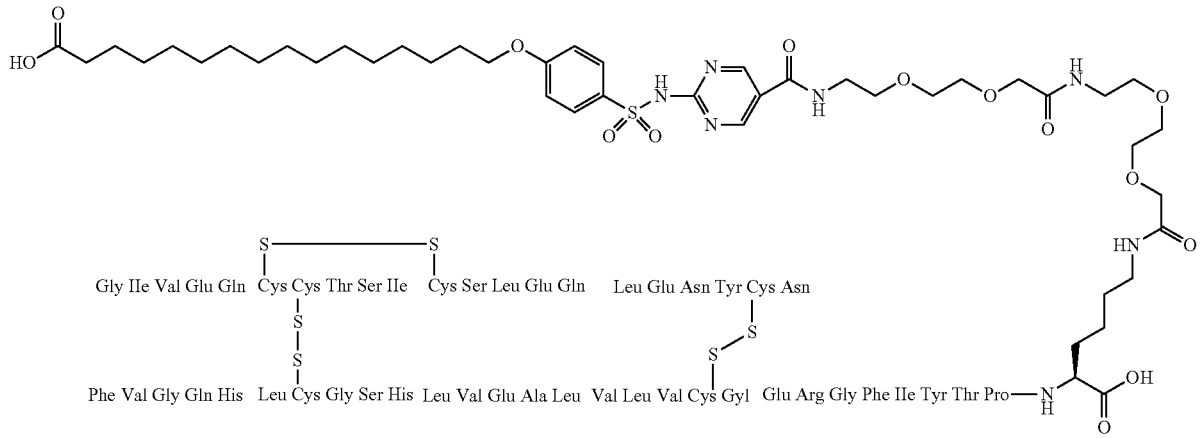

15. A process for preparing a conjugate comprising a sulfonamide of formula (I) and an insulin analog

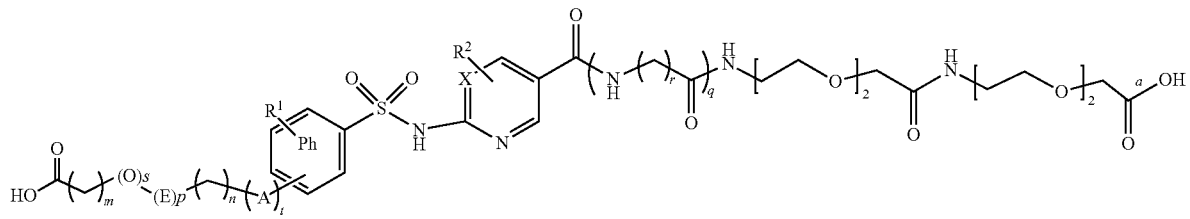

wherein in the sulfonamide of formula (I):
A is selected from the group consisting of oxygen atom, —CH$_2$CH$_2$— group, —OCH$_2$— group and —CH$_2$O— group;
E represents a —C$_6$H$_3$R— group with R being a hydrogen atom or a halogen atom, wherein the halogen atom is selected from the group consisting of fluorine, chlorine, bromine and iodine atom, optionally a fluorine atom;
X represents a nitrogen atom or a —CH— group;
m is an integer in the range from 5 to 17;
n is zero or an integer in the range from 1 to 3;
p is zero or 1;
q is zero or 1;
r is an integer in the range from 1 to 6;
s is zero or 1;
t is zero or 1;
R$^1$ represents at least one residue selected from the group of hydrogen atom, halogen atom, C$_1$ to C$_3$ alkyl group and halogenated C$_1$ to C$_3$ alkyl group;
R$^2$ represents at least one residue selected from the group of hydrogen atom, halogen atom, C$_1$ to C$_3$ alkyl group and halogenated C$_1$ to C$_3$ alkyl group;
wherein the sulfonamide of formula (I) is covalently bound to the active pharmaceutical ingredient in that the terminal carboxy group "a" of the sulfonamide of formula (I) is covalently bound to an amino group of the active pharmaceutical ingredient; comprising:
(a) providing a sulfonamide of formula (Aa)

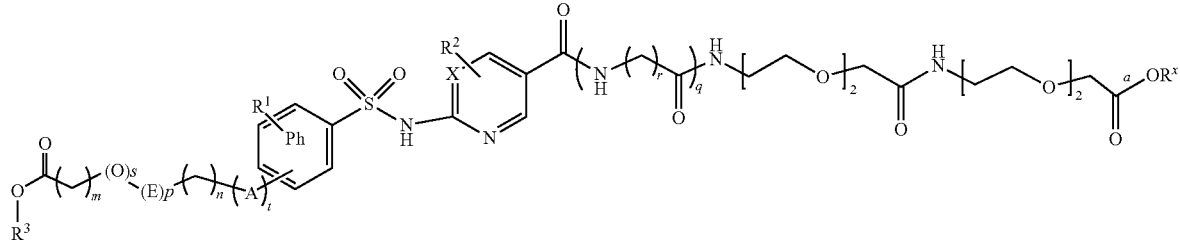

wherein X, Y, A, E, $R^1$, $R^2$ and the indices m, n, p, q, r, s, t have the meaning as defined in embodiment 1, $R^x$ is a hydrogen atom or an activation group, optionally an activation group selected from the group consisting of 7-azabenzotriazole (optionally derived from HATU or HBTU), 4-nitro benzene and N-succinimidyl-group, wherein $R^x$ is optionally a N-succinimidyl-group; and $R^3$ is a protective group or a hydrogen atom, optionally a hydrogen atom; and an insulin analog having a protected or unprotected C terminus;

(b) reacting the sulfonamide of formula (Aa) and the insulin analog having a protected or unprotected C terminus under conditions suitable to form an amide bond between the free or activated, optionally activated, carboxy group "a" of the sulfonamide of formula (Aa) and an amino group of the insulin analog having a protected or unprotected C terminus;

(c) optionally removing one or both protection groups.

16. A conjugate comprising a sulfonamide of formula (I) and an insulin analog obtained or obtainable from the process according to embodiment 15.

17. Pharmaceutical composition comprising in a pharmaceutically effective amount the conjugate comprising a sulfonamide of formula (I) and an insulin analog according to any of embodiments 1 to 15 or according to embodiment 16.

18. The conjugate comprising a sulfonamide of formula (I) and an insulin analog according to any of embodiments 1 to 15 or according to embodiment 16 for use as a medicament.

19. The conjugate comprising a sulfonamide of formula (I) and an insulin analog according to any of embodiments 1 to 15 or according to embodiment 16 for use as a medicament for treatment of a disease selected from the group consisting of gestational diabetes, diabetes mellitus type 1, diabetes mellitus type 2, and hyperglycemia and/or for lowering blood glucose levels.

20. A method of treating a disease selected from the group consisting of gestational diabetes, diabetes mellitus type 1, diabetes mellitus type 2, and hyperglycemia and/or for lowering blood glucose levels comprising administering to a patient in need thereof a conjugate comprising an insulin analog and a sulfonamide of formula (I)

m is an integer in the range from 5 to 17;
n is zero or an integer in the range from 1 to 3;
p is zero or 1;
q is zero or 1;
r is an integer in the range from 1 to 6;
s is zero or 1;
t is zero or 1;
$R^1$ represents at least one residue selected from the group of hydrogen atom, halogen atom, C1 to C3 alkyl group and halogenated C1 to C3 alkyl group;
$R^2$ represents at least one residue selected from the group of hydrogen atom, halogen atom, C1 to C3 alkyl group and halogenated C1 to C3 alkyl group,
wherein the sulfonamide of formula (I) is covalently bound to the insulin analog in that terminal carboxy group "a" of the sulfonamide of formula (I) is covalently bound to an amino group of the insulin analog, thereby treating the disease.

The present invention is further illustrated by the following examples.

EXAMPLES

1. List of Used Abbreviations

| | |
|---|---|
| Ac | Acetyl |
| Boc | tert-Butyloxycarbonyl |
| DCM | Dichlormethane |
| DIAD | Diisopropyl azodicarboxylate |
| DIPEA | N,N-diisopropylethylamine |
| DMAP | 4-Dimethylaminopyridine |
| DMF | Dimethylformamide |
| DMSO | Dimethyl sulfoxide |
| EA | Ethyl acetate |
| HMPA | Hexamethylphosphoramide |
| HPLC | High performance liquid chromatography |
| LC | Liquid chromatography |
| LCMS | Liquid chromatography/mass spectrometry |
| MeCN | MeCN |
| NMM | N-methylmorpholine |
| NMP | N-methyl-2-pyrrolidone |
| PE | Petroleum ether |
| RP | Reversed phase |
| RT | Room temperature (25° C.) |
| TEA | Triethylamine |

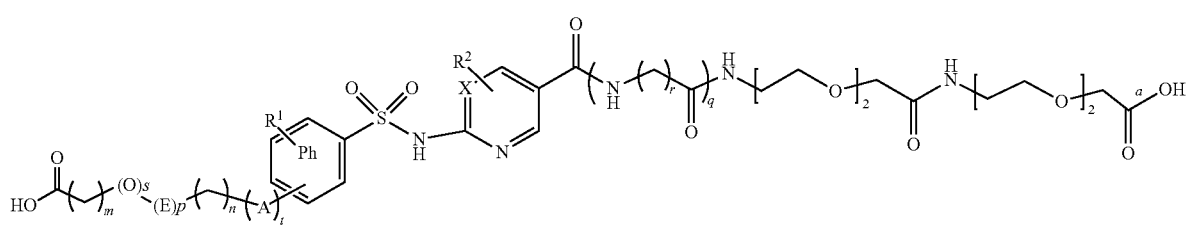

(I)

wherein:

A is selected from the group consisting of oxygen atom, —$CH_2CH_2$— group, —$OCH_2$— group and —$CH_2O$— group;

E represents a —$C_6H_3R$— group with R being a hydrogen atom or a halogen atom, wherein the halogen atom is selected from the group consisting of fluorine, chlorine, bromine and iodine atom;

X represents a nitrogen atom or a —CH— group;

-continued

| | |
|---|---|
| TEMPO | 2,2,6,6-Tetramethylpiperidine-N-oxide |
| TFA | Trifluoroacetic acid |
| TFAA | Trifluoroacetic anhydride |
| TMS | Trimethyl silyl |
| Ts | Tosyl |
| TSTU | O-(N-Succinimidyl)-N,N,N,N-tetramethyluronium tetrafluoroborate |

General processes suitable for preparing compounds of the formula (I) are described below. The compounds of the formula I were prepared by different chemical processes. The groups and indices mentioned in the following methods, especially in the schemes, have the abovementioned meaning indicated for formula (I) unless they are explicitly defined otherwise.

2. General Synthesis of Compounds of Formula (I)

Compounds of the formula (I) were synthesized starting from the corresponding intermediate I (scheme 1). After activation with TSTU the intermediate I was coupled either with amino acid (4) (step3) or compound (2) (step2) to give species (3) and (6), respectively. In case in step3 an alkyl ester (R=alkyl) was utilized, saponification with LiOH was achieved. Both carboxylic acids (6) and (7) were activated with TSTU and coupled with (2) to yield species (3). To finish the synthesis of compounds of the formula (I), tert-butyl ester of (3) was cleaved in the final step7 by treatment with $CF_3CO_2H$. The synthesis of intermediate I is shown in scheme 2.

Scheme 1
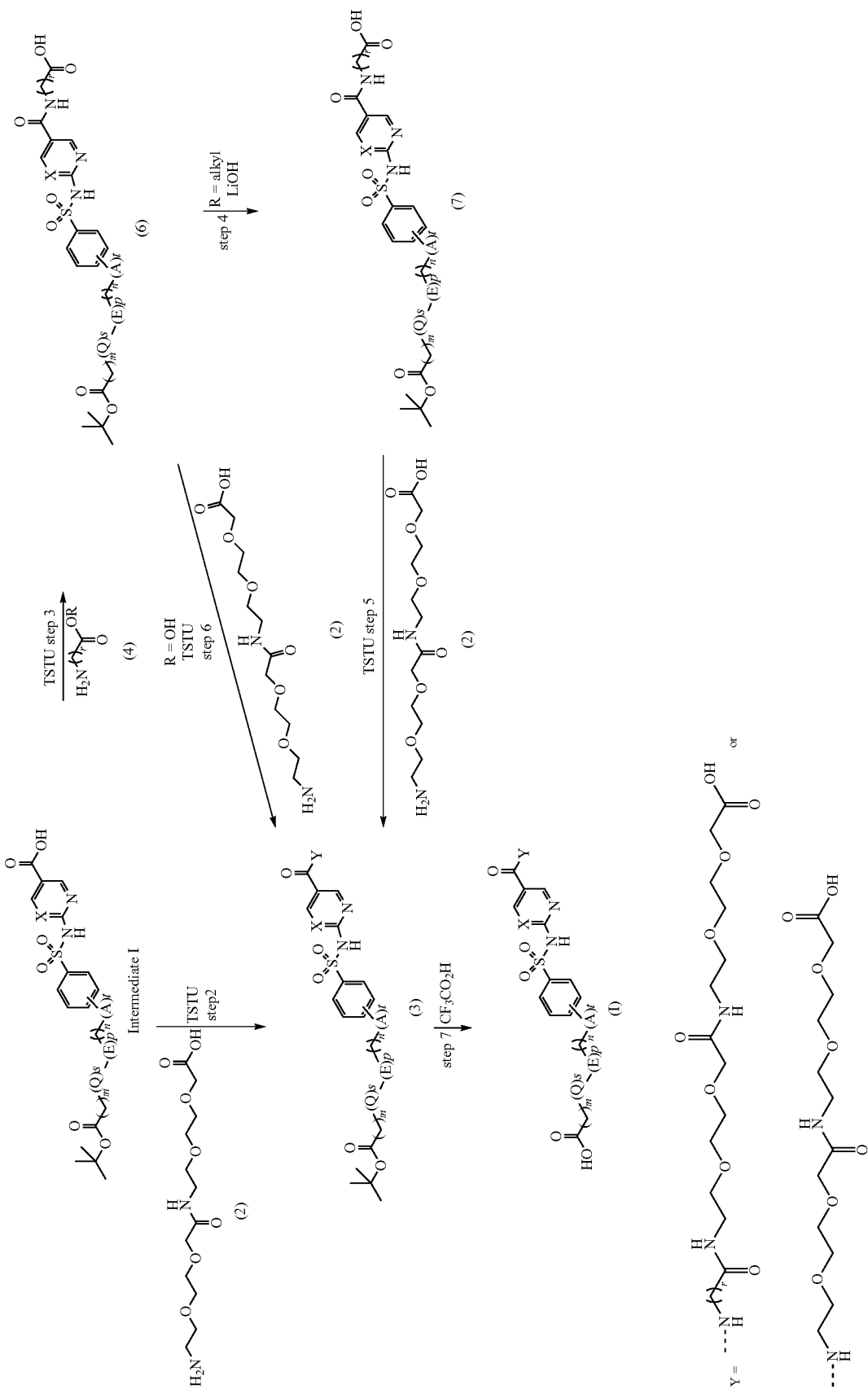

2.1 General Synthesis of Intermediate I

Intermediate I was synthesized as shown in scheme 2. Starting from Bromide I or Tosylate I alkylation of intermediate III was achieved in the presence of $K_2CO_3$ (step 8). Alternatively species (8) was isolated after a sequence of reactions starting with a Sonogashira reaction of alkyne I and intermediate II (step 11) followed by a hydrogenation of the resulting (11) under a hydrogen atmosphere catalyzed by palladium and platinum, respectively (step 12). Species (8) was then condensed either with 2-chloro pyridine (9) (step 9) in a palladium catalyzed reaction or thermally condensed with 2-chloro pyrimidine (10) (step 10). In both cases the alkyl ester was subsequently hydrolyzed with LiOH to obtain the desired intermediate I.

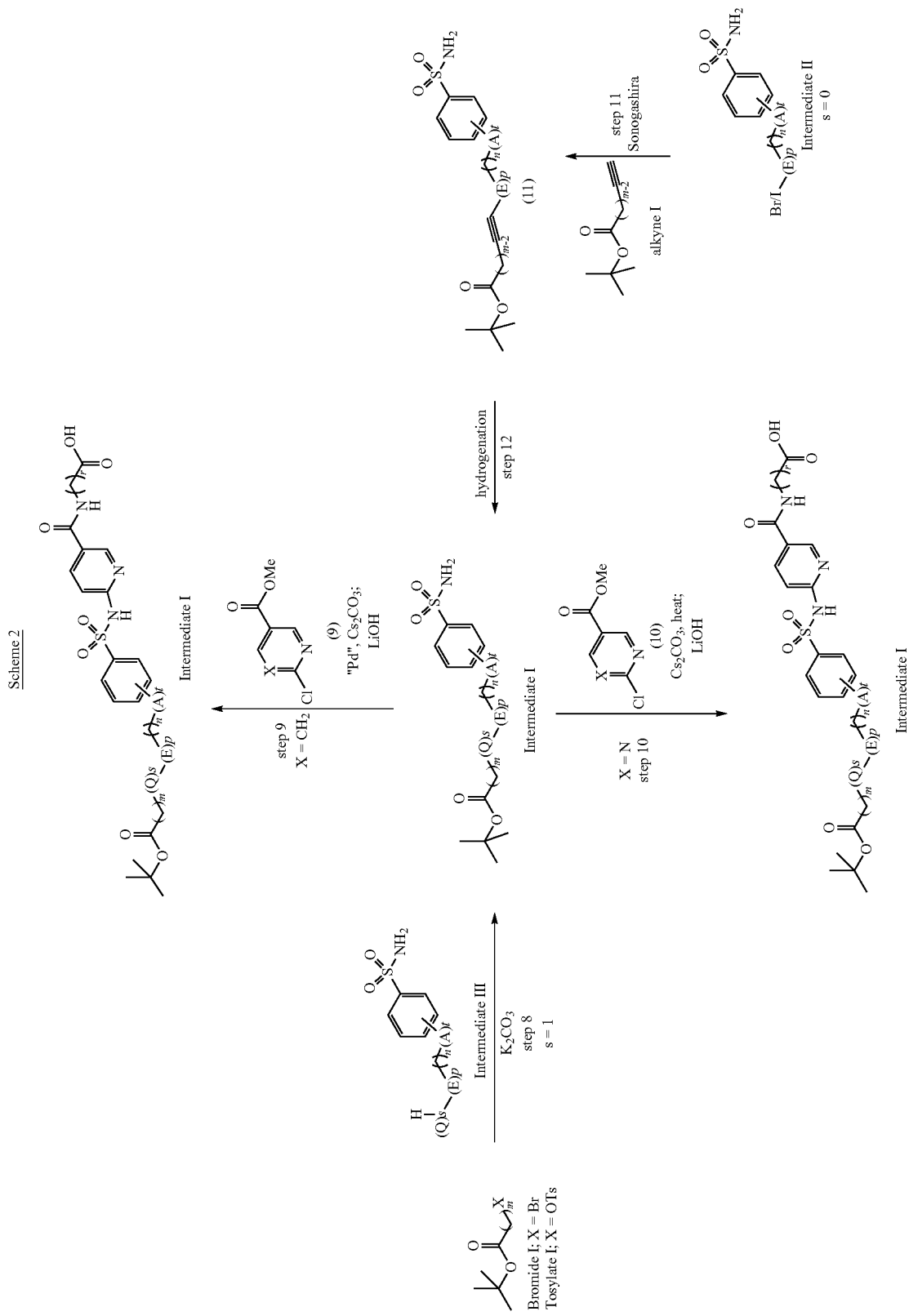

2.2 General Synthesis of Intermediate II

As shown in scheme 3, intermediate II was isolated after a Mitsunobu reaction of phenol (13) and alcohol (12) (step 13). Alternatively, intermediate II was synthesized via alkylation of either phenol (13) (step14) or phenol (15) (step 15) in the presence of $K_2CO_3$. Suitable alkylating agents were (14) and (16), respectively. Nucleophilic aromatic substitution of fluoride (18) with phenol (17) also yielded intermediate II (step16).

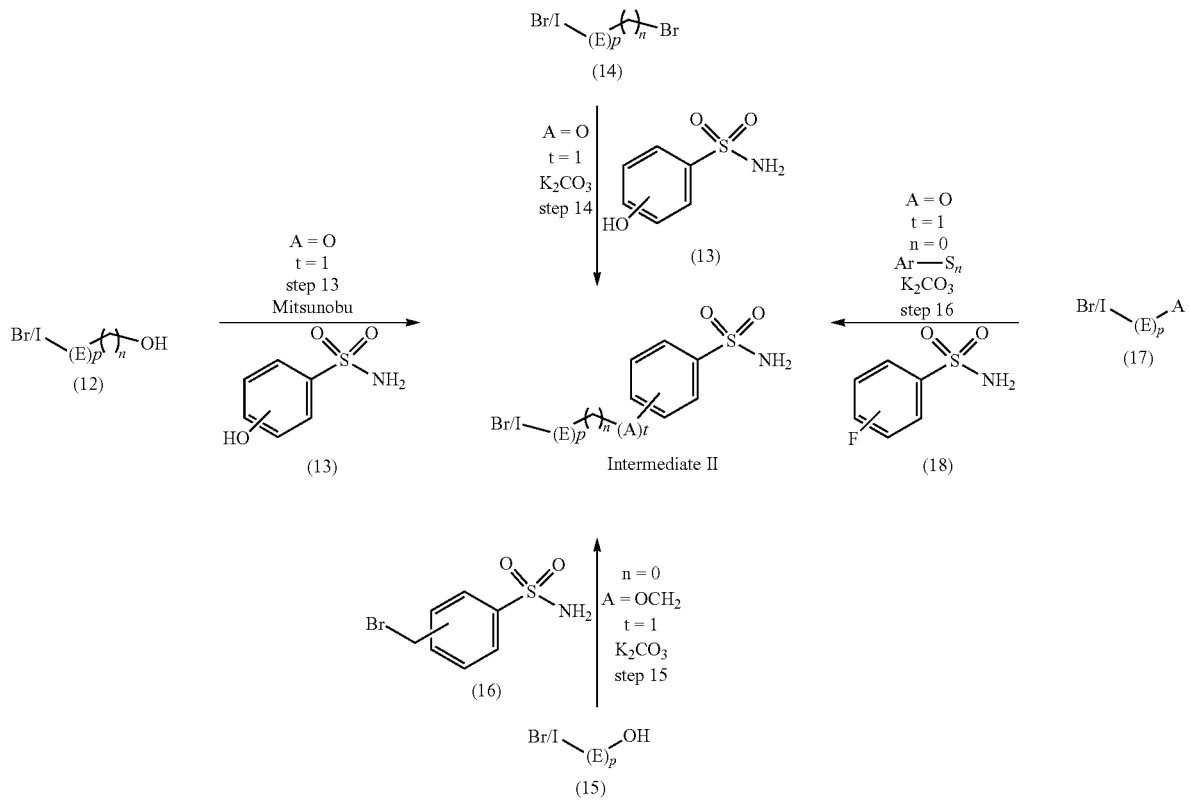

Scheme 3

2.3 General Synthesis of Intermediate III

Intermediate III was obtained after a linear reaction sequence as described in scheme 4. Starting with an alkylation of alkyne (20) with bromide (19), TMS protected alkyne (21) was isolated. Alkyne (21) was deprotected under basic conditions using NaOH.

Subsequent Sonogashira reaction of the isolated alkyne (22) with a corresponding aromatic halide (23) (step19) yielded species (24). A suitable protecting group for species (24) was for example acetyl (PG=Ac), which was cleaved upon treatment with NaOH (step20). The final hydrogenation step 21 was catalyzed by palladium or platinum under a $H_2$ atmosphere to provide the desired intermediate III.

Scheme 4

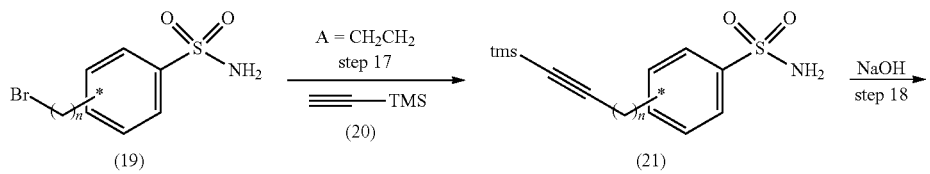

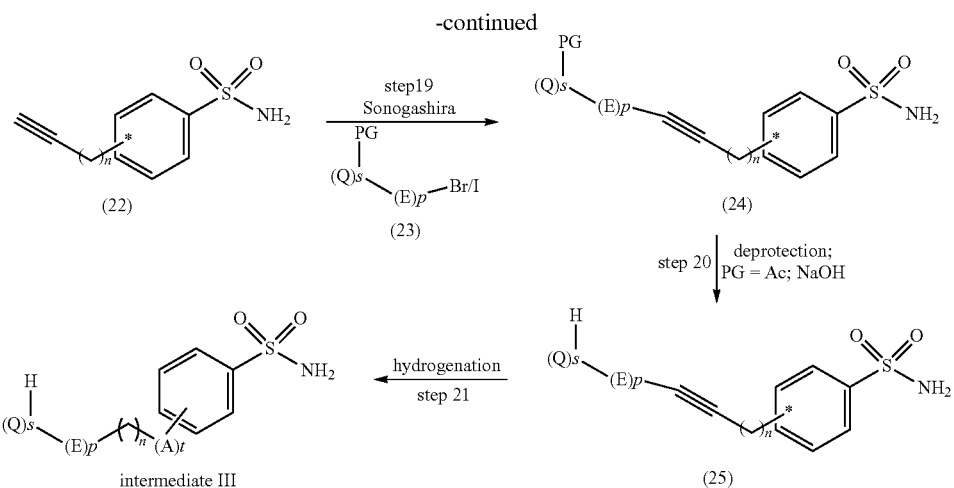

2.4 General Synthesis of Alkyne I and Bromide I

Starting materials bromide I and alkyne I were synthesized as shown in scheme 5. For alkyne I two different synthetic routes were utilized. Carboxylic acid (28) was either isolated after oxidation of alcohol (29)—the mentioned oxidation was achieved through a mixture of NaOCl and NaClO₂ in the presence of a catalytic amount of TEMPO (step24)—or by an alkylation/deprotection sequence of bromide (26). For the alkylation reagent (20) was used. The isolated product (27) was than treated with NaOH to cleave the TMS protecting group. The necessary protection of carboxylic acid (28) as a tert-Butyl ester to obtain desired alkyne I was achieved after activation with (CF₃CO)₂O and reaction with tert-butanol.

For the synthesis of bromide I a similar sequence as described for the convertion of (29) to alkyne I was used (step24 and 25). Oxidation of alcohol (30) and subsequent protection of the resulting carboxylic acid (31) yielded the desired bromide I.

Tosylate I can be synthezised by a tosylation of the alcohol (33) (step29). (33) was isolated after a reduction of the carboxylic acid (32), which was in situ transferred into the mixed anhydride and subsequently reduced with NaBH₄ (step28).

Scheme 5

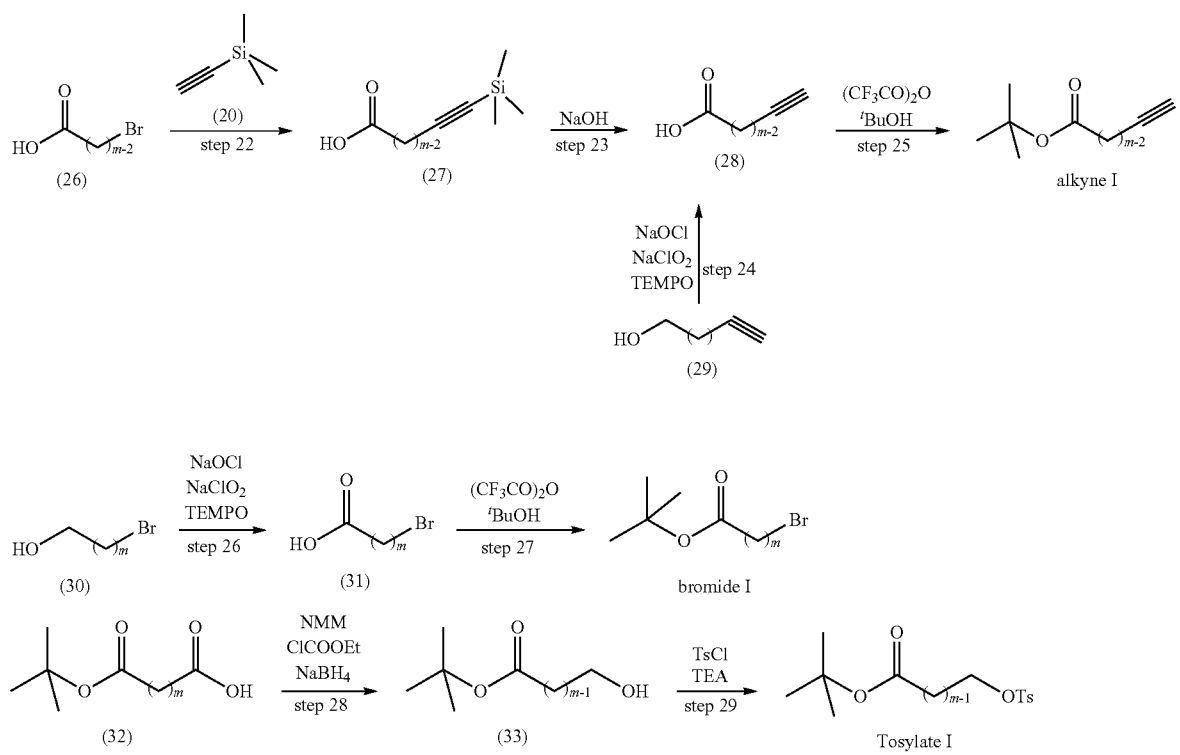

Scheme 5

2.5 Examples for the Synthesis of Alkynes I and Bromides I According to Scheme 5

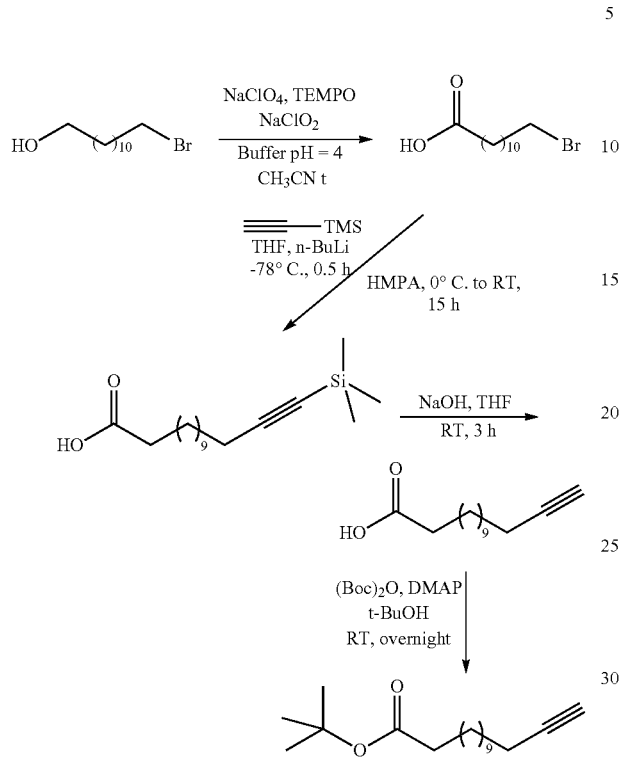

2.5.1 Synthesis of 12-bromododecanoic Acid

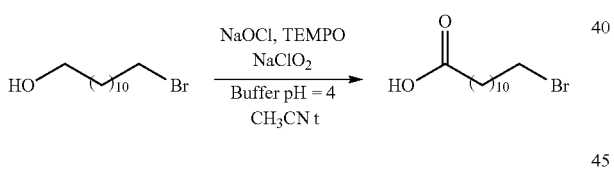

A solution of NaClO$_2$ (37.5 g, 414.8 mmol) in H$_2$O (60 ml) and a 10% solution of NaOCl (28 g, 37.7 mmol) were simultaneously added to a solution of 12-bromo-dodecan-1-ol (20 g, 75.4 mmol) and TEMPO (5.9 g, 37.7 mmol) in CH$_3$CN (400 ml) and pH 4-buffer solution (60 ml). The reaction mixture was stirred at RT overnight. The mixture was diluted with EA (1200 ml), washed with water (1000 ml) and brine, dried over Na$_2$SO$_4$, and concentrated under vacuum to afford the desired product 12-bromododecanoic acid (20 g, 71.6 mmol, yield, 95%) as a yellow solid.

$^1$H NMR (400 MHz, DMSO) δ 11.96 (s, 1H), 3.52 (t, J=6.6 Hz, 2H), 2.18 (t, J=7.2 Hz, 2H), 1.85-1.72 (m, 2H), 1.55-1.43 (m, 2H), 1.37 (s, 2H), 1.21 (d, J=32.6 Hz, 12H).

Following compounds were synthesized accordingly:

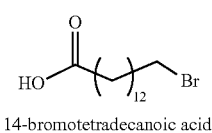

14-bromotetradecanoic acid

2.5.2 Synthesis of 14-(trimethylsilyl)tetradec-13-ynoic Acid

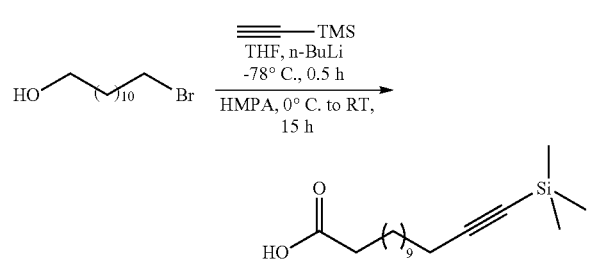

To a mixture of ethynyl-trimethyl-silane (63.3 g, 644.7 mmol) in THE (300 ml), n-butyllithium (2.5M in hexane) (258 ml, 644.7 mmol) was added at −78° C. under N$_2$. After 10 min, HMPA (115.5 g, 644.7 mmol) was added and the mixture was warmed to 0° C. for 30 min. Then 12-bromododecanoic acid (30 g, 107.45 mmol) in THE (300 ml) was added. Then the mixture was stirred at RT overnight. Water (1200 ml) was added into the mixture slowly at 0° C., then pH value was adjusted to 3 with aqueous HCl solution, extracted with EA (800 ml). The organic phase was washed with brine, dried over Na$_2$SO$_4$, concentrated under vacuum to afford the crude product 14-(trimethylsilyl)tetradec-13-ynoic acid (35 g) as a brown oil and used for next step.

Following compounds were synthesized accordingly:

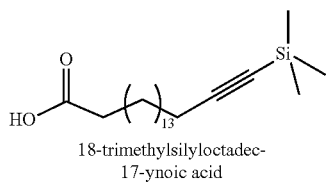

18-trimethylsilyloctadec-17-ynoic acid

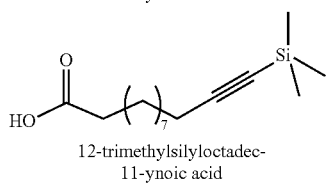

12-trimethylsilyloctadec-11-ynoic acid

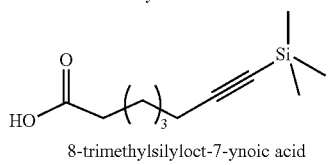

8-trimethylsilyloct-7-ynoic acid

2.5.3 Synthesis of tetradec-13-ynoic Acid

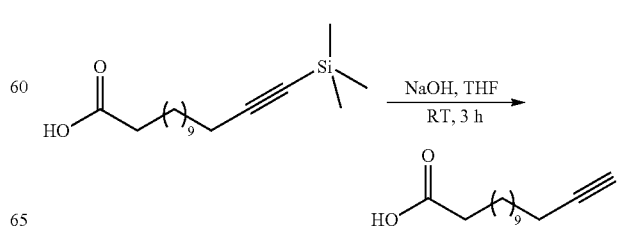

NaOH (8.6 g, 214.9 mmol) was added to a mixture of 14-(trimethylsilyl)tetradec-13-ynoic acid (35 g, 107.45 mmol) in H$_2$O (150 ml) and THF (150 ml). Then the mixture was stirred at RT for 3 h. Then pH value was adjusted to 4 with aqueous HCl solution, extracted with EA (2×300 ml). The organic phases were washed with brine, dried over Na$_2$SO$_4$, concentrated under vacuum. The crude was purified by silica gel chromatography (PE:EA=4:1) to afford the desired product tetradec-13-ynoic acid (23 g, 102.5 mmol, 2 step yield: 95%) as a yellow solid.

$^1$H NMR (400 MHz, DMSO) δ 11.96 (s, 1H), 2.73 (s, 1H), 2.17 (dd, J=16.3, 8.9 Hz, 4H), 1.51-1.21 (m, 18H).

Following compounds were synthesized accordingly:

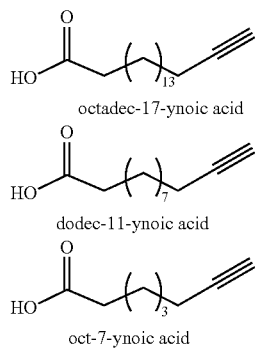

octadec-17-ynoic acid dodec-11-ynoic acid oct-7-ynoic acid

2.5.4 Synthesis of dec-9-ynoic Acid

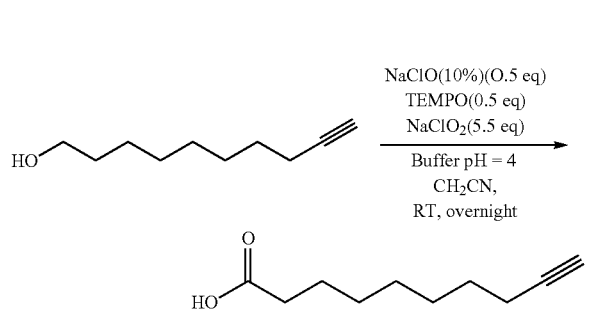

A solution of NaClO$_2$ (48.2 g, 536 mmol) and NaOCl (36.0 g, 48.7 mmol) was simultaneously added to a solution of dec-9-yn-1-ol (15 g, 97.4 mmol) and TEMPO (7.6 g, 48.7 mmol) in CH$_3$CN (300 ml) and pH 4-buffer solution (75 ml). The reaction mixture was stirred at RT overnight, diluted with EA (900 ml), washed with water (900 ml) and brine, dried over Na$_2$SO$_4$, concentrated under vacuum. The crude was purified by silica gel chromatography (PE/EA=1/1) to afford the desired dec-9-ynoic acid (20 g, crude) as a colourless oil.

$^1$H NMR (400 MHz, CDCl$_3$) δ 2.36 (t, J=7.3 Hz, 2H), 2.18 (td, J=6.9, 2.3 Hz, 2H), 1.93 (t, J=2.3 Hz, 1H), 1.72-1.59 (m, 2H), 1.54 (td, J=14.1, 7.2 Hz, 2H), 1.48-1.30 (m, 6H) ppm.

Following compounds were synthesized accordingly:

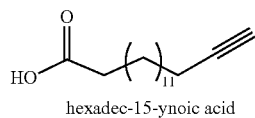

hexadec-15-ynoic acid

2.5.5 Synthesis of tert-butyl tetradec-13-ynoate

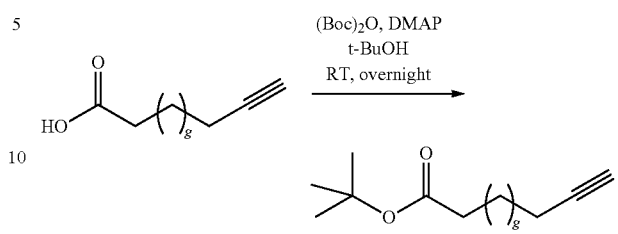

(Boc)$_2$O (33.6 g, 153.8 mmol) and DMAP (3.7 g, 30.7 mmol) were added to a mixture of tetradec-13-ynoic acid (23 g, 102.5 mmol) in t-BuOH (200 ml). Then the mixture was stirred at RT overnight. The solvent was removed under vacuum. Water (400 ml) was added to the mixture, and extracted with EA (400 ml). The organic phase was washed with brine, dried over Na$_2$SO$_4$, filtered and concentrated. The residue was purified by silica gel chromatography (PE:EA=30:1) to give the desired product tert-butyl tetradec-13-ynoate (23.5 g, 83.8 mmol, 82% yield) as a yellow liquid.

$^1$H NMR (400 MHz, DMSO) δ 2.72 (s, 1H), 2.15 (d, J=8.4 Hz, 4H), 1.49-1.21 (m, 27H).

Following compounds were synthesized accordingly:

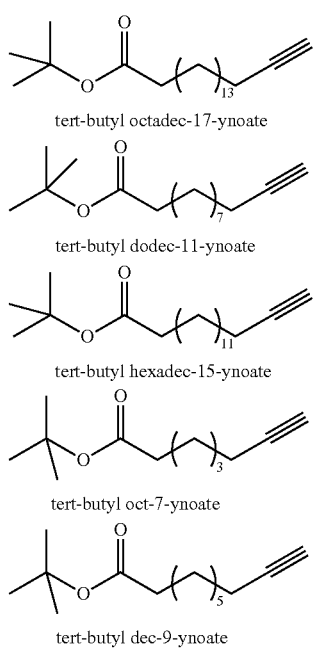

tert-butyl octadec-17-ynoate tert-butyl dodec-11-ynoate tert-butyl hexadec-15-ynoate tert-butyl oct-7-ynoate tert-butyl dec-9-ynoate

2.5.6 Synthesis of tert-butyl 6-bromohexanoate

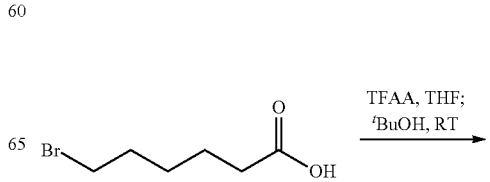

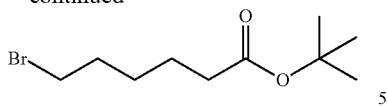

6-bromohexanoic acid (6.0 g, 31 mmol), TFAA (26.0 g, 124 mmol) was added to THF (60 ml), the mixture reacted at RT for 1 h. Then tert-butanol (30 ml) was added to the mixture, and stirred for 16 h at RT. Then the pH of reaction mixture was adapted to pH=8 with NaHCO$_3$ solution, the mixture was extracted with EA (3×150 ml), dried over Na$_2$SO$_4$, concentrated to afford the target compound tert-butyl 6-bromohexanoate (7.6 g, 30.4 mmol, 98% yield).

$^1$H NMR (400 MHz, DMSO) δ 3.52 (t, J=6.6 Hz, 2H), 2.20 (dd, J=15.0, 7.8 Hz, 2H), 1.85-1.74 (m, 2H), 1.52 (ddd, J=19.3, 10.9, 5.7 Hz, 2H), 1.44-1.32 (m, 9H).

2.5.6 Synthesis of Tosylates I

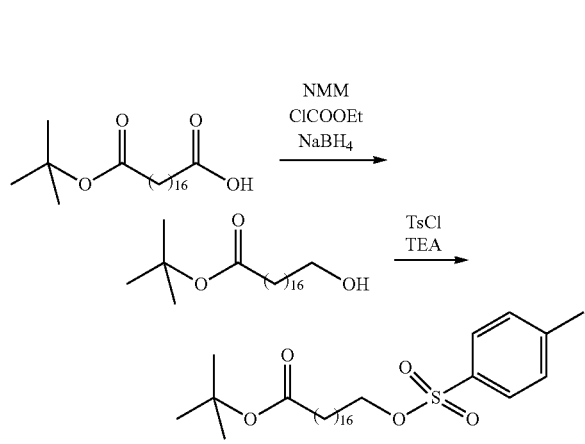

2.5.7 Synthesis of tert-butyl 18-hydroxyoctadecanoate

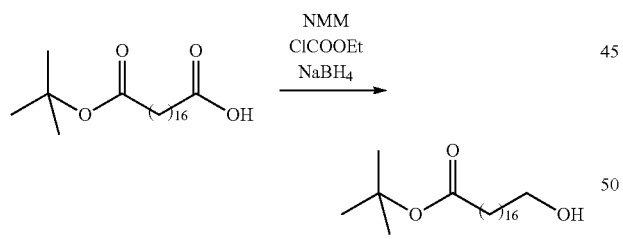

N-methylmorpholine (1638 mg, 16.5 mmol) was added to a solution of 18-tert-butoxy-18-oxo-octadecanoic acid (5 g, 13.5 mmol) in THF (150 ml). The mixture was cooled to −25° C. before adding ethyl chloroformate (1277 mg, 13.5 mmol) dropwise. The mixture was stirred at −25° C. for 20 minutes and the solid was removed by filtration. The solution was carefully added to a solution of NaBH$_4$ (770 mg, 20.25 mmol) in water (15 mL) at 0° C. The mixture was stirred for 1 hour at room temperature. THF was removed under vacuum and the aqueous phase was extracted with EA (3×50 mL). The combined organic phases were dried over MgSO$_4$ and concentrated under vacuum to give tert-butyl 18-hydroxyoctadecanoate as a white solid (4.7 g, 99.8% yield).

$^1$H NMR (400 MHz, CDCl$_3$) δ 3.63 (t, J=6.6 Hz, 2H), 2.19 (t, J=7.5 Hz, 2H), 1.57 (dd, J=13.0, 6.5 Hz, 4H), 1.43 (d, J=3.9 Hz, 9H), 1.38-1.20 (m, 27H).

Following compounds were synthesized accordingly:

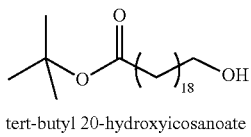

tert-butyl 20-hydroxyicosanoate

2.5.8 Synthesis of tert-butyl 18-(p-tolylsulfonyloxy)octadecanoate

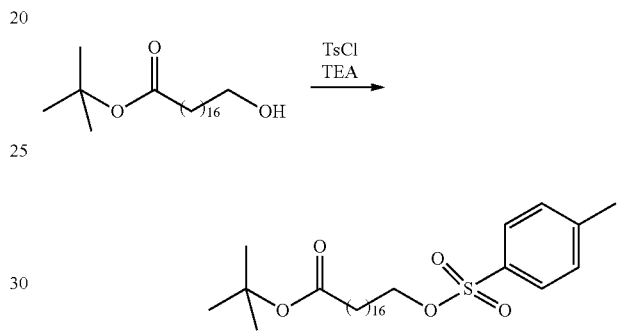

TEA (400 mg, 39.6 mmol) was added to a solution of tert-butyl 18-hydroxyoctadecanoate (4700 mg, 13.2 mmol) and TsCl (2508 mg, 13.2 mmol) in DCM (100 mL). The reaction mixture was stirred at room temperature overnight. Water (50 mL) was added, and extracted with DCM (2×50 ml). The combined organic phase was washed with brine (100 mL), dried over Na$_2$SO$_4$, filtrated and concentrated. The crude was purified by silica gel column (EA/n-hexane=1:20) to afford tert-butyl 18-(p-tolylsulfonyloxy) octadecanoate (4.5 g, 67% yield).

$^1$H NMR (400 MHz, CDCl$_3$) δ 7.79 (d, J=8.2 Hz, 2H), 7.34 (d, J=8.1 Hz, 2H), 4.02 (t, J=6.5 Hz, 2H), 2.45 (s, 3H), 2.20 (t, J=7.5 Hz, 2H), 1.69-1.57 (m, 4H), 1.44 (s, 9H), 1.25 (t, J=12.1 Hz, 24H).

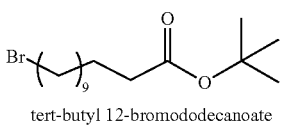

tert-butyl 12-bromododecanoate

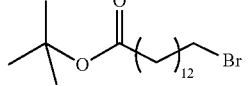

tert-butyl 14-bromotetradecanoate

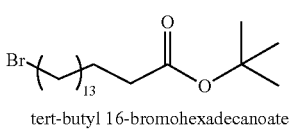

tert-butyl 16-bromohexadecanoate

Following compounds were synthesized accordingly:

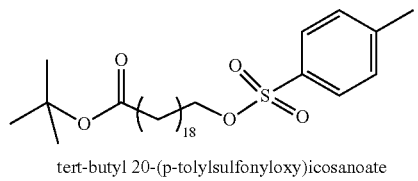

tert-butyl 20-(p-tolylsulfonyloxy)icosanoate

2.6 Examples for the Synthesis of Intermediates III According to Scheme 4

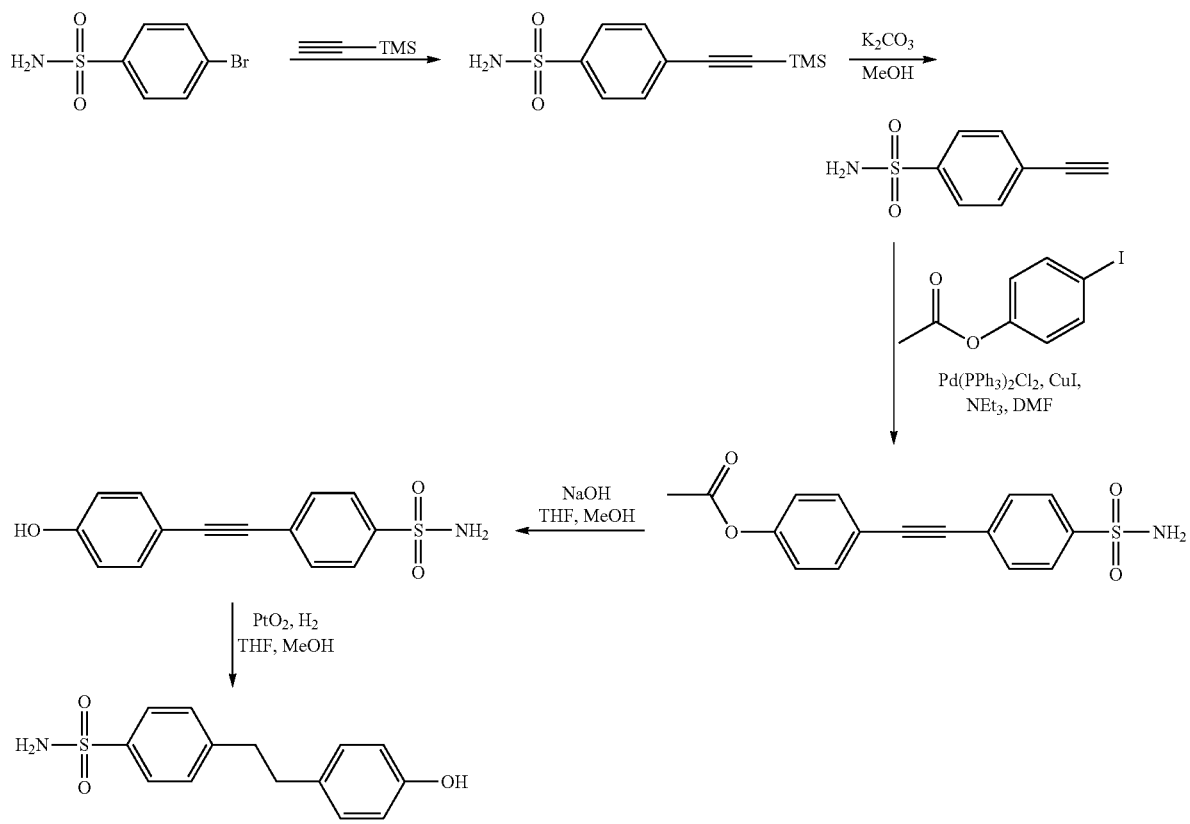

2.6.1 Synthesis of 4-((trimethylsilyl)ethynyl)benzenesulfonamide

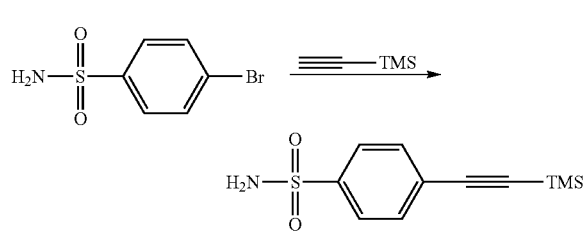

A mixture of 4-bromobenzenesulfonamide (61 g, 260 mmol), trimethylsilylacetylene (38.2 g, 0.09 mol), tetrakis(triphenylphosphine) palladium (7.5 g, 6.5 mmol) and copper iodide (2.5 g, 13 mmol) in triethylamine (500 ml) was heated to 80° C. under a nitrogen atmosphere for 8 h. The mixture was concentrated in vacuo and extracted with EA (300 ml). The combined organic layers were dried (Na$_2$SO$_4$) and concentrated under reduced pressure. The crude was purified by silica gel chromatography (eluting with 70% DCM in PE) to afford 4-((trimethylsilyl)ethynyl)benzenesulfonamide (50 g, 75%).

LC-Mass Method: Mobile phase: A=10 mM TFA/H$_2$O, B=MeCN; Gradient: B=5%-95% in 1.5 min; Flow rate: 2.0 ml/min; Column: Xbridge-C$_{18}$, 50×4.6 mm, 3.5 μm. LC purity: 90% (214 nm); Mass: find peak 254.0 (M+H)$^+$ at 1.98 min.

2.6.2 Synthesis of 4-ethynylbenzenesulfonamide

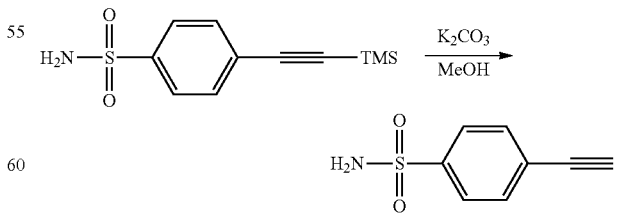

4-((trimethylsilyl)ethynyl)benzenesulfonamide (40 g, 158 mmol), K$_2$CO$_3$ (2.2 g, 15.8 mmol), and methanol (400 ml) were stirred at RT for 12 h. After the reaction was completed (monitored by LCMS), diluted with water (200 ml), and extracted with EA (2×200 ml). The combined organic layers were dried (Na$_2$SO$_4$) and concentrated under reduced pressure. The crude was purified by silica gel chromatography (eluting with 100% DCM in PE) to afford 4-ethynylbenzenesulfonamide (22 g, 77%).

LC-Mass Method: Mobile phase: A=10 mM TFA/H$_2$O, B=MeCN; Gradient: B=5%-95% in 1.5 min; Flow rate: 2.0 ml/min; Column: Xbridge-C$_{18}$, 50×4.6 mm, 3.5 μm. LC purity: 90% (214 nm); Mass: find peak 182.1 (M+H)$^+$ at 1.65 min.

2.6.3 Synthesis of 4-((4-sulfamoylphenyl)ethynyl)phenyl Acetate

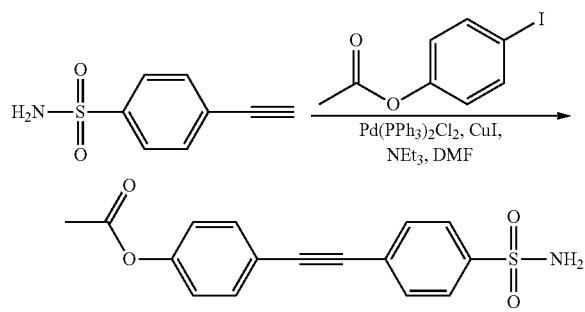

Pd(PPh$_3$)$_2$Cl$_2$ (5.8 g, 8.3 mmol), CuI (1.6 g, 8.3 mmol), Et$_3$N (25 g, 249 mmol) and (4-iodophenyl) acetate (27 g, 103 mmol) were added to a mixture of 4-ethynylbenzenesulfonamide (15 g, 83 mmol) in DMF (150 ml). The flask was evacuated and backfilled with N$_2$. Then the mixture was stirred at RT overnight. Water (200 ml) was added into the mixture, suction filtration and drying in air provides 4-((4-sulfamoylphenyl)ethynyl)phenyl acetate as brown solid (18 g, 70%).

LC-Mass Method: Mobile phase: A=10 mM TFA/H$_2$O, B=MeCN; Gradient: B=5%-95% in 1.5 min; Flow rate: 2.0 ml/min; Column: Xbridge-C$_{18}$, 50×4.6 mm, 3.5 μm. LC purity: 90% (214 nm); Mass: find peak 338 (M+Na)$^+$ at 1.88 min.

2.6.4 Synthesis of 4-((4-hydroxyphenyl)ethynyl)benzenesulfonamide

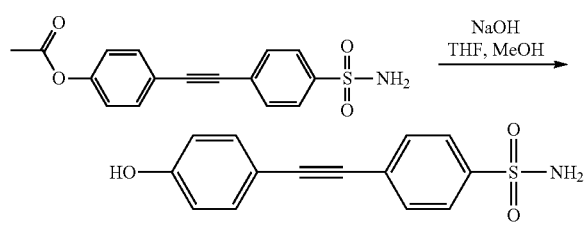

At 0° C., NaOH (4.5 g, 114 mmol) was added to a solution of 4-((4-sulfamoylphenyl)ethynyl)phenyl acetate (18 g, 57 mmol) in THF (60 ml), MeOH (60 ml) and H$_2$O (30 ml). The mixture was stirred at RT for 2 h. After the reaction was completed (monitored by LCMS), upon the solution was diluted with EA (50 ml) and washed with water (20 ml), and saturated aqueous NaCl, dried over MgSO$_4$. The filtrate was concentrated in vacuo to provide crude product. The crude product was slurried with DCM. Suction filtration and drying in air provides 4-((4-hydroxyphenyl) ethynyl)benzenesulfonamide as brown solid (10.9 g, 70%).

LC-Mass Method: Mobile phase: A=10 mM TFA/H$_2$O, B=MeCN; Gradient: B=5%-95% in 1.5 min; Flow rate: 2.0 ml/min; Column: Xbridge-C$_{18}$, 50×4.6 mm, 3.5 μm. LC purity: 95% (214 nm); Mass: find peak 296.1 (M+Na)$^+$ at 1.75 min.

2.6.5 Synthesis of 4-(4-hydroxyphenethyl)benzenesulfonamide

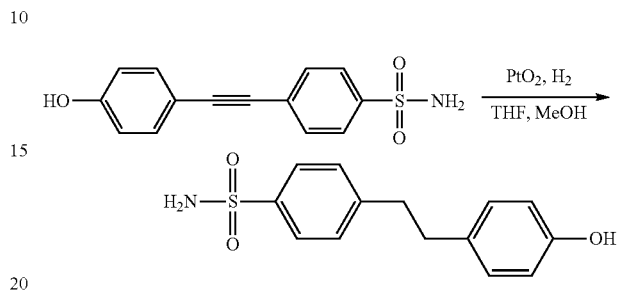

PtO$_2$ (1 g) was added to a solution of 4-((4-hydroxyphenyl)ethynyl)benzenesulfonamide (10.9 g, 40 mmol) in 40 ml of THF and 40 ml of MeOH. The reaction mixture was stirred at RT under H$_2$ for 24 h. After the reaction was completed (monitored by LCMS), the mixture was then filtered. The filtrate was concentrated in vacuo to provide 4-(4-hydroxyphenethyl)benzenesulfonamide (9.5 g, 86%).

LC-Mass Method: Mobile phase: A=10 mM TFA/H$_2$O, B=MeCN; Gradient: B=5%-95% in 1.5 min; Flow rate: 2.0 ml/min; Column: Xbridge-C$_{18}$, 50×4.6 mm, 3.5 μm. LC purity: 100% (214 nm); Mass: find peak 278.1 (M+H)$^+$ at 1.67 min.

$^1$H NMR (400 MHz, DMSO) δ 9.14 (s, 1H), 7.71 (d, J=8.3 Hz, 2H), 7.38 (d, J=8.3 Hz, 2H), 7.26 (s, 2H), 7.00 (d, J=8.4 Hz, 2H), 6.72-6.60 (m, 2H), 2.96-2.84 (dd, J=9.2, 6.2 Hz, 2H), 2.77 (dd, J=9.2, 6.3 Hz, 2H).

2.7 Examples for the Synthesis of Intermediates II According to Scheme 3

2.7.1 Synthesis of 4-(3-bromo-4-fluorophenoxy)benzenesulfonamide

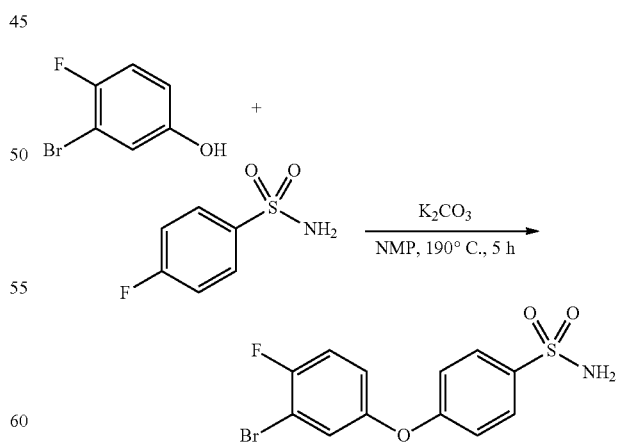

A mixture of 3-bromo-4-fluoro-phenol (12.8 g, 66.8 mmol), 4-fluorobenzene sulfonamide (9.00 g, 51.4 mmol) and K$_2$CO$_3$ (14.2 g, 103 mmol) in NMP (50 ml) was stirred at 190° C. for 5 h. The reaction mixture was diluted with EA (500 ml), washed with water (50 ml), brine (3×50 ml), dried over Na$_2$SO$_4$, filtered and concentrated. The residue was purified by flash chromatography on silica gel (eluting with PE/EA=3/1) to afford 4-(3-bromo-4-fluorophenoxy)benzenesulfonamide as a white solid (10.8 g, 31.3 mmol, 61% yield).

LC-Mass Method: Mobile phase: A=2.5 mM TFA/H$_2$O, B=2.5 mM TFA/MeCN; Gradient: B=10%-95% in 1.0 min; Flow rate: 1.5 ml/min; Column: Xbridge-C$_{18}$, 30×4.6 mm, 2.5 μm. LC (desired product) purity: 88% (214 nm); Mass: find peak 368.0 (M+Na)$^+$ at 1.74 min.

Following compounds were synthesized accordingly:

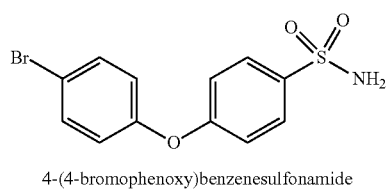 [SMILES: NS(=O)(=O)c1ccc(Oc2ccc(Br)cc2)cc1]

4-(4-bromophenoxy)benzenesulfonamide

2.7.2 Synthesis of 4-(4-bromophenethoxy)benzenesulfonamide

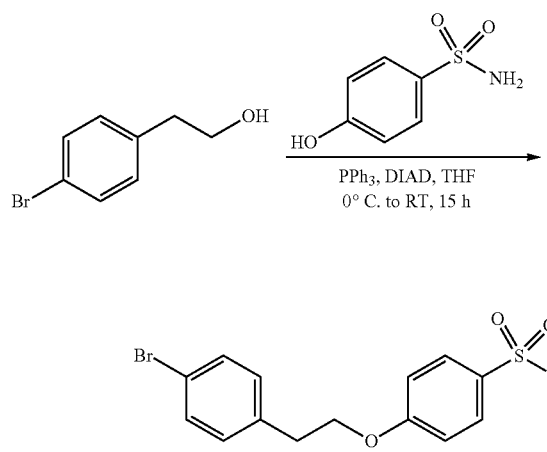

DIAD (11.1 g, 54.7 mmol) was added, at 0° C. and dropwise, to a solution of 2-(4-bromophenyl)ethanol (10 g, 49.8 mmol), 4-hydroxybenzene sulfonamide (8.6 g, 49.8 mmol) and PPh$_3$ (14.3 g, 54.795 mmol) in dry THF (200 ml). The reaction was allowed to warm to RT with stirring for 20 h. The solvent was removed under reduced pressure and the residue was dissolved in EA (200 ml) and then washed with water (50 ml) and brine (50 ml). The organic phase dried over Na$_2$SO$_4$. After filtration, the solvent was removed under reduced pressure and the residue was purified by column chromatography (silica gel, eluting with EA in PE from 0 to 40%) to obtain 4-(4-bromophenethoxy) benzenesulfonamide (6.8 g as white solid) in 39% yield.

LC-Mass Method: Mobile phase: H$_2$O (0.01% TFA (A)/ MeCN (0.01% TFA), (B); Gradient: 5% B for 0.2 min, increase to 95% B within 1.3 min; Flow rate: 1.8 ml/min; Column: SunFire, 50×4.6 mm, 3.5 μm. LC purity: 95% (214 nm); Mass: find peak 356 (M+H)$^+$ at 2.08 min

2.7.3 Synthesis Scheme 4-((4-iodophenoxy)methyl)benzenesulfonamide

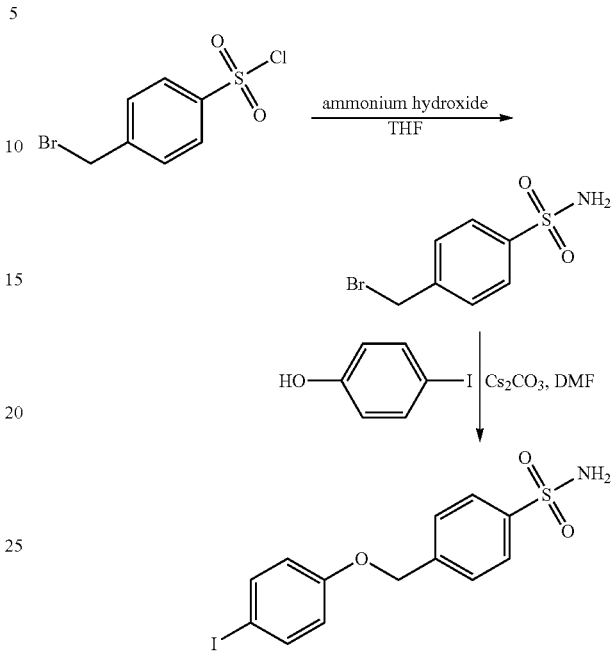

2.7.4 Synthesis of 4-(bromomethyl)benzenesulfonamide

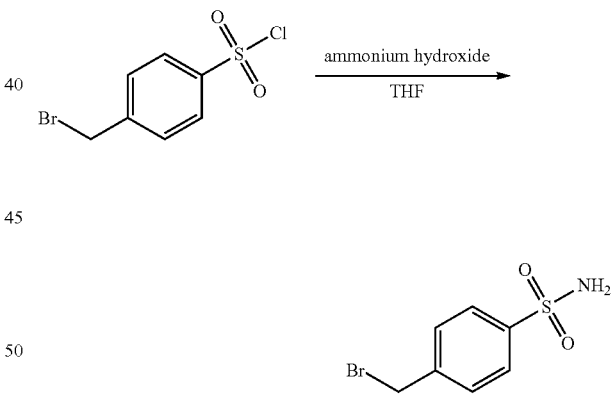

A solution of 4-(bromomethyl)benzenesulfonyl chloride (7 g, 26 mmol) in THF (80 ml) was cooled to 0° C., 28% aqueous ammonia (6.5 ml) was added thereto and the mixture was stirred at RT for 2 h. The reaction solution was concentrated and ethyl acetate (200 ml) was added. The organic layer was separated, dried and concentrated. The crude 4-(bromomethyl)benzenesulfonamide was used directly without further purification. (5.5 g, 86%)

LC-Mass Method: Mobile phase: A=10 mM TFA/H$_2$O, B=MeCN; Gradient: B=5%-95% in 1.5 min; Flow rate: 2.0 ml/min; Column: Xbridge-C$_{18}$, 50×4.6 mm, 3.5 μm. LC purity: 90% (214 nm); Mass: find peak 250.1 (M+H)$^+$ at 1.64 min.

2.7.5 Synthesis of 4-((4-iodophenoxy)methyl)benzenesulfonamide

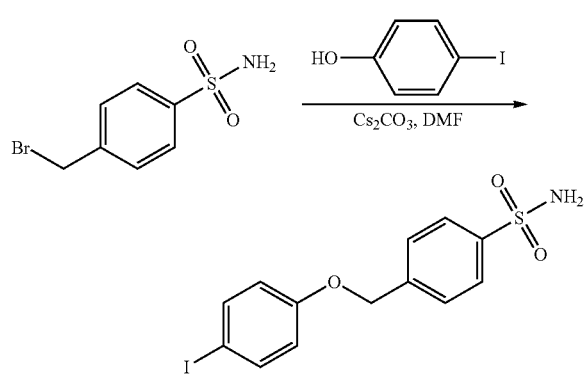

Cs₂CO₃ (10.7 g, 33 mmol) and 4-iodophenol (6 g, 27.5 mmol) were added to a mixture of 4-(bromomethyl)benzenesulfonamide (5.5 g, 22 mmol) in DMF (50 ml). Then the mixture was stirred at RT for 12 h. Water (200 ml) was added into the mixture, the resulting solid filtered, and then slurried with Et₂O (50 ml); suction filtration and drying in air provides the desired product as a white solid (5.5 g, 65%).

LC-Mass Method: Method: Mobile phase: A=10 mM TFA/H₂O, B=MeCN; Gradient: B=5%-95% in 1.5 min; Flow rate: 1.8 ml/min; Column: Xbridge-C$_{18}$, 50×4.6 mm, 3.5 µm. LC purity: 80% (214 nm); Mass: find peak 389.7 (M+H)⁺ at 1.98 min.

2.7.6 Synthesis of 4-(4-bromobenzyloxy)benzenesulfonamide

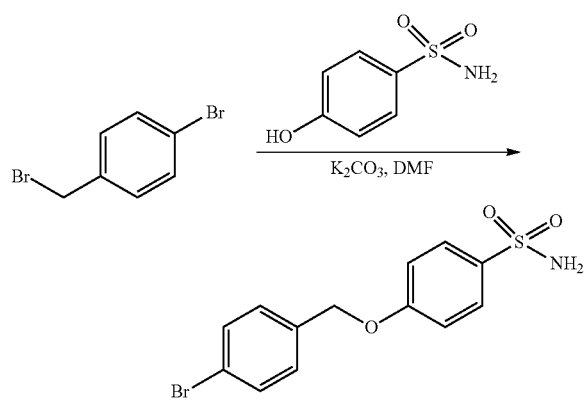

To a mixture of 1-bromo-4-(bromomethyl)benzene (6.5 g, 26 mmol) in DMF (50 ml) was added K₂CO₃ (5.5 g, 40 mmol), and 4-hydroxybenzenesulfonamide (4.5 g, 26 mmol). Then the mixture was stirred at 50° C. for 2 h. Water (200 ml) was added into the mixture, the solid was filtered. Then the solid was slurried with PE:EA=1:2 (50 ml), suction filtration and drying in air provides the desired product as a white solid. (5.3 g, 60%).

LC-Mass Method: Method: Mobile phase: A=10 mM TFA/H₂O, B=MeCN; Gradient: B=5%-95% in 1.5 min; Flow rate: 1.8 ml/min; Column: Xbridge-C$_{18}$, 50×4.6 mm, 3.5 µm. LC purity: 80% (214 nm); Mass: find peak 364 (M+Na)⁺ at 1.81 min.

2.8 Examples for the Synthesis of Intermediates I According to Scheme 2

2.8.1 Synthesis of tert-butyl 12-(4-sulfamoylphenoxy)dodecanoate

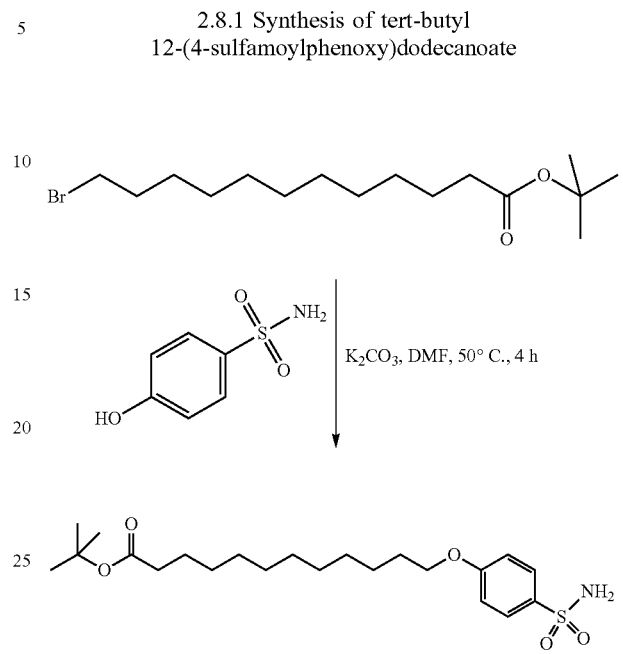

A mixture of tert-butyl 12-bromododecanoate (6 g, 18 mmol), 4-hydroxybenzene sulfonamide (3 g, 18 mmol) and K₂CO₃ (5 g, 36 mmol) in DMF (50 ml) was heated to 50° C. and stirred for 4 h. Then water (300 ml) was added. The resulting precipitate was collected and dried to give the crude tert-butyl 12-(4-sulfamoylphenoxy)dodecanoate, which was slurried with EA/PE (1/5, 100 ml) to yield 7 g (93%) of 12-(4-sulfamoylphenoxy) dodecanoate:

LC-Mass Method: Mobile phase: A: water (0.01% TFA) B: MeCN (0.01% TFA). Gradient: 5% B for 0.2 min, increase to 95% B within 1.3 min, 95% B for 1.5 min, back to 5% B within 0.01 min; Flow Rate: 1.8 ml/min; Column: Sunfire, 50*4.6 mm, 3.5 µm Column Temperature: 50° C. LC-MS purity: 100% (214 nm); Mass: find peak 450.2 (M+Na)⁺ at 2.23 min.

¹H NMR (400 MHz, CDCl₃) δ 7.83 (t, J=14.8 Hz, 2H), 6.96 (d, J=8.8 Hz, 2H), 4.89 (s, 2H), 4.03 (dt, J=13.0, 6.6 Hz, 2H), 2.20 (t, J=7.5 Hz, 2H), 1.73-1.80 (m, 2H), 1.50-1.57 (m, 2H), 1.40-1.48 (m, 11H), 1.37-1.19 (m, 12H).

Following compounds were synthesized accordingly:

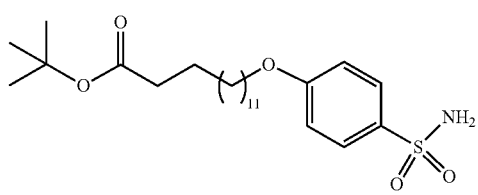

tert-butyl 14-(4-sulfamoylphenoxy) tetradecanoate

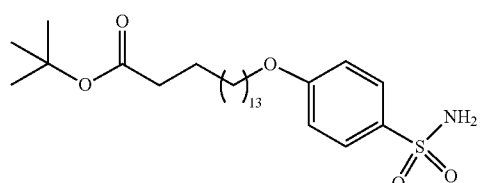

tert-butyl
16-(4-sulfamoylphenoxy)
hexadecanoate

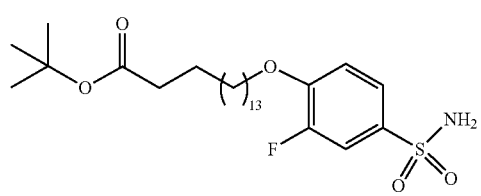

tert-butyl
16-(2-fluoro-4-sulfamoyl-
phenoxy) hexadecanoate

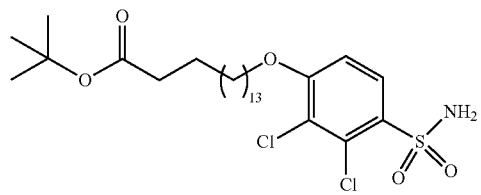

tert-butyl
16-(2,3-dichloro-4-sulfamoyl-
phenoxy) hexadecanoate

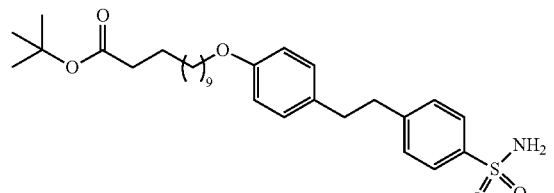

tert-butyl
12-[4-[2-(4-sulfamoylphenyl)
ethyl]phenoxy]dodecanoate

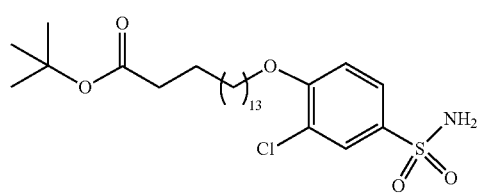

tert-butyl
16-(2-chloro-4-sulfamoyl-
phenoxy) hexadecanoate

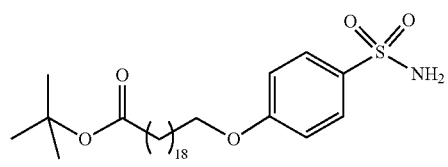

tert-butyl
20-(4-sulfamoylphenoxy)
icosanoate

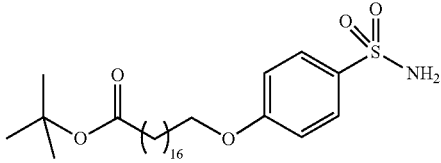

tert-butyl
18-(4-sulfamoyl-phenoxy)
octadecanoate

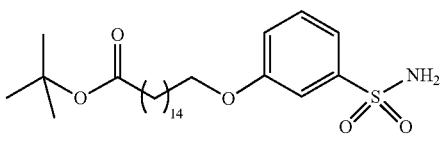

tert-butyl
16-(3-
sulfamoylphenoxy)hexadecanoate

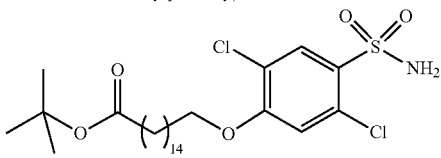

tert-butyl
16-(2,5-dichloro-4-sulfamoyl-
phenoxy)hexadecanoate

Synthetic Scheme: Synthesis of
14-(4-sulfamoylphenyl)tetradecanoate

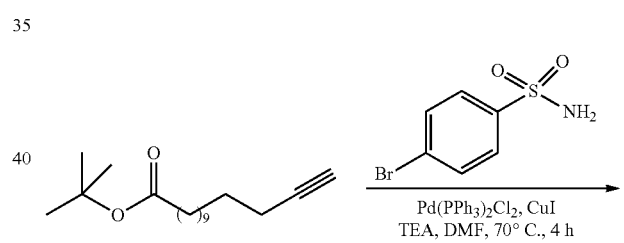

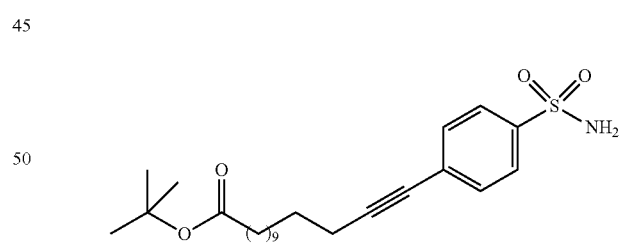

2.8.2 Synthesis of tert-butyl 14-(4-sulfamoylphenyl)tetradec-13-ynoate

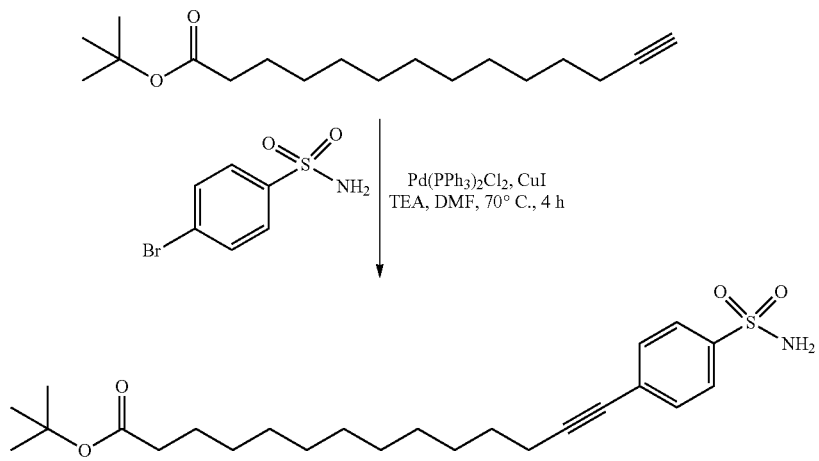

Pd(PPh₃)₂Cl₂ (0.47 g, 0.68 mmol), CuI (0.13 g, 0.68 mmol), Et₃N (2 g, 20.33 mmol) and tert-butyl tetradec-13-ynoate (2.2 g, 7.8 mmol) were added to a mixture of 4-bromobenzenesulfonamide (1.6 g, 6.8 mmol) in DMF (20 ml). The flask was evacuated and backfilled with N₂. Then the mixture was stirred at 70° C. for 4 h. Water (80 ml) was added into the mixture, extracted by EA (2×80 ml). The combined organic phase was washed with brine, dried over Na₂SO₄, concentrated under the vacuum. The crude was purified by silica gel chromatography (PE:EA=4:1) to give tert-butyl 14-(4-sulfamoylphenyl)tetradec-13-ynoate (2.2 g, 5.05 mmol, yield: 76%) as a yellow solid.

LC-Mass Method: Method: Mobile phase: A=10 mM TFA/H₂O, B=MeCN; Gradient: B=5%-95% in 1.5 min; Flow rate: 1.8 ml/min; Column: Xbridge-C₁₈, 50×4.6 mm, 3.5 μm. LC purity: 98% (214 nm); Mass: find peak 458 (M+H)⁺ at 2.37 min.

Following compounds were synthesized accordingly:

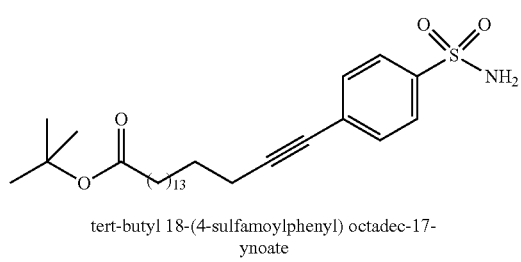

tert-butyl 18-(4-sulfamoylphenyl) octadec-17-ynoate

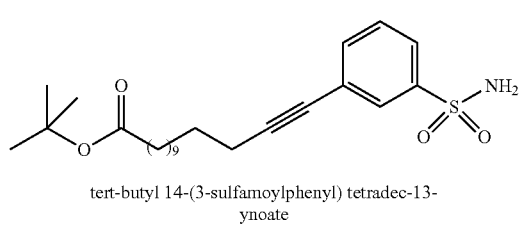

tert-butyl 14-(3-sulfamoylphenyl) tetradec-13-ynoate

-continued

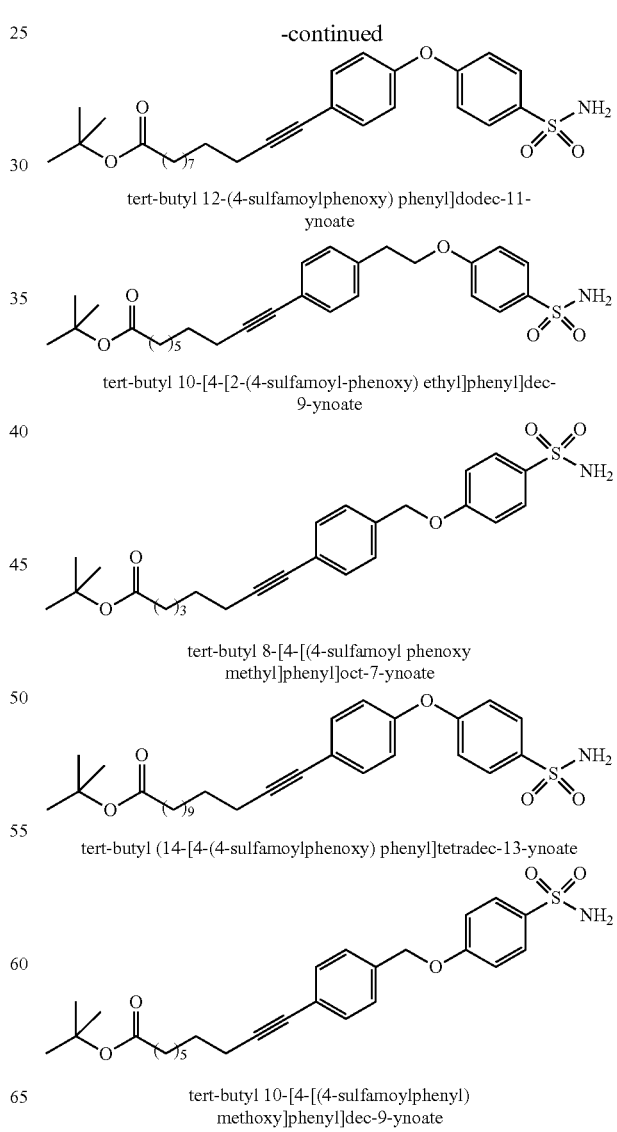

tert-butyl 12-(4-sulfamoylphenoxy) phenyl]dodec-11-ynoate tert-butyl 10-[4-[2-(4-sulfamoyl-phenoxy) ethyl]phenyl]dec-9-ynoate tert-butyl 8-[4-[(4-sulfamoyl phenoxy methyl]phenyl]oct-7-ynoate tert-butyl (14-[4-(4-sulfamoylphenoxy) phenyl]tetradec-13-ynoate tert-butyl 10-[4-[(4-sulfamoylphenyl) methoxy]phenyl]dec-9-ynoate

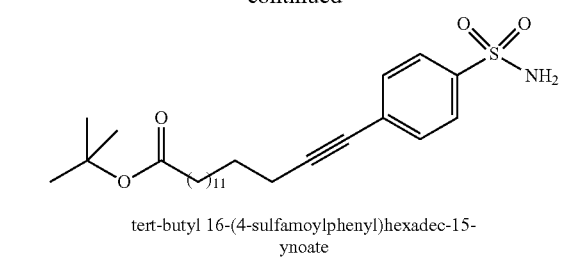

tert-butyl 16-(4-sulfamoylphenyl)hexadec-15-ynoate

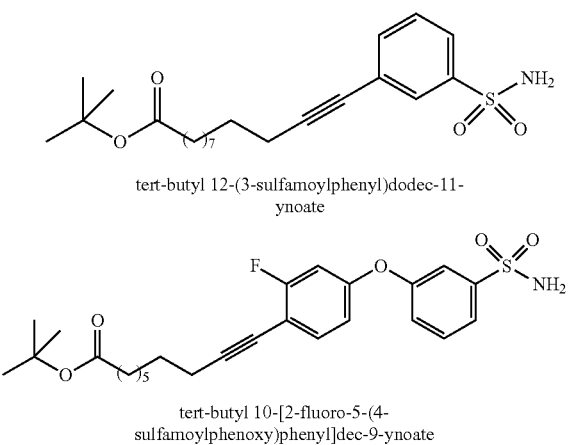

tert-butyl 12-(3-sulfamoylphenyl)dodec-11-ynoate tert-butyl 10-[2-fluoro-5-(4-sulfamoylphenoxy)phenyl]dec-9-ynoate

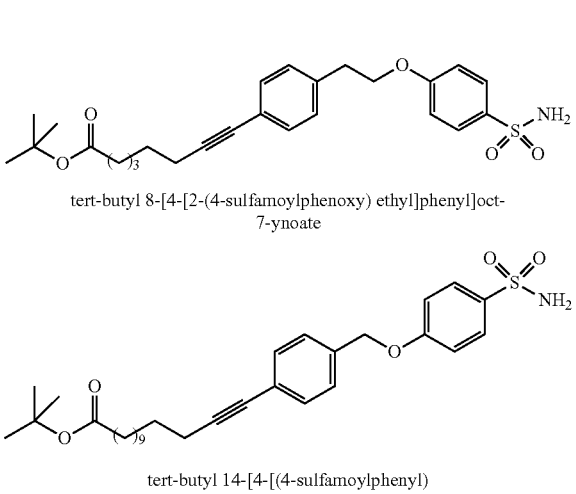

tert-butyl 8-[4-[2-(4-sulfamoylphenoxy) ethyl]phenyl]oct-7-ynoate tert-butyl 14-[4-[(4-sulfamoylphenyl)methoxy]phenyl]tetradec-13-ynoate

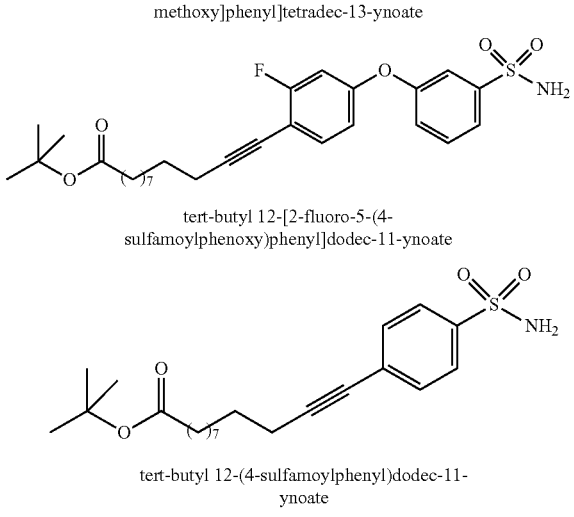

tert-butyl 12-[2-fluoro-5-(4-sulfamoylphenoxy)phenyl]dodec-11-ynoate tert-butyl 12-(4-sulfamoylphenyl)dodec-11-ynoate

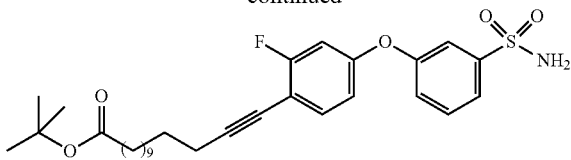

tert-butyl 14-[2-fluoro-5-(4-sulfamoylphenoxy)phenyl]tetradec-13-ynoate

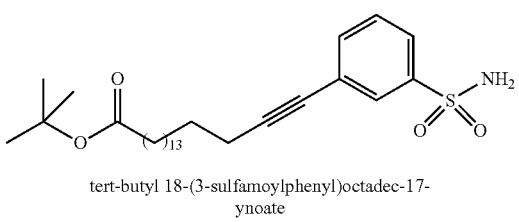

tert-butyl 18-(3-sulfamoylphenyl)octadec-17-ynoate

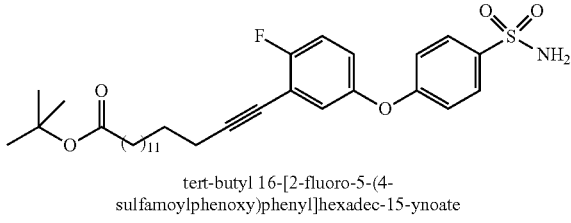

tert-butyl 16-[2-fluoro-5-(4-sulfamoylphenoxy)phenyl]hexadec-15-ynoate

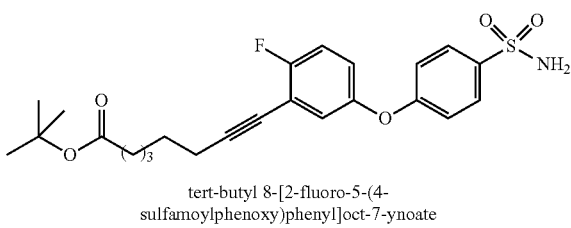

tert-butyl 8-[2-fluoro-5-(4-sulfamoylphenoxy)phenyl]oct-7-ynoate

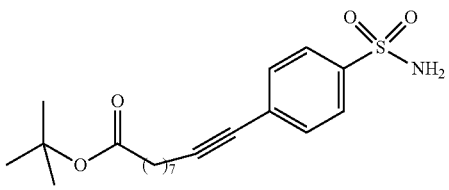

tert-butyl 10-(4-sulfamoylphenyl)dec-9-ynoate

2.8.3 Synthesis of tert-butyl 14-(4-sulfamoylphenyl)tetradecanoate

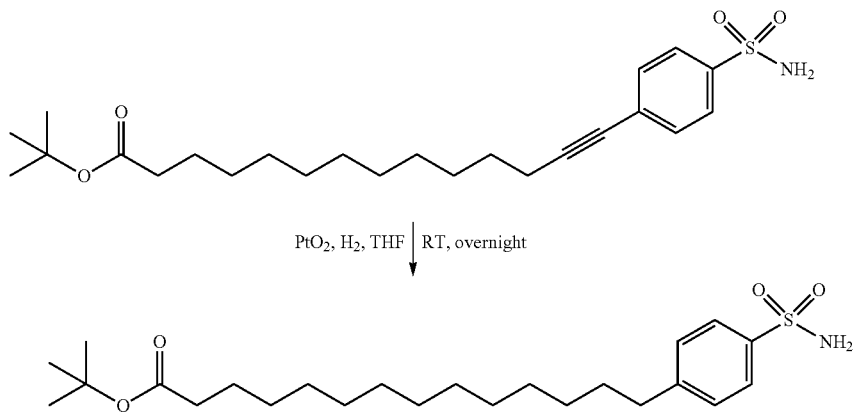

PtO₂ (0.23 g, 1.01 mmol) was added to a mixture of tert-butyl 14-(4-sulfamoylphenyl)tetradec-13-ynoate (2.2 g, 5.05 mmol) in THE (30 ml). The flask was evacuated and backfilled with H₂. Then the mixture was stirred at RT overnight. Filtered, concentrated under the vacuum to afford 14-(4-sulfamoylphenyl)tetradecanoate (2 g, 4.55 mmol, yield: 90%) as a gray solid.

LC-Mass Method: Mobile phase: A=10 mM TFA/H₂O, B=MeCN; Gradient: B=5%-95% in 1.5 min; Flow rate: 1.8 ml/min; Column: Xbridge-C$_{18}$, 50×4.6 mm, 3.5 μm. LC purity: 93% (214 nm); Mass: find peak 462 (M+H)⁺ at 2.44 min.

¹HNMR (400 MHz, DMSO) δ 7.72 (d, J=8.1 Hz, 2H), 7.37 (d, J=8.1 Hz, 2H), 7.26 (s, 2H), 2.63 (t, J=7.6 Hz, 2H), 2.16 (t, J=7.3 Hz, 2H), 1.57 (s, 2H), 1.51-1.43 (m, 2H), 1.38 (s, 9H), 1.25 (d, J=14.5 Hz, 18H).

Following compounds were synthesized accordingly:

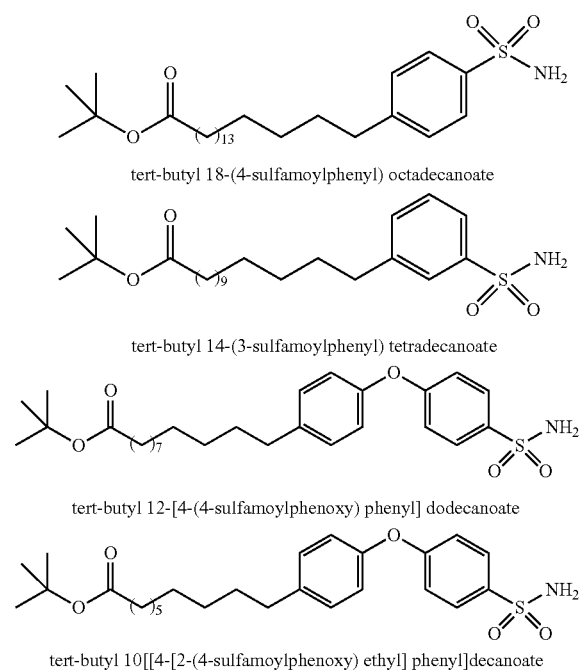

-continued

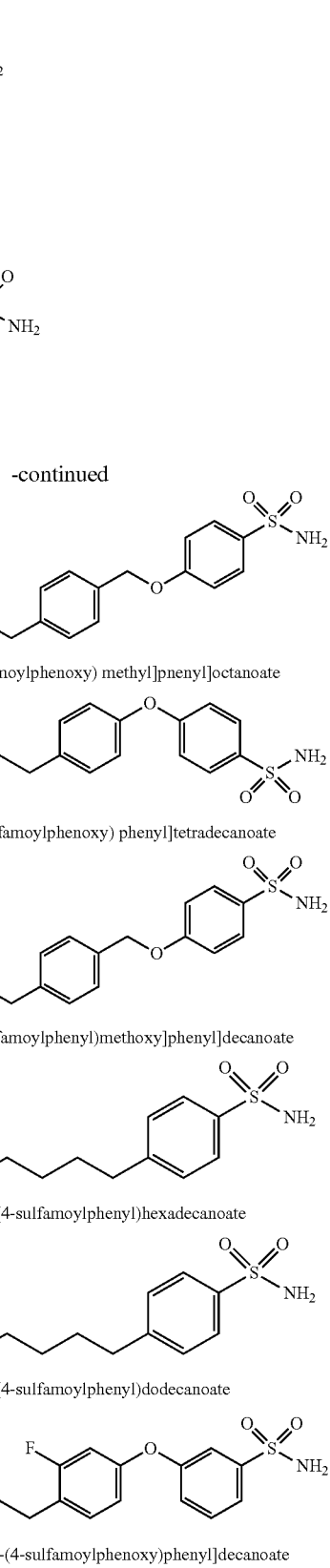

107
-continued
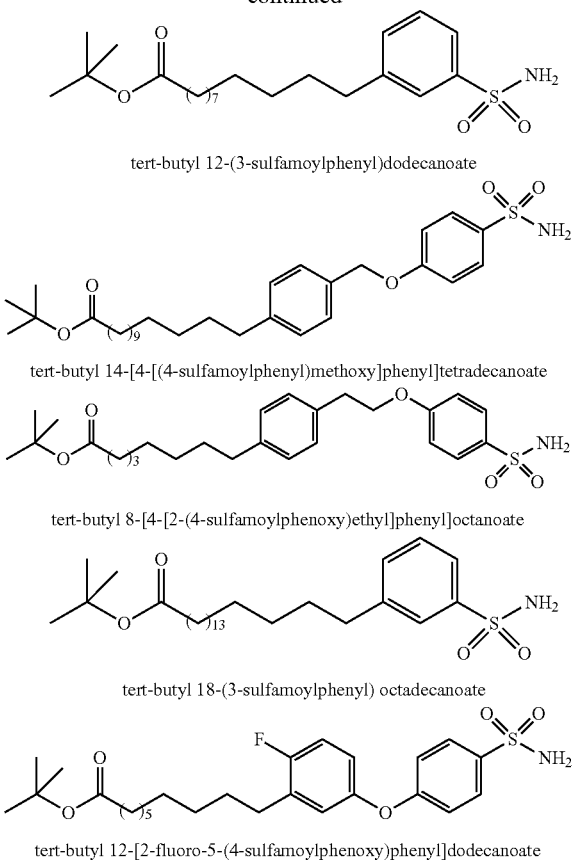
2.8.4 Synthesis of 2-[[4-[3-(12-tert-butoxy-12-oxo-dodecyl)-4-fluoro-phenoxy]phenyl]sulfonyl amino] pyrimidine-5-carboxylic Acid
108
-continued
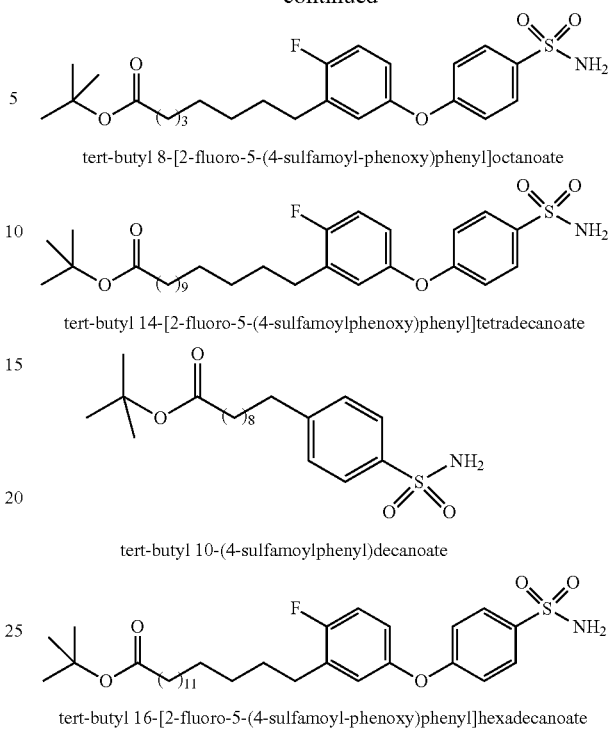
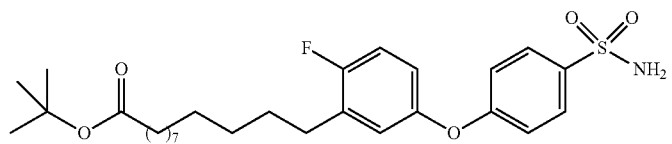
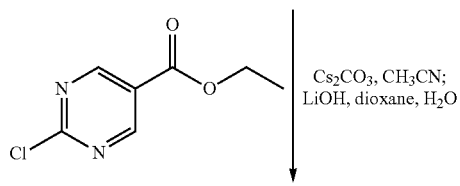
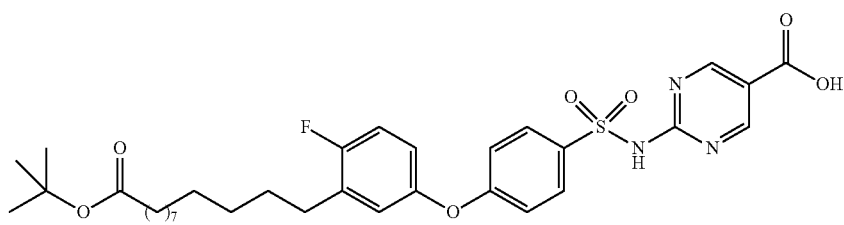

A mixture of tert-butyl 12-[2-fluoro-5-(4-sulfamoylphenoxy)phenyl]dodecanoate (300 mg, 575 µmol), ethyl 2-chloropyrimidine-5-carboxylate (112 mg, 603 µmol) and Cs$_2$CO$_3$ (656 mg, 2.01 mmol) in MeCN (6 ml) was heated to 60° C. and stirred for 3 h (TLC control). The reaction mixture was used in the next saponification step without further purification.

The suspension was diluted with dioxane (6 ml) and a solution of LiOH (37 mg, 1.56 mmol) in water (6 ml) was added. The mixture was stirred at RT for 16 h and additional LiOH (37 mg, 1.56 mmol) was added. Overall the mixture was stirred at RT for 36 h. The suspension was poured on an aqueous solution of citric acid (10 percent, 50 ml).

The suspension was filtered and the filter cake washed with water and dried in vacuum. The title compound 2-[[4-[3-(12-tert-butoxy-12-oxo-dodecyl)-4-fluoro-phenoxy]phenyl]sulfonylamino] pyrimidine-5-carboxylic acid was obtained as white solid (350 mg, quan.).

$^1$H NMR (400.23 MHz, DMSO-d$_6$) δ ppm 12.2 (bs, 2H), 8.89 (s, 2H), 7.99 (d, J=8.93 Hz, 2H), 7.21 (t, J=9.17 Hz, 1H), 7.05 (m, 4H), 2.58 (br t, J=7.46 Hz, 2H), 2.15 (t, J=7.27 Hz, 2H), 1.53 (m, 2H), 1.47 (m, 2H), 1.38 (s, 9H), 1.26-1.22 (in, 14H).

In case the desired product did not precipitate upon pouring on aqueous citric acid, the aqueous layer was extracted with ethyl acetate, the combined organic layers dried with Na$_2$SO$_4$, filtered and concentrated in vacuo. The crude products were subjected to column chromatography using MeOH/CH$_2$Cl$_2$ as eluent.

Following compounds were synthesized accordingly:

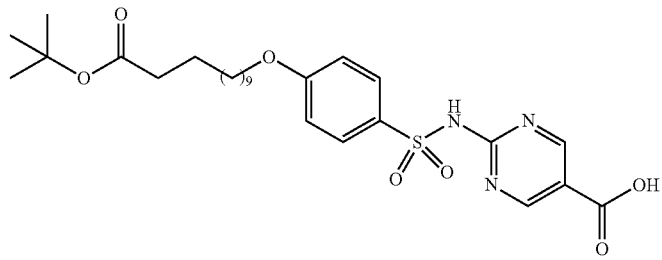

5-[[4-(12-tert-butoxy-12-oxo-dodecoxy)phenyl]sulfonylamino]pyrimidine-2-carboxylic acid

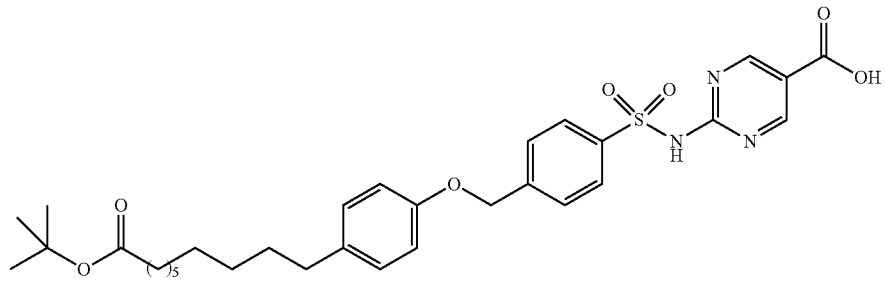

5-[[4-[[4-(10-tert-butoxy-10-oxo-decyl)phenoxy]methyl]phenyl]sulfonylamino]pyrimidine-2-carboxylic acid

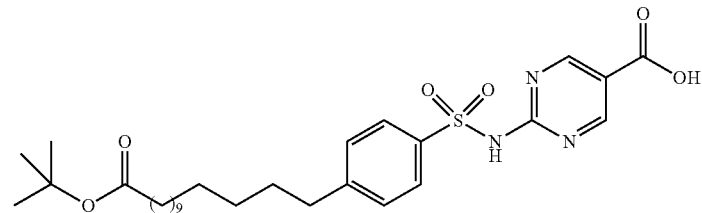

5-[[4-(14-tert-butoxy-14-oxo-tetradecyl)phenyl]sulfonylamino]pyrimidine-2-carboxylic acid

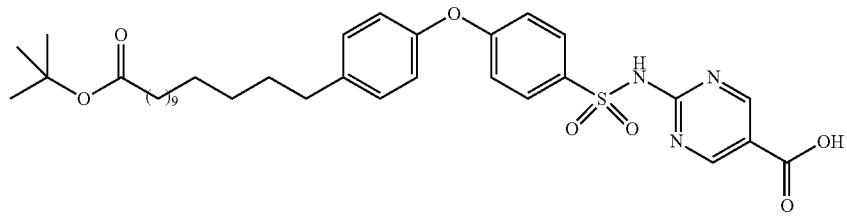

5-[[4-[4-(14-tert-butoxy-14-oxo-tetradecyl)phenoxy]phenyl]sulfonylamino]pyrimidine-2-carboxylic acid -continued

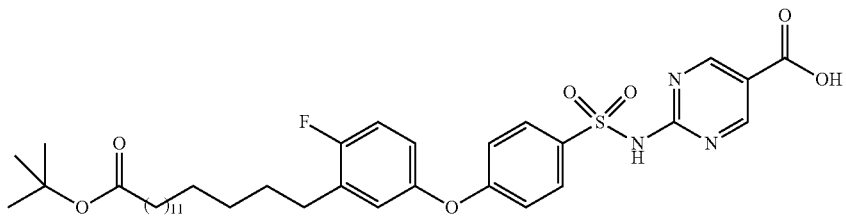

5-[[4-[3-(16-tert-butoxy-16-oxo-hexadecyl)-4-fluoro-phenoxy]phenyl
sulfonylamino]pyrimidine-2-carboxylic acid

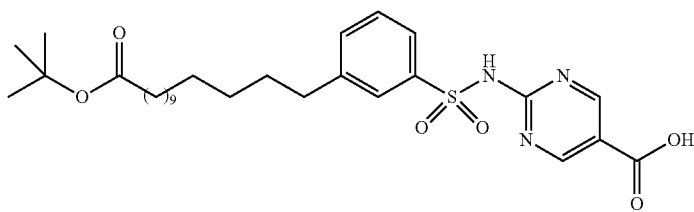

5-[[3-(14-tert-butoxy-14-oxo-tetradecyl)phenyl]sulfonylamino]pyrimidine-2-
carboxylic acid

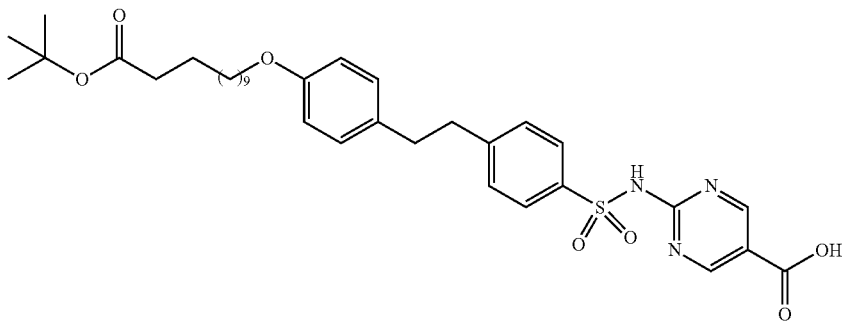

5-[[4-[2-[4-(12-tert-butoxy-12-oxo-dodecoxy)phenyl]ethyl]
dodecoxy)phenyl]ethyl]phenyl]sulfonylamino]pyrimidine-2-carboxylic acid

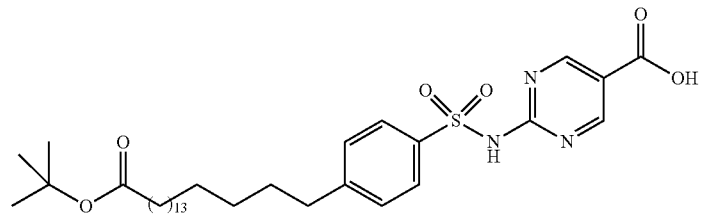

5-[[4-(18-tert-butoxy-18-oxo-octadecyl)phenyl]sulfonylamino]pyrimidine-2-carboxylic acid

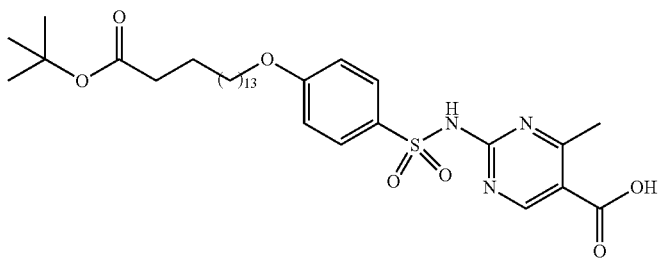

2-[[4-(16-tert-butoxy-16-oxo-hexadecoxy)phenyl]sulfonylamino]-4-methyl-
pyrimidine-5-carboxylic acid -continued

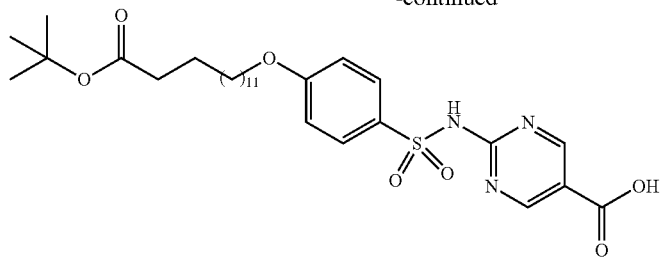

5-[[4-(14-tert-butoxy-14-oxo-tertradecoxy)phenyl]sulfonylamino]
pyrimidine-2-carboxylic acid

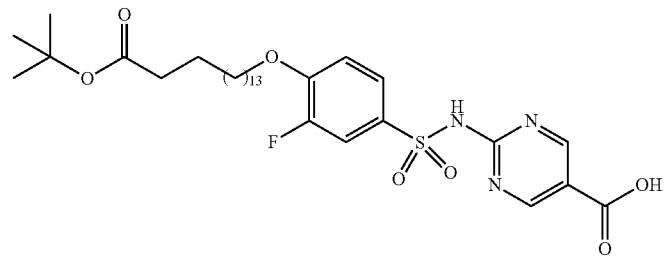

2-[[4-(16-tert-butoxy-16-oxo-hexadecoxy)-3-fluoro-phenyl] sulfonylamino]pyrimidine-
5-carboxylic acid

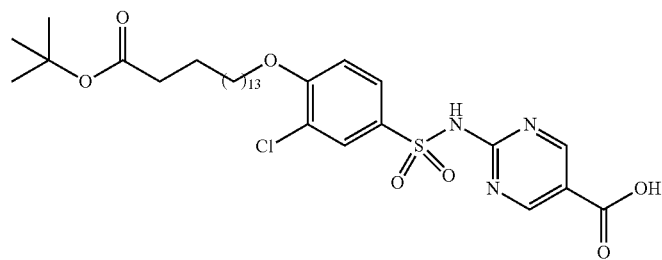

2-[[4-(16-tert-butoxy-16-oxo-hexadecoxy)-3-chloro-phenyl]sulfonylamino]pyrimidine-5-
carboxylic acid

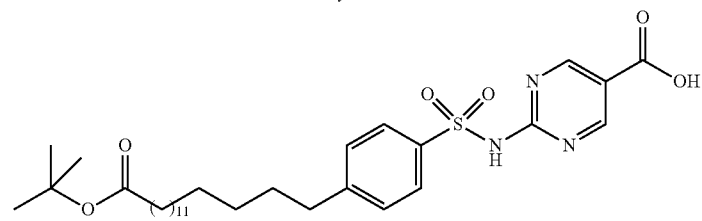

2-[[4-(16-tert-butoxy-16-oxo-hexadecyl]phenyl]sulfonylamino]pyrimidine-5-carboxylic acid

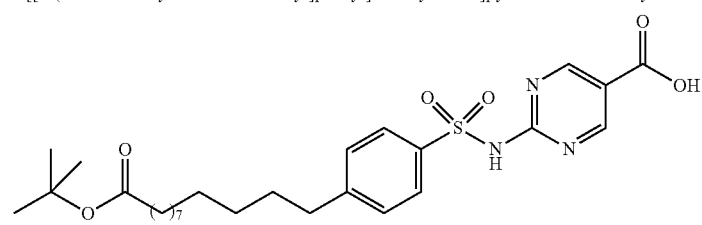

2-[[4-(12-tert-butoxy-12-oxo-dodecyl]phenyl]sulfonylamino]pyrimidine-5-carboxylic acid

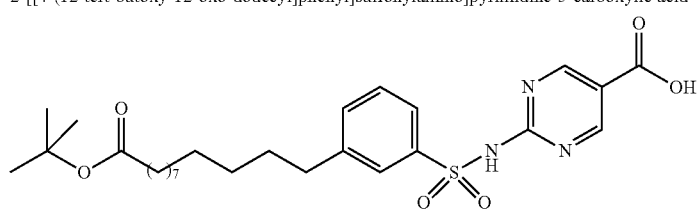

2-[[3-(12-tert-butoxy-12-oxo-dodecyl)phenyl]sulfonylamino]pyrimidine-5-carboxylic acid

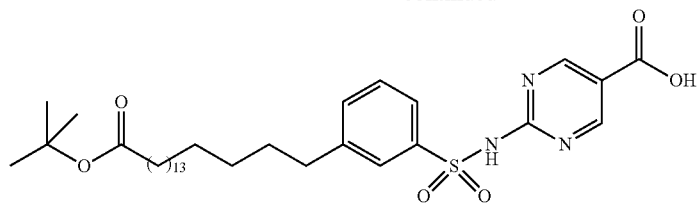

2-[[3-(18-tert-butoxy-18-oxo-octadecyl)phenyl]sulfonylamino]pyrimidine-5-carboxylic acid

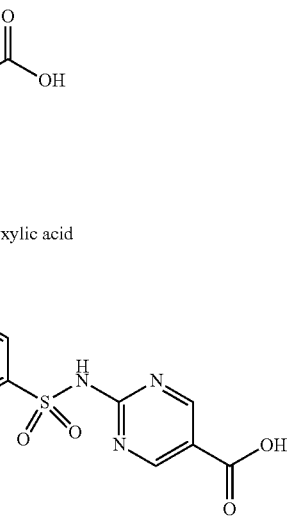

5-[[4-[2-[4-(10-tert-butoxy-10-oxo-decyl)phenyl]ethoxy] phenylsulfonylamino]pyrimidine-2-carboxylic acid

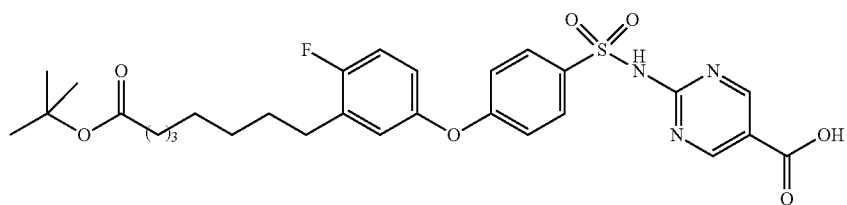

2-[[4-[3-(8-tert-butoxy-8-oxo-octyl)-4-fluoro-phenoxy]phenyl]sulfonylanino]pyrimidine-5-carboxylic acid

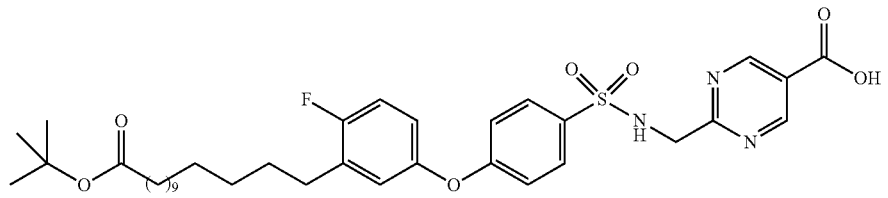

5-[[4-[3-(14-tert-butoxy-14-oxo-tetradecyl-4-fluoro-phenoxy]phenyl]sulfonylamino]pyrimidine-2-carboxylic acid

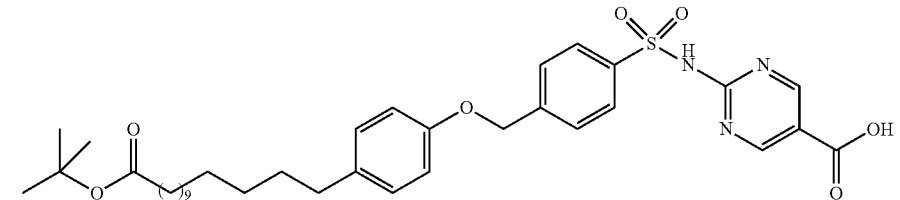

2-[[4-[[4-(14-tert-butoxy-14-oxo-octyl)tetradecyl)phenoxy]methyl]phenyl]sulfonylamino]pyrimidine-5-carboxylic acid

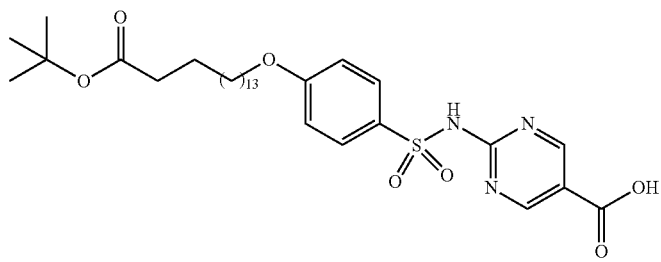

5-[[4-(16-tert-butoxy-16-oxo-hexadecoxy)phenyl] sulfonylamino]pyrimidine-2-carboxylic acid -continued

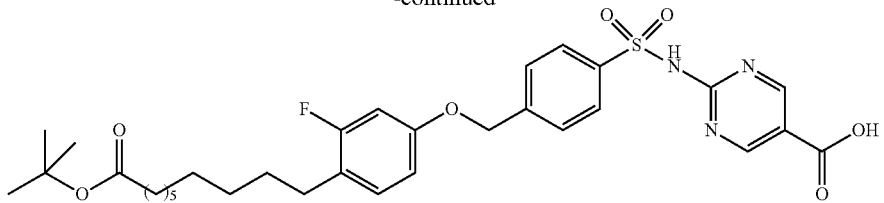

2-[[4-[3-(10-tert-butoxy-10-oxo-decyl)-4-fluoro-phenoxy]phenyl] sulfonylamino] pyrimidine-5-carboxylic acid

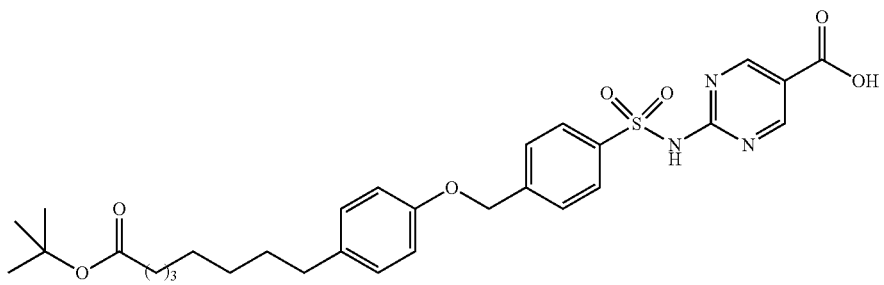

5-[[4-[[4-(8-tert-butoxy-8-oxo-octyl)phenyl]methoxy]phenyl]sulfonylamino]pyrimidine-2-carboxylic acid

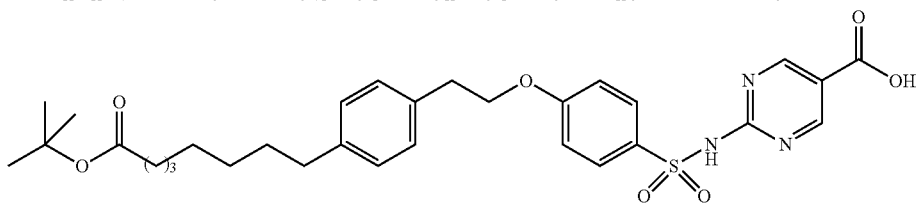

2-[[4-[2-[4-(8-tert-butoxy-8-oxo-octyl)phenyl]ethoxy]phenyl]sulfonylamino]pyrimidine-5-carboxylic acid

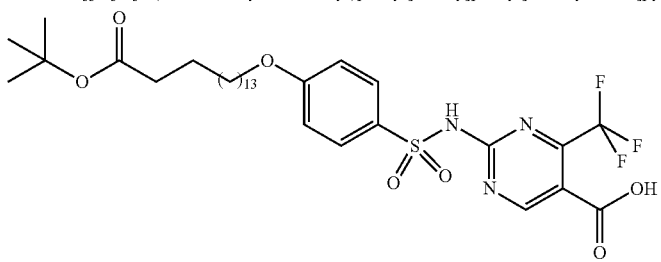

2-[[4-(16-tert-butoxy-16-oxo-hexadecoxy)phenyl]sulfonylamino]-4-(trifluoromethyl) pyrimidine-5-carboxylic acid

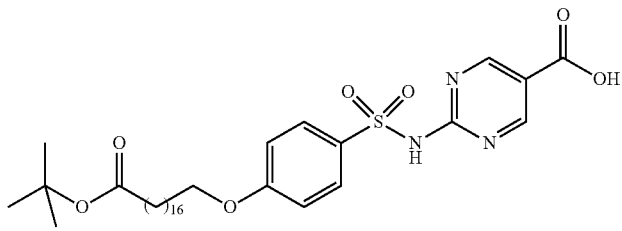

2-[[4-(18-tert-butoxy-18-oxo-octadecoxy)phenyl]sulfonylamino]pyrimidine-5-carboxylic acid

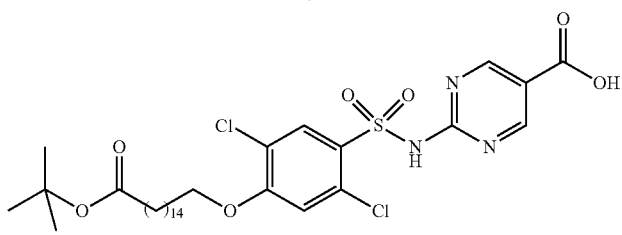

2-[[4-(16-tert-butoxy-16-oxo-hexadecoxy)-2,5-dichloro-phenyl] sulfonylamino]pyrimidine-5-carboxylic acid

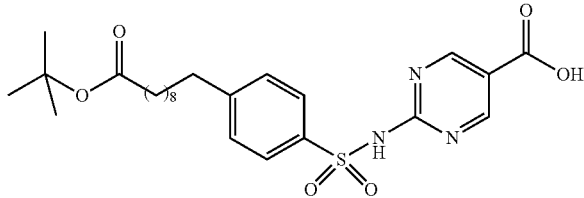

2-[[4-(10-tert-butoxy-10-oxo-decyl)phenyl]sulfonylamino]pyrimidine-5-carboxylic acid

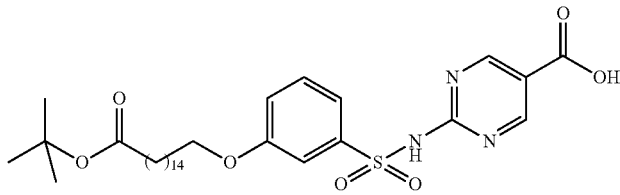

2-[[3-(16-tert-butoxy-16-hexadecoxy)phenyl]sulfonylamino]pyrimidine-5-carboxylic acid 2.8.5 Synthesis of 6-[[4-[3-(12-tert-butoxy-12-oxo-dodecyl)-4-fluoro-phenoxy]phenyl]sulfonyl-amino]pyridine-3-carboxylic Acid

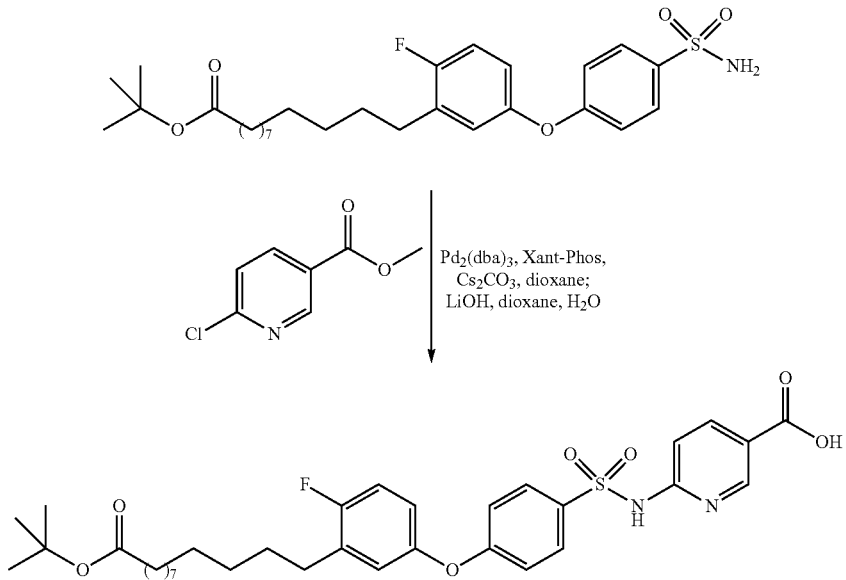

A mixture of tert-butyl 12-[2-fluoro-5-(4-sulfamoylphenoxy)phenyl]dodecanoate (300 mg, 575 μmol), methyl 6-chloronicotinoate (102 mg, 603 μmol), Cs$_2$CO$_3$ (468 mg, 1.44 mmol), tris(dibenzylideneacetone)dipalladium (26 mg, 29 μmol) and 4,5-bis(diphenyl-phosphino)-9,9-dimethyl-xanthene ("xantphos", 17 mg, 29 μmol) in dioxane (6 ml) was heated to 80° C. in an argon atmosphere for 3 h (TLC control). The reaction mixture was used in the next saponification step without further purification.

The suspension was diluted with dioxane (6 ml) and a solution of LiOH (37 mg, 1.56 mmol) in water (6 ml) was added. The mixture was stirred at RT for 16 h and additional LiOH (37 mg, 1.56 mmol) was added. Overall the mixture was stirred at RT for 36 h. The suspension was poured on a aqueous solution of citric acid (10 percent, 50 ml). The suspension was filtered and the filter cake washed with water and dried in vacuum. The title compound 6-[[4-[3-(12-tert-butoxy-12-oxo-dodecyl)-4-fluoro-phenoxy]phenyl]sulfonyl-amino]pyridine-3-carboxylic acid was obtained as white solid (350 mg, quan.).

$^1$H NMR (400.23 MHz, DMSO-d$_6$) δ ppm 12.5 (br s, 1H), 8.54 (br s, 1H), 8.11 (dd, J=8.93, 2.20 Hz, 1H), 7.91 (br d, J=8.68 Hz, 2H), 7.80 (m, 1H), 7.19 (m, 2H), 7.04 (m, 4H), 2.58 (br t, J=7.46 Hz, 2H), 2.15 (t, J=7.27 Hz, 2H), 1.48 (m, 4H), 1.38 (s, 9H), 1.26-1.22 (m, 14H).

In case the desired product did not precipitate upon pouring on aqueous citric acid, the aqueous layer was extracted with ethyl acetate, the combined organic layers dried with Na$_2$SO$_4$, filtered and concentrated in vacuo. The crude products were subjected to column chromatography using MeOH/CH$_2$Cl$_2$ as eluent.

Following compounds were synthesized accordingly:

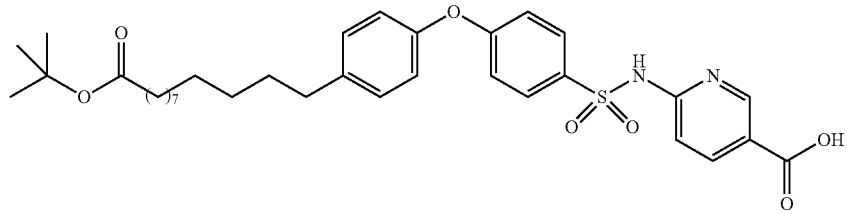

6-[[4-[4-(12-tert-butoxy-12-oxo-dodecyl)phenoxy]phenyl]sulfonylamino]pyridine-3-carboxylic acid

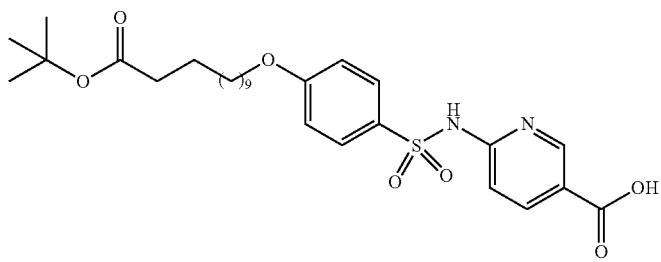

6-[[4-(12-tert-butoxy-12-oxo-dodecoxy)phenyl]sulfonylamino]pyridine-3-carboxylic acid

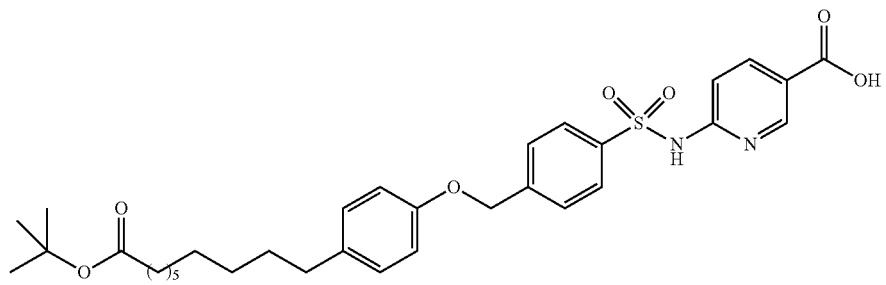

6-[[4-[[4-(10-tert-butoxy-10-oxo-decyl)phenoxy]methyl]phenyl]sulfonylamino]pyrimidine-3-carboxylic acid

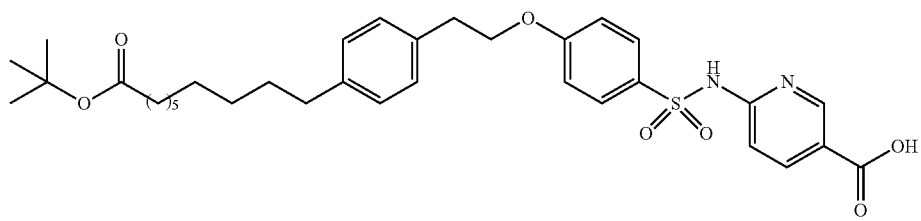

6-[[4-[2-[4-(10-tert-butoxy-10-oxo-decyl)phenyl]ethoxy] phenylsulfonylamino]pyrimidine-3-carboxylic acid

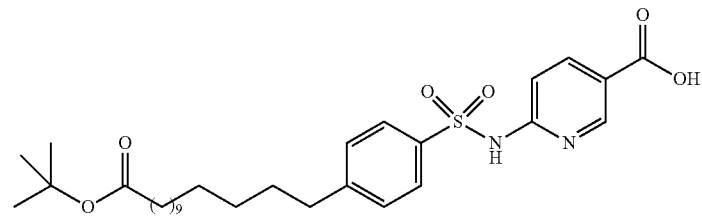

6-[[4-(14-tert-butoxy-14-oxo-tetradecyl)phenyl]sulfonylamino]pyrimidine-3-carboxylic acid

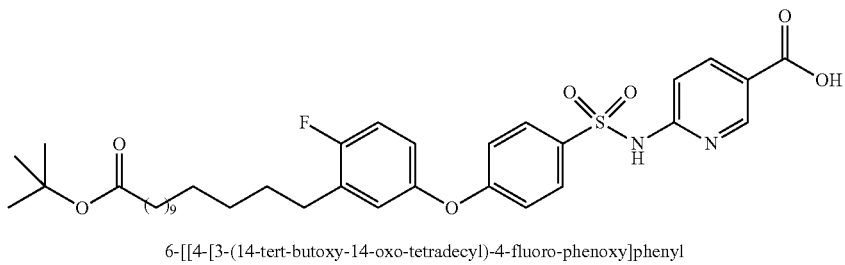

6-[[4-[3-(14-tert-butoxy-14-oxo-tetradecyl)-4-fluoro-phenoxy]phenyl sulfonylamino]pyrimidine-2-carboxylic acid

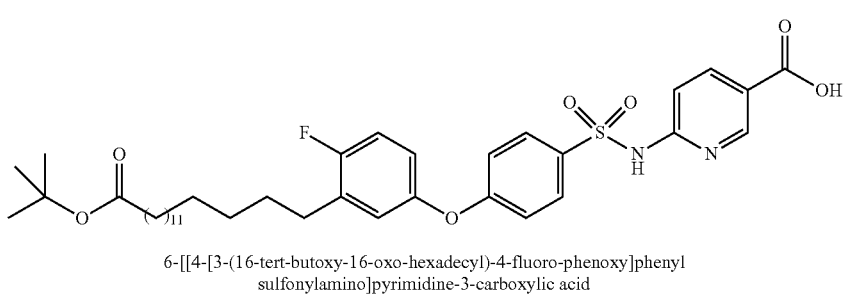

6-[[4-[3-(16-tert-butoxy-16-oxo-hexadecyl)-4-fluoro-phenoxy]phenyl sulfonylamino]pyrimidine-3-carboxylic acid

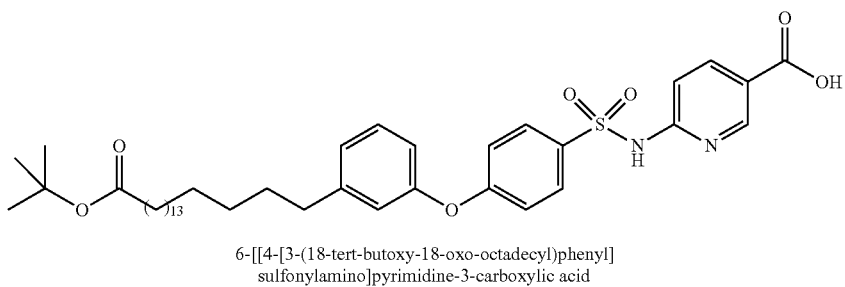

6-[[4-[3-(18-tert-butoxy-18-oxo-octadecyl)phenyl] sulfonylamino]pyrimidine-3-carboxylic acid

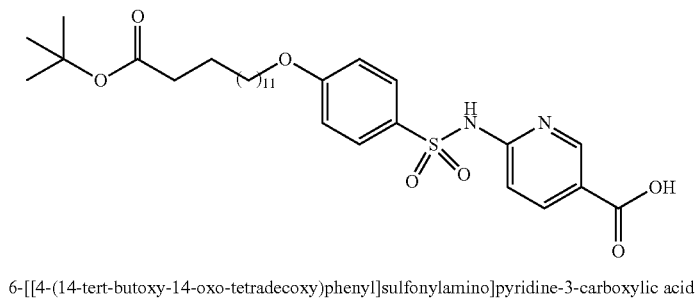

6-[[4-(14-tert-butoxy-14-oxo-tetradecoxy)phenyl]sulfonylamino]pyridine-3-carboxylic acid

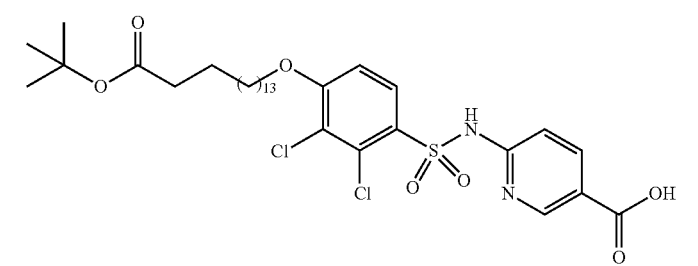

6-[[4-(16-tert-butoxy-16-oxo-hexadecoxy)-2,3-dichloro-phenyl] sulfonylamino] pyridine-3-carboxylic acid

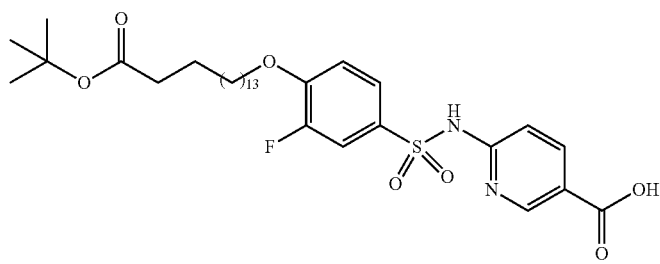

6-[[4-(16-tert-butoxy-16-oxo-hexadecoxy)-3-fluoro-phenyl]sulfonylamino]pyridine-3-carboxylic acid

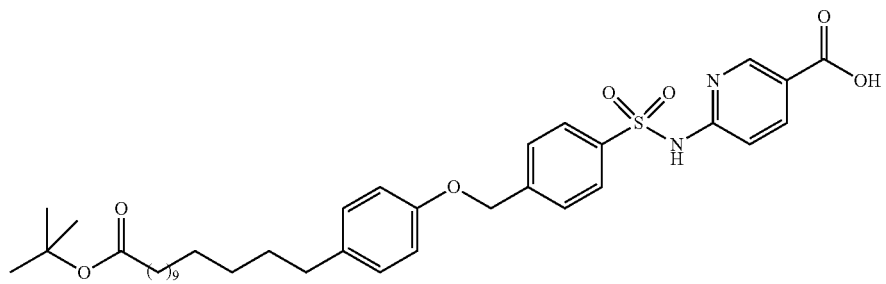

6-[[4-[[4-(14-tert-butoxy-14-oxo-tetradecyl)phenoxy]methyl]phenyl]sulfonylamino]pyridine-3-carboxylic acid

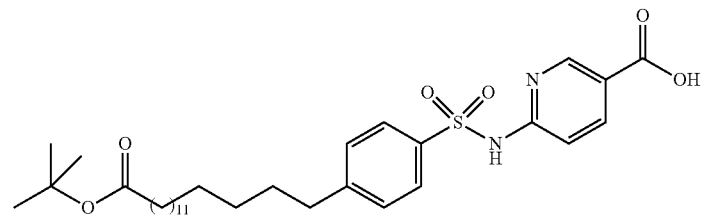

6-[[4-(14-tert-butoxy-16-oxo-hexadecyl)phenyl]sulfonylamino]pyrimidine-3-carboxylic acid

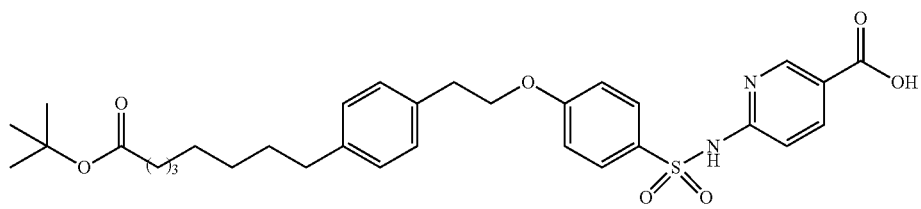

6-[[4-[2-[4-(8-tert-butoxy-8-oxo-octyl)phenyl]ethoxy] phenyl]sulfonylamino]pyridine-3-carboxylic acid

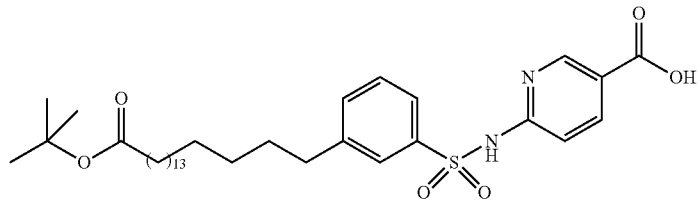

6-[[3-(18-tert-butoxy-18-oxo-octadecyl)phenyl]sulfonylamino]pyridine-3-carboxylic acid -continued

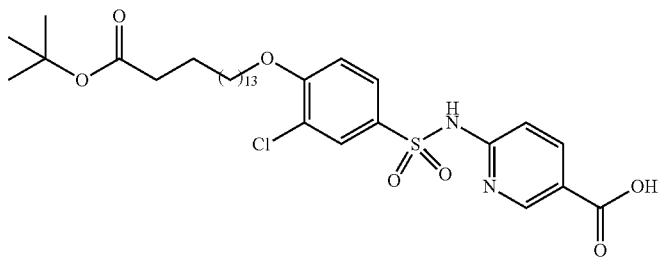

6-[[4-(16-tert-butoxy-16-oxo-hexadecoxy)-3-chloro-phenyl]sulfonylamino]pyridine-3-carboxylic acid

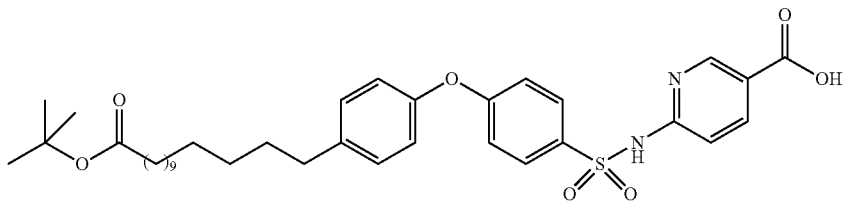

6-[[4-[4-(14-tert-butoxy-14-oxo-tetradecyl)phenoxy]phenyl]sulfonylamino]pyridine-3-carboxylic acid

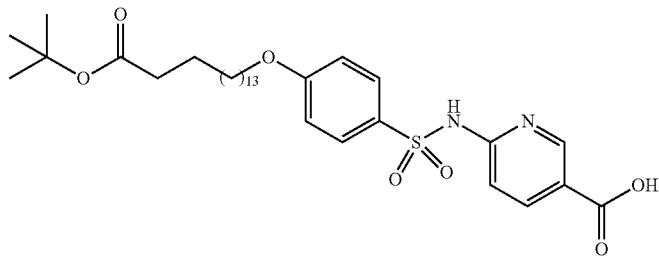

6-[[4-(16-tert-butoxy-16-oxo-hexadecoxy)phenyl]sulfonylamino]pyridine-3-carboxylic acid

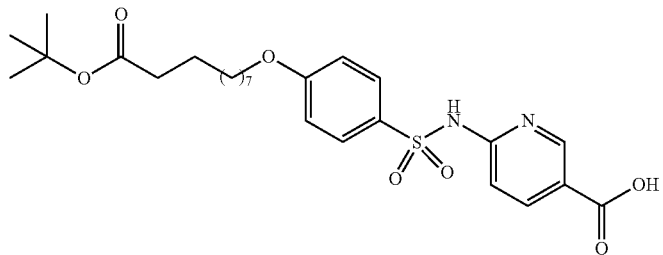

6-[[4-(10-tert-butoxy-10-oxo-decoxy)phenyl]sulfonylamino]pyridine-3-carboxylic acid

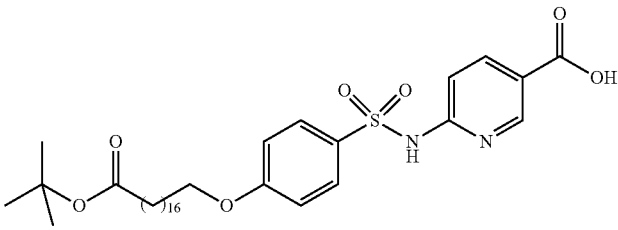

6-[[4-(18-tert-butoxy-18-oxo-octadecoxy)phenyl]sulfonylamino]pyrimidine-3-carboxylic acid

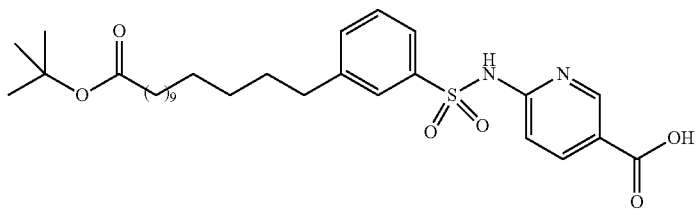

6-[[3-(14-tert-butoxy-14-oxo-tetradecyl)phenyl]sulfonylamino]pyridine-3-carboxylic acid

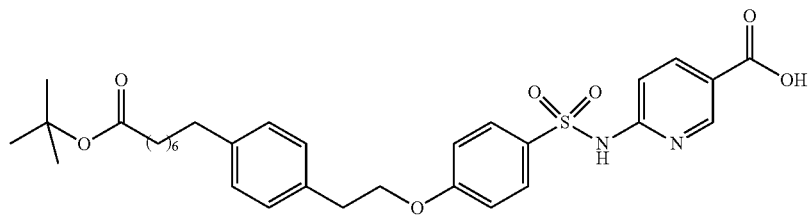

6-[[4-[2-[4-(8-tert-butoxy-8-oxo-octyl)phenyl]ethoxy]phenyl]sulfonylamino]pyridine-3-carboxylic acid

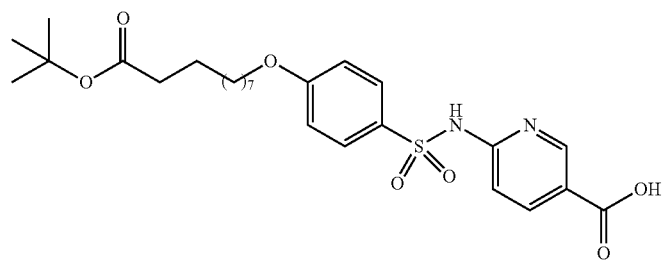

6-[[4-(10-tert-butoxy-10-oxo-decoxy)phenyl]sulfonylamino]pyridine-3-carboxylic acid

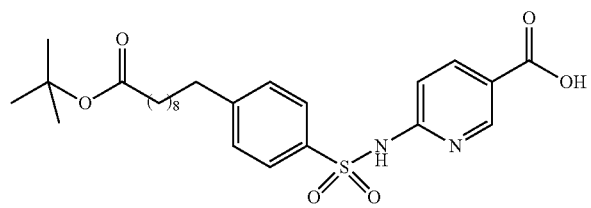

6-[[4-(10-tert-butoxy-10-oxo-decyl)phenyl]sulfonylamino]pyridine-3-carboxylic acid

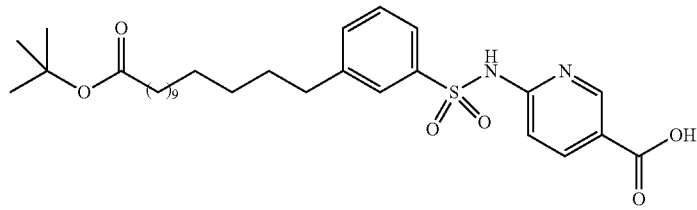

6-[[3-(14-tert-butoxy-14-oxo-tetradecyl)phenyl]sulfonylamino]pyridine-3-carboxylic acid

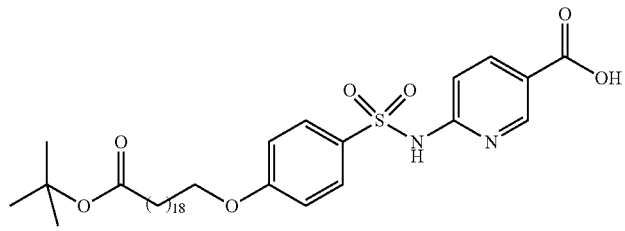

6-[[4-(20-tert-butoxy-20-oxo-icosoxy)phenyl]sulfonylamino]pyrimidine-3-carboxylic acid

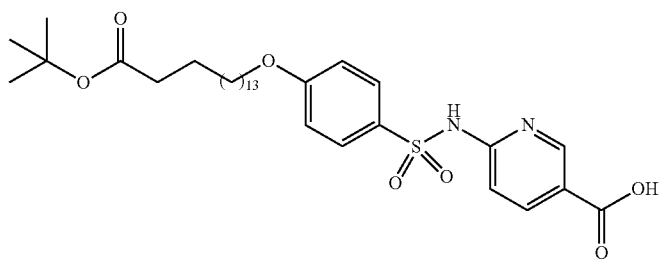

6-[[4-(16-tert-butoxy-16-oxo-hexadecoxy)phenyl]sulfonylamino]pyridine-3-carboxylic acid

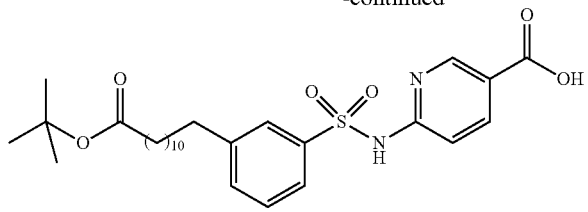

6-[[3-(12-tert-butoxy-12-oxo-dodecyl)phenyl]sulfonylamino]pyrimidine-3-carboxylic acid

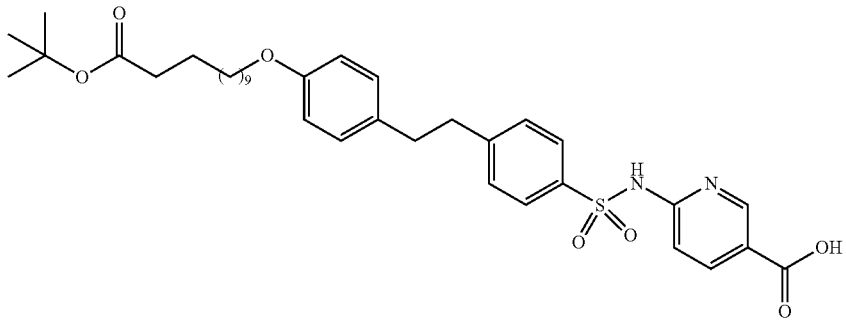

6-[[4-[2-[4-(12-tert-butoxy-12-oxo-dodecoxy)phenyl]ethyl]phenyl]sulfonylamino]pyridine-3-carboxylic acid 2.9 Examples for the Synthesis of Compounds with Formula I According to Scheme 1

2.9.1 Synthesis of 2-[2-[2-[[2-[2-[2-[[6-[[4-[3-(14-tert-butoxy-14-oxo-tetradecyl)-4-fluoro-phenoxy]phenyl] sulfonylamino]pyridine-3-carbonyl]amino]ethoxy]ethoxy]acetyl]amino] ethoxy]ethoxy]acetic Acid

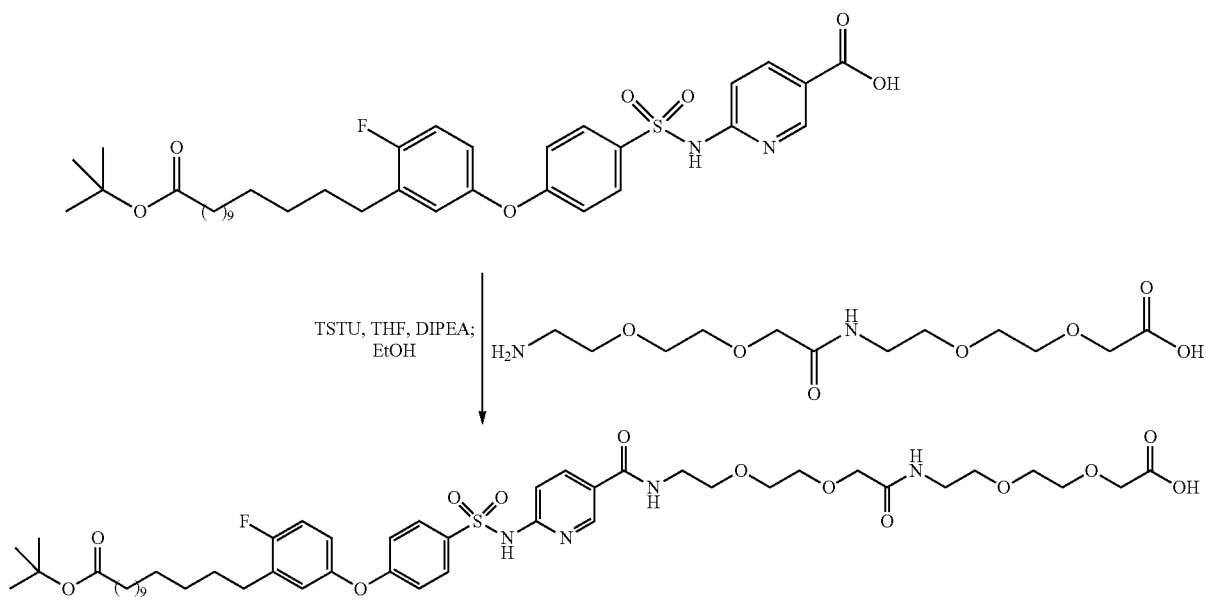

A mixture of 6-[[4-[3-(14-tert-butoxy-14-oxo-tetradecyl)-4-fluoro-phenoxy]phenyl]sulfonyl amino]pyridine-3-carboxylic acid (169 mg, 251 μmol), TSTU (80 mg, 264 μmol) and DIPEA (132 μl, 97 mg, 1.25 mmol) in 6 ml of THF was stirred at RT for 16 h. After 16 h, the solvent was removed under reduced pressure and a solution of [2-(2-{2-[2-(2-amino-ethoxy)-ethoxy]-acetylamino}-ethoxy)-ethoxy]-acetic acid (85 mg, 277 μmol) in 6 ml abs. EtOH was added and the mixture was stirred at RT for 16 h. Volatile components were removed under reduced pressure, the resulting residue dissolved in CH$_2$Cl$_2$ and washed with aq. 10% KHSO$_4$ solution. The organic layer was washed with water and brine, dried over anhydrous Na$_2$SO$_4$, filtered and concentrated under reduced pressure. The crude product was purified by RP HPLC to afford 2-[2-[2-[[2-[2-[2-[[6-[[4-[3-(14-tert-butoxy-14-oxo-tetradecyl)-4-fluoro-phenoxy]phenyl]sulfonylamino]pyridine-3-carbonyl]amino]ethoxy]ethoxy]acetyl]amino]ethoxy] ethoxy]acetic acid (106 mg, 44%).

$^1$H NMR (400.23 MHz, DMSO-d$_6$) δ ppm 12.29 (br s, 1H), 8.52 (m, 2H), 8.09 (dd, J=8.93, 2.32 Hz, 1H), 7.89 (d, J=8.80 Hz, 2H), 7.61 (br t, J=5.69 Hz, 1H), 7.18 (m, 2H), 7.03 (m, 4H), 4.01 (s, 2H), 3.86 (s, 2H), 3.20-3.68 (m, 16H), 2.58 (br t, J=7.52 Hz, 2H), 2.15 (t, J=7.27 Hz, 2H), 1.49 (m, 4H), 1.38 (s, 9H), 1.25 (m, 18H).

The following compounds were synthesized accordingly:

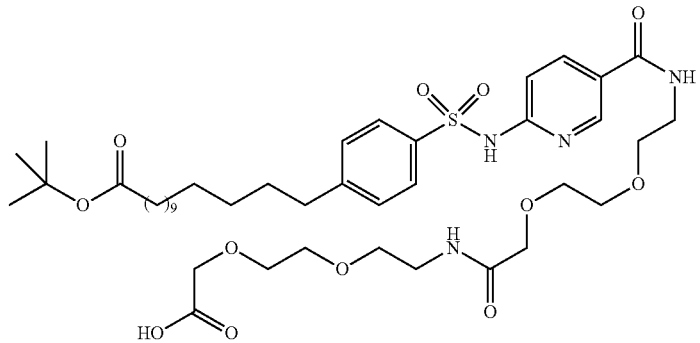

2-[2-[2-[[2-[2-[2-[[6-[[4-(14-tert-butoxy-14-oxo-tetradecyl) phenyl]sulfonylamino]pyridine-3-carbonyl]amino]ethoxy]ethoxy]acetyl]amino]ethoxy]ethoxy]acetic acid

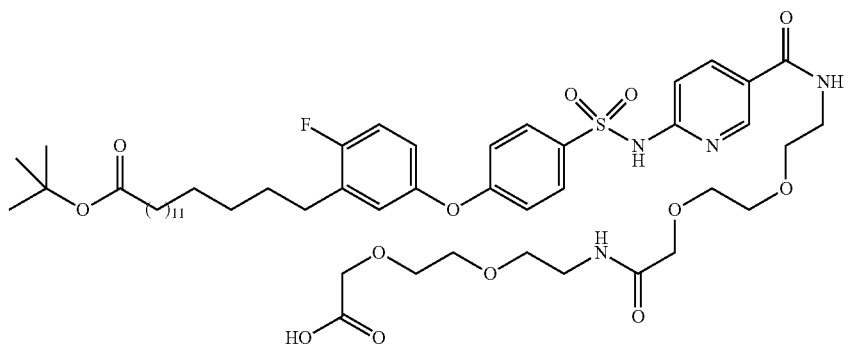

2-[2-[2-[[2-[2-[2-[[6-[[4-[3-(16-tert-butoxy-16-oxo-hexadecyl)-4-fluoro-phenoxy]phenyl]sulfonylamino]pyridine-3-carbonyl]amino]ethoxy]ethoxy]acetyl]amino]ethoxy]ethoxy]acetic acid

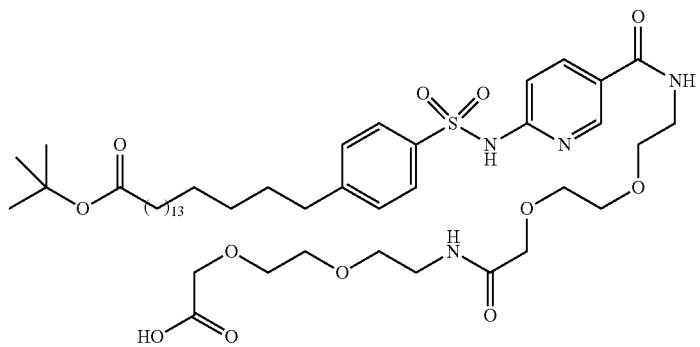

2-[2-[2-[[2-[2-[2-[[6-[[4-(18-tert-butoxy-18-oxo-octadecyl)phenyl]sulfonylamino]pyridine-3-carbonyl]amino]ethoxy]ethoxy]acetyl]amino]ethoxy]ethoxy]acetic acid -continued

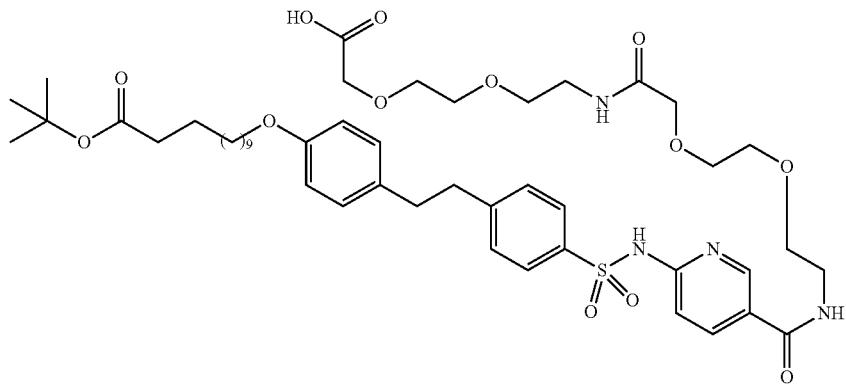

2-[2-[2-[[2-[2-[2-[[6-[[4-[2-[4-(12-tert-butoxy-12-oxo-dodecoxy)phenyl]ethyl]phenyl]sulfonylamino]pyridine-3-carbonyl]amino]ethoxy]ethoxy]acetyl]amino]ethoxy]ethoxy]acetic acid

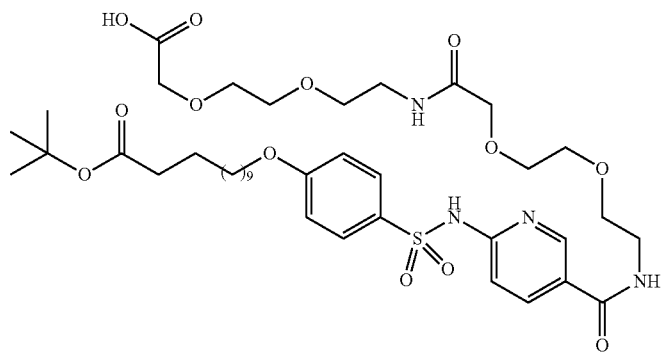

2-[2-[2-[[2-[2-[2-[[6-[[4-[2-[4-(12-tert-butoxy-12-oxo-dodecoxy)phenyl]sulfonylamino]pyridine-3-carbonyl]amino]ethoxy]ethoxy]acetyl]amino]ethoxy]ethoxy]acetic acid

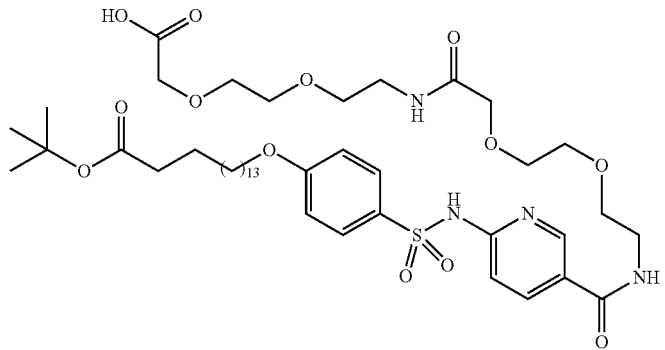

2-[2-[2-[[2-[2-[2-[[6-[[4-(16-tert-butoxy-16-oxo-hexadecoxy)phenyl]sulfonylamino]pyridine-3-carbonyl]amino]ethoxy]ethoxy]acetyl]amino]ethoxy]ethoxy]acetic acid

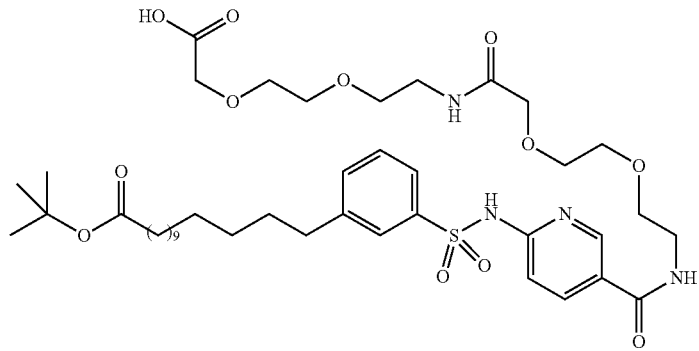

2-[2-[2-[[2-[2-[2-[[6-[[3-(14-tert-butoxy-14-oxo-tetradecyl)phenyl]sulfonylamino]pyridine-3-carbonyl]amino]ethoxy]ethoxy]acetyl]amino]ethoxy]ethoxy]acetic acid -continued

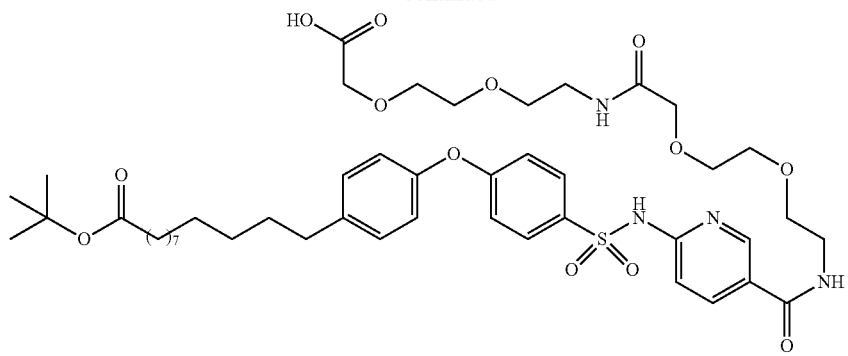

2-[2-[2-[[2-[2-[2-[[6-[[4-[4-(12-tert-butoxy-12-oxo-dodecyl)phenoxy]phenyl]sulfonylamino]
pyridine-3-carbonyl]amino]ethoxy]ethoxy]acetyl]amino]ethoxy]ethoxy]acetic acid

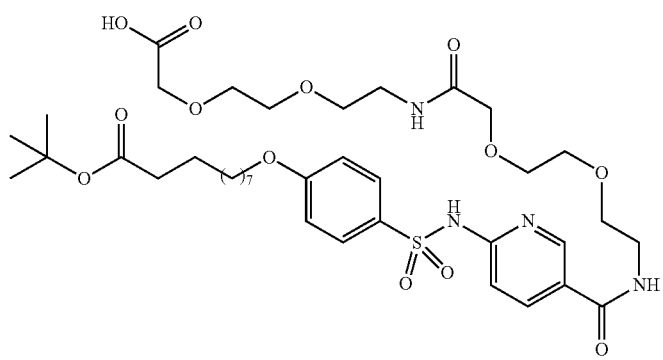

2-[2-[2-[[2-[2-[2-[[6-[[4-(10-tert-butoxy-10-oxo-decoxy)phenyl]sulfonylamino]
pyridine-3-carbonyl]amino]ethoxy]ethoxy]acetyl]amino]ethoxy]ethoxy]acetic acid

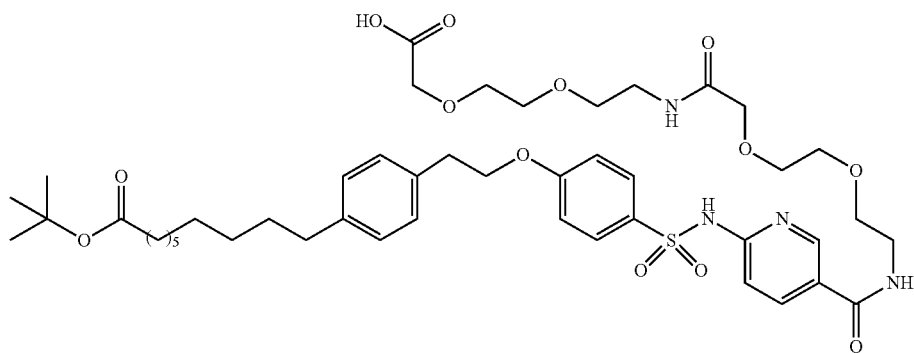

2-[2-[2-[[2-[2-[2-[[6-[[4-[2-[4-(10-tert-butoxy-10-oxo-decyl)phenyl]ethoxy]sulfonylamino]
pyridine-3-carbonyl]amino]ethoxy]ethoxy]acetyl]amino]ethoxy]ethoxy]acetic acid

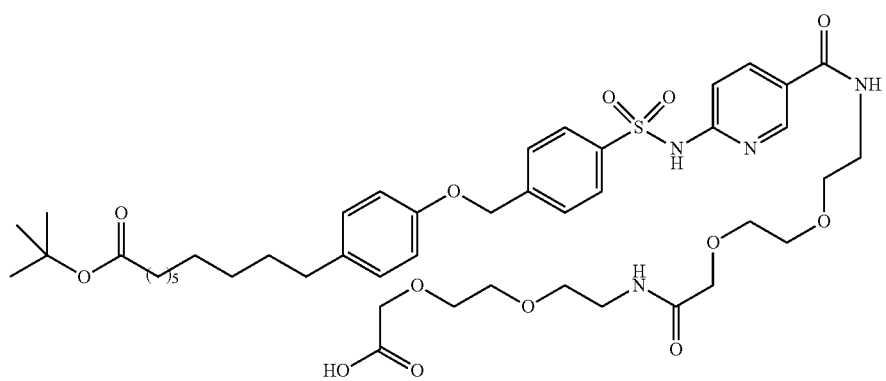

2-[2-[2-[[2-[2-[2-[[6-[[4-[[4-(10-tert-butoxy-10-oxo-decyl) phenoxy]methyl]phenyl]sulfonylamino]
pyridine-3-carbonyl]amino]ethoxy]ethoxy]acetyl]amino]ethoxy]ethoxy]acetic acid

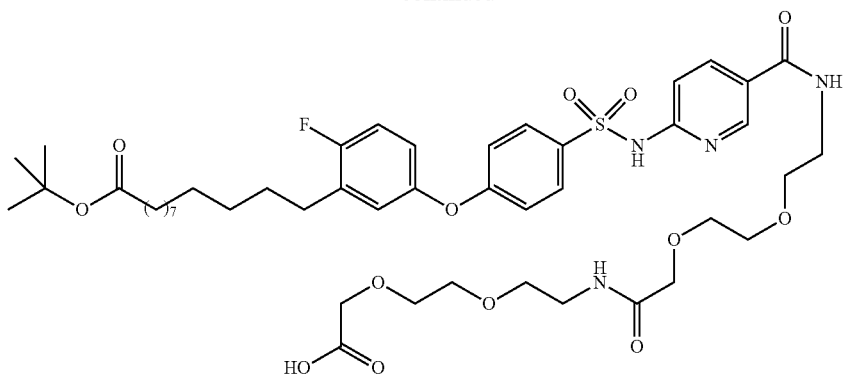

2-[2-[2-[[2-[2-[2-[[6-[[4-[3-(12-tert-butoxy-12-oxo-dodecyl)-4-fluoro-phenoxy]phenyl]sulfonylamino]pyridine-3-carbonyl]amino]ethoxy]ethoxy]acetyl]amino]ethoxy]ethoxy]acetic acid

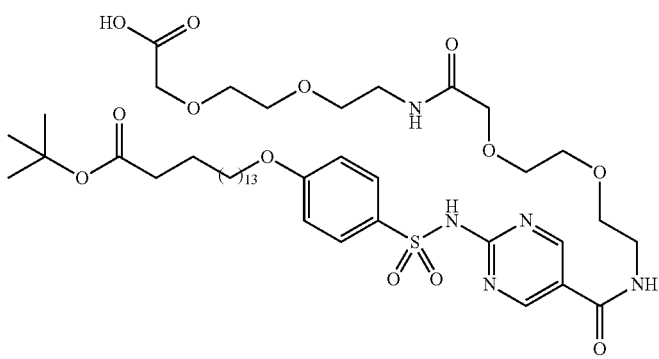

2-[2-[2-[[2-[2-[2-[[5-[[4-(16-tert-butoxy-16-oxo-hexadecoxy)phenyl]sulfonylamino]pyridine-3-carbonyl]amino]ethoxy]ethoxy]acetyl]amino]ethoxy]ethoxy]acetic acid

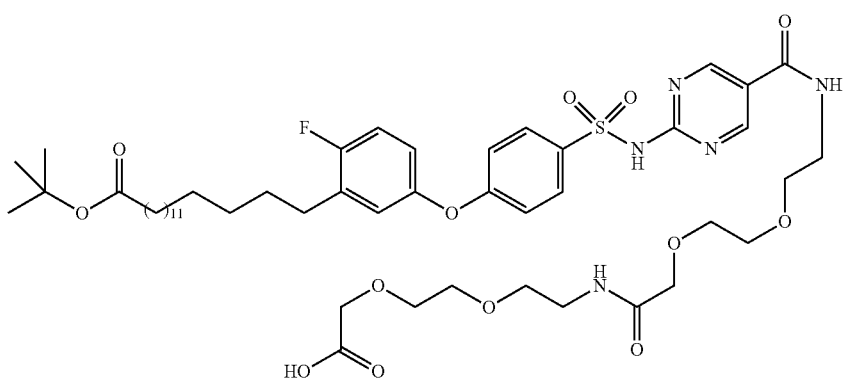

2-[2-[2-[[2-[2-[2-[[5-[[4-[3-(16-tert-butoxy-16-oxo-hexadecyl)-4-fluoro-phenoxy]phenyl]sulfonylamino]pyridine-3-carbonyl]amino]ethoxy]ethoxy]acetyl]amino]ethoxy]ethoxy]acetic acid

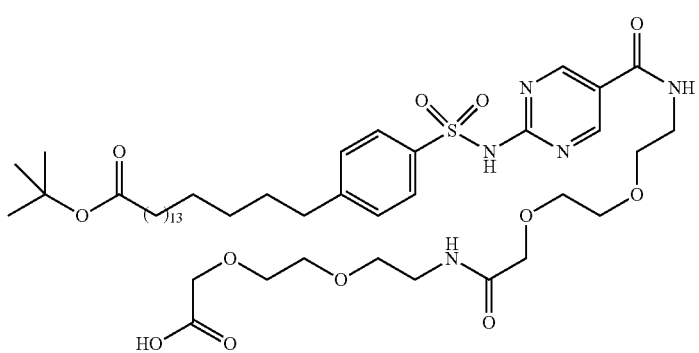

2-[2-[2-[[2-[2-[2-[[5-[[4-(18-tert-butoxy-18-oxo-octadecyl)phenyl]sulfonylamino]pyridine-3-carbonyl]amino]ethoxy]ethoxy]acetyl]amino]ethoxy]ethoxy]acetic acid

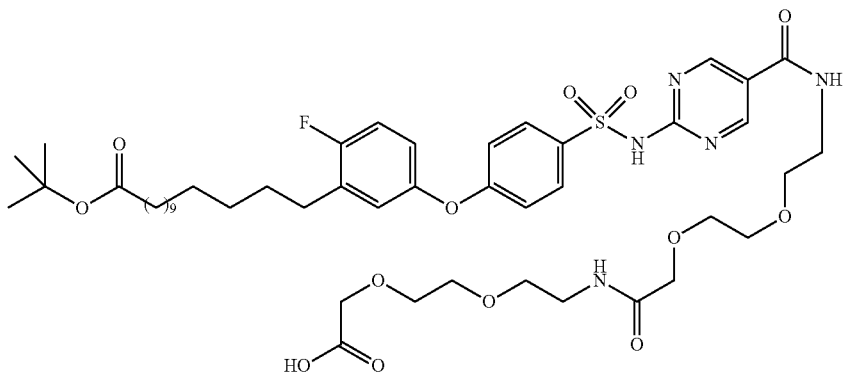

2-[2-[2-[[2-[2-[2-[[5-[[4-[3-(14-tert-butoxy-14-oxo-tetradecyl)-4-fluoro-phenoxy]phenyl]sulfonylamino]
pyridine-3-carbonyl]amino]ethoxy]ethoxy]acetyl]amino]ethoxy]ethoxy]acetic acid

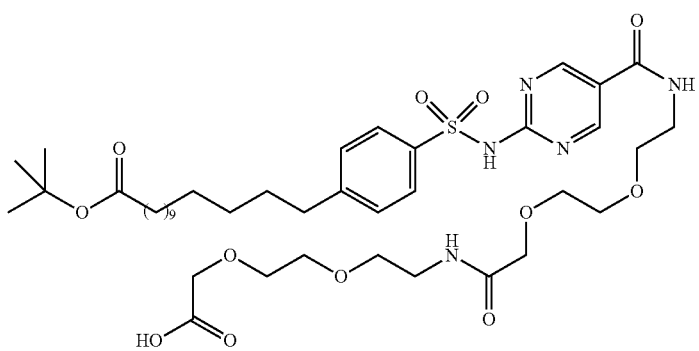

2-[2-[2-[[2-[2-[2-[[5-[[4-(14-tert-butoxy-14-oxo-tetradecyl)phenyl]sulfonylamino]
pyridine-2-carbonyl]amino]ethoxy]ethoxy]acetyl]amino]ethoxy]ethoxy]acetic acid

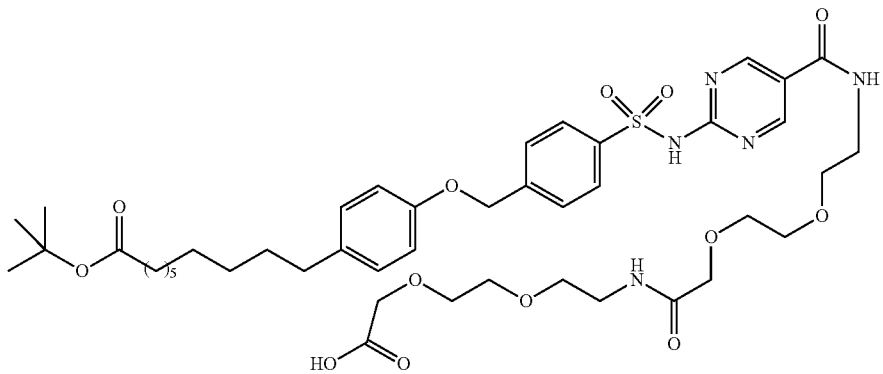

2-[2-[2-[[2-[2-[2-[[5-[[4-[[4-(10-tert-butoxy-10-oxo-decyl) phenoxy]methyl]phenyl]sulfonylamino]
pyridine-3-carbonyl]amino]ethoxy]ethoxy]acetyl]amino]ethoxy]ethoxy]acetic acid

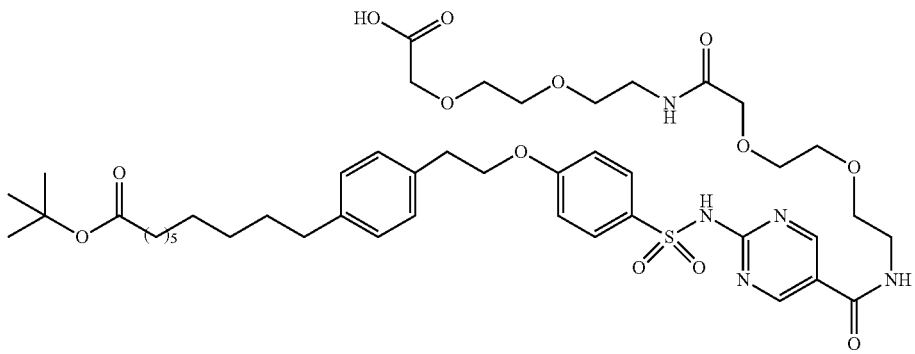

2-[2-[2-[[2-[2-[2-[[5-[[4-[2-[4-(10-tert-butoxy-10-oxo-decyl)phenyl]sulfonylamino]
pyridine-2-carbonyl]amino]ethoxy]ethoxy]acetyl]amino]ethoxy]acetic acid

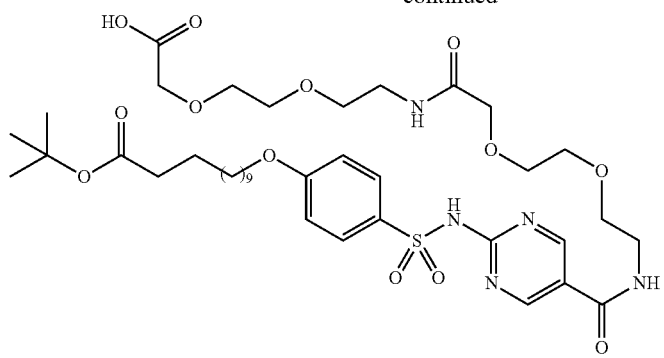

2-[2-[2-[[2-[2-[2-[[5-[[4-(12-tert-butoxy-12-oxo-dodecoxy)phenyl]sulfonylamino]
pyridine-3-carbonyl]amino]ethoxy]ethoxy]acetyl]amino]ethoxy]ethoxy]acetic acid

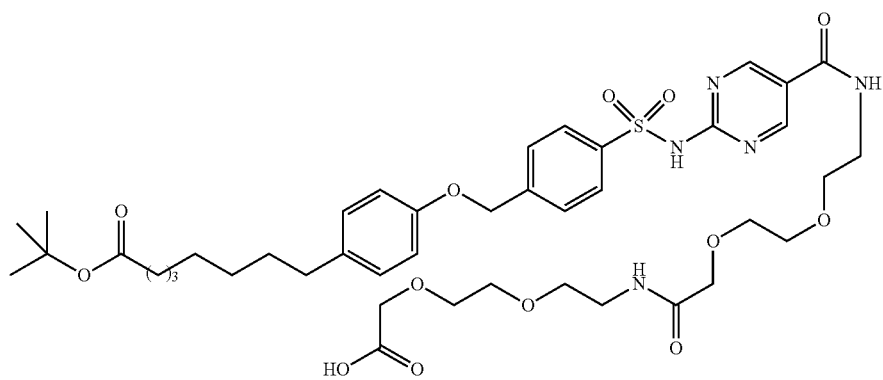

2-[2-[2-[[2-[2-[2-[[5-[[4-[[4-(8-tert-butoxy-8-octylphenyl]methoxy]phenyl]sulfonylamino]
pyridine-2-carbonyl]amino]ethoxy]ethoxy]amino]ethoxy]ethoxy]acetic acid

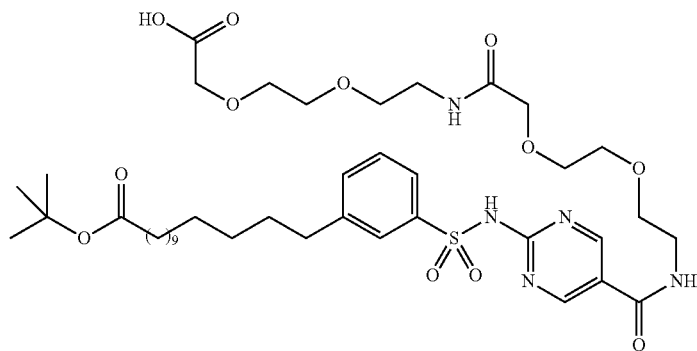

2-[2-[2-[[2-[2-[2-[[5-[[3-(14-tert-butoxy-14-oxo-tetradecyl)phenyl]sulfonylamino]
pyridine-2-carbonyl]amino]ethoxy]ethoxy]acetyl]amino]ethoxy]ethoxy]acetic acid

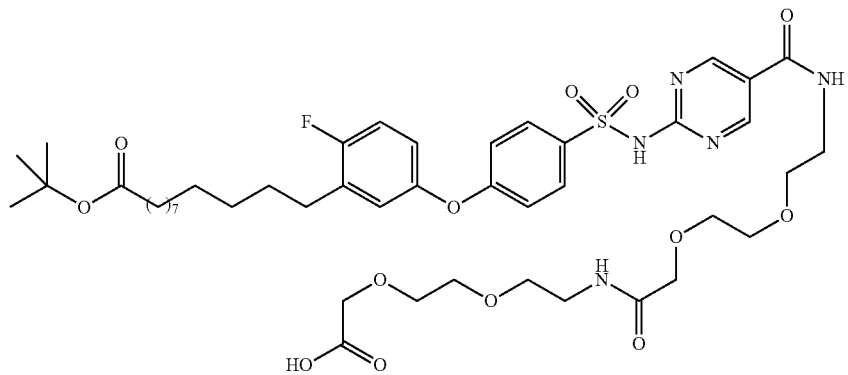

2-[2-[2-[[2-[2-[2-[[5-[[4-[3-(12-tert-butoxy-12-oxo-dodecyl)-4-fluoro-phenoxy]phenyl]sulfonylamino]
pyridine-2-carbonyl]amino]ethoxy]ethoxy]acetyl]amino]ethoxy]ethoxy]acetic acid

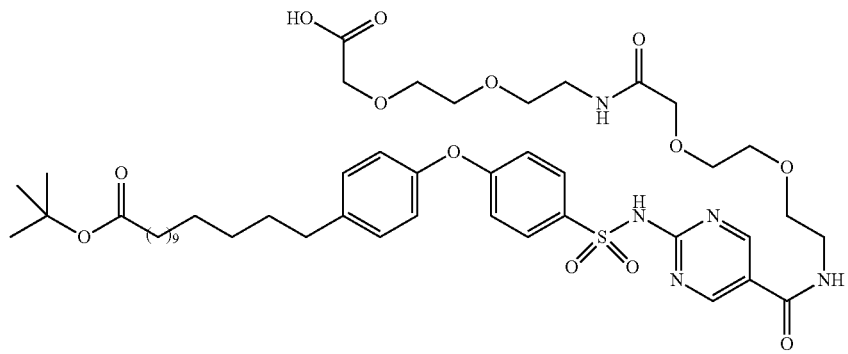

2-[2-[2-[[2-[2-[2-[[5-[[4-[4-(14-tert-butoxy-14-oxo-tetradecyl)pheny]sulfonylamino]
pyridine-2-carbonyl]amino]ethoxy]ethoxy]acetyl]amino]ethoxy]ethoxy]acetic acid

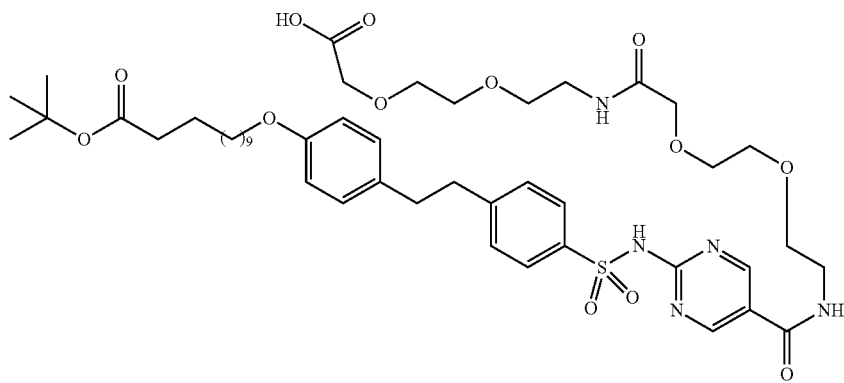

2-[2-[2-[[2-[2-[2-[[5-[[4-[2-[4-(12-tert-butoxy-12-oxododecoxy)phenyl]sulfonylamino]
pyridine-2-carbonyl]amino]ethoxy]ethoxy]acetyl]amino]ethoxy]ethoxy]acetic acid

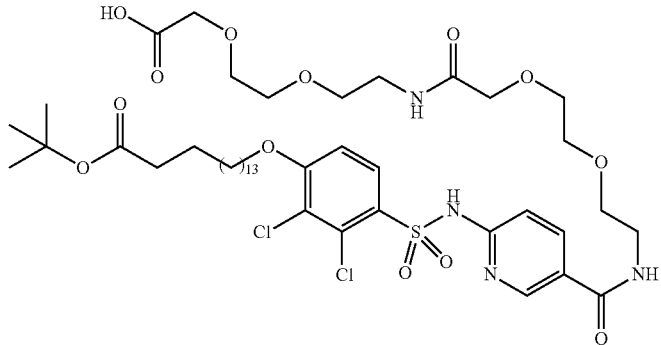

2-[2-[2-[[2-[2-[2-[[6-[[4-(16-tert-butoxy-16-oxo-hexadecoxy)-2,3-dichloro-phenyl]sulfonylamino]
pyridine-3-carbonyl]amino]ethoxy]ethoxy]acetyl]amino]ethoxy]ethoxy]acetic acid

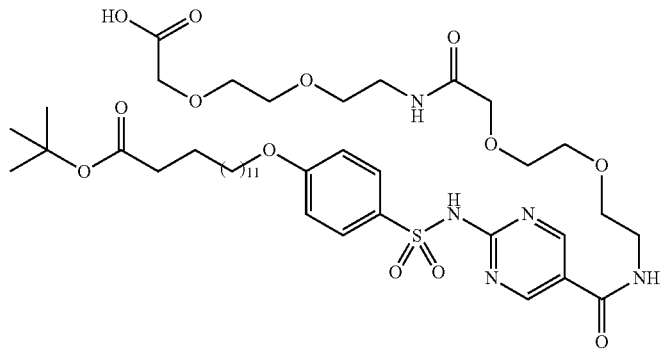

2-[2-[2-[[2-[2-[2-[[5-[[4-(14-tert-butoxy-14-oxo-tetradecoxy)phenyl]sulfonylamino]
pyridine-2-carbonyl]amino]ethoxy]ethoxy]acetyl]amino]ethoxy]ethoxy]acetic acid

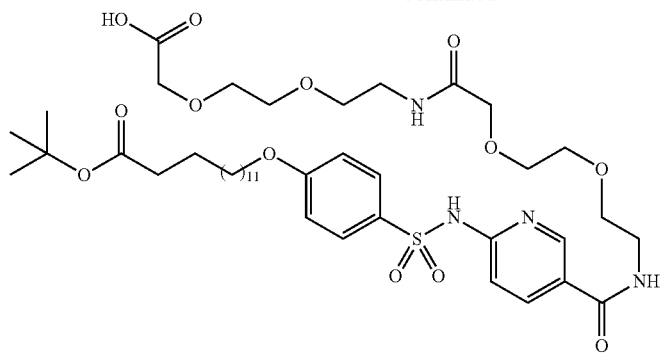

2-[2-[2-[[2-[2-[2-[[6-[[4-(14-tert-butoxy-14-oxo-tetradecoxy)phenyl]sulfonylamino]
pyridine-3-carbonyl]amino]ethoxy]ethoxy]acetyl]amino]ethoxy]ethoxy]acetic acid

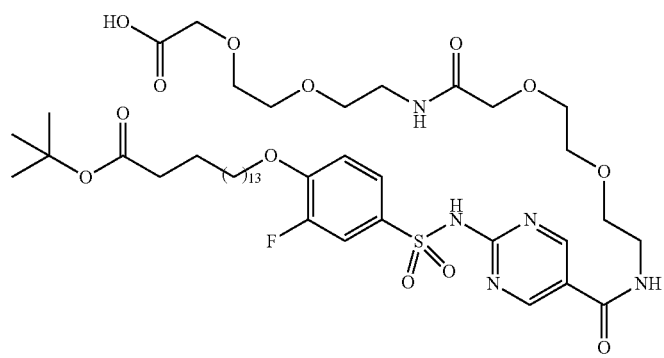

2-[2-[2-[[2-[2-[2-[[4-(16-tert-butoxy-16-oxo-hexadecoxy)-3-fluoro-phenyl]sulfonylamino]
pyridine-5-carbonyl]amino]ethoxy]ethoxy]acetyl]amino]ethoxy]ethoxy]acetic acid

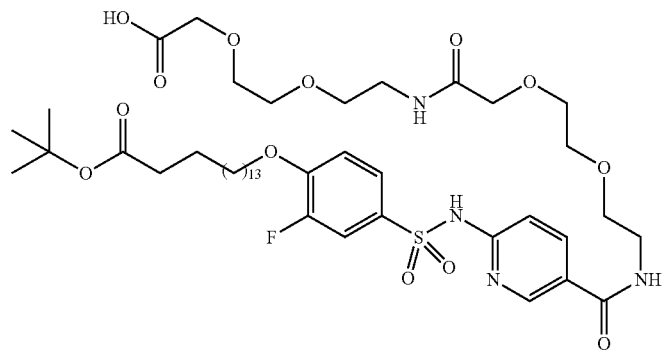

2-[2-[2-[[2-[2-[2-[[4-(16-tert-butoxy-16-oxo-hexadecoxy)-3-fluoro-phenyl]sulfonylamino]
pyridine-3-carbonyl]amino]ethoxy]ethoxy]acetyl]amino]ethoxy]ethoxy]acetic acid

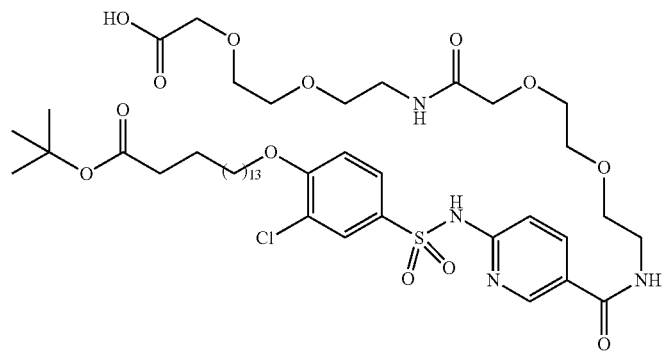

2-[2-[2-[[2-[2-[2-[[4-(16-tert-butoxy-16-oxo-hexadecoxy)-3-chloro-phenyl]sulfonylamino]
pyridine-3-carbonyl]amino]ethoxy]ethoxy]acetyl]amino]ethoxy]ethoxy]acetic acid -continued

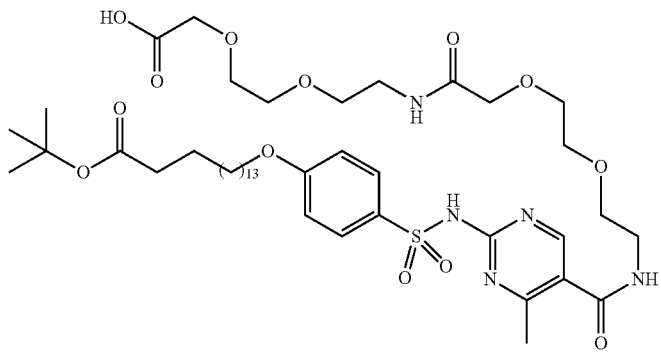

2-[2-[2-[[2-[2-[2-[[4-(16-tert-butoxy-16-oxo-hexadecoxy)phenyl]sulfonylamino]-4-methyl-
pyrimidine-5-carbonyl]amino]ethoxy]ethoxy]acetyl]amino]ethoxy]ethoxy]acetic acid

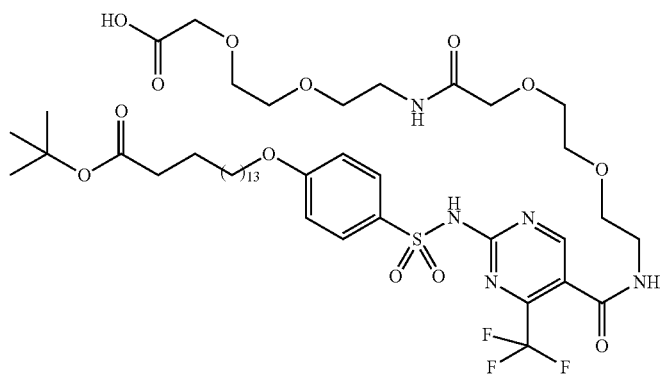

2-[2-[2-[[2-[2-[2-[[4-(16-tert-butoxy-16-oxo-hexadecoxy)phenyl]sulfonylamino]-4-(trifluoromethyl)
pyrimidine-5-carbonyl]amino]ethoxy]ethoxy]acetyl]amino]ethoxy]ethoxy]acetic acid

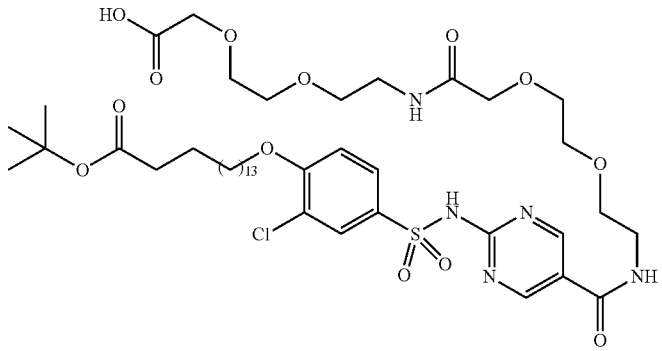

2-[2-[2-[[2-[2-[2-[[4-(16-tert-butoxy-16-oxo-hexadecoxy)-3-chloro-
phenyl]sulfonylamino]pyrimidine-5-carbonyl]amino]ethoxy]ethoxy]acetyl]amino]ethoxy]
ethoxy]acetic acid

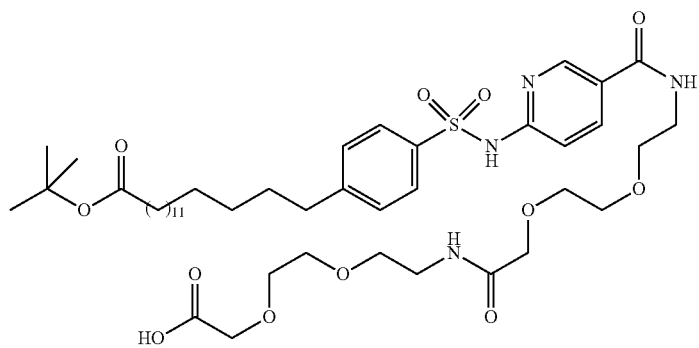

2-[2-[2-[[2-[2-[2-[[6-[[4-(16-tert-butoxy-16-oxo-hexadecyl)phenyl]sulfonylamino]
pyridine-3-carbonyl]amino]ethoxy]ethoxy]acetyl]amino]ethoxy]ethoxy]acetic acid

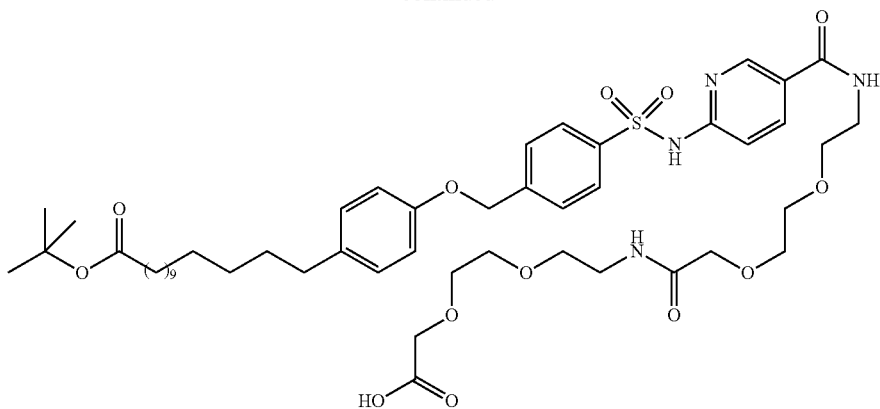

2-[2-[2-[[2-[2-[2-[[5-[[4-[[4-(14-tert-butoxy-14-oxo-tetradecyl)phenoxy]methyl]phenyl]sulfonylamino]
pyridine-3-carbonyl]amino]ethoxy]ethoxy]amino]ethoxy]ethoxy]acetic acid

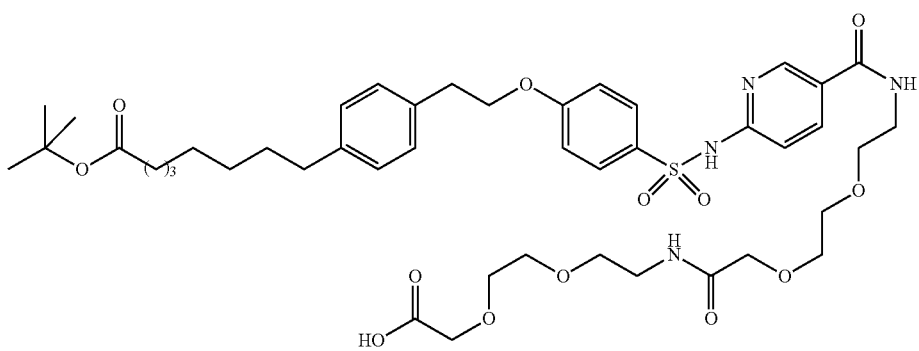

2-[2-[2-[[2-[2-[2-[[6-[[4-[2-[4-(8-tert-butoxy-8-oxo-octyl)phenyl]ethoxy]phenyl]sulfonylamino]
pyrimidine-3-carbonyl]amino]ethoxy]ethoxy]acetyl]amino]ethoxy]ethoxy]acetic acid

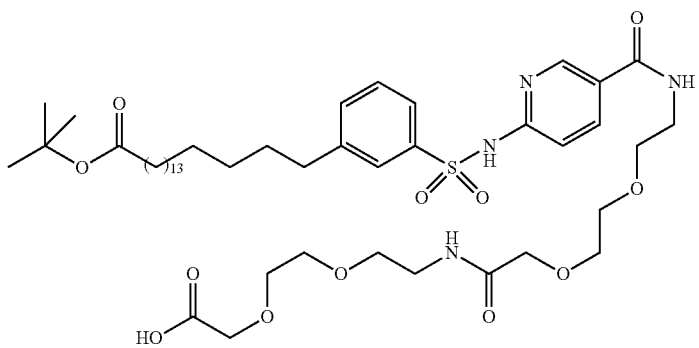

2-[2-[2-[[2-[2-[2-[[6-[[3-(18-tert-butoxy-18-oxo-octadecyl)phenyl]sulfonylamino]
pyrimidine-3-carbonyl]amino]ethoxy]ethoxy]acetyl]amino]ethoxy]ethoxy]acetic acid

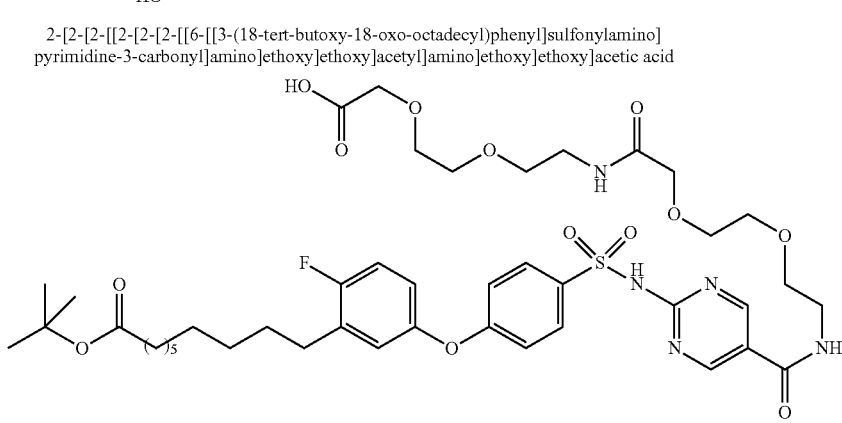

2-[2-[2-[[2-[2-[2-[[4-[[3-(10-tert-butoxy-10-oxo-decyl)-4-fluoro-phenoxy]pheny]sulfonylamino]
pyrimidine-5-carbonyl]amino]ethoxy]ethoxy]acetyl]amino]ethoxy]ethoxy]acetic acid

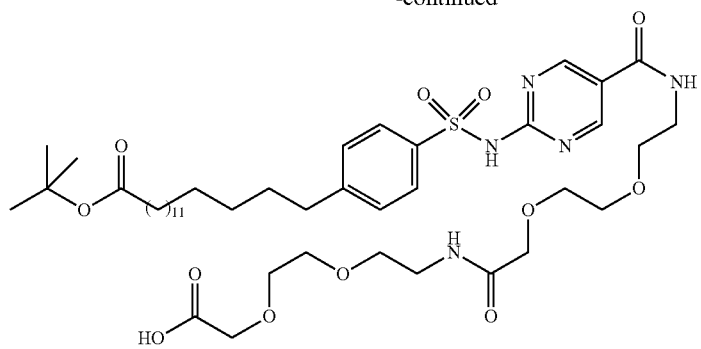

2-[2-[2-[[2-[2-[2-[[6-[[4-(16-tert-butoxy-16-oxo-hexadecyl)phenyl]sulfonylamino]
pyrimidine-5-carbonyl]amino]ethoxy]ethoxy]acetyl]amino]ethoxy]ethoxy]acetic acid

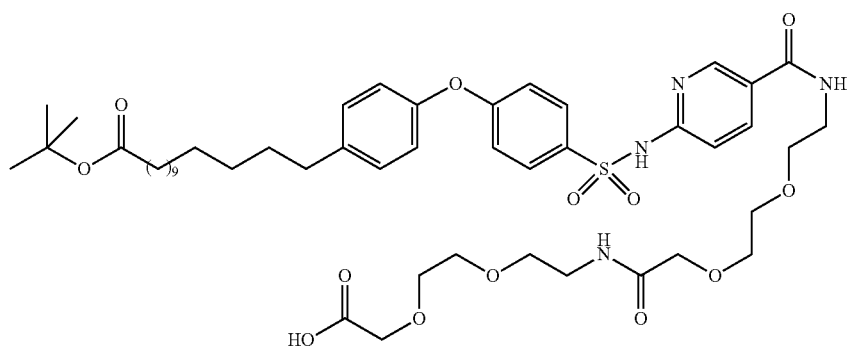

2-[2-[2-[[2-[2-[2-[[6-[[4-[4-[4-(14-tert-butoxy-14-oxo-tetradecyl)phenoxy]phenyl]sulfonylamino]
pyridine-3-carbonyl]amino]ethoxy]ethoxy]acetyl]amino]ethoxy]ethoxy]acetic acid

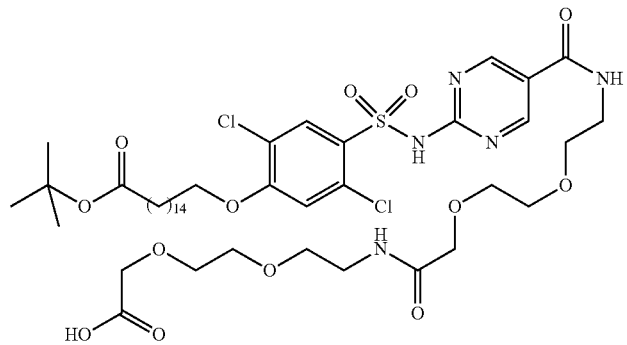

2-[2-[2-[[2-[2-[2-[[6-[[4-(16-tert-butoxy-16-oxo-hexadecyl)-2,5-dichloro-phenyl]sulfonylamino]
pyrimidine-5-carbonyl]amino]ethoxy]ethoxy]acetyl]amino]ethoxy]ethoxy]acetic acid

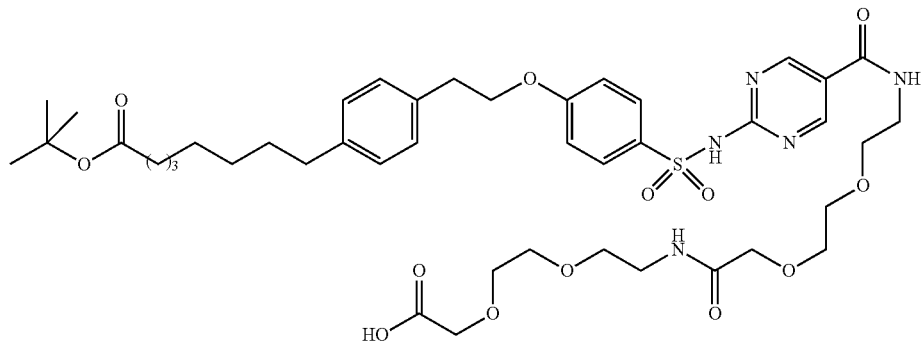

2-[2-[2-[[2-[2-[2-[[2-[[4-[2-[4-(8-tert-butoxy-8-oxo-octyl)phenyl]ethoxy]sulfonylamino]
pyrimidine-5-carbonyl]amino]ethoxy]ethoxy]acetyl]amino]ethoxy]ethoxy]acetic acid

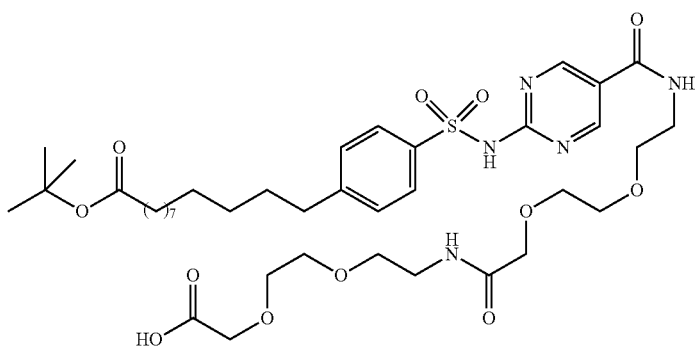

2-[2-[2-[[2-[2-[2-[[6-[[4-(12-tert-butoxy-12-oxo-dodecyl)phenyl]sulfonylamino]
pyrimidine-5-carbonyl]amino]ethoxy]ethoxy]acetyl]amino]ethoxy]ethoxy]acetic acid

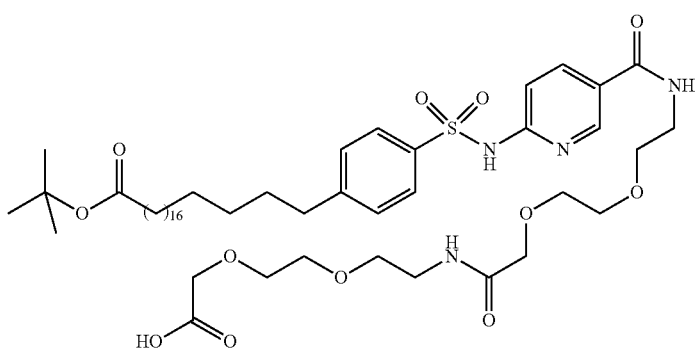

2-[2-[2-[[2-[2-[2-[[6-[[4-(18-tert-butoxy-18-oxo-octadecoxy)phenyl]sulfonylamino]
pyrimidine-3-carbonyl]amino]ethoxy]ethoxy]acetyl]amino]ethoxy]ethoxy]acetic acid

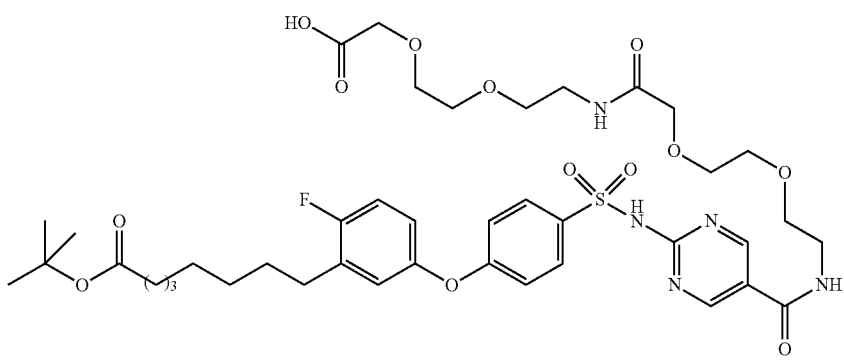

2-[2-[2-[[2-[2-[2-[[4-[[3-(8-tert-butoxy-8-oxo-octyl)-4-fluoro-phenoxy]pheny]sulfonylamino]
pyrimidine-5-carbonyl]amino]ethoxy]ethoxy]acetyl]amino]ethoxy]ethoxy]acetic acid

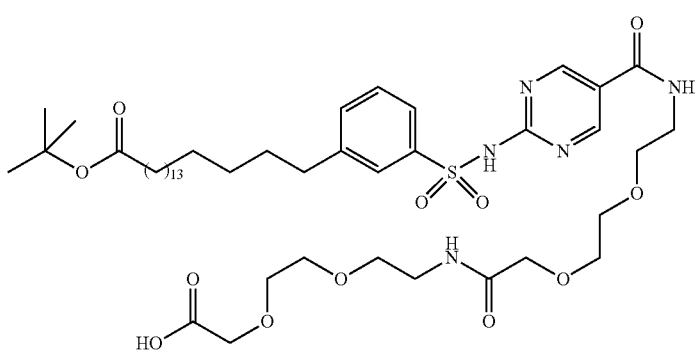

2-[2-[2-[[2-[2-[2-[[2-[[3-(18-tert-butoxy-18-oxo-octadecyl)phenyl]sulfonylamino]
pyridine-5-carbonyl]amino]ethoxy]ethoxy]acetyl]amino]ethoxy]ethoxy]acetic acid -continued

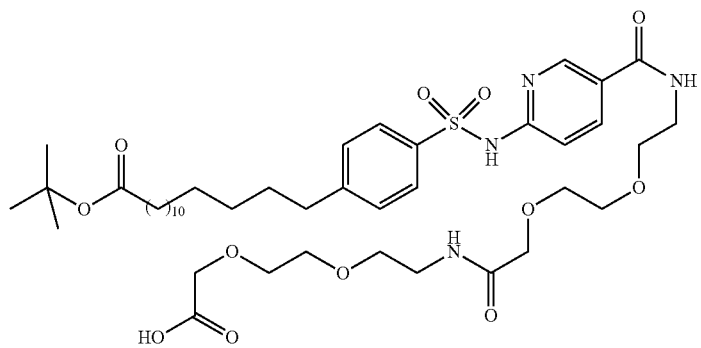

2-[2-[2-[[2-[2-[2-[[6-[[3-(12-tert-butoxy-12-oxo-dodecyl)phenyl]sulfonylamino]pyrimidine-3-carbonyl]amino]ethoxy]ethoxy]acetyl]amino]ethoxy]ethoxy]acetic acid

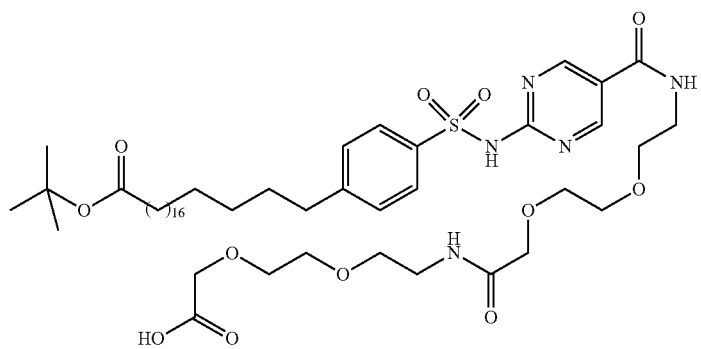

2-[2-[2-[[2-[2-[2-[[4-(18-tert-butoxy-18-oxo-octadecoxy)phenyl]sulfonylamino]pyrimidine-5-carbonyl]amino]ethoxy]ethoxy]acetyl]amino]ethoxy]ethoxy]acetic acid

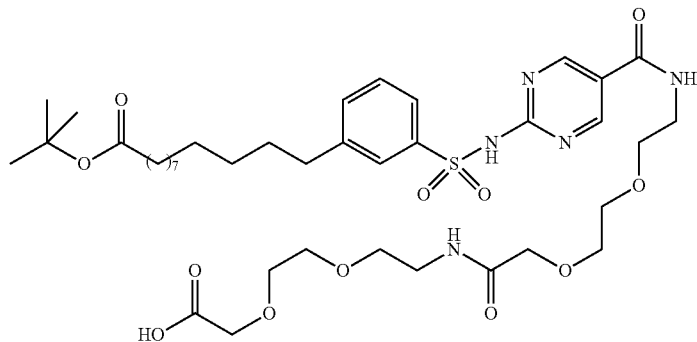

2-[2-[2-[[2-[2-[2-[[2-[3-(12-tert-butoxy-12-oxo-dodecyl)phenyl]sulfonylamino]pyrimidine-5-carbonyl]amino]ethoxy]ethoxy]acetyl]amino]ethoxy]ethoxy]acetic acid

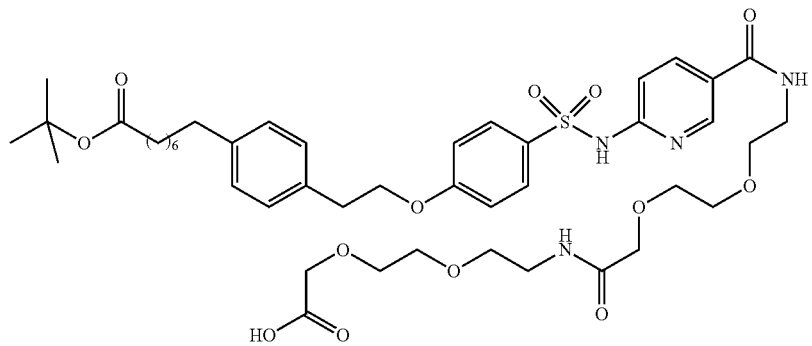

2-[2-[2-[[2-[2-[2-[[6-[[4-[2-[4-(8-tert-butoxy-8-oxo-octyl)phenyl]ethoxy]phenyl]sulfonylamino]pyrimidine-3-carbonyl]amino]ethoxy]ethoxy]acetyl]amino]ethoxy]ethoxy]acetic acid

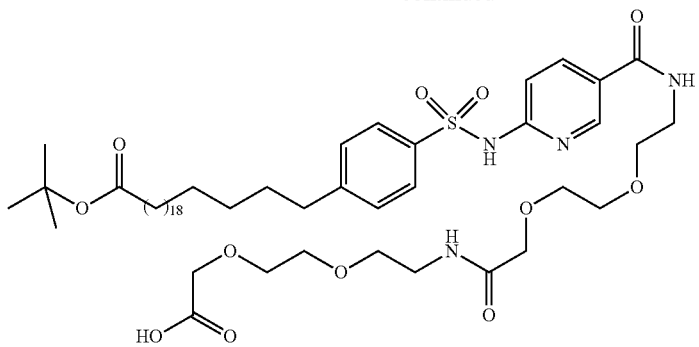

2-[2-[2-[[2-[2-[2-[[6-[[4-(20-tert-butoxy-20-oxo-icosoxy)sulfonylamino]
pyridine-3-carbonyl]amino]ethoxy]ethoxy]acetyl]amino]ethoxy]ethoxy]acetic acid

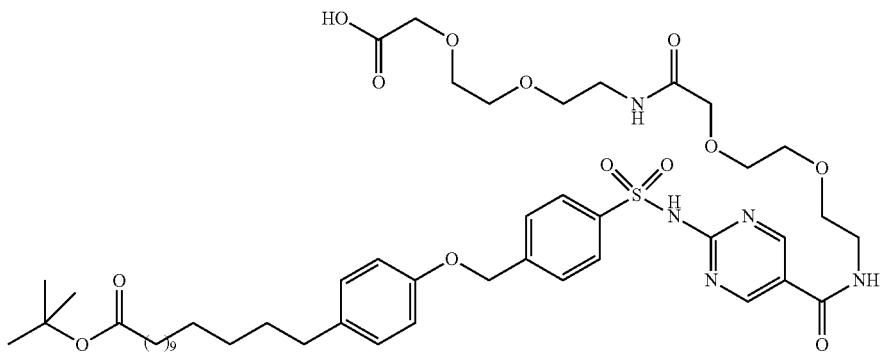

2-[2-[2-[[2-[2-[2-[[4-[[4-(14-tert-butoxy-14-oxo-terradecyl)phenoxy]methyl]pheny]sulfonylamino]
pyrimidine-5-carbonyl]amino]ethoxy]ethoxy]acetyl]amino]ethoxy]ethoxy]acetic acid

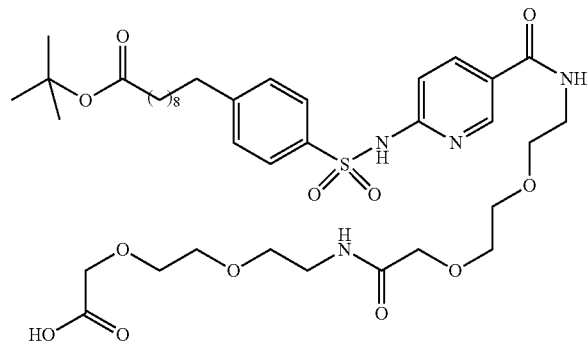

2-[2-[2-[[2-[2-[2-[[6-[[4-(10-tert-butoxy-10-oxo-decyl)phenyl]sulfonylamino]
pyrimidine-3-carbonyl]amino]ethoxy]ethoxy]acetyl]amino]ethoxy]ethoxy]acetic acid

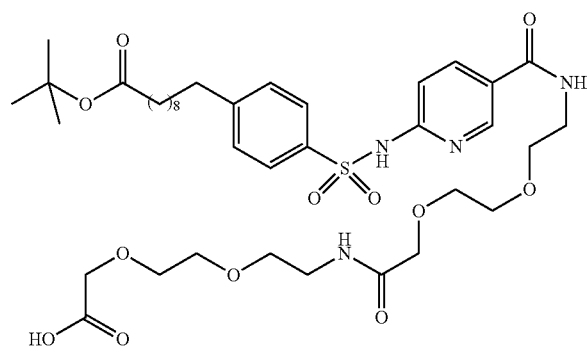

2-[2-[2-[[2-[2-[2-[[2-[4-(10-tert-butoxy-10-oxo-decyl)phenyl]sulfonylamino]
pyrimidine-5-carbonyl]amino]ethoxy]ethoxy]acetyl]amino]ethoxy]ethoxy]acetic acid

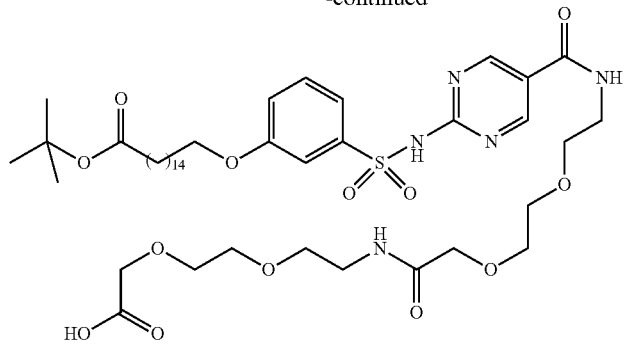

2-[2-[2-[[2-[2-[2-[[2-[[3-(16-tert-butoxy-16-oxo-decyl)hexadecoxy]phenyl]sulfonylamino]
pyrimidine-5-carbonyl]amino]ethoxy]ethoxy]acetyl]amino]ethoxy]ethoxy]acetic acid 2.9.2 Synthesis of 2-[2-[2-[[2-[2-[2-[6-[[5-[[4-(16-tert-butoxy-16-oxo-hexadecoxy)phenyl] sulfonylamino] pyrimidine-2-carbonyl]amino]-hexanoylamino]ethoxy]ethoxy]acetyl]amino]ethoxy]ethoxy] acetic Acid

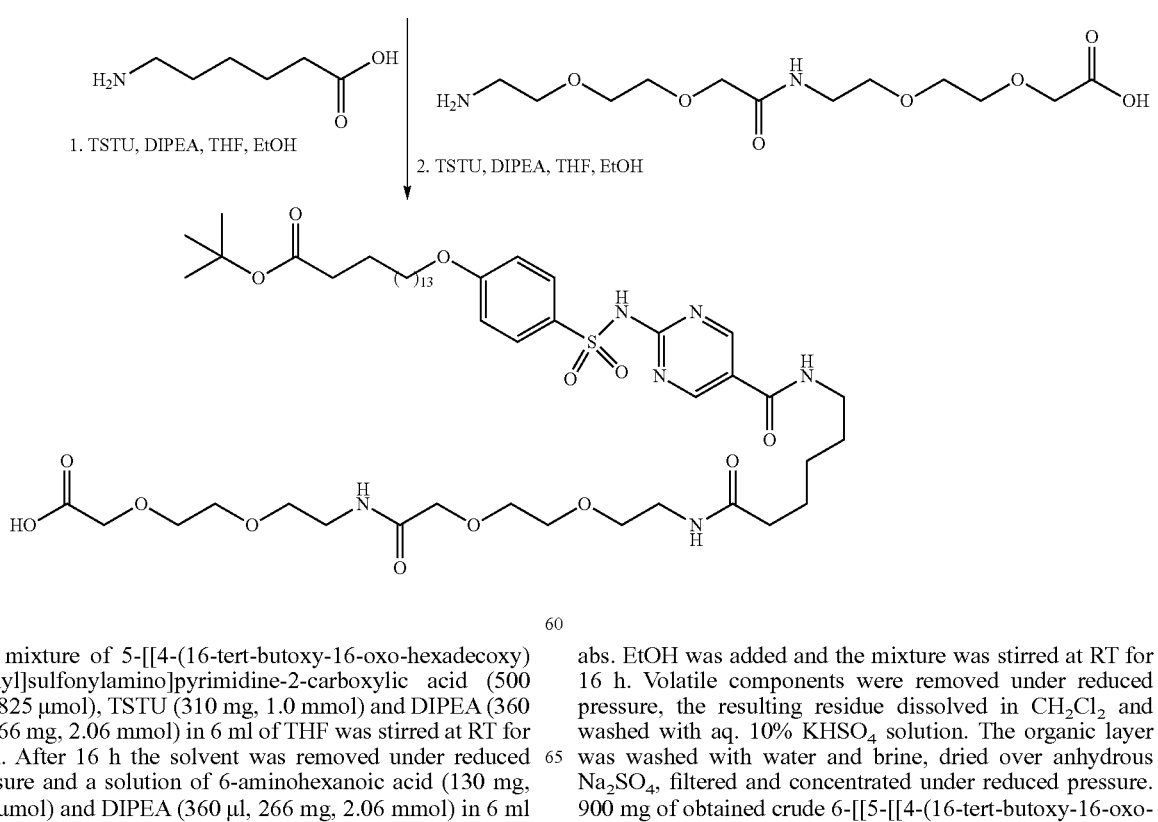

A mixture of 5-[[4-(16-tert-butoxy-16-oxo-hexadecoxy)phenyl]sulfonylamino]pyrimidine-2-carboxylic acid (500 mg, 825 μmol), TSTU (310 mg, 1.0 mmol) and DIPEA (360 μl, 266 mg, 2.06 mmol) in 6 ml of THF was stirred at RT for 16 h. After 16 h the solvent was removed under reduced pressure and a solution of 6-aminohexanoic acid (130 mg, 990 μmol) and DIPEA (360 μl, 266 mg, 2.06 mmol) in 6 ml abs. EtOH was added and the mixture was stirred at RT for 16 h. Volatile components were removed under reduced pressure, the resulting residue dissolved in CH$_2$Cl$_2$ and washed with aq. 10% KHSO$_4$ solution. The organic layer was washed with water and brine, dried over anhydrous Na$_2$SO$_4$, filtered and concentrated under reduced pressure. 900 mg of obtained crude 6-[[5-[[4-(16-tert-butoxy-16-oxohexadecoxy)phenyl] sulfonylamino] pyrimidine-2-carbonyl]amino]hexanoic acid were used in the next step without further purification.

A mixture of 6-[[5-[[4-(16-tert-butoxy-16-oxo-hexadecoxy)phenyl]sulfonylamino]pyrimidine-2-carbonyl] amino]hexanoic acid (900 mg crude, 65% purity, 814 µmol), TSTU (306 mg, 1.02 mmol) and DIPEA (355 µl, 262 mg, 2.03 mmol) in 6 ml of THF was stirred at RT for 16 h. After 16 h the solvent was removed under reduced pressure and a solution of 2-[2-[2-[[2-[2-(2-aminoethoxy)ethoxy]acetyl] amino]ethoxy]ethoxy]acetic acid (301 mg, 976 µmol) and DIPEA (355 µl, 262 mg, 2.03 mmol) in 6 ml abs. EtOH was added and the mixture was stirred at RT for 16 h. Volatile components were removed under reduced pressure, the resulting residue dissolved in $CH_2Cl_2$ and washed with aq. 10% $KHSO_4$ solution. The organic layer was washed with water and brine, dried over anhydrous $Na_2SO_4$, filtered and concentrated under reduced pressure. The crude product was purified by RP HPLC to afford 2-[2-[2-[[2-[2-[2-[6-[[5-[[4-(16-tert-butoxy-16-oxo-hexadecoxy)phenyl]sulfonylamino] pyrimidine-2-carbonyl]amino]hexanoylamino]ethoxy] ethoxy]acetyl]amino]ethoxy]ethoxy] acetic acid (78 mg, 10%).

$^1$H NMR (400.23 MHz, DMSO-$d_6$) δ ppm 12.29 (br s, 1H), 8.82 (s, 2H), 8.47 (br s, 1H), 7.90 (d, J=8.93 Hz, 2H), 7.79 (t, J=5.50 Hz, 1H), 7.63 (t, J=5.75 Hz, 1H), 7.07 (d, J=8.93 Hz, 2H), 4.01 (m, 4H), 3.87 (s, 2H), 3.20-3.68 (m, 18H), 2.15 (t, J=7.27 Hz, 2H), 2.05 (t, J=7.34 Hz, 2H), 1.70 (m, 2H), 1.48 (m, 6H), 1.38 (s, 9H), 1.25 (m, 24H).

The following compound was synthesized accordingly:

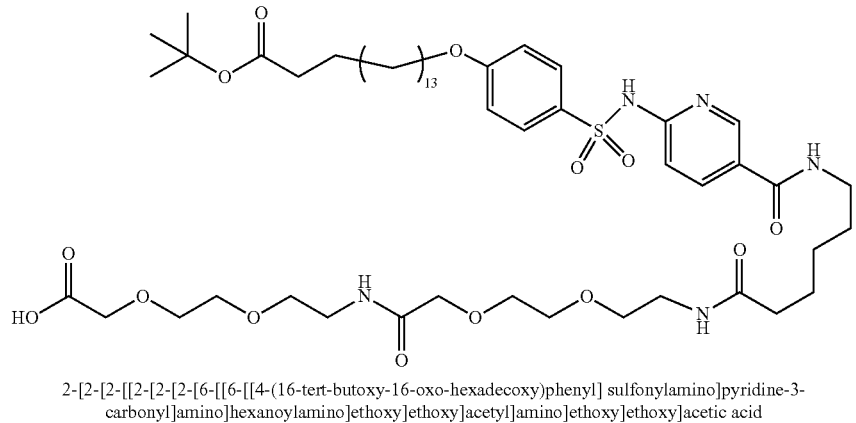

2-[2-[2-[[2-[2-[2-[6-[[6-[[4-(16-tert-butoxy-16-oxo-hexadecoxy)phenyl] sulfonylamino]pyridine-3-carbonyl]amino]hexanoylamino]ethoxy]ethoxy]acetyl]amino]ethoxy]ethoxy]acetic acid

2.10 Incorporation of Species (2)

2.10.1 Synthesis of 2-[2-[2-[[2-[2-[2-[3-[[5-[[4-[4-(14-tert-butoxy-14-oxo-tetradecyl)phenoxy] phenyl] sulfonyl amino]pyrimidine-2-carbonyl]-amino]propanoylamino]ethoxy]ethoxy]acetyl] amino]ethoxy]ethoxy]acetic Acid

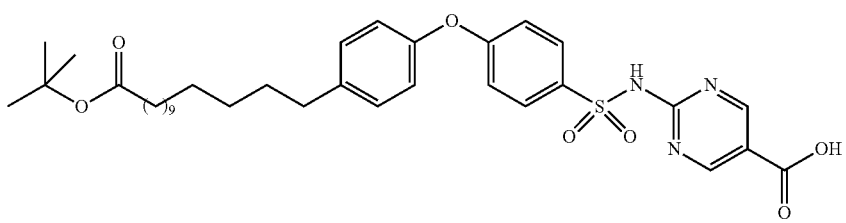

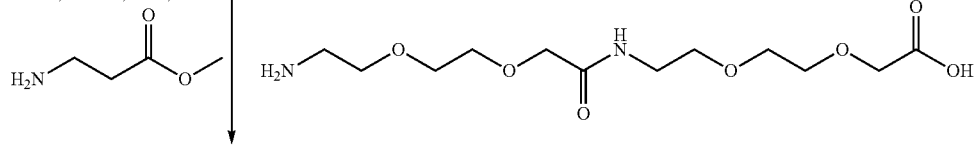

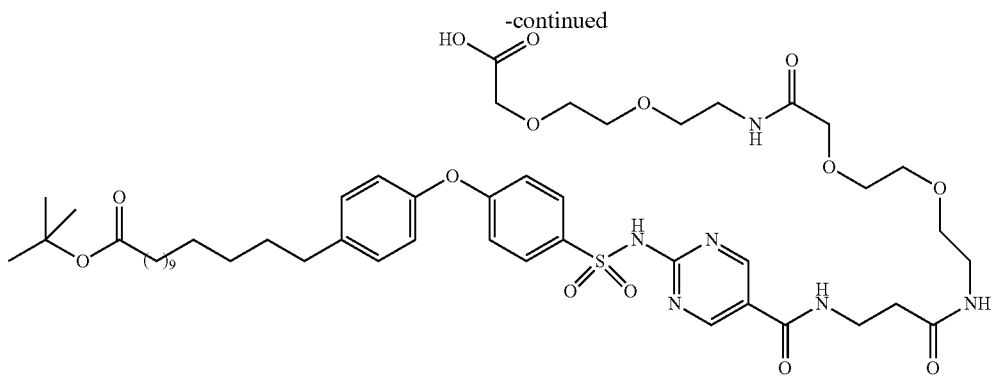

2.10.2 Synthesis of tert-butyl 14-[4-[4-[[5-[(3-methoxy-3-oxo-propyl)carbamoyl]pyrimidin-2-yl]sulfamoyl] phenoxy]phenyl]tetradecanoate

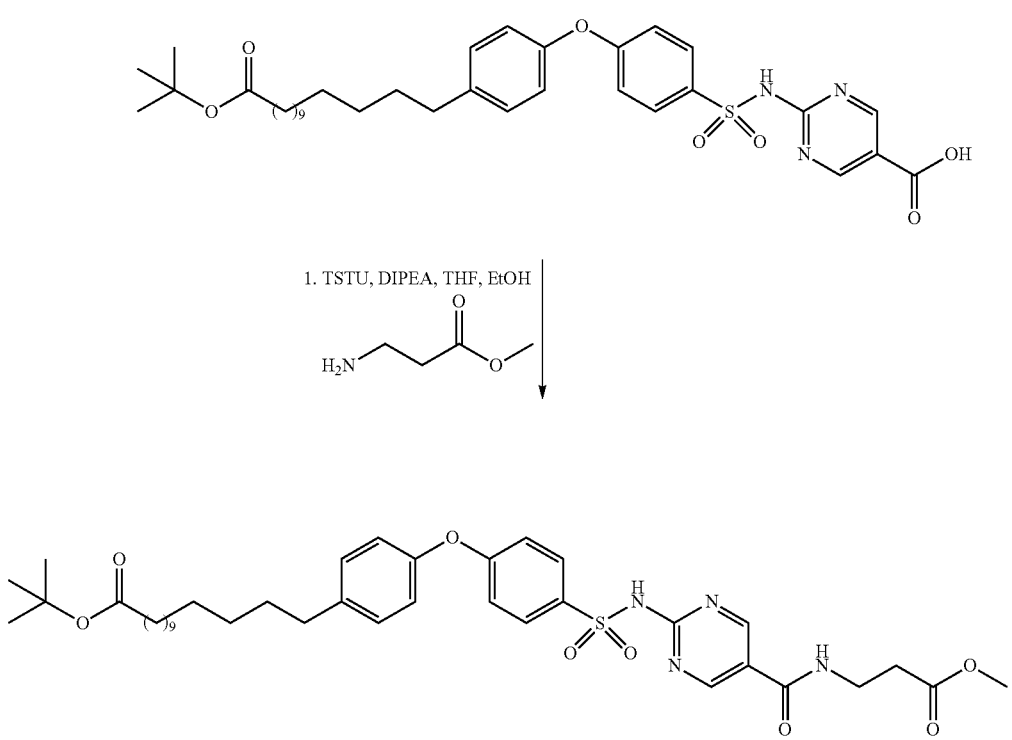

A mixture of 5-[[4-[4-(14-tert-butoxy-14-oxo-tetradecyl)phenoxy]phenyl]sulfonyl amino]pyrimidine-2-carboxylic acid (1.0 g, 764 µmol), TSTU (241 mg, 803 µmol) and DIPEA (494 mg, 3.82 mmol) in 10 ml of THF was stirred at RT for 16 h. Additional TSTU was added (80 mg, 267 µmol) and stirring at RT was continued for 2 h. Methyl 3-aminopropanoate hydrochloride (117 mg, 841 µmol) was added and stirring at RT was continued for 16 h. Volatile components were removed under reduced pressure, the resulting residue dissolved in CH$_2$Cl$_2$ and washed with aq. 10% KHSO$_4$ solution. The organic layer was washed with water and brine, dried over anhydrous Na$_2$SO$_4$, filtered and concentrated under reduced pressure. The crude product was purified by RP preparative HPLC to afford 14-[4-[4-[[5-[(3-methoxy-3-oxo-propyl) carbamoyl]pyrimidin-2-yl]sulfamoyl]phenoxy]phenyl] tetradecanoate (235 mg, 42%).

$^1$H NMR (400.23 MHz, DMSO-d$_6$) δ ppm 12.11 (brs, 1H), 8.84 (s, 2H), 8.66 (t, J=5.44 Hz, 1H), 7.98 (d, J=8.93 Hz, 2H), 7.26 (d, J=8.44 Hz, 2H), 7.04 (m, 4H), 3.60 (s, 3H), 3.46 (m, 2H), 2.57 (m, 4H), 2.15 (t, J=7.27 Hz, 2H), 1.56 (m, 2H), 1.46 (m, 2H), 1.38 (s, 9H), 1.29 (m, 18H).

2.10.3 Synthesis of 2-[2-[2-[[2-[2-[2-[3-[[5-[[4-[4-(14-tert-butoxy-14-oxo-tetradecyl)phenoxy] phenyl] sulfonyl amino]pyrimidine-2-carbonyl]amino]propanoylamino]ethoxy]ethoxy]acetyl]amino]ethoxy] ethoxy]acetic Acid

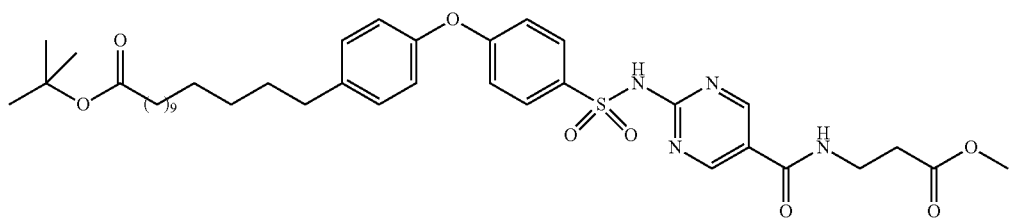

1. LiOH, THF/H$_2$O
2. TSTU, DIPEA, THF, EtOH

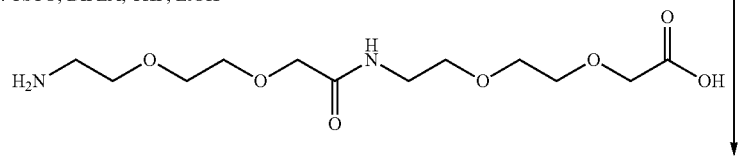

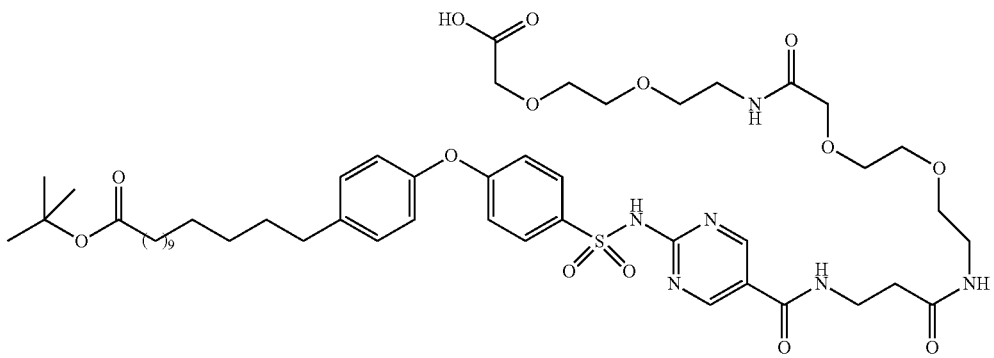

A mixture of 14-[4-[4-[[5-[(3-methoxy-3-oxo-propyl)carbamoyl] pyrimidin-2-yl]sulfamoyl] phenoxy]phenyl] tetradecanoate (235 mg, 318 µmol), LiOH (38 mg, 1.59 mmol), THF (5 ml) and H$_2$O (5 ml) was stirred at RT for 2 h. The reaction mixture was acidified to approx. pH=1.0 with HCl (2.0 M) and extracted with CH$_2$Cl$_2$. The organic layer was washed with brine dried with Na$_2$SO$_4$, filtered and concentrated to afford 3-[[5-[[4-[4-(14-tert-butoxy-14-oxo-tetradecyl)phenoxy]phenyl]sulfonylamino]pyrimidine-2-carbonyl]amino]propanoic acid (207 mg, 89% yield) as a white solid, which was used in the next reaction without further purification.

A mixture of 3-[[5-[[4-[4-(14-tert-butoxy-14-oxo-tetradecyl)phenoxy]phenyl]sulfonyl amino]pyrimidine-2-carbonyl]amino]propanoic acid (207 mg, 285 µmol), TSTU (90 mg, 300 µmol) and DIPEA (150 µl, 110 mg, 850 µmol) in 6 ml of THF was stirred at RT for 1 h. After 1 h, the solvent was removed under reduced pressure and a solution of 2-[2-[2-[[2-[2-(2-aminoethoxy)ethoxy]acetyl]amino]ethoxy]ethoxy]acetic acid (97 mg, 314 µmol) and DIPEA (150 µl, 110 mg, 850 µmol) in 6 ml abs. EtOH was added and the mixture was stirred at RT for 16 h. Volatile components were removed under reduced pressure, the resulting residue dissolved in CH$_2$Cl$_2$ and washed with aq. 10% KHSO$_4$ solution. The organic layer was washed with water and brine, dried over anhydrous Na$_2$SO$_4$, filtered and concentrated under reduced pressure. The crude product was purified by RP HPLC to afford 2-[2-[2-[[2-[2-[2-[3-[[5-[[4-[4-(14-tert-butoxy-14-oxo-tetradecyl)phenoxy]phenyl]sulfonylamino]pyrimidine-2-carbonyl]amino]propanoylamino]ethoxy]ethoxy]acetyl]amino]ethoxy]ethoxy]acetic acid (163 mg, 56%).

$^1$H NMR (400.23 MHz, DMSO-d$_6$) δ ppm 12.11 (br s, 2H), 8.84 (s, 2H), 8.61 (t, J=5.62 Hz, 1H), 7.97 (m, 3H), 7.62 (t, J=5.56 Hz, 1H), 7.26 (d, J=8.44 Hz, 2H), 7.04 (m, 4H), 4.01 (s, 2H), 3.86 (s, 2H), 3.20-3.60 (m, 18H), 2.58 (m, 2H), 2.34 (t, J=7.03 Hz, 2H), 2.15 (t, J=7.27 Hz, 2H), 1.56 (m, 2H), 1.46 (m, 2H), 1.38 (s, 9H), 1.29 (m, 18H).

2.11 Deprotection Synthesis of 14-[5-[4-[[5-[2-[2-[2-[2-[2-(carboxymethyloxy)ethoxy]ethylamino]-2-oxo-ethoxy]ethoxy] ethylcarbamoyl]-2-pyridyl]sulfamoyl]phenoxy]-2-fluoro-phenyl]tetradecanoic Acid

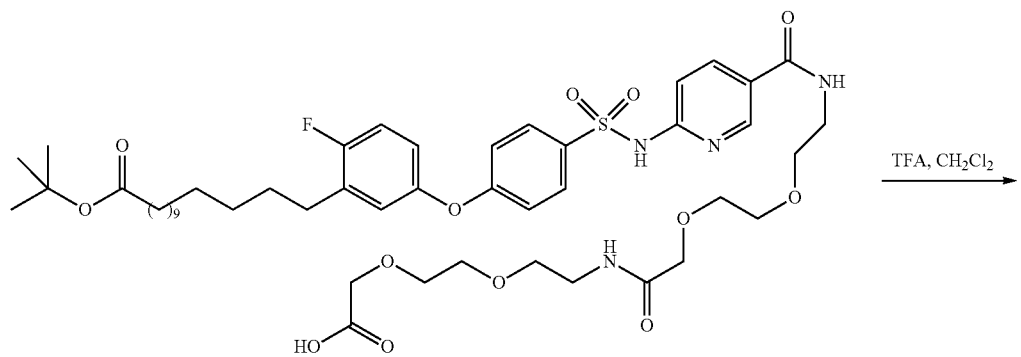

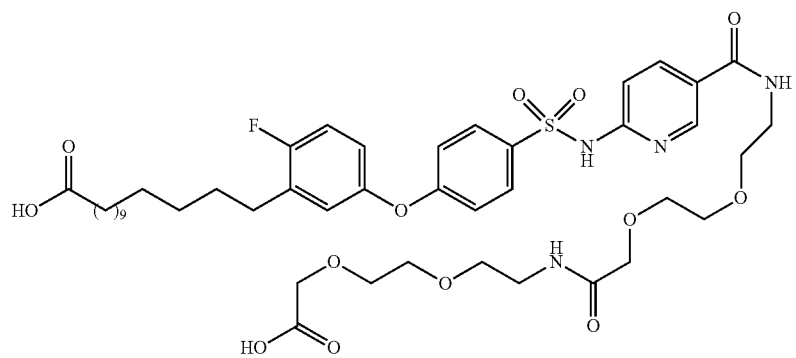

2-[2-[2-[[2-[2-[2-[[6-[[4-[3-(14-tert-butoxy-14-oxo-tetradecyl)-4-fluoro-phenoxy] phenyl]sulfonylamino]pyridine-3-carbonyl]amino] ethoxy]ethoxy] acetyl]amino]ethoxy] ethoxy]acetic acid (20 mg, 21 μmol) was dissolved in DCM (3.0 ml) and TEA (0.5 ml) was added at RT. Stirring was continued at RT for 16 h. Volatile components were removed under reduced pressure and the resulting residue dissolved in DCM and reevaporated twice. The crude product was purified by RP preparative HPLC. The title compound 14-[5-[4-[[5-[2-[2-[2-[2-[2-(carboxymethyloxy)ethoxy]ethylamino]-2-oxo-ethoxy]ethoxy]ethylcarbamoyl]-2-pyridyl]sulfamoyl]phenoxy]-2-fluoro-phenyl]tetradecanoic acid was obtained as a colourless solid (19 mg, 21 μmol, quan.). $^1$H NMR (400.23 MHz, DMSO-$d_6$) δ ppm 12.19 (br s, 1H), 8.51 (m, 2H), 8.09 (dd, J=8.93, 2.32 Hz, 1H), 7.89 (d, J=8.93 Hz, 2H), 7.61 (br t, J=5.56 Hz, 1H), 7.20 (t, J=8.93 Hz, 1H), 7.15 (d, J=8.19 Hz, 1H), 7.03 (m, 4H), 4.01 (s, 2H), 3.86 (s, 2H), 3.20-3.68 (m, 16H), 2.58 (br t, J=7.52 Hz, 2H), 2.17 (t, J=7.34 Hz, 2H), 1.49 (m, 4H), 1.25 (m, 18H).

The following compounds were synthesized accordingly:

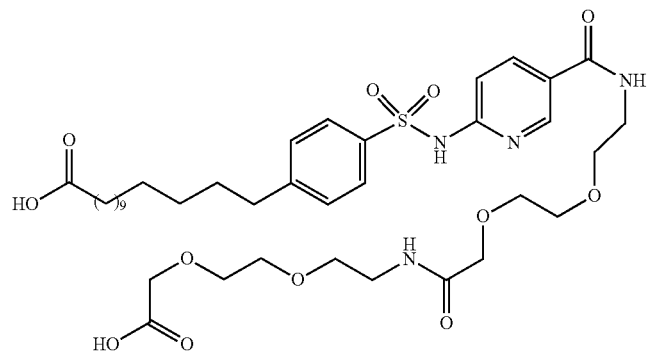

14-[4-[[5-[2-[2-[2-[2-[2-(carboxymethyloxy)ethoxy]ethylamino]-2-oxo-ethoxy]ethoxy]ethyl carbamoyl]-2-pyridyl]sulfamoyl]phenyl]tetradecanoic acid

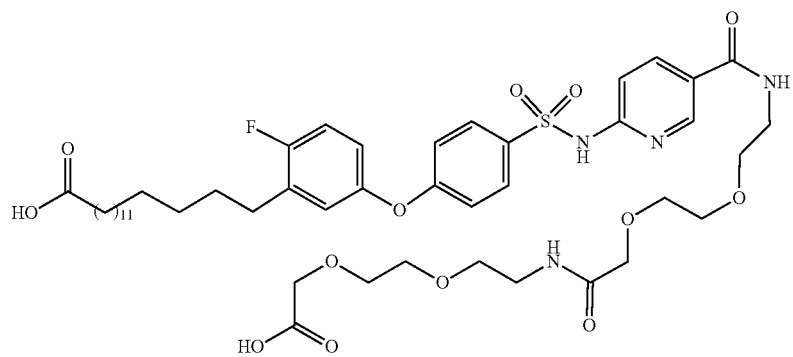

16-[5-4-[[5-[2-[2-[2-[2-[2-(carboxymethyloxy)ethoxy]ethoxy]ethylamino]-2-oxo-ethoxy]ethoxy]
ethylcarbamoyl]-2-pyridyl]sulfamoyl]phenoxy]-2-fluoro-phenyl]hexadecanoic acid

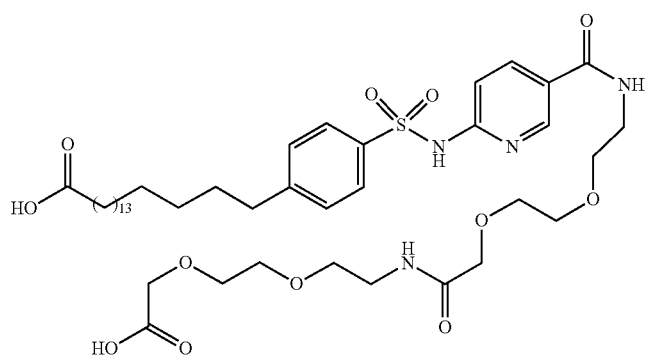

18-[4-[[5-[2-[2-[2-[2-[2-(carboxymethyloxy)ethoxy]ethoxy]ethylamino]-2-oxo-ethoxy]ethoxy]
ethylcarbamoyl]-2-pyridyl]sulfamoyl]phenyl]octadecanoic acid

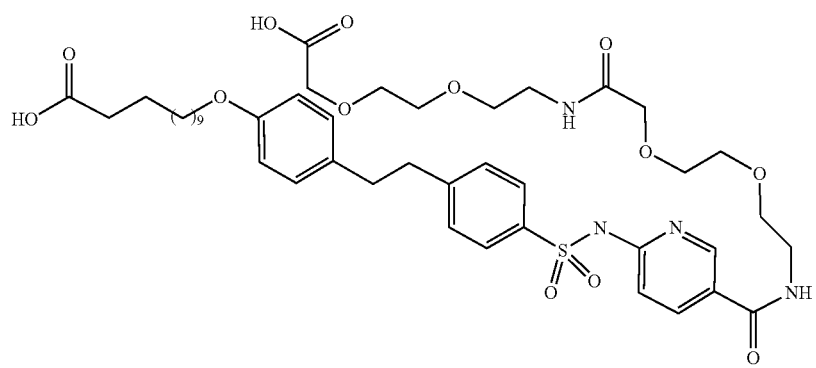

12-[4-[2-[4-[[5-[2-[2-[2-[2-[2-(carboxymethyloxy)ethoxy]ethoxy]ethylamino]-2-oxo-ethoxy]ethoxy]
ethylcarbamoyl]-2-pyridyl]sulfamoyl]phenyl]ethyl]phenoxy]dodecanoic acid

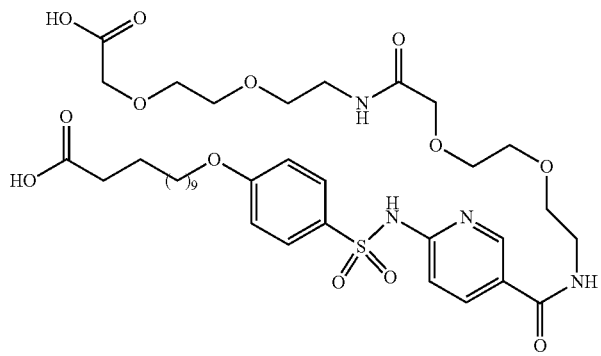

12-[4-[[5-[2-[2-[2-[2-[2-(carboxymethyloxy)ethoxy]ethoxy]ethylamino]-2-oxo-ethoxy]ethoxy]
ethylcarbamoyl]-2-pyridyl]sulfamoyl]phenoxy]dodecanoic acid

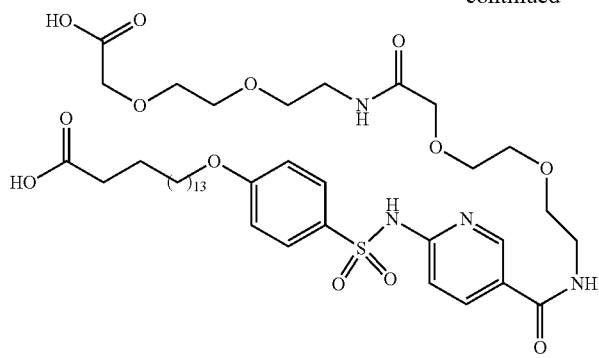

16-[4-[[5-[2-[2-[2-[2-[2-(carboxymethyloxy)ethoxy]ethylamino]-2-oxo-ethoxy]ethoxy]
ethylcarbamoyl]-2-pyridyl]sulfamoyl]phenoxy]hexadecanoic acid

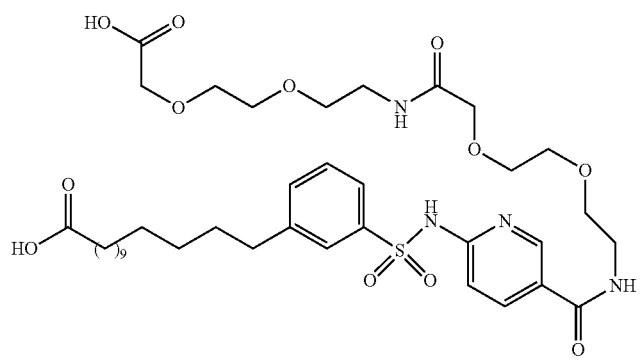

14-[3-[[5-[2-[2-[2-[2-[2-(carboxymethyloxy)ethoxy]ethylamino]-2-oxo-ethoxy]ethoxy]
ethylcarbamoyl]-2-pyridyl]sulfamoyl]phenyl]tetradecanoic acid

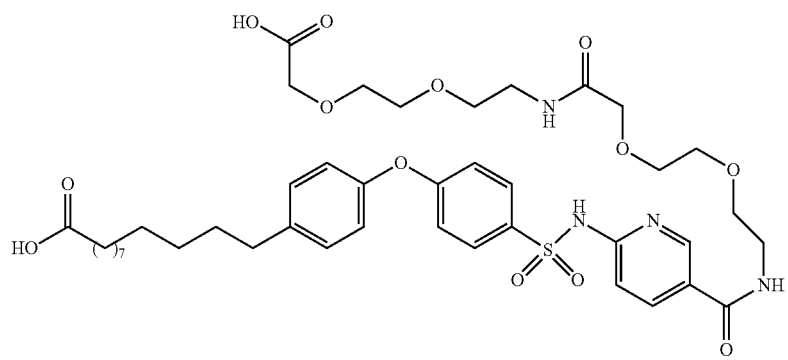

12-[4-[4-[[5-[2-[2-[2-[2-[2-(carboxymethyloxy)ethoxy]ethylamino]-2-oxo-ethoxy]ethoxy]
ethylcarbamoyl]-2-pyridyl]sulfamoyl]phenoxy]phenyl]dodecanoic acid

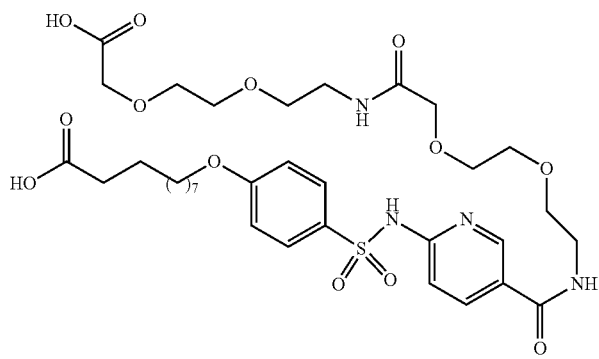

10-[4-[[5-[2-[2-[2-[2-[2-(carboxymethyloxy)ethoxy]ethylamino]-2-oxo-ethoxy]ethoxy]
ethylcarbamoyl]-2-pyridyl]sulfamoyl]phenoxy]dodecanoic acid

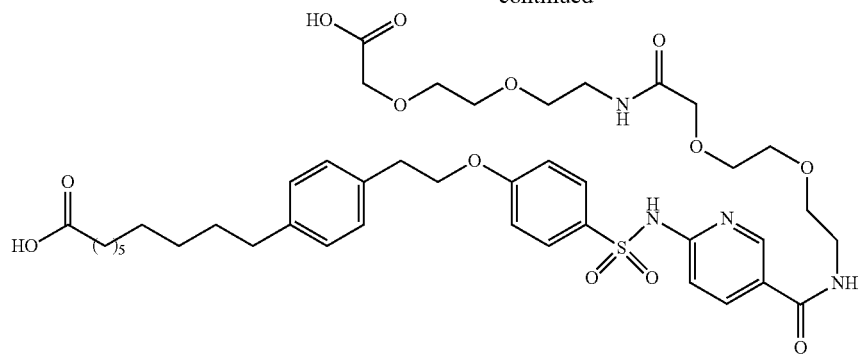

10-[4-[2-[4-[[5-[2-[2-[2-[2-[2-(carboxymethyloxy)ethoxy]ethylamino]-2-oxo-ethoxy]ethoxy]
ethylcarbamoyl]-2-pyridyl]sulfamoyl]ethyl]phenyl]dodecanoic acid

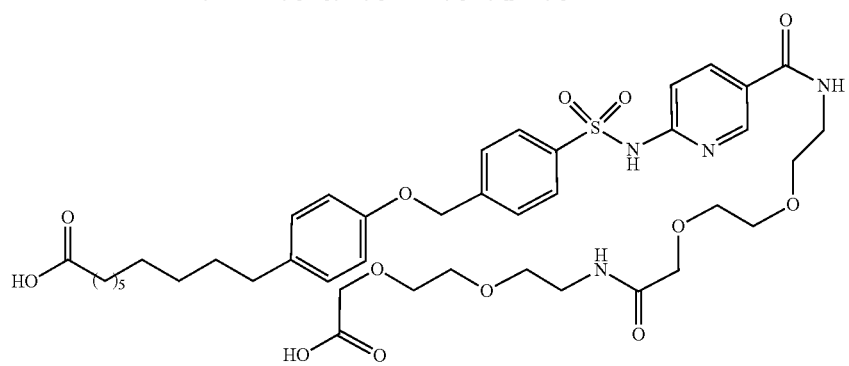

10-[4-[2-[4-[[5-[2-[2-[2-[2-[2-(carboxymethyloxy)ethoxy]ethylamino]-2-oxo-ethoxy]ethoxy]
ethylcarbamoyl]-2-pyridyl]sulfamoyl]phenyl]ethyl]phenoxy]dodecanoic acid

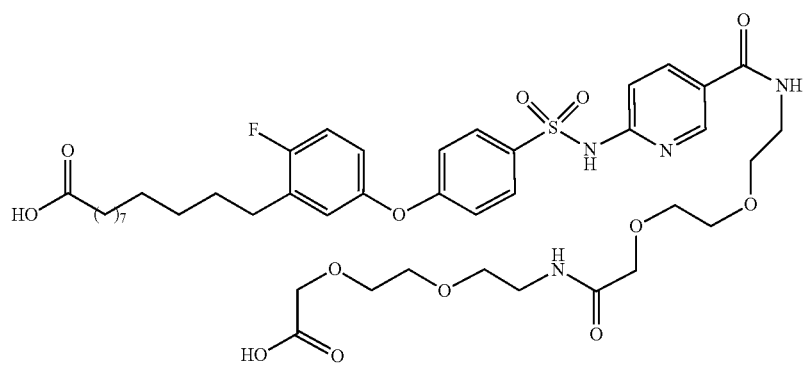

12-[5-[4-[[5-[2-[2-[2-[2-[2-(carboxymethyloxy)ethoxy]ethylamino]-2-oxo-ethoxy]ethoxy]
ethylcarbamoyl]-2-pyridyl]sulfamoyl]phenoxy]-2-fluoro-phenyl]dodecanoic acid

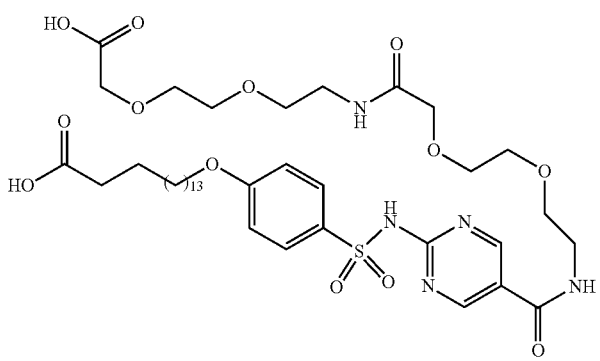

16-[4-[[5-[2-[2-[2-[2-[2-(carboxymethyloxy)ethoxy]ethylamino]-2-oxo-ethoxy]ethoxy]
ethylcarbamoyl]pyrimidin-2-yl]sulfamoyl]phenoxy]hexadecanoic acid

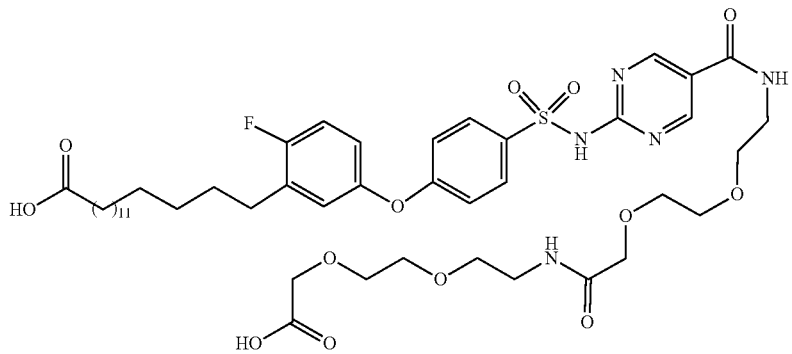

16-[5-[4-[[5-[2-[2-[2-[2-[2-(carboxymethyloxy)ethoxy]ethoxy]ethylamino]-2-oxo-ethoxy]ethoxy]
ethylcarbamoyl]pyrimidin-2-yl]sulfamoyl]phenoxy]-2-fluoro-phenyl]hexadecanoic acid

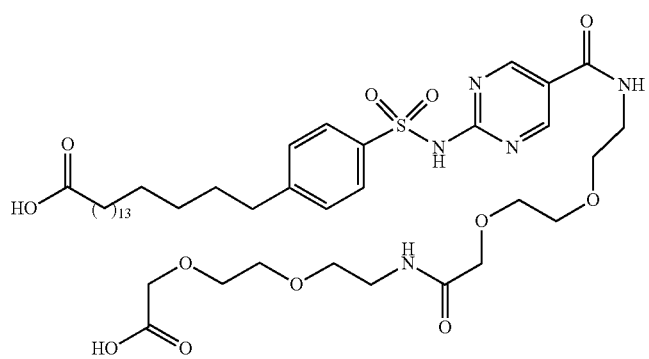

18-[4-[[5-[2-[2-[2-[2-[2-(carboxymethyloxy)ethoxy]ethoxy]ethylamino]-2-oxo-ethoxy]ethoxy]
ethylcarbamoyl]pyrimidin-2-yl]sulfamoyl]phenyl]octadecanoic acid

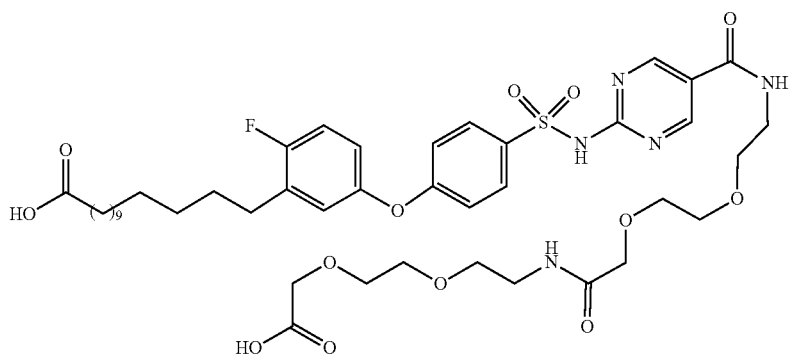

14-[5-[4-[[5-[2-[2-[2-[2-[2-(carboxymethyloxy)ethoxy]ethoxy]ethylamino]-2-oxo-ethoxy]ethoxy]
ethylcarbamoyl]pyrimidin-2-yl]sulfamoyl]phenoxy]-2-fluoro-phenyl]tetradecanoic acid

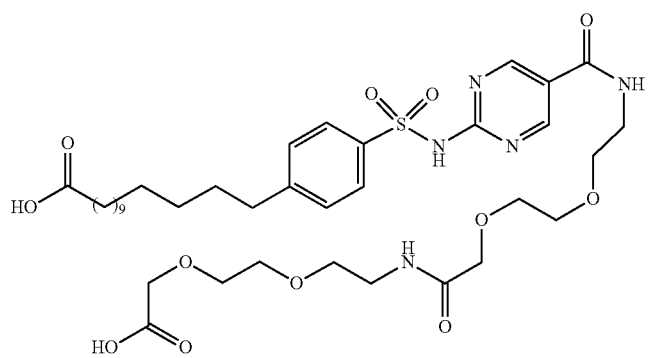

14-[4-[[5-[2-[2-[2-[2-[2-(carboxymethyloxy)ethoxy]ethoxy]ethylamino]-2-oxo-ethoxy]ethoxy]
ethylcarbamoyl]pyrimidin-2-yl]sulfamoyl]phenyl]tetradecanoic acid

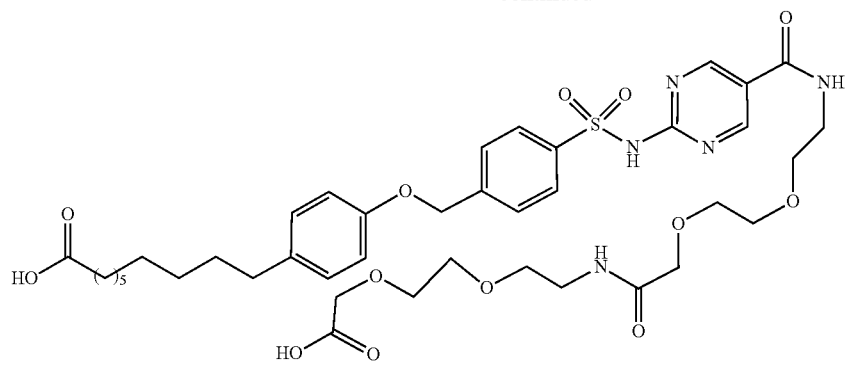

10-[4-[[4-[[5-[2-[2-[2-[2-[2-(carboxymethyloxy)ethoxy]ethylamino]-2-oxo-ethoxy]ethoxy]ethylcarbamoyl]pyrimidin-2-yl]sulfamoyl]phenyl]methoxy]pheny]decanoic acid

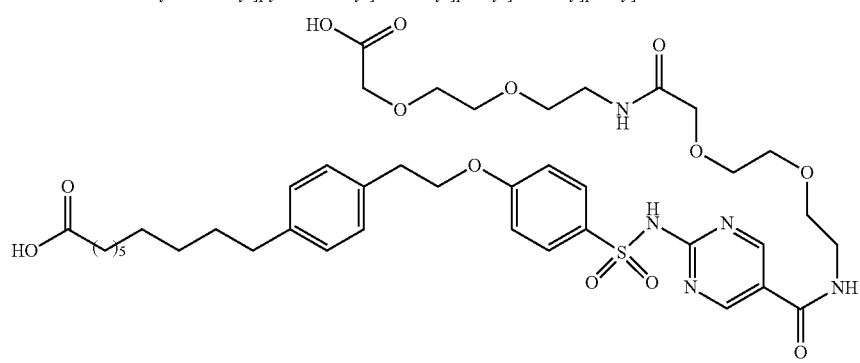

10-[4-[2-[4-[[5-[2-[2-[2-[2-[2-(carboxymethyloxy)ethoxy]ethylamino]-2-oxo-ethoxy]ethoxy]ethylcarbamoyl]pyrimidin-2-yl]sulfamoyl]phenoxy]ethyl]phenyl]decanoic acid

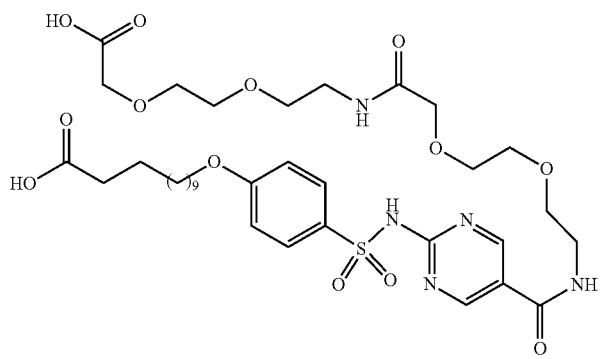

12-[4-[[5-[2-[2-[2-[2-[2-(carboxymethyloxy)ethoxy]ethylamino]-2-oxo-ethoxy]ethoxy]ethylcarbamoyl]pyrimidin-2-yl]sulfamoyl]phenoxy]dodecanoic acid

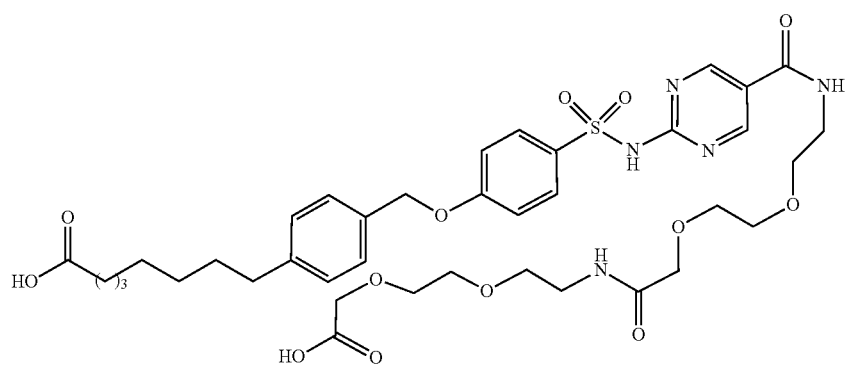

8-[4-[[4-[[5-[2-[2-[2-[2-[2-(carboxymethyloxy)ethoxy]ethylamino]-2-oxo-ethoxy]ethoxy]ethylcarbamoyl]pyrimidin-2-yl]sulfamoyl]phenoxy]methyl]pheny]octanoic acid

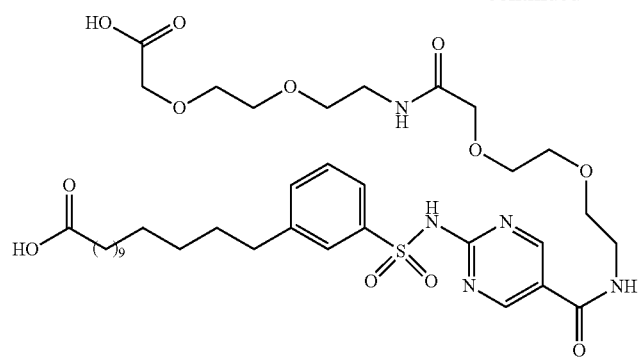

14-[3-[[5-[2-[2-[2-[2-[2-(carboxymethyloxy)ethoxy]ethoxy]ethylamino]-2-oxo-ethoxy]ethoxy]
ethylcarbamoyl]pyrimidin-2-yl]sulfamoyl]phenyl]tetradecanoic acid

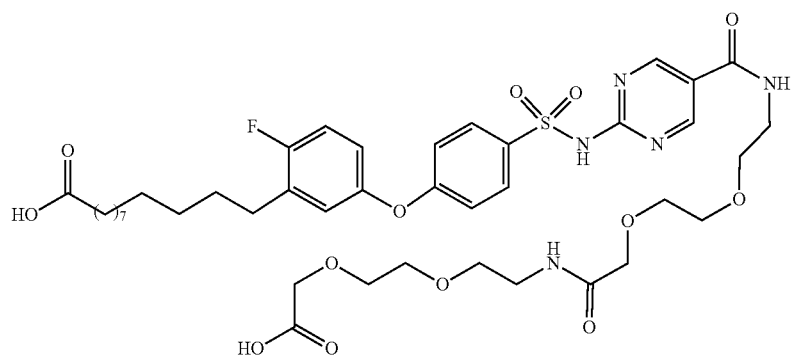

12-[5-[4-[[5-[2-[2-[2-[2-[2-(carboxymethyloxy)ethoxy]ethoxy]ethylamino]-2-oxo-ethoxy]ethoxy]
ethylcarbamoyl]pyrimidin-2-yl]sulfamoyl]phenoxy]-2-fluoro-phenyl]dodecanoic acid

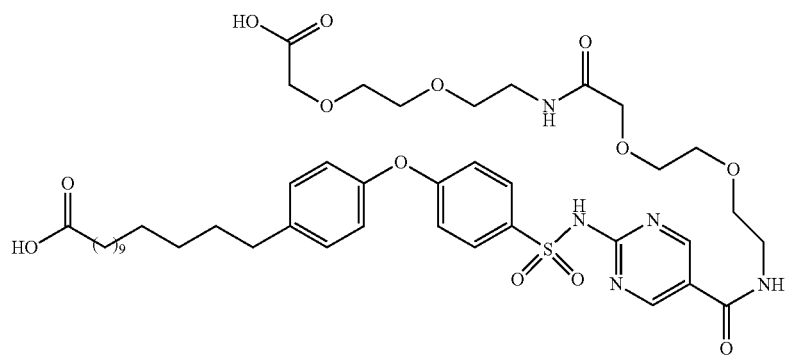

14-[4-[4-[[5-[2-[2-[2-[2-[2-(carboxymethyloxy)ethoxy]ethoxy]ethylamino]-2-oxo-ethoxy]ethoxy]
ethylcarbamoyl]pyrimidin-2-yl]sulfamoyl]phenoxy]phenyl]tetradecanoic acid

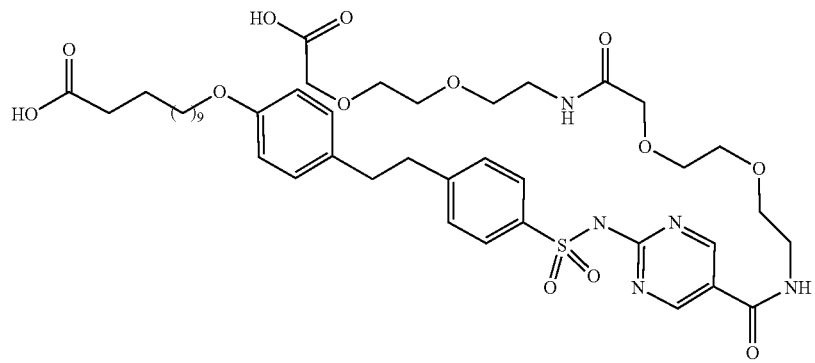

12-[4-[2-[4-[[5-[2-[2-[2-[2-[2-(carboxymethyloxy)ethoxy]ethoxy]ethylamino]-2-oxo-ethoxy]ethoxy]
ethylcarbamoyl]pyrimidin-2-yl]sulfamoyl]phenyl]ethyl]phenoxy]dodecanoic acid

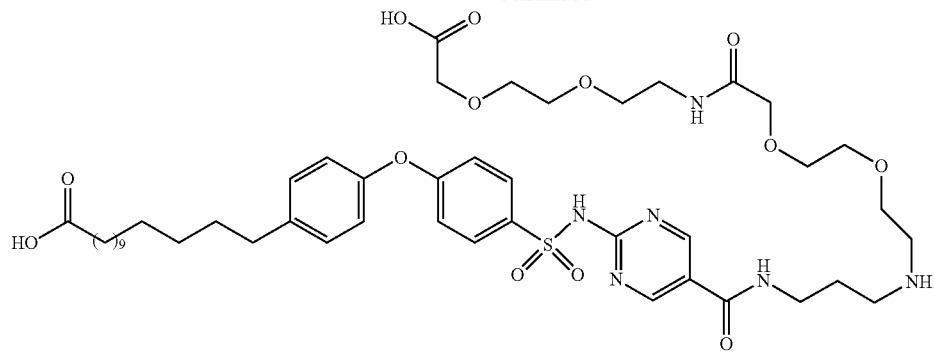

14-[4-[2-[4-[[5-[2-[2-[2-[2-(carboxymethyloxy)ethoxy]ethylamino]-2-oxo-ethoxy]ethoxy]ethylamino]-3-oxo-propyl]carbamoyl]pyrimidin-2-yl]sulfamoyl]phenoxy]phenyl]tetradecanoic acid

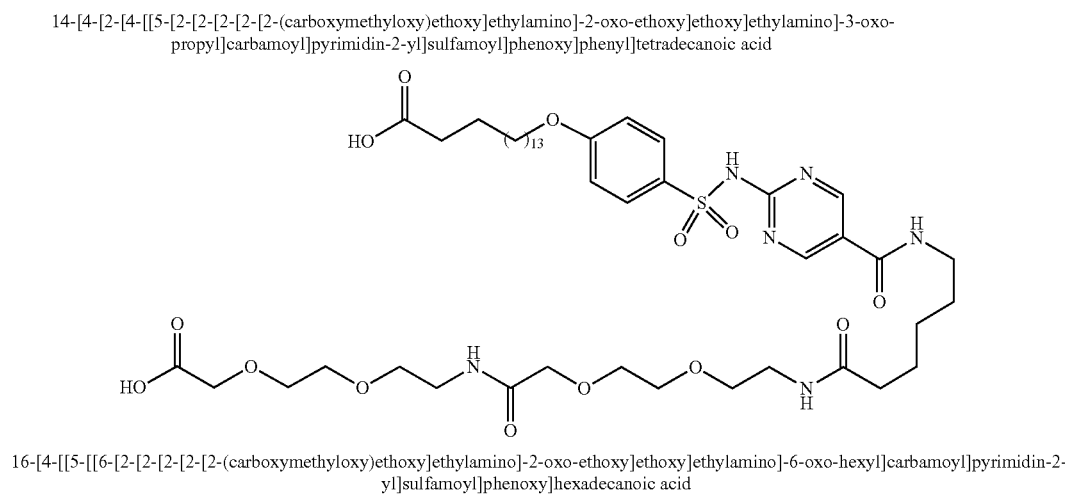

16-[4-[[5-[[6-[2-[2-[2-[2-(carboxymethyloxy)ethoxy]ethylamino]-2-oxo-ethoxy]ethoxy]ethylamino]-6-oxo-hexyl]carbamoyl]pyrimidin-2-yl]sulfamoyl]phenoxy]hexadecanoic acid

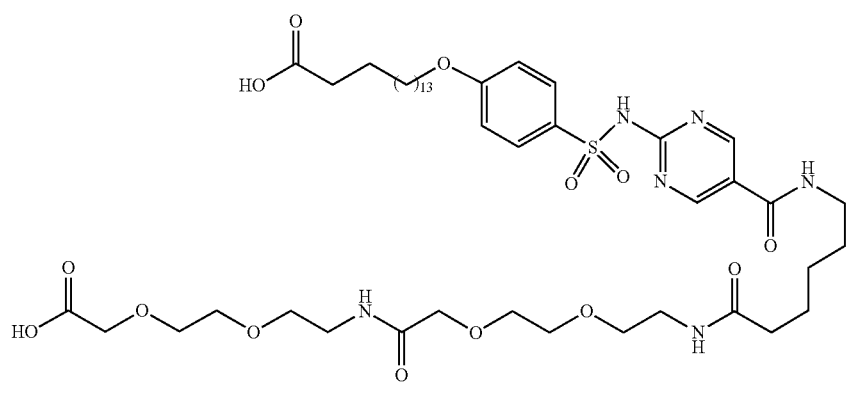

16-[4-[[5-[[6-[2-[2-[2-[2-(carboxymethyloxy)ethoxy]ethylamino]-2-oxo-ethoxy]ethoxy]ethylamino]-6-oxo-hexyl]carbamoyl]-2-pyridyl]sulfamoyl]phenoxy]hexadecanoic acid

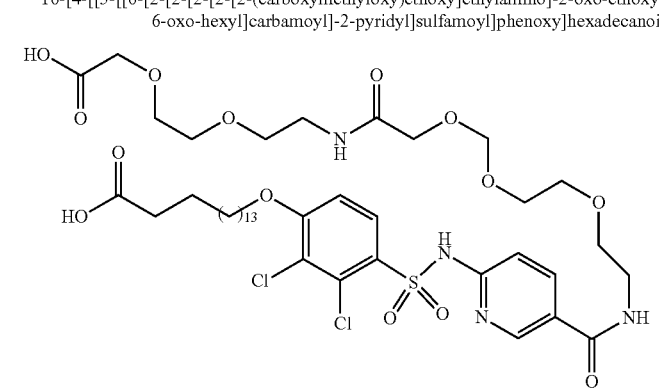

16-[4-[[5-[2-[2-[2-[2-[2-(carboxymethyloxy)ethoxy]ethylamino]-2-oxo-ethoxy]ethoxy]ethylcarbamoyl]-2-pyridyl]sulfamoyl]-2,3-dichloro-phenoxy]hexadecanoic acid

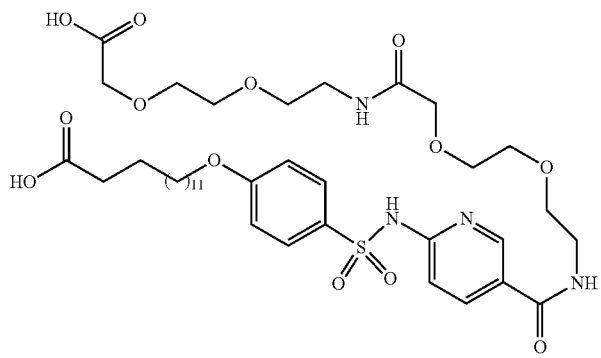

14-[4-[[5-[2-[2-[2-[2-[2-(carboxymethyloxy)ethoxy]ethylamino]-2-oxo-ethoxy]ethoxy]
ethylcarbamoyl]-2-pyridyl]sulfamoyl]phenoxy]tetradecanoic acid

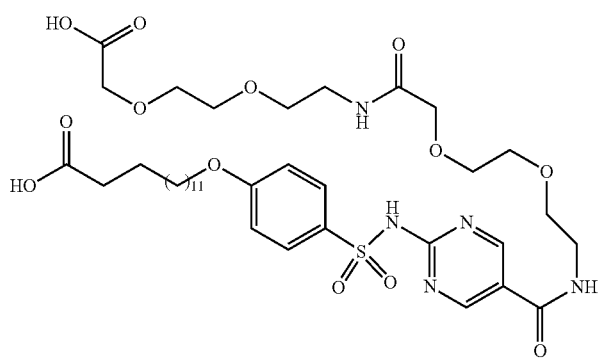

14-[4-[[5-[2-[2-[2-[2-[2-(carboxymethyloxy)ethoxy]ethylamino]-2-oxo-ethoxy]ethoxy]
ethylcarbamoyl]pyrimidin-2-yl]sulfamoyl]phenoxy]tetradecanoic acid

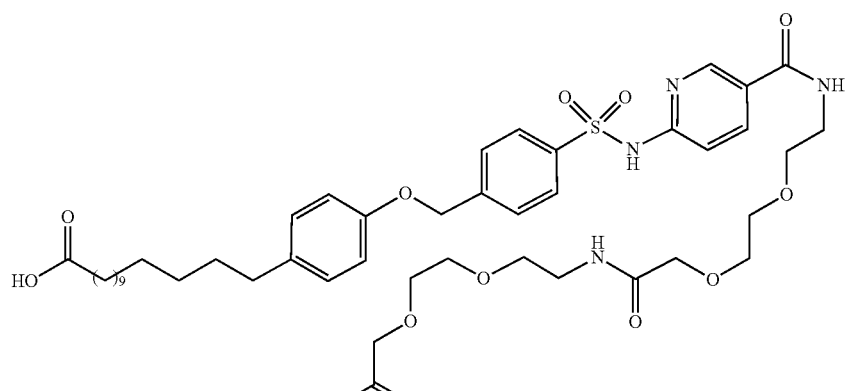

14-[4-[[4-[[5-[2-[2-[2-[2-[2-(carboxymethyloxy)ethoxy]ethylamino]-2-oxo-ethoxy]ethoxy]
ethylcarbamoyl]-2-pyridyl]sulfamoyl]phenyl]methoxy]pheny]tetradecanoic acid

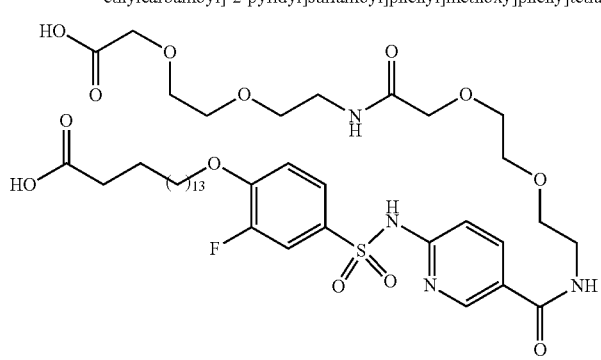

16-[4-[[5-[2-[2-[2-[2-[2-(carboxymethyloxy)ethoxy]ethylamino]-2-oxo-ethoxy]ethoxy]
ethylcarbamoyl]-2-pyridyl]sulfamoyl]-2-fluoro-phenoxy]hexadecanoic acid

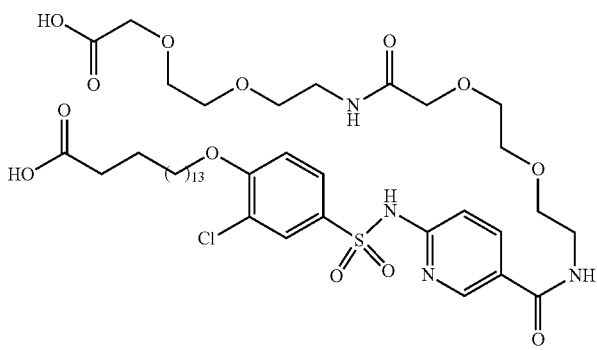

16-[4-[[5-[2-[2-[2-[2-(carboxymethyloxy)ethoxy]ethoxy]ethylamino]-2-oxo-ethoxy]ethoxy]
ethylcarbamoyl]-2-pyridyl]sulfamoyl]-2-chloro-phenoxy]hexadecanoic acid

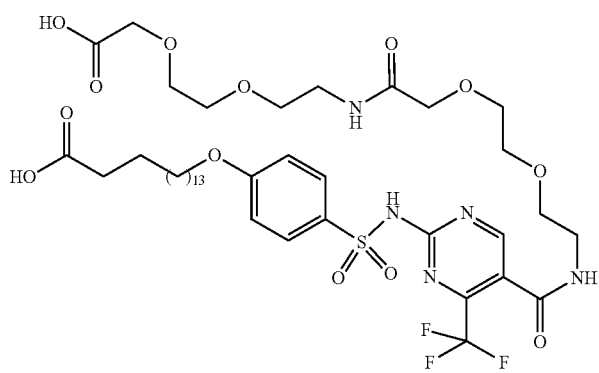

16-[4-[[5-[2-[2-[2-[2-(carboxymethyloxy)ethoxy]ethoxy]ethylamino]-2-oxo-ethoxy]ethoxy]
ethylcarbamoyl]-4-(trifluoromethyl)pyrimidin-2-yl]sulfamoyl]phenoxy]hexadecanoic acid

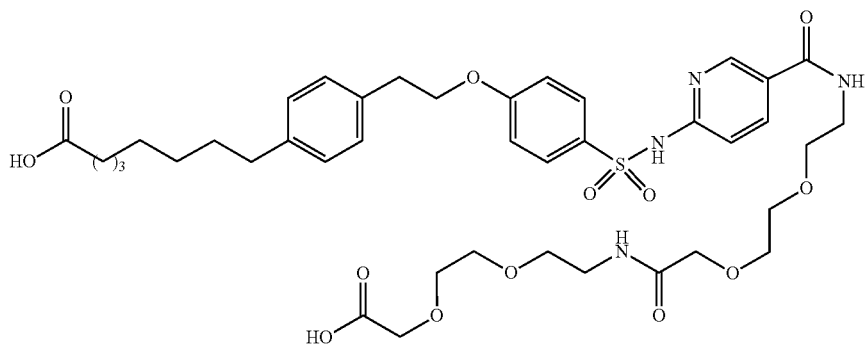

8-[4-[2-[4-[[5-[2-[2-[2-[2-(carboxymethyloxy)ethoxy]ethoxy]ethylamino]-2-oxo-ethoxy]ethoxy]
ethylcarbamoyl]-2-pyridyl]sulfamoyl]phenoxy]ethyl]phenyl]octanoic acid

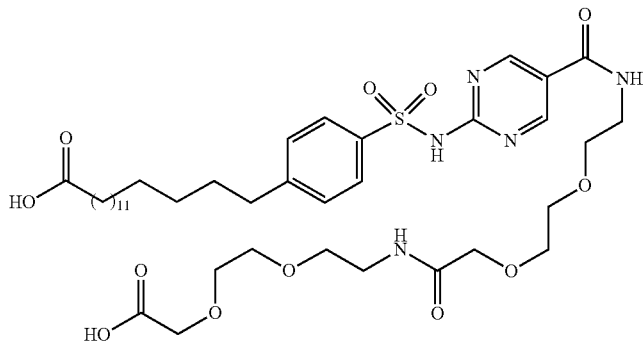

16-[4-[[5-[2-[2-[2-[2-(carboxymethyloxy)ethoxy]ethoxy]ethylamino]-2-oxo-ethoxy]ethoxy]ethyl
carbamoyl]-2-pyridyl]sulfamoyl]phenyl]hexadecanoic acid

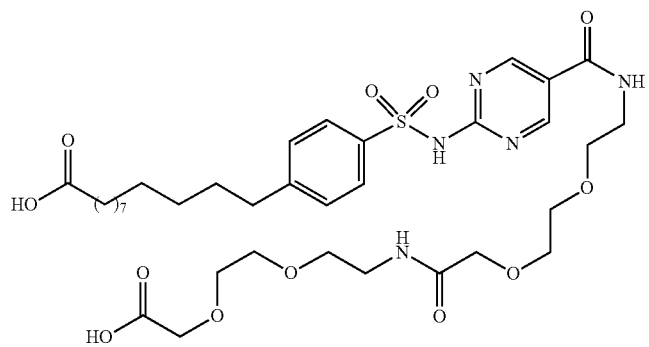

12-[4-[[5-[2-[2-[2-[2-[2-(carboxymethyloxy)ethoxy]ethoxy]ethylamino]-2-oxo-ethoxy]ethoxy]ethyl carbamoyl]pyrimidin-2-yl]sulfamoyl]phenyl]dodecanoic acid

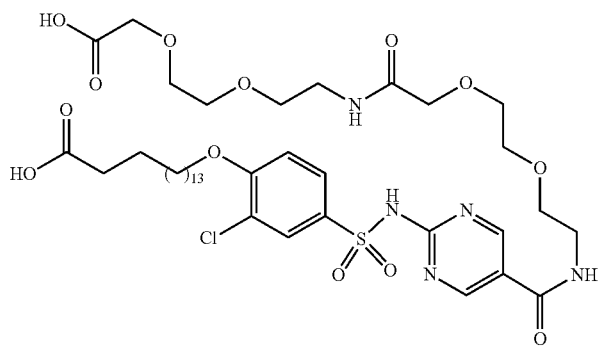

16-[4-[[5-[2-[2-[2-[2-[2-(carboxymethyloxy)ethoxy]ethylamino]-2-oxo-ethoxy]ethoxy] ethylcarbamoyl]pyrimidin-2-yl]sulfamoyl]-2-chloro-phenoxy]hexadecanoic acid

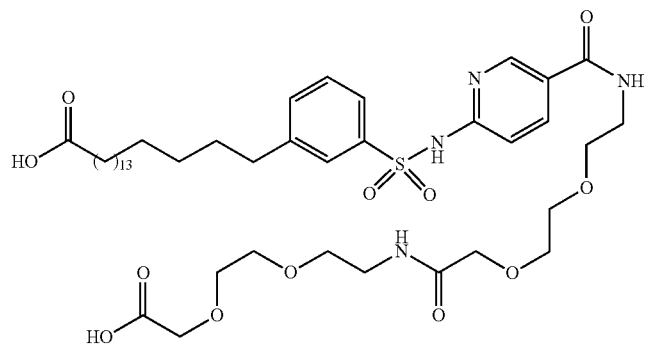

18-[3-[[5-[2-[2-[2-[2-[2-(carboxymethyloxy)ethoxy]ethoxy]ethylamino]-2-oxo-ethoxy]ethoxy] ethylcarbamoyl]-2-pyridyl]sulfamoyl]phenyl]octadecanoic acid

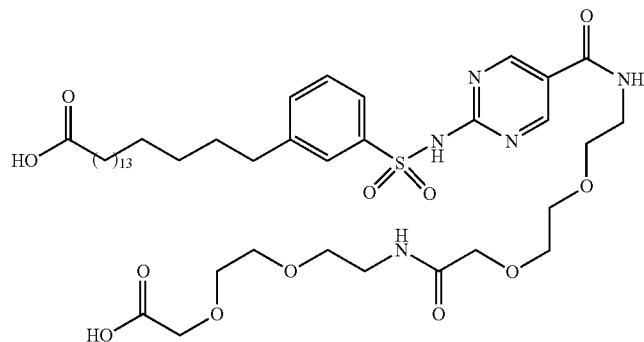

18-[3-[[5-[2-[2-[2-[2-[2-(carboxymethyloxy)ethoxy]ethoxy]ethylamino]-2-oxo-ethoxy]ethoxy] ethylcarbamoyl]pyrimidin-2-yl]sulfamoyl]phenyl]octadecanoic acid

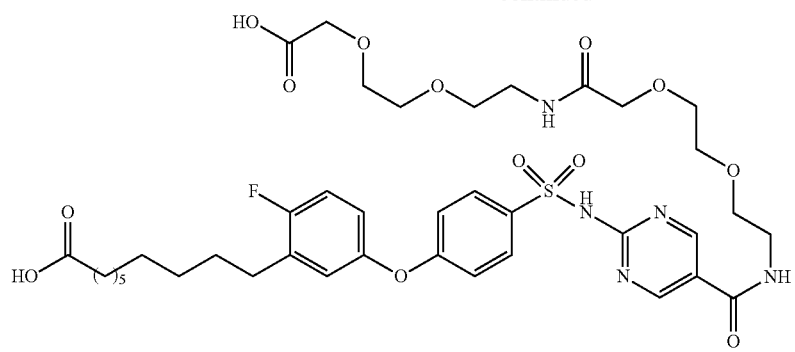

10-[4-[4-[[5-[2-[2-[2-[2-[2-(carboxymethyloxy)ethoxy]ethoxy]ethylamino]-2-oxo-ethoxy]ethoxy]
ethylcarbamoyl]pyrimidin-2-yl]sulfamoyl]phenoxy]phenyl]decanoic acid

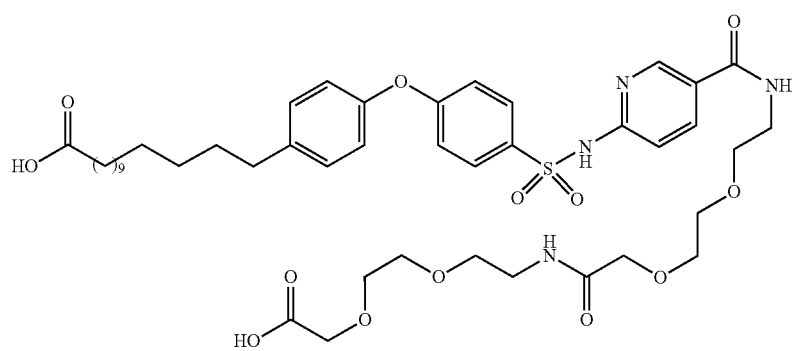

14-[4-[[5-[2-[2-[2-[2-[2-(carboxymethyloxy)ethoxy]ethoxy]ethylamino]-2-oxo-ethoxy]ethoxy]
ethylcarbamoyl]-2-pyridyl]sulfamoyl]phenoxy]phenyl]tetradecanoic acid

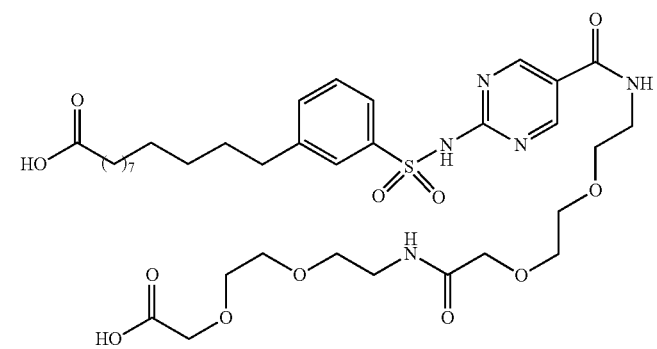

12-[3-[[5-[2-[2-[2-[2-[2-(carboxymethyloxy)ethoxy]ethoxy]ethylamino]-2-oxo-ethoxy]ethoxy]
ethylcarbamoyl]pyrimidin-2-yl]sulfamoyl]phenyl]dodecanoic acid

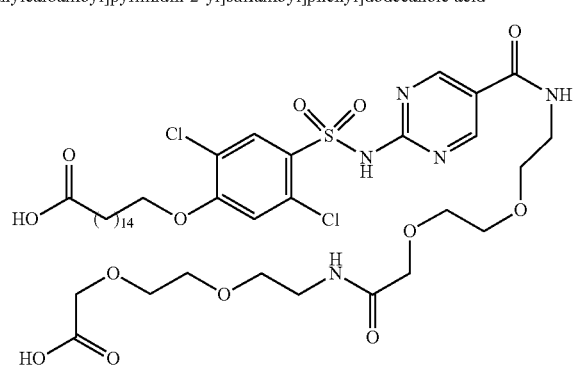

16-[4-[[5-[2-[2-[2-[2-[2-(carboxymethyloxy)ethoxy]ethoxy]ethylamino]-2-oxo-ethoxy]ethoxy]ethyl
carbamoyl]pyrimidin-2-yl]sulfamoyl]-2,5-dichloro-phenoxy]hexadecanoic acid

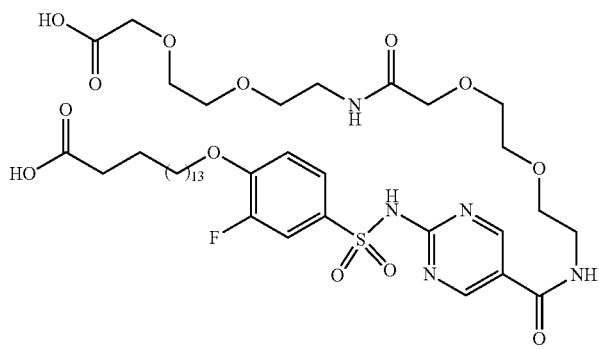

16-[4-[[5-[2-[2-[2-[2-[2-(carboxymethyloxy)ethoxy]ethylamino]-2-oxo-ethoxy]ethoxy]
ethylcarbamoyl]pyrimidin-2-yl]sulfamoyl]-2-fluoro-phenoxy]hexadecanoic acid

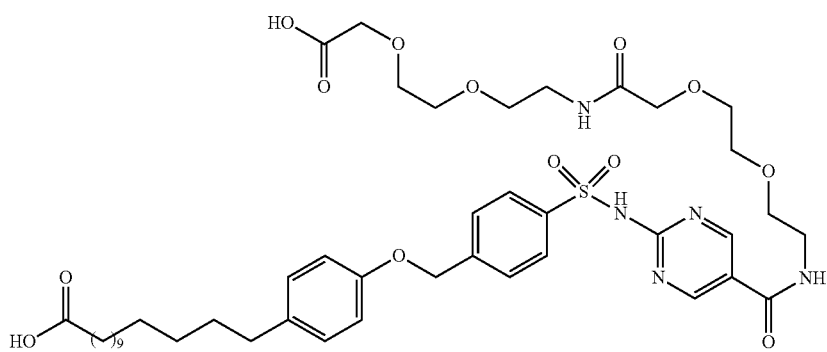

14-[4-[[4-[[5-[2-[2-[2-[2-[2-(carboxymethyloxy)ethoxy]ethylamino]-2-oxo-ethoxy]ethoxy]
ethylcarbamoyl]pyrimidin-2-yl]sulfamoyl]phenyl]methoxy]phenyl]tetradecanoic acid

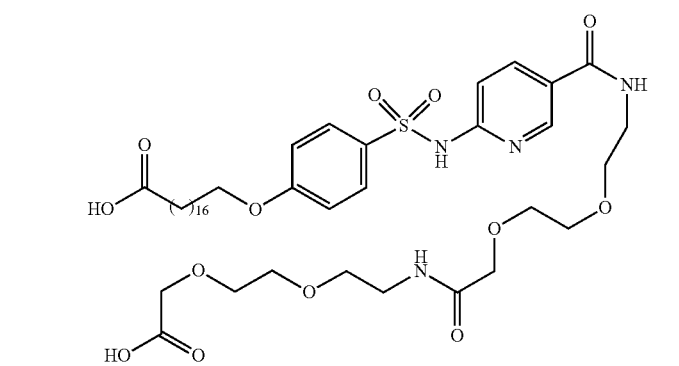

18-[4-[[5-[2-[2-[2-[2-[2-(carboxymethyloxy)ethoxy]ethylamino]-2-oxo-ethoxy]ethoxy]ethyl
carbamoyl]-2-pyridyl]sulfamoyl]phenoxy]octadecanoic acid

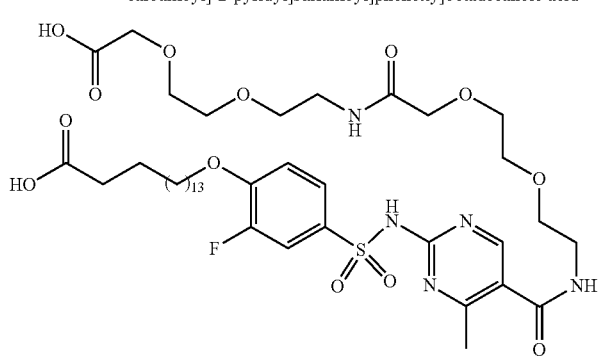

16-[4-[[5-[2-[2-[2-[2-[2-(carboxymethyloxy)ethoxy]ethylamino]-2-oxo-ethoxy]ethoxy]
ethylcarbamoyl]-4-methyl-pyrimidin-2-yl]sulfamoyl]phenoxy]hexadecanoic acid

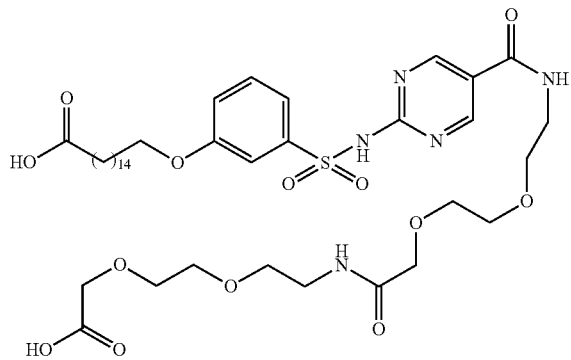

16-[3-[[5-[2-[2-[2-[2-[2-(carboxymethyloxy)ethoxy]ethylamino]-2-oxo-ethoxy]ethoxy]ethyl carbamoyl]pyrimidin-2-yl]sulfamoyl]phenoxy]hexadecanoic acid

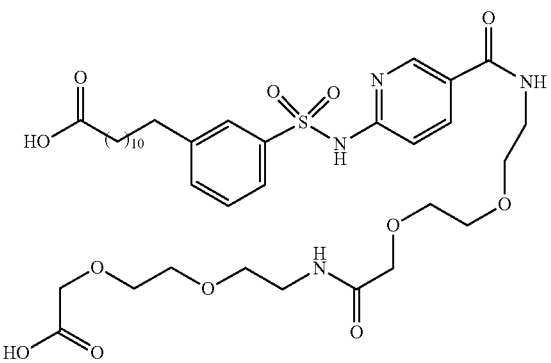

12-[3-[[5-[2-[2-[2-[2-[2-(carboxymethyloxy)ethoxy]ethylamino]-2-oxo-ethoxy]ethoxy]ethyl carbamoyl]-2-pyridyl]sulfamoyl]phenyl]dodecanoic acid

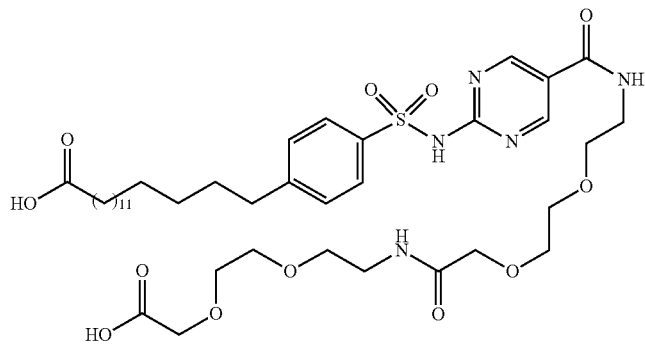

16-[4-[[5-[2-[2-[2-[2-[2-(carboxymethyloxy)ethoxy]ethylamino]-2-oxo-ethoxy]ethoxy]ethyl carbamoyl]pyrimidin-2-yl]sulfamoyl]phenyl]-hexadecanoic acid

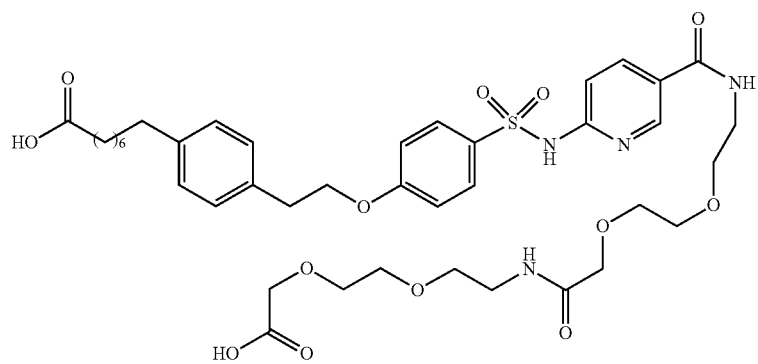

8-[4-[2-[4-[[5-[2-[2-[2-[2-[2-(carboxymethyloxy)ethoxy]ethylamino]-2-oxo-ethoxy]ethoxy]ethyl carbamoyl]-2-pyridyl]sulfamoyl]phenoxy]ethyl]phenyl]octanoic acid -continued

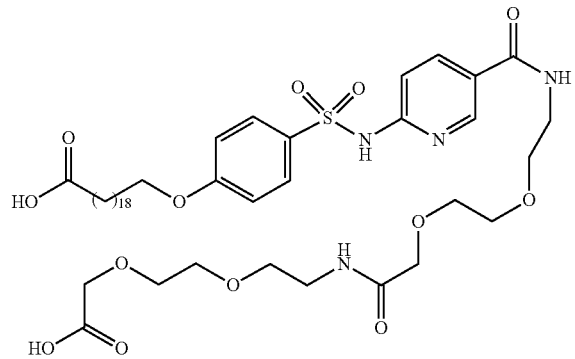

20-[4-[[5-[2-[2-[2-[2-[2-(carboxymethyloxy)ethoxy]ethylamino]-2-oxo-ethoxy]ethoxy]ethyl carbamoyl]-2-pyridyl]sulfamoyl]phenoxy]icosanoic acid

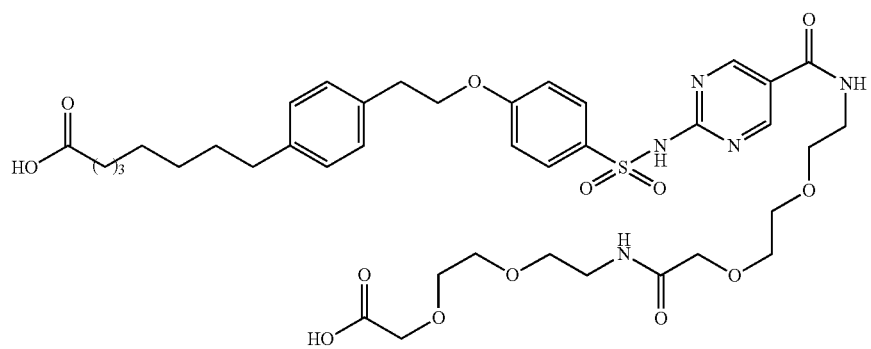

8-[4-[2-[4-[[5-[2-[2-[2-[2-[2-(carboxymethyloxy)ethoxy]ethylamino]-2-oxo-ethoxy]ethoxy]ethyl carbamoyl]pyrimidin-2-yl]sulfamoyl]phenoxy]hexadecanoic acid

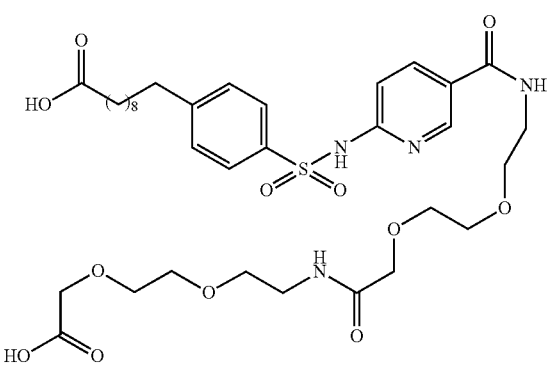

10-[4-[[5-[2-[2-[2-[2-[2-(carboxymethyloxy)ethoxy]ethylamino]-2-oxo-ethoxy]ethoxy]ethyl carbamoyl]-2-pyridyl]sulfamoyl]phenyl]decanoic acid

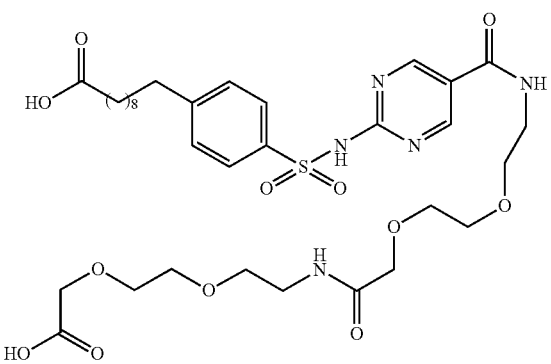

10-[4-[[5-[2-[2-[2-[2-[2-(carboxymethyloxy)ethoxy]ethylamino]-2-oxo-ethoxy]ethoxy]ethyl carbamoyl]pyrimidin-2-yl]sulfamoyl]phenyl]decanoic acid -continued

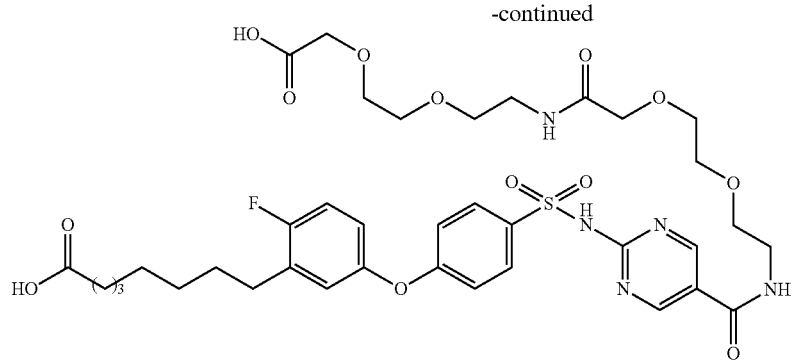

8-[5-[4-[[5-[2-[2-[2-[2-[2-(carboxymethyloxy)ethoxy]ethylamino]-2-oxo-ethoxy]ethoxy]
ethylcarbamoyl]pyrimidin-2-yl]sulfamoyl]phenoxy]-2-fluoro-phenyl]octanoic acid

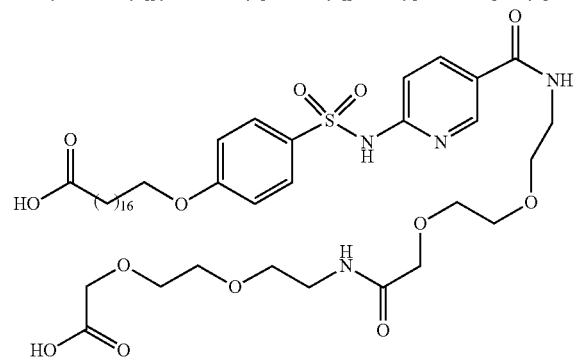

18-[4-[[5-[2-[2-[2-[2-[2-(carboxymethyloxy)ethoxy]ethylamino]-2-oxo-ethoxy]ethoxy]ethyl
carbamoyl]pyrimidin-2-yl]sulfamoyl]phenoxy]octadecanoic acid

3. Insulins and Conjugate Synthesis

3.1 Human Insulin

The amino acid sequences of the A and B chain of human insulin are:

A-chain:
(SEQ ID NO: 102)
GIVEQCCTSICSLYQLENYCN

B-chain:
(SEQ ID NO: 103)
FVNQHLCGSHLVEALYLVCGERGFFYTPKT

An intrachenar disulfide bridge is present between Cys (A6) amd Cys(A11), two interchenar disulfide bridges are present between Cys(A7) and Cys(B7) and between Cys (A20) and (Cys(B19).

3.2 Insulin Analog 41

Insulin analog 41 is based on human insulin with mutations in positions A14, B16, B25 and a removal of the amino acid at position B30:
Glu(A14): The amino acid at position 14 of the A-chain of human insulin (Y, tyrosine, Tyr) is substituted by glutamic acid (E, Glu),
His(B16): The amino acid at position 16 of the B-chain of human insulin (Y, tyrosine, Tyr) is substituted by histidine (H, His),
His(B25): The amino acid at position 25 of the B-chain of human insulin (F, phenylalanine, Phe) is substituted by histidine (H, His), Des(B30): The amino acid at position 30 of the B-chain of human insulin is deleted.

The complete amino acid sequence of insulin analog 41 in view of A and B chain is:

A-chain:
(SEQ ID NO: 104)
GIVEQCCTSICSLEQLENYCN

B-chain:
(SEQ ID NO: 105)
FVNQHLCGSHLVEALHLVCGERGFHYTPK-

The one intrachenar and the two interchenar disulfide bridges are in accordance with human insulin.

3.3 Conjugate with Human Insulin/Synthesis of [16-[4-[[5-[2-[2-[2-[2-[2-(carboxymethyloxy)ethoxy]ethylamino]-2-oxo-ethoxy]ethoxy]ethylcarbamoyl]pyrimidin-2-yl]sulfamoyl]phenoxy]hexadecanoic acid]Lys(B29)-insulin A conjugate was prepared from human insulin according to 3.1 and 2-[2-[2-[[2-[2-[2-[[2-[[4-(16-tert-butoxy-16-oxo-hexadecoxy) phenyl]sulfonylamino]pyrimidine-5-carbonyl]amino]ethoxy]ethoxy]acetyl]amino]ethoxy]ethoxy]acetic acid from Example 2.9:

Synthesis of 16-[4-[[5-[2-[2-[2-[2-[2-[2-(2,5-di-oxopyrrolidin-1-yl) oxy-2-oxo-ethoxy]ethoxy]ethylamino]-2-oxo-ethoxy]ethoxy]ethylcarbamoyl]pyrimidin-2-yl]sulfamoyl]phenoxy]hexadecanoate To a solution of 296 mg 2-[2-[2-[[2-[2-[2-[[4-(16-tert-butoxy-16-oxo-hexadecoxy) phenyl]sulfonylamino]pyrimidine-5-carbonyl]amino]ethoxy]ethoxy]acetyl]amino]-ethoxy]ethoxy]acetic acid in 9 ml DMF, 92.7 µl triethylamine, 106 mg TSTU and a trace of DMAP were added. The solution was stirred for one hour. 100 ml methylene chloride were added and the resulting solution was washed three times with 50 ml brine. The organic layer was separated, dried with sodium sulfate, filtered and concentrated in vacuo. The crude product was taken up in 11 ml methylene chloride and 5.5 ml trifluoro acetic acid and stored overnight in at 5° C.

The solution was concentrated. Then, the crude product was three times dissolved in 30 ml methylene chloride and evaporated. The solid material was suspended in 5 ml methyl tert-butyl ether, the ether decanted. The residue was dried in vacuo and used without further purification.

A solution of 480 mg insulin was suspended in 25 ml water and then 0.45 ml triethylamine was added. To the clear solution, 25 ml MeCN and then 0.9 ml (45.89 mM in DMF) 16-[4-[[5-[2-[2-[2-[2-[2-[2-(2,5-dioxopyrrolidin-1-yl)oxy-2-oxo-ethoxy]ethoxy]ethylamino]-2-oxo-ethoxy]ethoxy]ethylcarbamoyl]pyrimidin-2-yl]sulfamoyl]phenoxy]hexadecanoate were added. The solution was stirred for 3 hours at room temperature. The reaction was analyzed with waters UPLC H-class at 214 nm in a sodium chloride phosphate buffer. Waters BEH300 10 cm. Retention time insulin: 3.85 min. Rentention time insulin conjugate 6.46 min. The product was purified by HPLC with ÄKTA avant 25. Kinetex 5 µm C18 100 A 250×21.2 mm. Column volume (CV) 88 ml.

Column volume (CV) 88 ml.
Solvent A: 0.5% acetic acid in water
Solvent B: 0.5 acetic acid in water/MeCN 2:8
Gradient: 95% A5% B to 40% A 60% B in 14 CV The reaction was analyzed with Waters UPLC H-class at 214 nm in a sodium chloride phosphate buffer. Waters BEH300 10 cm. Retention time insulin conjugate: 6.419 min. The solution was lyophilized and gave the desired product. 93 mg 34% yield. Mass spec.: 6629.6 g/mol.

3.4 Conjugates with Insulin Analog 41

Conjugates of insulin analog 41 according to 3.2 were prepared with binder molecules from Example 2.9 (for the structure, see also Table 1):

Binder 5: 16-[4-[[5-[2-[2-[2-[2-[2-(carboxymethyloxy)ethoxy]ethylamino]-2-oxo-ethoxy]ethoxy] ethylcarbamoyl]pyrimidin-2-yl]sulfamoyl]phenoxy]hexadecanoic acid; tert-butyl ester: 2-[2-[2-[[2-[2-[2-[[2-[[4-(16-tert-butoxy-16-oxo-hexadecoxy) phenyl]sulfonylamino]pyrimidine-5-carbonyl]amino]ethoxy]ethoxy]acetyl]amino]ethoxy]ethoxy]acetic acid Binder 8: 14-[5-[4-[[5-[2-[2-[2-[2-[2-(carboxymethyloxy)ethoxy]ethylamino]-2-oxo-ethoxy]ethoxy] ethylcarbamoyl]pyrimidin-2-yl]sulfamoyl]phenoxy]-2-fluoro-phenyl] tetradecanoic acid; tert-butyl ester: 2-[2-[2-[[2-[2-[2-[[5-[[4-[3-(14-tert-butoxy-14-oxo-tetradecyl)-4-fluoro-phenoxy]phenyl] sulfonylamino] pyrimidine-2-carbonyl]amino]ethoxy]ethoxy]acetyl]amino]ethoxy]ethoxy]acetic acid Binder 50: 16-[4-[[5-[2-[2-[2-[2-[2-(carboxymethyloxy)ethoxy]ethylamino]-2-oxo-ethoxy]ethoxy]ethylcarbamoyl]pyrimidin-2-yl]sulfamoyl]-2-chloro-phenoxy]hexadecanoic acid; tert-butyl ester: 2-[2-[2-[[2-[2-[2-[[2-[[4-(16-tert-butoxy-16-oxo-hexadecoxy)-3-chloro-phenyl] sulfonylamino]pyrimidine-5-carbonyl]amino]ethoxy]ethoxy]acetyl]amino]ethoxy]ethoxy]acetic acid Binder 54: 16-[4-[[5-[2-[2-[2-[2-[2-(carboxymethyloxy)ethoxy]ethylamino]-2-oxo-ethoxy]ethoxy]ethylcarbamoyl]pyrimidin-2-yl]sulfamoyl]phenyl]hexadecanoic acid; and tert-butyl ester: 2-[2-[2-[[2-[2-[2-[[2-[[4-(16-tert-butoxy-16-oxo-hexadecyl)phenyl]sulfonylamino]pyrimidine-5-carbonyl]amino]ethoxy]ethoxy]acetyl]amino]ethoxy]ethoxy]acetic acid

3.4.1 Synthesis of Glu(A14)His(B16)His(B25)[16-[4-[[5-[2-[2-[2-[2-[2-(carboxymethyloxy)ethoxy]ethylamino]-2-oxoethoxy]ethoxy]-ethylcarbamoyl]pyrimidin-2-yl]sulfamoyl]phenoxy]hexadecanoic acid]Lys(B29)Des(B30)-insulin An amide bond was formed between the ε-amino group of lysine B29 and the activated acetic acid residue of the binder in its tert-butyl ester form 2-[2-[2-[[2-[2-[2-[[2-[[4-(16-tert-butoxy-16-oxo-hexadecoxy) phenyl]sulfonylamino]pyrimidine-5-carbonyl]amino]-ethoxy]ethoxy]acetyl]amino]ethoxy]ethoxy]acetic as follows:

A solution of 400 mg of insulin analog 41 (Glu(A14)His(B16)His(B25)Des(B30)-insulin according to Example 3.2) was suspended in 20 ml water and then 0.4 ml triethylamine was added. To the clear solution, 20 ml DMF and then 5 ml (17.04 mM in DMF) tert-butyl 16-[4-[[5-[2-[2-[2-[2-[2-[2-(2,5-dioxopyrrolidin-1-yl)oxy-2-oxo-ethoxy]ethoxy]ethylamino]-2-oxo-ethoxy]ethoxy]ethylcarbamoyl]pyrimidin-2-yl]sulfamoyl]phenoxy]hexadecanoate) were added. The solution was stirred for 2 hours at room temperature. The reaction was analyzed with Waters UPLC H-class at 214 nm in a sodium chloride phosphate buffer.

Waters BEH300 10 cm.

Retention time insulin: 2.643 min.

Rentention time insulin conjugate 6.224 min.

The product was purified by HPLC with ÄKTA avant 25. Kinetex 5 µm C18 100 A 250×21.2 mm. Column volume (CV) 88 ml.

Solvent A: 0.5% acetic acid in water

Solvent B: 0.5% acetic acid in water/MeCN 4:6

Gradient: 80% A 20% B to 20% A 80% B in 10 CV

After lyophylisation of the product, the powder was dissolved in 2 ml trifluoroacetic acid. After one hour, the solution was neutralized with diluted sodium bicarbonate. The product was purified by HPLC with ÄKTA avant 25. Kinetex 5 µm C18 100 A 250×21.2 mm. Column volume (CV) 88 ml.

Solvent A: 0.5% acetic acid in water

Solvent B: 0.5% acetic acid in water/MeCN 4:6

Gradient: 70% A 30% B to 30% A 70% B in 8 CV

The reaction was analyzed with waters UPLC H-class at 214 nm in a sodium chloride phosphate buffer.

Waters BEH300 10 cm.

Retention time insulin conjugate: 5.121 min.

The solution was lyophilized and gave the desired product.

63 mg 14% yield.

Mass spec.: 6453.9 g/mol.

Conjugates of Binders 8, 50 and 54 and insulin analog 41 were prepared accordingly.

4. Analytical Data

4.1 Liquid Chromatography Mass Spectrometry (LCMS) Analysis

| Mass spectrometry Method | Method description | Mass spectrometry type |
|---|---|---|
| a | Waters SQD Single Quadrupol, 0.13 s scantime for mass 100-1400 | UPLC esi |
| b | Waters SQD Single Quadrupol, 0.5 s scantime for mass 100-1400 | UPLC esi |

| Liquid chromatography Method | Method description |
|---|---|
| A | Waters ACQUITY UPLC BEH C18 1.7um 2.1 × 50 mm MV Kit; H2O + 0.05% TFA:MeCN + 0.035% TFA 98:2(0 min) to 98:2(0.2 min) to 2:98(3.8 min) to 2:98(4.3 min) to 98:2(4.5 min), 1 ml/min 55° C. |
| B | Waters ACQUITY UPLC BEH C18 1.7 um 2.1 × 50 mm; H2O + 0.05% TFA:MeCN + 0.035% TFA 95:5(0 min) to 5:95(2 min) to 5:95(2.6 min) to 95:5(2.7 min) to 95:5(3 min), 0.9 ml/min 55° C. |
| C | Waters ACQUITY UPLC BEH C18 1.7 um 2.1 × 50 mm; H2O + 0.05% TFA:MeCN + 0.035% TFA 98:2(0 min) to 98:2(0.2 min) to 2:98(3.8 min) to 2:98(4.3 min) to 98:2(4.5 min), 1 ml/min 55° C. |

Table 1 in section 4.2 shows the LCMS analysis results of the isolated binders.

4.2 Analysis of Albumin Binding

Instrument: Waters Alliance 2795/Waters PDA 2996 or Waters H-Class UPLC equipped with a Waters Acquity photodiode-array detector
Software: Waters Empower 3
Column: CHIRALPAK® HSA 50×4 mm; 5 µm Particle size
 Chiraltech Order Numbers: HSA: 34712
Eluent A: Phosphate Buffer saline (PBS) at pH=7.4
 Gibco PBS pH7.4 (10×) Phosphate Buffered Saline 500 ml;
 Order Number: 70011-036 (500 ml)
Eluent B: Isopropanol
 Fisher Order Number: A461-1 (1 L)

| Time [min] | % A | % B |
|---|---|---|
| 0 | 98 | 2 |
| 2 | 98 | 2 |
| 17 | 60 | 40 |
| 22 | 60 | 40 |
| 22.2 | 98 | 2 |
| 30 | 98 | 2 |
| 31 | 95 | 5 |

Column temperature: 25° C.
Flow rate: 1.0 ml/min
Detection: $\lambda$=220 nm
Injection volume: 20 µL
Sample Conc.: 1 mg/ml insulin solution in PBS for insulin samples
 5 µL of 10 mM DMSO stock solution (DMSO evaporated and re-dissolved in 200 µL i-propanol/water 1:1 v/v) for isolated binder samples (250 µM, 0.2 mg/ml at 800 Da MolWeight)
t0 marker Sodium Nitrate (NaNO$_3$) solution in water, 0.05 mg/ml Diluted from aqueous 1 mg/ml stock solution (Fluka Order Number: 74246-100ML)
Reported Value Net retention time of sample: RetTime Sample−RetTime t0 marker Affinity chromatography was carried out i) for insulin conjugates according to Examples 3.3 and 3.4 on a Waters Alliance Separation Module 2695 equipped with a Waters photodiode-array detector 2996 or Waters H-Class UPLC equipped with a Waters Acquity photodiode-array detector and ii) for isolated binders according to Example 2.11 on a Waters Alliance Separation Module 2795 equipped with a Waters photodiode-array detector 2996 or Waters H-Class UPLC equipped with a Waters Acquity photodiode-array detector.

Waters Empower 3 was used for all measurements as data processing software.

Columns with immobilized human serum albumin (50×4 mm; 5 µm particle size) were purchased from Chiralpak and used for separations.

Phosphate Buffer Saline (PBS) was purchased from Gibco and used as Eluent A, isopropanol was purchased from Fisher and used as Eluent B.

The applied gradient with a flow of 1.0 ml/min is shown below:

| Time [min] | % Eluent A | % Eluent B |
|---|---|---|
| 0 | 98 | 2 |
| 2 | 98 | 2 |
| 17 | 60 | 40 |
| 22 | 60 | 40 |
| 22.2 | 98 | 2 |
| 30 | 98 | 2 |
| 31 | 95 | 5 |

The columns with immobilized serum albumin were kept at 25° C. during the LC run, UV detection was carried out at 220 nm and injection volume was 20 µL.

The net retention time of the samples was reported according to

Net retention time=RetTime Sample−RetTime t0 marker

Table 1 shows the albumin binding results of the isolated binders, together with the LCMS data from section 4.1.

The abbreviations used in Table 1 are defined as follows:
NRT: Net retention time on columns with immobilized human serum albumin
    LCMS: Liquid chromatography mass spectrometry
    MSM: Mass spectrometry method
    OIM: Observed ion mass
    OIT: Observed ion type
    IM: Ionization method
    LCRT: Liquid chromatography Retention time
    LCM: Liquid chromatography Method

TABLE 1

Results from Columns with immobilized serum albumin and LCMS data

| No. | Structure |
|---|---|
| 1 | 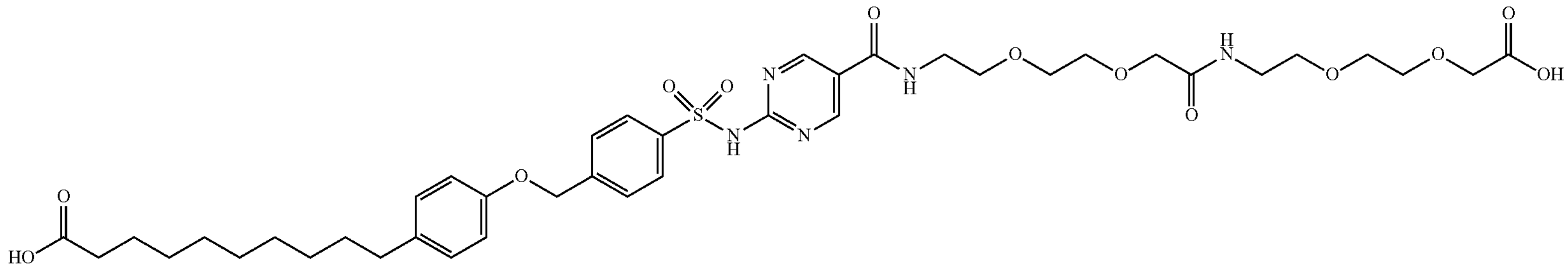 [SMILES: O=C(O)CCCCCCCCCc1ccc(OCc2ccc(S(=O)(=O)Nc3ncc(C(=O)NCCOCCOCC(=O)NCCOCCOCC(=O)O)cn3)cc2)cc1] |
| 2 | 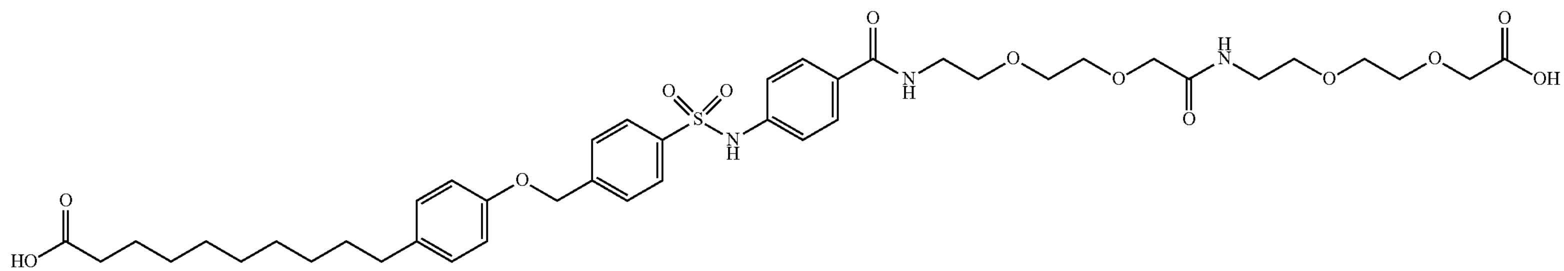 [SMILES: O=C(O)CCCCCCCCCc1ccc(OCc2ccc(S(=O)(=O)Nc3ccc(C(=O)NCCOCCOCC(=O)NCCOCCOCC(=O)O)cc3)cc2)cc1] |
| 3 | 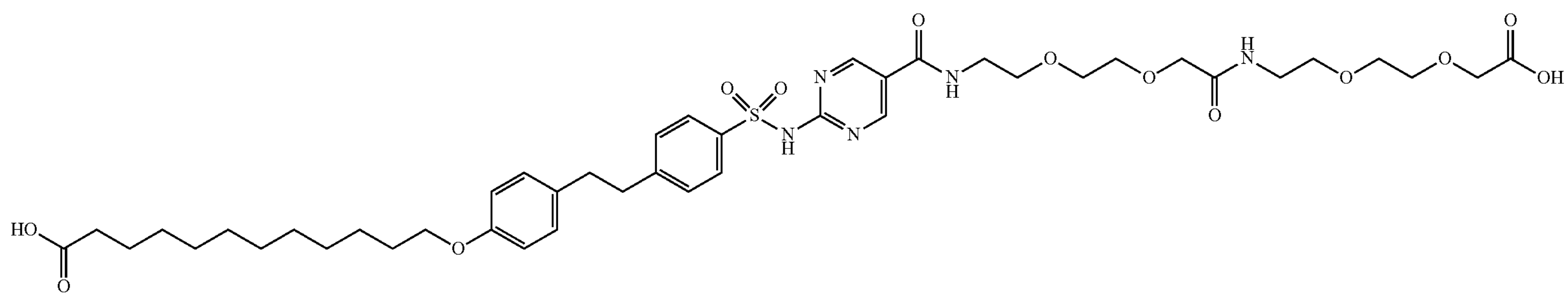 [SMILES: O=C(O)CCCCCCCCCCCOc1ccc(CCc2ccc(S(=O)(=O)Nc3ccc(C(=O)NCCOCCOCC(=O)NCCOCCOCC(=O)O)cn3)cc2)cc1] |

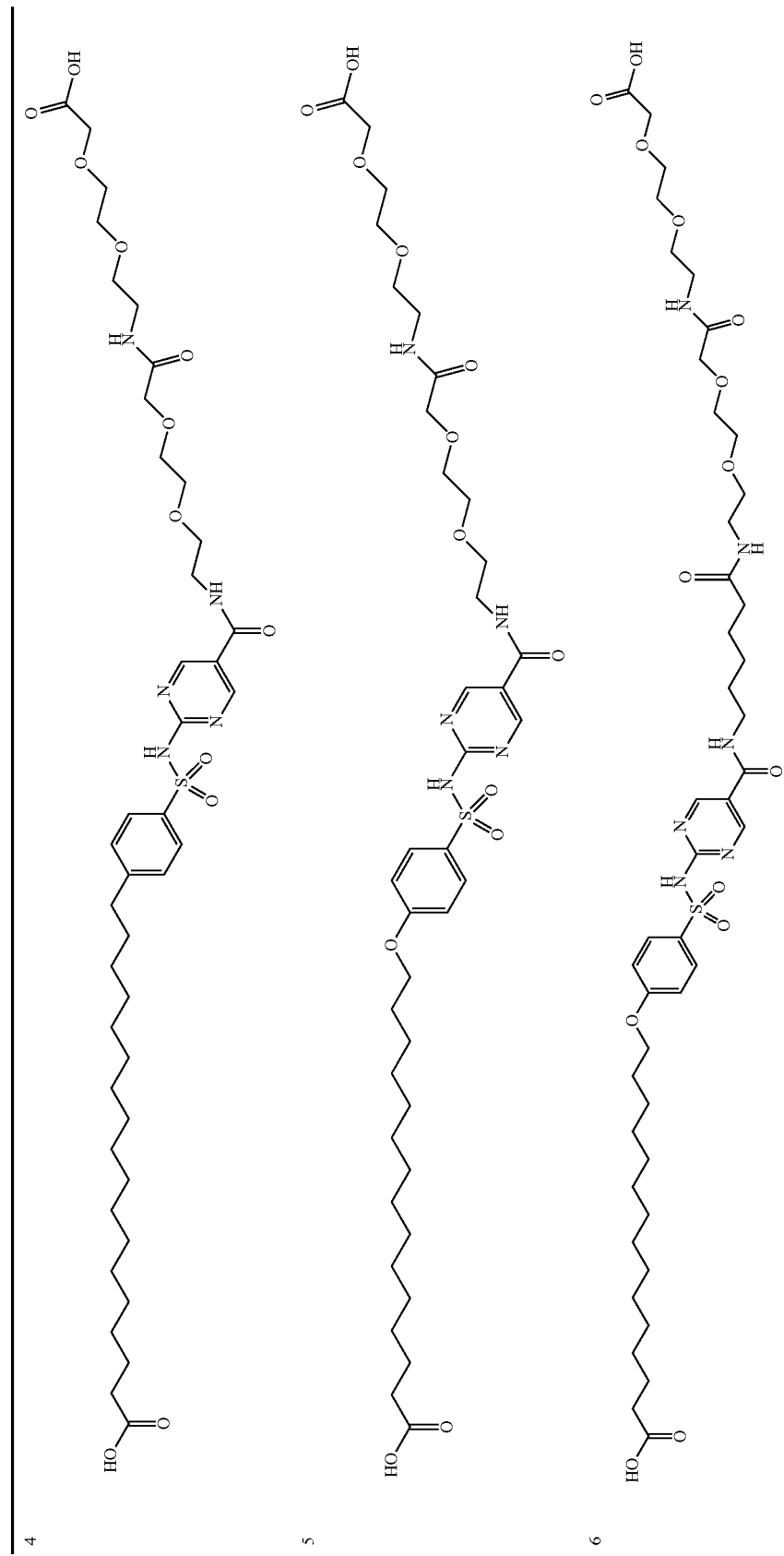

TABLE 1-continued
Results from Columns with immobilized serum albumin and LCMS data
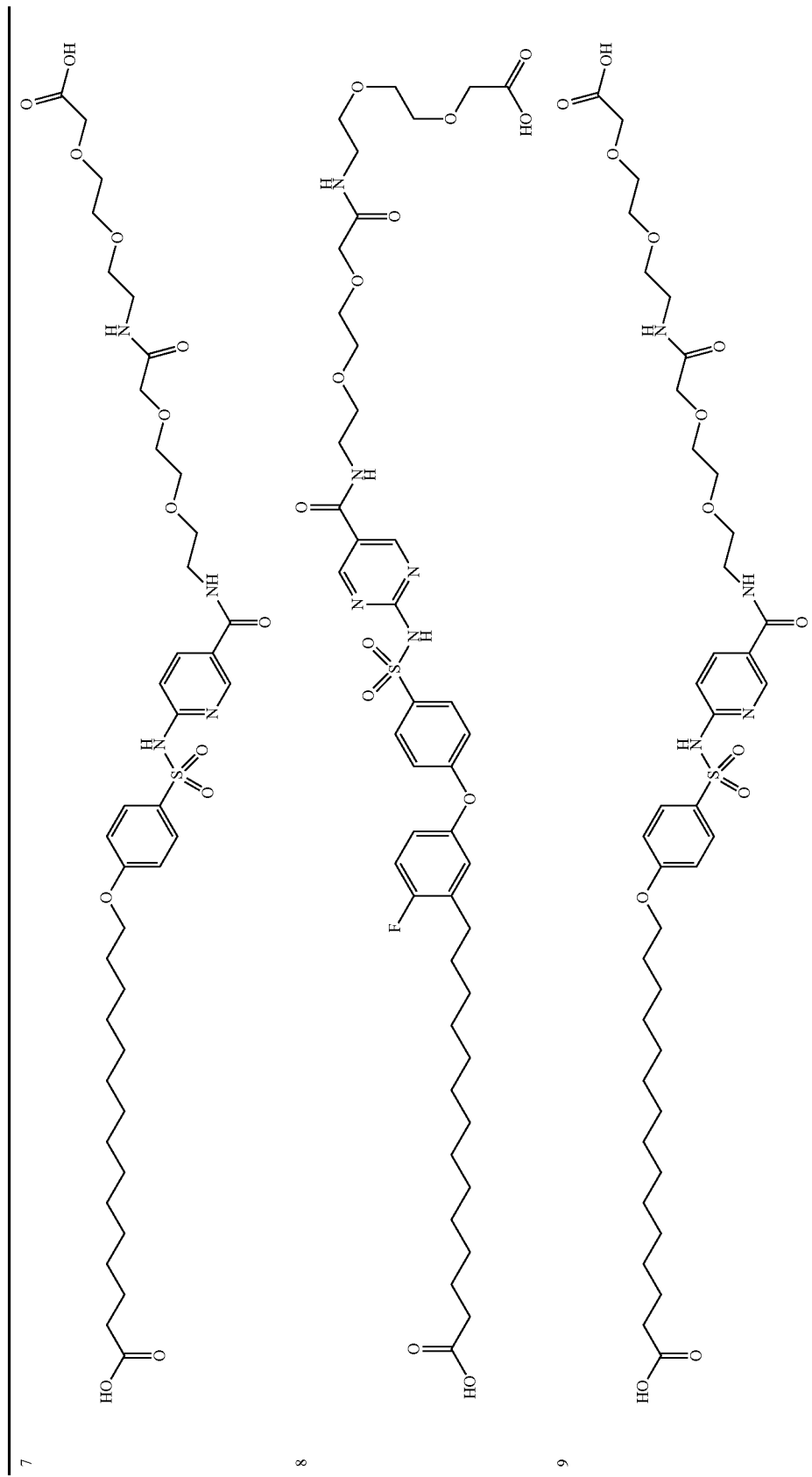

TABLE 1-continued

Results from Columns with immobilized serum albumin and LCMS data

| 10 | (structure) |
| 11 | (structure) |
| 12 | (structure) |
| 13 | (structure) |

TABLE 1-continued
Results from Columns with immobilized serum albumin and LCMS data
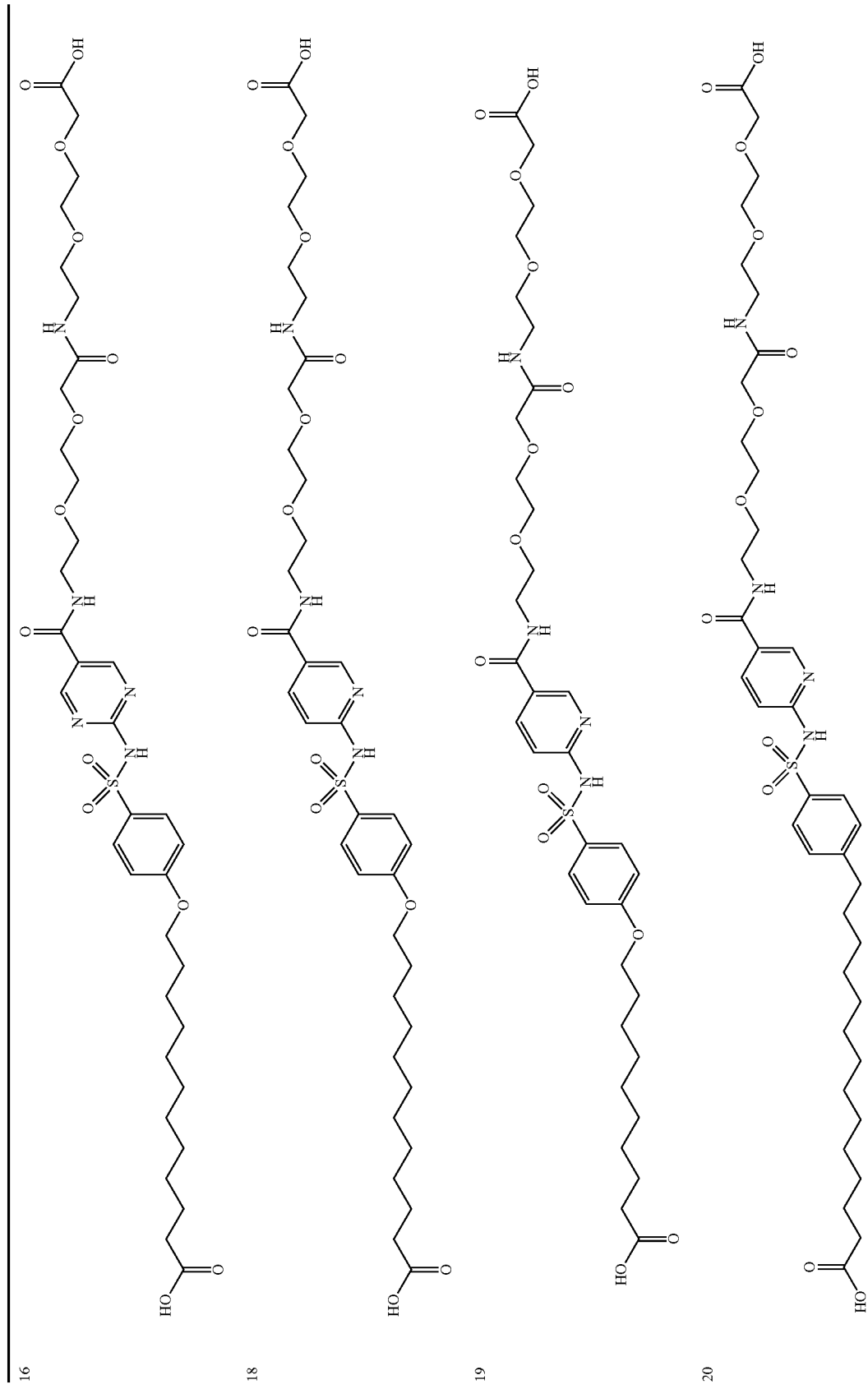

TABLE 1-continued

Results from Columns with immobilized serum albumin and LCMS data

| | |
|---|---|
| 21 | (structure) |
| 22 | (structure) |
| 23 | (structure) |
| 24 | (structure) |

TABLE 1-continued
Results from Columns with immobilized serum albumin and LCMS data
| 25 | 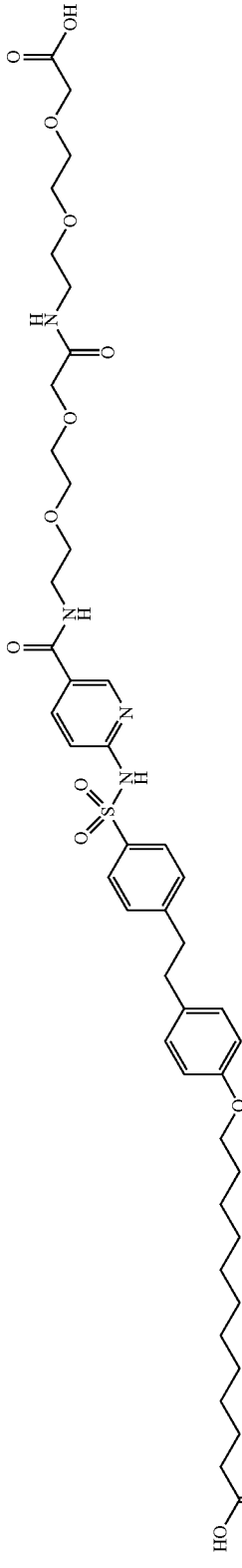 |
| 26 | 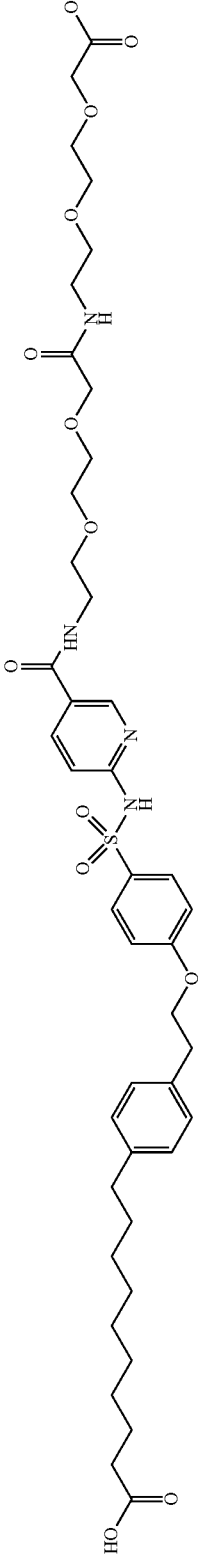 |
| 27 | 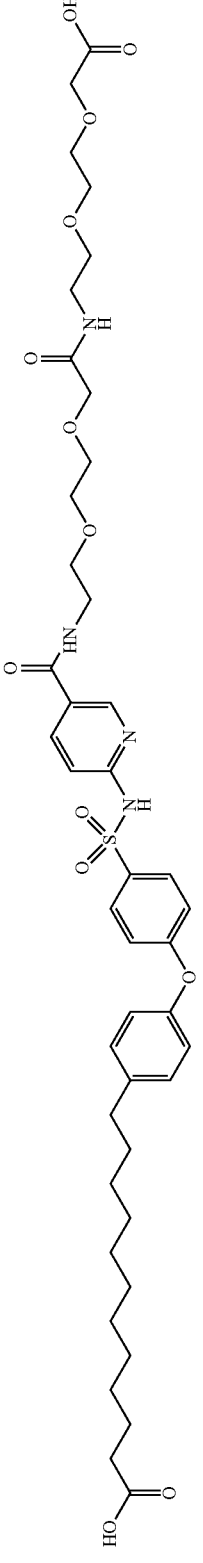 |
| 28 | 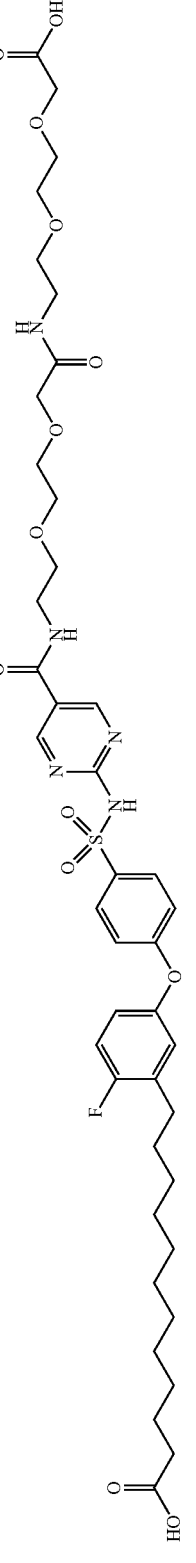 |

TABLE 1-continued
Results from Columns with immobilized serum albumin and LCMS data
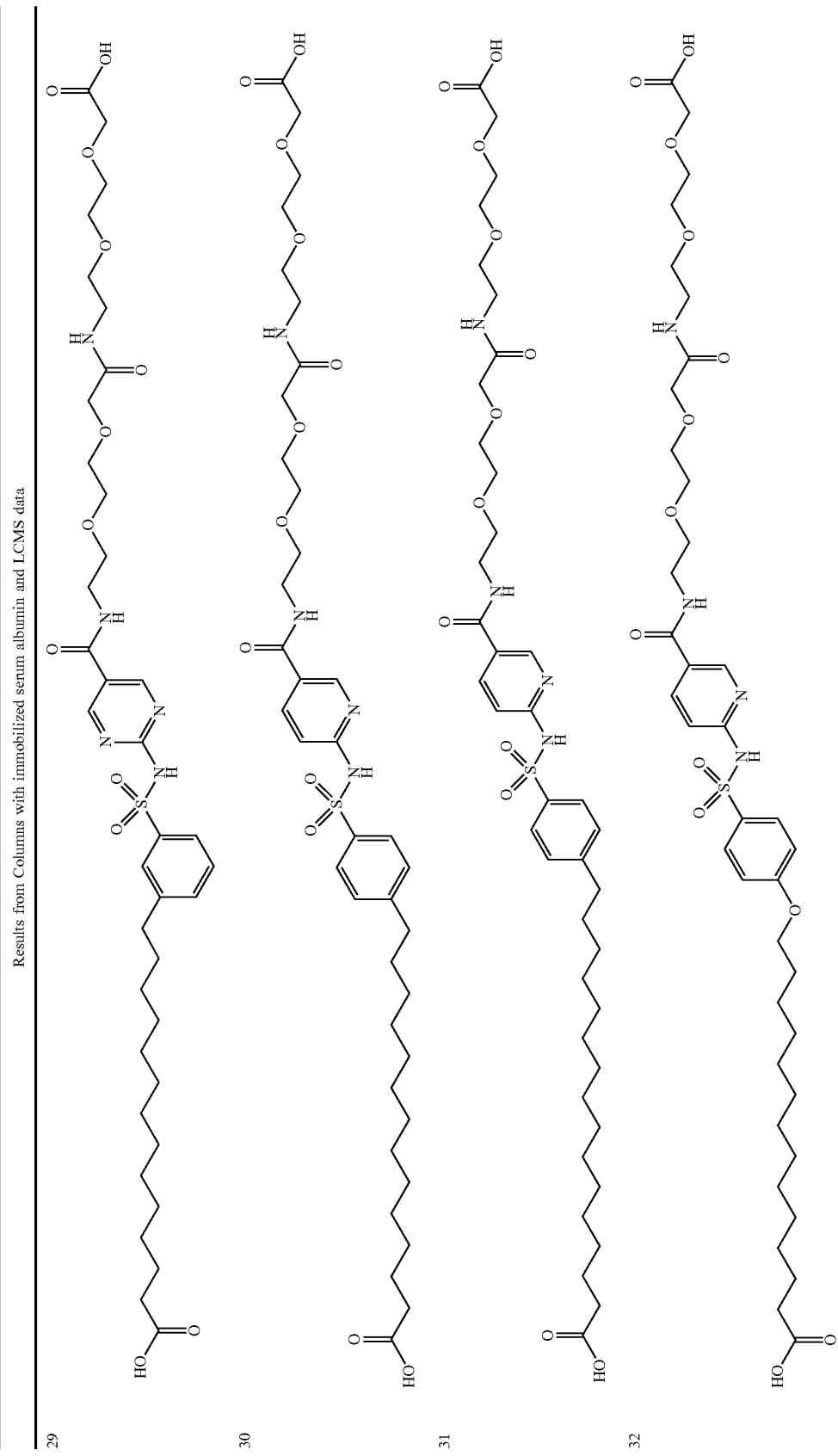

TABLE 1-continued

Results from Columns with immobilized serum albumin and LCMS data

| | |
|---|---|
| 33 | |
| 36 | |
| 38 | |
| 39 | |

TABLE 1-continued
Results from Columns with immobilized serum albumin and LCMS data
| | |
|---|---|
| 40 | 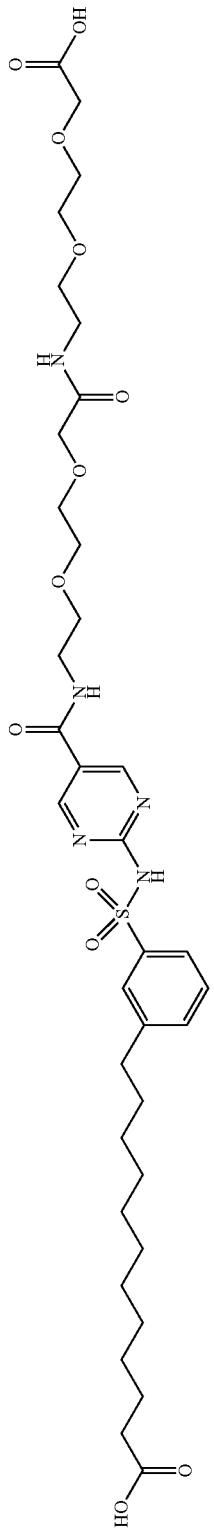 |
| 41 | 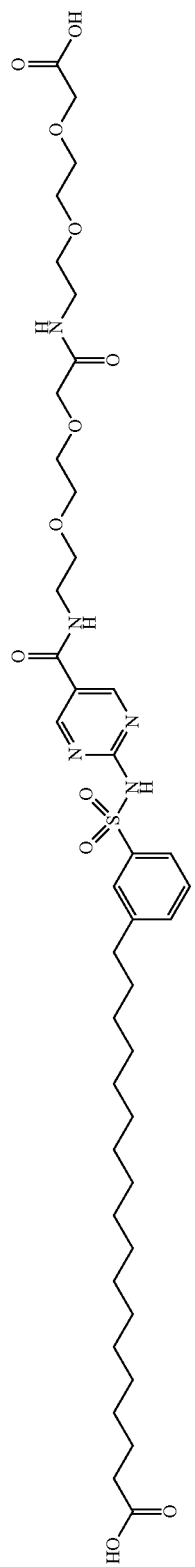 |
| 42 | 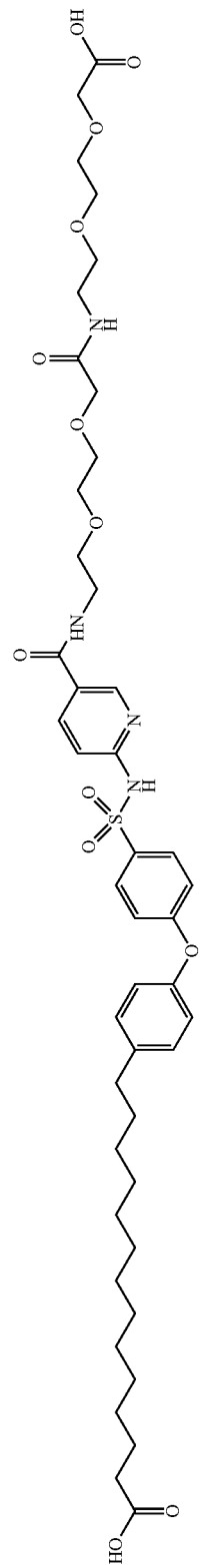 |
| 43 | 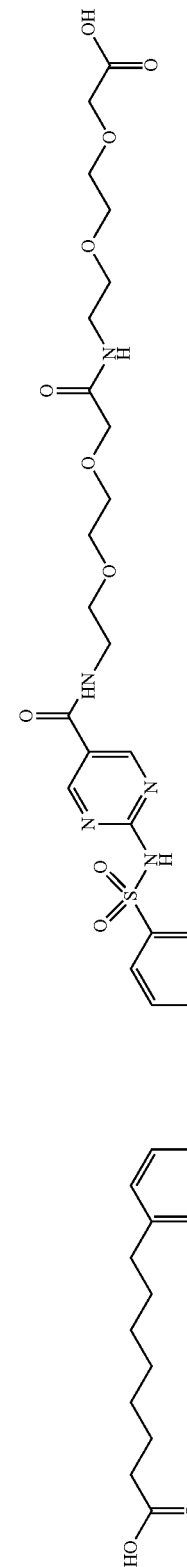 |
| 44 | 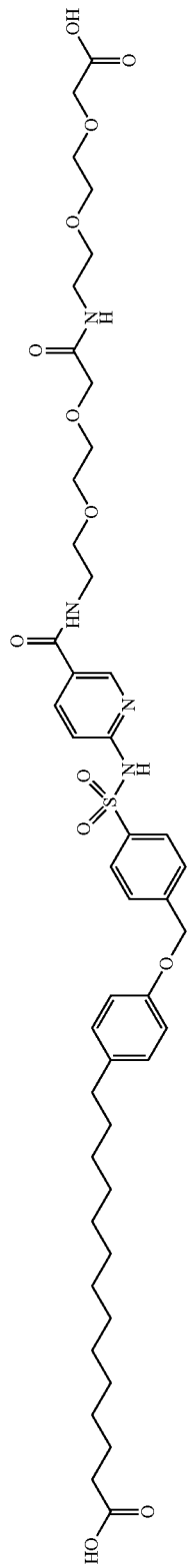 |

TABLE 1-continued

Results from Columns with immobilized serum albumin and LCMS data

| 45 | (structure) |
| 46 | (structure) |
| 47 | (structure) |
| 50 | (structure) |

TABLE 1-continued

Results from Columns with immobilized serum albumin and LCMS data

| 51 | 52 | 53 | 54 |

TABLE 1-continued
Results from Columns with immobilized serum albumin and LCMS data
| | |
|---|---|
| 55 | 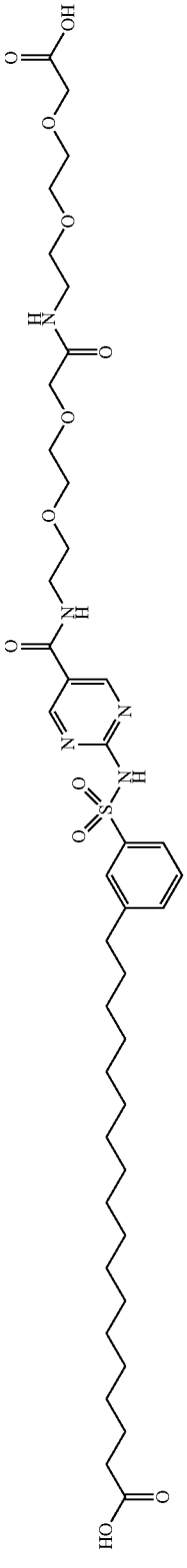 |
| 59 | 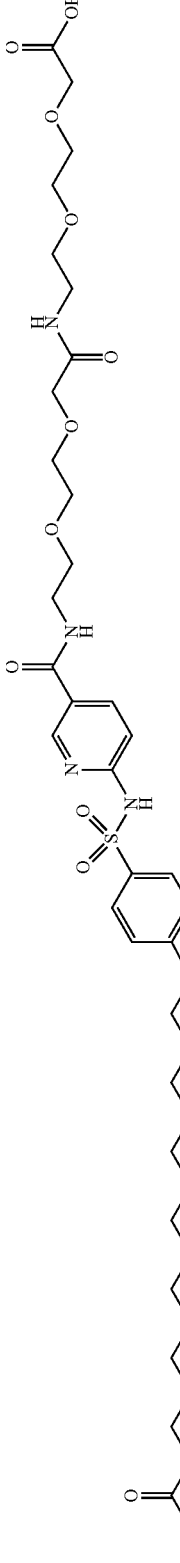 |
| 63 | 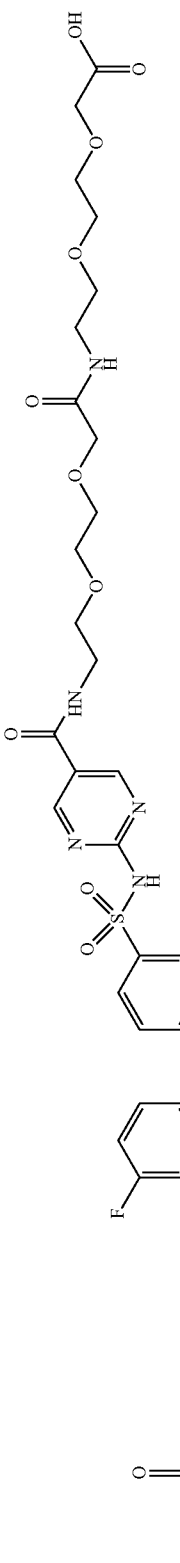 |
| 64 | 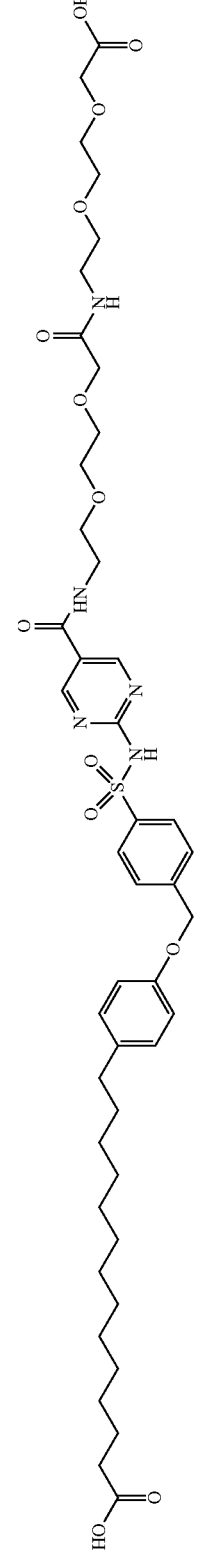 |
| 65 | 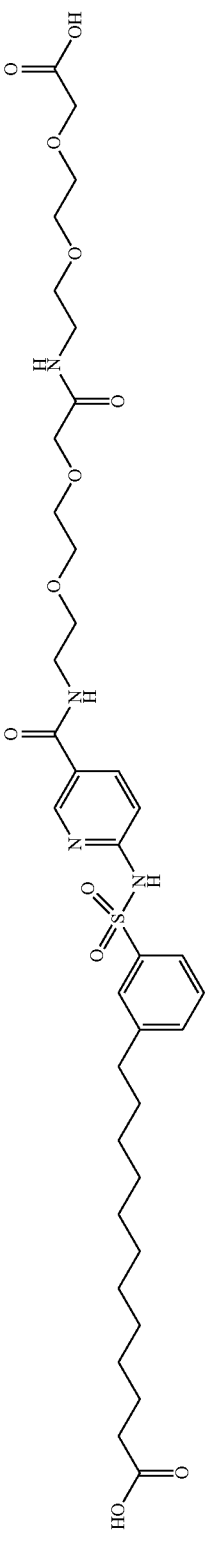 |

TABLE 1-continued

Results from Columns with immobilized serum albumin and LCMS data

TABLE 1-continued

Results from Columns with immobilized serum albumin and LCMS data

| No. | NRT [min] | MSM | OIM | OIT | IM | LCRT [min] | LCM |
|---|---|---|---|---|---|---|---|
| 1 | 16.76 | b | 846.37 | [M + H]+ | ES+ | 1.78 | B |
| 2 | 17.88 | b | 845.37 | [M + H]+ | ES+ | 2.28 | C |
| 3 | 17.51 | b | 888.35 | [M + H]+ | ES+ | 2.52 | C |
| 4 | 15.75 | b | 852.7 | [M + H]+ | ES+ | 2.88 | A |
| 5 | 14.32 | b | 840.35 | [M + H]+ | ES+ | 2.59 | C |
| 6 | 14.31 | b | 953.46 | [M + H]+ | ES+ | 2.58 | C |
| 7 | 14.65 | b | 839.4 | [M + H]+ | ES+ | 2.58 | C |
| 8 | 15.29 | b | 906.52 | [M + H]+ | ES+ | 2.77 | C |
| 9 | 14.01 | b | 952.4 | [M + H]+ | ES+ | 2.57 | C |
| 10 | 15.65 | b | 860.32 | [M + H]+ | ES+ | 2.38 | A |
| 11 | 14.52 | b | 888.7 | [M + H]+ | ES+ | 2.78 | A |
| 12 | 14.95 | b | 957.7 | [M − H]− | ES+ | 2.73 | A |
| 13 | 15.29 | b | 934.78 | [M + H]+ | ES+ | 2.99 | C |
| 16 | 11.88 | a | 784.28 | [M + H]+ | ES+ | 2.14 | C |
| 18 | 12.37 | a | 783.34 | [M + H]+ | ES+ | 2.13 | C |
| 19 | 10.82 | a | 755.28 | [M + H]+ | ES+ | 1.87 | C |
| 20 | 14.8 | a | 795.37 | [M + H]+ | ES+ | 2.4 | C |
| 21 | 16.26 | a | 795.37 | [M + H]+ | ES+ | 2.38 | C |
| 22 | 15.55 | a | 905.47 | [M + H]+ | ES+ | 2.77 | C |
| 23 | 15.61 | a | 933.54 | [M + H]+ | ES+ | 2.99 | C |
| 24 | 15.76 | a | 877.44 | [M + H]+ | ES+ | 2.55 | C |
| 25 | 17.48 | a | 887.49 | [M + H]+ | ES+ | 2.54 | C |
| 26 | 14.98 | a | 859.44 | [M + H]+ | ES+ | 2.41 | C |
| 27 | 15.01 | a | 859.45 | [M + H]+ | ES+ | 2.55 | C |
| 28 | 15.39 | a | 878.4 | [M + H]+ | ES+ | 2.57 | C |
| 29 | 15.66 | a | 796.4 | [M + H]+ | ES+ | 2.39 | C |
| 30 | 14.36 | a | 796.44 | [M + H]+ | ES+ | 2.41 | C |
| 31 | 15.77 | a | 851.51 | [M + H]+ | ES+ | 2.88 | C |
| 32 | 13.9 | a | 811.29 | [M + H]+ | ES+ | 2.36 | C |

TABLE 1-continued

Results from Columns with immobilized serum albumin and LCMS data

| | | | | | |
|---|---|---|---|---|---|
| 33 | 13.57 | a | 812.23 | [M + H]+ | ES+ | 2.37 |
| 36 | 13.89 | a | 907.59 | [M + H]+ | ES+ | 2.74 |
| 38 | 13.53 | a | 858.6 | [M + H]+ | ES+ | 2.62 |
| 39 | 13.68 | a | 857.62 | [M + H]+ | ES+ | 2.6 |
| 40 | 11.44 | a | 768.6 | [M + H]+ | ES+ | 2.14 |
| 41 | 14.98 | a | 851.7 | [M + H]+ | ES+ | 2.82 |
| 42 | 14.35 | a | 887.65 | [M + H]+ | ES+ | 2.76 |
| 43 | 11.36 | a | 832.6 | [M + H]+ | ES+ | 2.18 |
| 44 | 15.04 | a | 901.72 | [M + H]+ | ES+ | 2.76 |
| 45 | 13.8 | a | 908.66 | [M + H]+ | ES+ | 2.77 |
| 46 | 14.48 | a | 831.6 | [M + H]+ | ES+ | 2.16 |
| 47 | 13.73 | a | 854.7 | [M + H]+ | ES+ | 2.63 |
| 50 | 13.74 | a | 874.6 | [M + H]+ | ES+ | 2.7 |
| 51 | 13.59 | a | 871.6 | [M − H]− | ES− | 2.68 |
| 52 | 14.56 | a | 850.54 | [M + H]+ | ES+ | 2.33 |
| 53 | 12.29 | a | 768.5 | [M + H]+ | ES+ | 2.16 |
| 54 | 15.19 | a | 824.61 | [M + H]+ | ES+ | 2.64 |
| 55 | 15.01 | a | 852.58 | [M + H]+ | ES+ | 2.84 |
| 59 | 15.47 | a | 821.62 | [M − H]− | ES− | 2.62 |
| 63 | 13.42 | a | 822.52 | [M + H]+ | ES+ | 2.11 |
| 64 | 14.78 | a | 902.65 | [M + H]+ | ES+ | 2.78 |
| 65 | 12.21 | a | 767.61 | [M + H]+ | ES+ | 2.13 |
| 66 | 9.87 | a | 740.57 | [M + H]+ | ES+ | 1.92 |
| 67 | 10.99 | a | 739.57 | [M + H]+ | ES+ | 1.91 |
| 68 | 14.74 | a | 840.57 | [M + H]+ | ES+ | 2.60 |
| 69 | 14.24 | a | 868.82 | [M + H]+ | ES+ | 2.84 |
| 70 | 14.26 | a | 867.83 | [M + H]+ | ES+ | 2.83 |
| 71 | 14.42 | a | 895.81 | [M + H]+ | ES+ | 3.06 |
| 72 | 13.96 | a | 908.79 | [M + H]+ | ES+ | 2.77 |

5 Insulin Receptor Binding Affinity

Insulin receptor binding affinity for the insulin, insulin analog 41 and the respective conjugates listed in Table 2 was determined as described in Hartmann et al. (Effect of the long-acting insulin analogues glargine and degludec on cardiomyocyte cell signaling and function. Cardiovasc Diabetol. 2016; 15:96). Isolation of insulin receptor embedded plasma membranes (M-IR) and competition binding experiments were performed as previously described (Sommerfeld et al., PLoS One. 2010; 5(3): e9540). Briefly, CHO-cells overexpressing the IR were collected and re-suspended in ice-cold 2.25 STM buffer (2.25 M sucrose, 5 mM Tris-HCl pH 7.4, 5 mM $MgCl_2$, complete protease inhibitor) and disrupted using a Dounce homogenizer followed by sonication. The homogenate was overlaid with 0.8 STM buffer (0.8 M sucrose, 5 mM Tris-HCl pH 7.4, 5 mM $MgCl_2$, complete protease inhibitor) and ultra-centrifuged for 90 min at 100,000 g. Plasma membranes at the interface were collected and washed twice with phosphate buffered saline (PBS). The final pellet was re-suspended in dilution buffer (50 mM Tris-HCl pH 7.4, 5 mM $MgCl_2$, complete protease inhibitor) and again homogenized with a Dounce homogenizer. Competition binding experiments were performed in a binding buffer (50 mM Tris-HCl, 150 mM NaCl, 0.1% BSA, complete protease inhibitor, adjusted to pH 7.8) in 96-well microplates. In each well, 2 µg isolated membrane was incubated with 0.25 mg wheat germ agglutinin polyvinyltoluene polyethylenimine scintillation proximity assay (SPA) beads. Constant concentrations of [125I]-labelled human Ins (100 µM) and various concentrations of respective unlabelled Ins (0.001-1000 nM) were added for 12 h at room temperature (23° C.). The radioactivity was measured at equilibrium in a microplate scintillation counter (Wallac Microbeta, Freiburg, Germany)."

The insulin receptor binding affinity relative to human insulin for the analoga depicted in Table 2 comprises the following ranges: A (40%); B (<20%). Conjugate human insulin+binder no. 5 belongs to category A whereas all other conjugates and insulin analog 41 were classified under category B.

TABLE 2

Insulin receptor B binding affinity relative to human insulin

| No. of binder | Backbone | In vitro insulin receptor B activation |
|---|---|---|
| 5 | Human insulin | A |
| 5 | Insulin analog 41 | B |
| 8 | Insulin analog 41 | B |
| 50 | Insulin analog 41 | B |
| 54 | Insulin analog 41 | B |
| — | Insulin analog 41 | B |

6. In Vivo Testing—Evaluation of Pharmacokinetic Effects

Healthy, normoglycemic Göttingen minipigs (aged 8-11 months, body weight~12-18 kg) were used to evaluate the pharmacodynamic and pharmacokinetic effects of very long-acting insulin analogs in animals. The pigs were kept under standard animal house conditions and were fed once daily with access to tap water ad libitum. After overnight fasting, the pigs were treated with a single subcutaneous injection of a solution that contained either a placebo formulation, insulin or an insulin analog or the respective conjugate. Pure human insulin and pure insulin analog 41 as well as the conjugate of binder no. 5 with human insulin and the conjugates of binders 5, 50 and 54 with insulin analog 41 were tested.

Blood collection was performed via pre-implanted central venous catheters for determination of blood glucose, pharmacokinetics and additional biomarkers from K-EDTA plasma. Blood sampling started before the administration of the test item (baseline) and was repeated 1-4 times per day until study end. During the study, the animals were fed after the last blood sampling of the day. All animals were handled regularly and clinical signs were recorded at least twice on the day of treatment and once daily for the remaining duration of the study. The animals were monitored carefully for any clinical signs of hypoglycemia, including behavior, coat, urine and fecal excretion, condition of body orifices and any signs of illness. In case of severe hypoglycemia, the investigator was allowed to offer food or infuse glucose solution intravenous (i.v.) in case food intake was not possible. After the last blood sampling, the animals were transported back to the non-GLP animal keeping facility.

For determination of the pharmacokinetic parameters following experimental conditions were used.

6.1 Materials and Chemicals

MeCN (hyperSolv chromanorm), dimethyl sulfoxide (uvasol), 2-propanol, methanol (hyperSolv chromanorm), water (hyperSolv chromanorm), formic acid (98-100%) were purchased from Merck (Darmstadt, Germany). Analyte and suitable internal reference were obtained from Sanofi. Blank plasma (K2-EDTA as anticoagulant) was obtained from Seralab (West Sussex, UK).

6.2 Stock and Working Solutions of Test Compound and Internal Standard

Stock solutions of the test compound and its internal standard were prepared in MeCN/water/formic acid (50:50:1, v/v/v) at a concentration of 1 mg/ml. The working solutions of the test compound and the corresponding internal standard were prepared in the same solvent at a concentration of respectively 100 µg/ml and 1250 ng/ml.

6.3 Plasma Sample Preparation

A 25 µl portion of plasma was spiked with 10 µl of internal standard working solution (1250 ng/ml) into a 1.5 ml Eppendorf tube. After sealing and mixing, 75 µl of MeCN/methanol (80:20, v/v) was added and the samples were vortexed for 5 s and vortexed for 10 min at approximately 5° C. and 3000 g. Then, 75 µl of supernatant was transferred into an autosampler vial containing 75 µl of water. The vials were sealed, mixed and analyzed.

6.4 LC-MS/MS Analysis

The LC-MS/MS analysis of the intact insulin was performed on an Agilent 1290 Series HPLC (Waldbronn, Germany), coupled to an ABSciex QqQ API 4000 mass spectrometer (Darmstadt, Germany). The LC was equipped with an Aeris PEPTIDE XB-C18 analytical column (100×2.1 mm, particle size 3.6 µm, Phenomenex) operated at 40° C. The mobile phase A consisted in water/formic acid/DMSO (100:0.1:1, v/v/v) and mobile phase B in MeCN/formic acid/DMSO (100:0.1:1, v/v/v). The HPLC program started by keeping the initial conditions of 2% B for 0.5 min, then a gradient of 2% B to 90% B within 7.5 minutes was applied and the column was re-equilibrated for 2 minutes. The flow rate was 600 µl/min and a volume of 40 µl was injected into the system. The mass spectrometer was operated in the positive mode at an ion spray voltage of 5500 V, and the declustering potential was optimized for efficient isolation of the 5-fold protonated molecules. The mass spectrometer was operating in positive mode and the MS compound specific parameters were optimized for best sensitivity. Nitrogen was used as collision gas.

The pharmacokinetic (PK) parameters half-life time ($t_{1/2}$) and Mean Residence Time (MRT) are shown in Table 3.

For human insulin, the literature MRT value obtained in chronic diabetic Yucatan minipigs is given (Senshang Lin, Li-Lan H. Chen and Yie W. Chien, The journal of pharmacology and experimental therapeutics, 1998, 286, 959-966). The listed $t_{1/2}$ has been calculated as an approximation using the formula $t_{1/2}*1.44$ according to the text book Clinical Pharmacokinetics Concepts and applications by Tozer and Rowland, 3rd edition (Publisher Lippincott Williams & Wilkins), 1995-Section II-6).

As can be seen, conjugation of insulin derivatives, here human insulin or insulin analog 41, with the binders of the invention had a significant impact in the PK (pharmacokinetic) properties of the resulting conjugates, leading in all cases to increased $t_{1/2}$ and MRTs.

TABLE 3

Pharmacokinetic results of pure insulins vs. conjugates

| No. of binder | Structure of binder | Backbone | PK $t_{1/2}$ | MRT |
|---|---|---|---|---|
| — | No binder | Human insulin | ~2 h** | 2.8 h* |
| 5 | [structure] | Human insulin | 30 h | 47.2 h |
| 5 | [structure] | Insulin analog 41 | 37 h | 57.7 h |
| 8 | [structure] | Insulin analog 41 | 38 h | 63.3 h |

TABLE 3-continued

Pharmacokinetic results of pure insulins vs. conjugates

| No. of binder | Structure of binder | Backbone | PK $t_{1/2}$ | MRT |
|---|---|---|---|---|
| 50 | | Insulin analog 41 | 52 h | 83 h |
| 54 | | Insulin analog 41 | 33 h | 56.5 h |

*From: Senshang Lin, Li-Lan H. Chen and Yie W. Chien, The journal of pharmacology and experimental therapeutics, 1998, 286, 959-966.

**Calculated from $t_{1/2}$ = MRT/1.44 according to Clinical Pharmacokinetics Concepts and applications by Tozer and Rowland, 3rd edition (Publisher Lippincott Williams & Wilkins), 1995-Section II-6).

Figure 2:
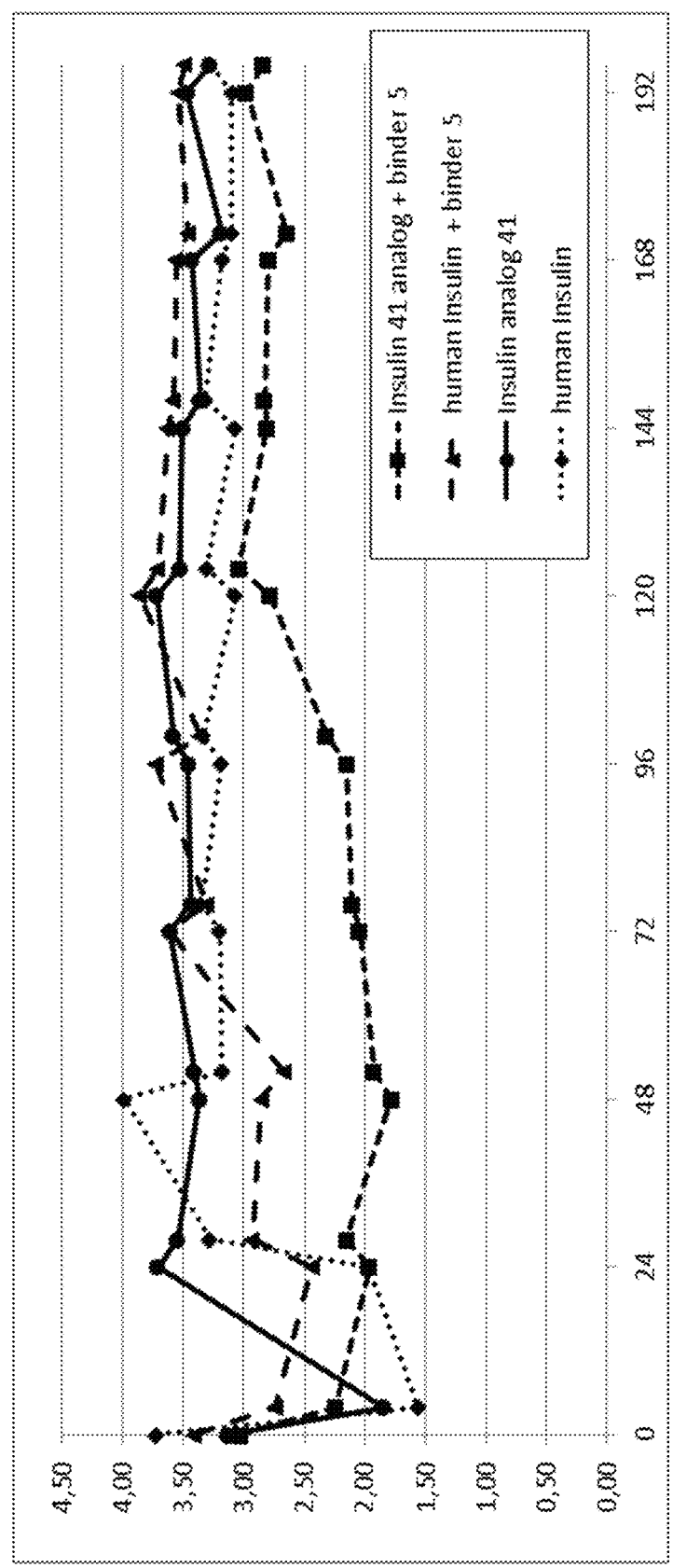
FIG. 2 shows blood glucose lowering effect after s.c. application of the insulins and insulin conjugates respectively in (Göttingen) minipigs (19-20 kg, n=3): Human insulin+binder no. 5 (18 nmol/kg), human insulin (3 nmol/kg), insulin analog 41+binder no. 5 (18 nmol/kg), insulin analog 41 (3 nmol/kg).

The pharmacodynamic effects of several insulins and conjugates are shown in FIGS. 1 and 2, i.e., the effect on blood glucose after s.c. administration is depicted. The data demonstrated a significant prolongation of the duration of action for all the insulin-binder conjugates tested (>48 h), in relation to insulin analog 41 and to human insulin respectively, for which a duration of action at the tested doses lower than 24 hr was observed. For the test insulin conjugates with a reduced insulin receptor binding affinity, the chosen in vivo dose was higher as for the corresponding parent insulins, which were not tested at higher doses to avoid hyploglychemic effects.

Example 7: Production of Human Insulin and Insulin Analogs

Human insulin as well as insulin analogs were produced recombinantly. Polynucleotides encoding pre-pro-insulin were ordered from Geneart®. The designed polynucleotides were optimized for expression in yeast. They were inserted into an expression vector by classical restriction cloning enabling functional expression and secretion in *Klyveromyces lactis* K. As secretion leader, the gene was C-terminally fused to a DNA sequence encoding the alpha mating factor signal of *Saccharomyces cerevisiae*. The recombinant gene expression was controlled by a lactose inducible *K. lactis* promoter.

Human insulin as well as insulin analogs were manufactured as a pre-pro-insulin. A genetically fused N-terminal pre-sequence was used to improve expression and secretion yields and to stabilize the peptide in the culture broth. A broad variety of sequences can be used for this purpose and were tested for efficiency. The proinsulin itself consists of a B-chain fused to a C-peptide followed by the C-terminal A-chain. As C-peptide, a variety of amino acid combinations are described. It was shown that short peptides of 1-10 amino acids work well as C-sequences. For later processing of the insulin the recognition sites for specific proteases, which flank the C-peptide to enable its excision, are important.

*K. lactis* cells were made competent by chemical means. Subsequently, the cells were transformed with the expression plasmid coding for the respective pre-pro-insulin. After insertion of the plasmid, cells were plated on selective agar plates containing geneticin. Grown colonies were isolated and tested for recombinant gene expression. Cells were grown to sufficiently high cell densities in yeast peptone dextrose medium supplemented with geneticin. After an initial growth phase, a salt-buffered yeast extract medium with geneticin supplemented with lactose was added to the cultures to induce expression of the recombinant gene. Cultures were grown several days and supernatants were harvested by centrifugation.

Purification of the functional insulin or insulin analogs was started by a filtration procedure. Initial chromatographic capturing procedure was made with an ion-exchange resin. Cleavage of pre-pro-insulin to insulin was performed with a highly specific protease. Depletion of host cell protein, pre-sequence and product related products were made by a cascade of two additional chromatographic steps. Next to a hydrophobic interaction chromatography another ion-exchange procedure was applied to achieve this goal. Final polishing was made by reverse phase chromatography. Filtration, precipitation and freeze drying were used to finish the production process of the insulin molecule.

After coupling reactions with an activated carboxylic acid derivative, the solution with conjugated insulin molecules was filtered. Final purification was made by reverse phase chromatography. Filtration, precipitation and freeze drying were used to finish the synthesis of the target molecule.

Various insulins analogs with mutations e.g. at positions B16, B25 and/or A14 were generated. Table 4 provides an overview of the generated insulins.

TABLE 4

Generated analogs of human Insulin

| Analog | Backbone | A14 | B16 | B25 | Amino acid sequence Chain A | SEQ ID NO (A chain) | Amino acid sequence Chain B | SEQ ID NO (B-Chain) |
|---|---|---|---|---|---|---|---|---|
| WT | Human Insulin (wild-type) | Tyr | Tyr | Phe | GIVEQCCTSICSLYQLEN YCN | 1 | FVNQHLCGSHLVEALYLVCGER GFFYTPKT | 2 |
| 2 | Glu(A14)Des(B30)-Insulin | Glu | Tyr | Phe | GIVEQCCTSICSLEQLEN YCN | 3 | FVNQHLCGSHLVEALYLVCGER GFFYTPK | 4 |
| 3 | Leu(B16)Des(B30)-Insulin | Tyr | Leu | Phe | GIVEQCCTSICSLYQLEN YCN | 5 | FVNQHLCGSHLVEALLLVCGER GFFYTPK | 6 |
| 4 | Gly(A21)Trp(B16)Des(B30)-Insulin | Tyr | Trp | Phe | GIVEQCCTSICSLYQLEN YCG | 7 | FVNQHLCGSHLVEALWLVCGE RGFFYTPK | 8 |
| 5 | His(B16)Des(B30)-Insulin | Tyr | His | Phe | GIVEQCCTSICSLYQLEN YCN | 9 | FVNQHLCGSHLVEALHLVCGER GFFYTPK | 10 |
| 6 | Val(B16)Des(B30)-Insulin | Tyr | Val | Phe | GIVEQCCTSICSLYQLEN YCN | 11 | FVNQHLCGSHLVEALVLVCGER GFFYTPK | 12 |
| 7 | Ala(B25)-Insulin | Tyr | Tyr | Ala | GIVEQCCTSICSLYQLEN YCN | 13 | FVNQHLCGSHLVEALYLVCGER GFAYTPKT | 14 |
| 8 | Ala(B25)Des(B30)-Insulin | Tyr | Tyr | Ala | GIVEQCCTSICSLYQLEN YCN | 15 | FVNQHLCGSHLVEALYLVCGER GFAYTPK | 16 |
| 9 | Glu(B25)Des(B30)-Insulin | Tyr | Tyr | Glu | GIVEQCCTSICSLYQLEN YCN | 17 | FVNQHLCGSHLVEALYLVCGER GFEYTPK | 18 |
| 10 | His(B25)Des(B30)-Insulin | Tyr | Tyr | His | GIVEQCCTSICSLYQLEN YCN | 19 | FVNQHLCGSHLVEALYLVCGER GFHYTPK | 20 |
| 11 | Leu(B25)Des(B30)-Insulin | Tyr | Tyr | Leu | GIVEQCCTSICSLYQLEN YCN | 21 | FVNQHLCGSHLVEALYLVCGER GFLYTPK | 22 |
| 12 | Val(B25)Des(B30)-Insulin | Tyr | Tyr | Val | GIVEQCCTSICSLYQLEN YCN | 23 | FVNQHLCGSHLVEALYLVCGER GFVYTPK | 24 |
| 13 | His(B16)His(B25)Des(B30)-Insulin | Tyr | His | His | GIVEQCCTSICSLYQLEN YCN | 25 | FVNQHLCGSHLVEALHLVCGER GFHYTPK | 26 |
| 14 | Gly(A21)Trp(B16)His(B25)Des(B30)-Insulin | Tyr | Trp | His | GIVEQCCTSICSLYQLEN YCG | 27 | FVNQHLCGSHLVEALWLVCGE RGFHYTPK | 28 |
| 15 | Gly(A21)Trp(B16)Trp(B25)Des(B30)-Insulin | Tyr | Trp | Trp | GIVEQCCTSICSLYQLEN YCG | 29 | FVNQHLCGSHLVEALWLVCGE RGFVVYTPK | 30 |
| 16 | Glu(A14)His(B16)Des(B30)-Insulin | Glu | His | Phe | GIVEQCCTSICSLEQLEN YCN | 31 | FVNQHLCGSHLVEALHLVCGER | 32 |

TABLE 4-continued

Generated analogs of human Insulin

| Analog | Backbone | A14 | B16 | B25 | Amino acid sequence Chain A | SEQ ID NO (A chain) | Amino acid sequence Chain B | SEQ ID NO (B-Chain) |
|---|---|---|---|---|---|---|---|---|
|  | Insulin |  |  |  | GIVEQCCTSICSLEQLEN YCN |  | GFFYTPK |  |
| 17 | Glu(A14)Gly(A21)Trp(B16)Des(B30)-Insulin | Glu | Trp | Phe | GIVEQCCTSICSLEQLEN YCG | 33 | FVNQHLCGSHLVEALWLVCGER GFFYTPK | 34 |
| 18 | Glu(A14)Ile(B16)Des(B30)-Insulin | Glu | Ile | Phe | GIVEQCCTSICSLEQLEN YCN | 35 | FVNQHLCGSHLVEALILVCGER GFFYTPK | 36 |
| 19 | Glu(A14)Val(B16)Des(B30)-Insulin | Glu | Val | Phe | GIVEQCCTSICSLEQLEN YCN | 37 | FVNQHLCGSHLVEALVLVCGER GFFYTPK | 38 |
| 20 | Glu(A14)Glu(B3)Val(B16)Des(B30)-Insulin | Glu | Val | Phe | GIVEQCCTSICSLEQLEN YCN | 39 | FVEQHLCGSHLVEALVLVCGER GFFYTPK | 40 |
| 21 | Glu(A14)His(B25)Des(B30)-Insulin | Glu | Tyr | His | GIVEQCCTSICSLEQLEN YCN | 41 | FVNQHLCGSHLVEALYLVCGER GFHYTPK | 42 |
| 22 | Glu(A14)Ile(B25)Des(B30)-Insulin | Glu | Tyr | Ile | GIVEQCCTSICSLEQLEN YCN | 43 | FVNQHLCGSHLVEALYLVCGER GFIYTPK | 44 |
| 23 | Glu(A14)Gly(A21)Trp(B25)Des(B30)-Insulin | Glu | Tyr | Trp | GIVEQCCTSICSLEQLEN YCG | 45 | FVNQHLCGSHLVEALYLVCGER GFVVTPK | 46 |
| 24 | Glu(A14)Val(B25)Des(B30)-Insulin | Glu | Tyr | Val | GIVEQCCTSICSLEQLEN YCN | 47 | FVNQHLCGSHLVEALYLVCGER GFVYTPK | 48 |
| 25 | Glu(A14)Gly(A21)Glu(B3)Val(B25)Des(B30)-Insulin | Glu | Tyr | Val | GIVEQCCTSICSLEQLEN YCG | 49 | FVEQHLCGSHLVEALYLVCGER GFVYTPK | 50 |
| 26 | Glu(A14)Glu(B16)His(B25)Des(B30)-Insulin | Glu | Glu | His | GIVEQCCTSICSLEQLEN YCN | 51 | FVNQHLCGSHLVEALELVCGER GFHYTPK | 52 |
| 27 | Glu(A14)His(B16)Ala(B25)Des(B30)-Insulin | Glu | His | Ala | GIVEQCCTSICSLEQLEN YCN | 53 | FVNQHLCGSHLVEALHLVCGER GFAYTPK | 54 |
| 28 | Glu(A14)His(B16)His(B25)Des(B30)-Insulin | Glu | His | His | GIVEQCCTSICSLEQLEN YCN | 55 | FVNQHLCGSHLVEALHLVCGER GFHYTPK | 56 |
| 29 | Glu(A14)Ile(B16)Ile(B25)Des(B30)-Insulin | Glu | Ile | Ile | GIVEQCCTSICSLEQLEN YCN | 57 | FVNQHLCGSHLVEALILVCGER GFIYTPK | 58 |
| 30 | Glu(A14)Glu(B3)Ile(B16)Ile(B25)Des(B30)-Insulin | Glu | Ile | Ile | GIVEQCCTSICSLEQLEN YCN | 59 | FVEQHLCGSHLVEALILVCGER GFIYTPK | 60 |
| 31 | Glu(A14)Gly(A21)Glu(B3)Ile(B16)Trp(B25)Des(B30)-Insulin | Glu | Ile | Trp | GIVEQCCTSICSLEQLEN YCG | 61 | FVEQHLCGSHLVEALILVCGER GFVVTPK | 62 |

TABLE 4-continued

Generated analogs of human Insulin

| Analog | Backbone | A14 | B16 | B25 | Amino acid sequence Chain A | SEQ ID NO (A chain) | Amino acid sequence Chain B | SEQ ID NO (B-Chain) |
|---|---|---|---|---|---|---|---|---|
| 32 | Glu(A14)Ile(B16)Val(B25) Des(B30)-Insulin | Glu | Ile | Val | GIVEQCCTSICSLEQLEN YCN | 63 | FVNQHLCGSHLVEALILVCGER GFVYTPK | 64 |
| 33 | Glu(A14)Gly(A21)Glu(B3)Ile (B16)Val(B25)Des(B30)-Insulin | Glu | Ile | Val | GIVEQCCTSICSLEQLEN YCG | 65 | FVEQHLCGSHLVEALILVCGER GFVYTPK | 66 |
| 34 | Glu(A14)Leu(B16)Ala(B25) Des(B30)-Insulin | Glu | Leu | Ala | GIVEQCCTSICSLEQLEN YCN | 67 | FVNQHLCGSHLVEALLLVCGER GFAYTPK | 68 |
| 35 | Glu(A14)Val(B16)Ile(B25) Des(B30)-Insulin | Glu | Val | Ile | GIVEQCCTSICSLEQLEN YCN | 69 | FVNQHLCGSHLVEALVLVCGER GFIYTPK | 70 |
| 36 | Glu(A14)Gly(A21)Val(B16) Trp(B25)Des(B30)-Insulin | Glu | Val | Trp | GIVEQCCTSICSLEQLEN YCG | 71 | FVNQHLCGSHLVEALVLVCGER GFVVTPK | 72 |
| 37 | Glu(A14)Gly(A21)Glu(B3)Val (B16)Trp(B25)Des(B30)-Insulin | Glu | Val | Trp | GIVEQCCTSICSLEQLEN YCG | 73 | FVEQHLCGSHLVEALVLVCGER GFVVTPK | 74 |
| 38 | Glu(A14)Val(B16)Val(B25) Des(B30)-Insulin | Glu | Val | Val | GIVEQCCTSICSLEQLEN YCN | 75 | FVNQHLCGSHLVEALVLVCGER GFVYTPK | 76 |
| 39 | Glu(A14)Glu(B3)Val(B16)Val (B25)Des(B30)-Insulin | Glu | Val | Val | GIVEQCCTSICSLEQLEN YCN | 77 | FVEQHLCGSHLVEALVLVCGER GFVYTPK | 78 |
| 40 | Glu(A14)Gly(A21)Glu(B3)Val (B16)Val(B25)Des(B30)-Insulin | Glu | Val | Val | GIVEQCCTSICSLEQLEN YCG | 79 | FVEQHLCGSHLVEALVLVCGER GFVYTPK | 80 |

Example 8: Insulin Receptor Binding Affinity Assays/Insulin Receptor Autophosphorylation Assays Insulin binding and signal transduction of various generated insulin analogs were determined by a binding assay and a receptor autophosphorylation assay.

A) Insulin Receptor Binding Affinity Assay

Insulin receptor binding affinity for the analogs listed in Table 4 was determined as described in Hartmann et al. (Effect of the long-acting insulin analogs glargine and degludec on cardiomyocyte cell signaling and function. Cardiovasc Diabetol. 2016; 15:96). Isolation of insulin receptor embedded plasma membranes (M-IR) and competition binding experiments were performed as previously described (Sommerfeld et al., PLoS One. 2010; 5(3): e9540). Briefly, CHO-cells overexpressing the IR were collected and re-suspended in ice-cold 2.25 STM buffer (2.25 M sucrose, 5 mM Tris-HCl pH 7.4, 5 mM $MgCl_2$, complete protease inhibitor) and disrupted using a Dounce homogenizer followed by sonication. The homogenate was overlaid with 0.8 STM buffer (0.8 M sucrose, 5 mM Tris-HCl pH 7.4, 5 mM $MgCl_2$, complete protease inhibitor) and ultra-centrifuged for 90 min at 100,000 g. Plasma membranes at the interface were collected and washed twice with phosphate buffered saline (PBS). The final pellet was re-suspended in dilution buffer (50 mM Tris-HCl pH 7.4, 5 mM $MgCl_2$, complete protease inhibitor) and again homogenized with a Dounce homogenizer. Competition binding experiments were performed in a binding buffer (50 mM Tris-HCl, 150 mM NaCl, 0.1% BSA, complete protease inhibitor, adjusted to pH 7.8) in 96-well microplates. In each well 2 µg isolated membrane was incubated with 0.25 mg wheat germ agglutinin polyvinyltoluene polyethylenimine scintillation proximity assay (SPA) beads. Constant concentrations of [125I]-labelled human insulin (100 µM) and various concentrations of respective unlabelled insulin (0.001-1000 nM) were added for 12 h at room temperature (23° C.). The radioactivity was measured at equilibrium in a microplate scintillation counter (Wallac Microbeta, Freiburg, Germany)."

The results of the insulin receptor binding affinity assays for the tested analogs relative to human insulin are shown in Table 5.

B) Insulin Receptor Autophosphorylation Assays (as a Measure for Signal Transduction)

In order to determine signal transduction of an insulin analog binding to insulin receptor B, autophosphorylation was measured in vitro.

CHO cells expressing human insulin receptor isoform B (IR-B) were used for IR autophosphorylation assays using In-Cell Western technology as previously described (Sommerfeld et al., PLoS One. 2010; 5(3): e9540). For the analysis of IGF1R autophosphorylation, the receptor was overexpressed in a mouse embryo fibroblast 3T3 Tet off cell line (BD Bioscience, Heidelberg, Germany) that was stably transfected with IGF1R tetracycline-regulatable expression plasmid. In order to determine the receptor tyrosine phosphorylation level, cells were seeded into 96-well plates and grown for 44 h. Cells were serum starved with serum-free medium Ham's F12 medium (Life Technologies, Darmstadt, Germany) for 2 h. The cells were subsequently treated with increasing concentrations of either human insulin or the insulin analog for 20 min at 37° C. After incubation the medium was discarded and the cells fixed in 3.75% freshly prepared para-formaldehyde for 20 min. Cells were permeabilised with 0.1% Triton X-100 in PBS for 20 min. Blocking was performed with Odyssey blocking buffer (LICOR, Bad Homburg, Germany) for 1 hour at room temperature. Anti-pTyr 4G10 (Millipore, Schwalbach, Germany) was incubated for 2 h at room temperature. After incubation of the primary antibody, cells were washed with PBS+0.1% Tween 20 (Sigma-Aldrich, St Louis, MO, USA). The secondary antimouse-IgG-800-CW antibody (LICOR, Bad Homburg, Germany) was incubated for 1 h. Results were normalized by the quantification of DNA with TO-PRO3 dye (Invitrogen, Karlsruhe, Germany). Data were obtained as relative units (RU).

The results of the insulin receptor autophosphorylation assays for the tested analogs relative to human insulin are shown in Table 5.

TABLE 5

Relative insulin receptor binding affinities and autophosphorylation activities of tested analogs of human insulin (for the sequences, please see Table 4).

| Analog | Backbone | A14 | B16 | B25 | Insulin-receptor binding affinity* | autophosphorylation activity* |
|---|---|---|---|---|---|---|
| WT | Human Insulin (wild-type) | Tyr | Tyr | Phe | 1 | 1 |
| 2 | Glu(A14)Des(B30)-Insulin | Glu | Tyr | Phe | 1.05 | 0.87 |
| 3 | Leu(B16)Des(B30)-Insulin | Tyr | Leu | Phe | 0.24 | 0.34 |
| 4 | Gly(A21)Trp(B16)Des(B30)-Insulin | Tyr | Trp | Phe | 0.57 | 0.4 |
| 5 | His(B16)Des(B30)-Insulin | Tyr | His | Phe | nd | nd |
| 6 | Val(B16)Des(B30)-Insulin | Tyr | Val | Phe | nd | 0.32 |
| 7 | Ala(B25)-Insulin | Tyr | Tyr | Ala | 0.05 | 0.2 |
| 8 | Ala(B25)Des(B30)-Insulin | Tyr | Tyr | Ala | nd | 0.17 |
| 9 | Glu(B25)Des(B30)-Insulin | Tyr | Tyr | Glu | nd | nd |
| 10 | His(B25)Des(B30)-Insulin | Tyr | Tyr | His | 0.37 | 0.31 |
| 11 | Leu(B25)Des(B30)-Insulin | Tyr | Tyr | Leu | 0.01 | 0.06 |
| 12 | Val(B25)Des(B30)-Insulin | Tyr | Tyr | Val | 0.01 | 0.06 |
| 13 | His(B16)His(B25)Des(B30)-Insulin | Tyr | His | His | 0.11 | 0.1 |
| 14 | Gly(A21)Trp(B16)His(B25)Des(B30)-Insulin | Tyr | Trp | His | 0.4 | 0.35 |
| 15 | Gly(A21)Trp(B16)Trp(B25)Des(B30)-Insulin | Tyr | Trp | Trp | 0.43 | 0.38 |

TABLE 5-continued

Relative insulin receptor binding affinities and autophosphorylation activities of tested analogs of human insulin (for the sequences, please see Table 4).

| Analog | Backbone | A14 | B16 | B25 | Insulin-receptor binding affinity* | autophosphorylation activity* |
|---|---|---|---|---|---|---|
| 16 | Glu(A14)His(B16)Des(B30)-Insulin | Glu | His | Phe | 0.36 | 0.29 |
| 17 | Glu(A14)Gly(A21)Trp(B16)Des(B30)-Insulin | Glu | Trp | Phe | 0.63 | 0.38 |
| 18 | Glu(A14)Ile(B16)Des(B30)-Insulin | Glu | Ile | Phe | 0.23 | 0.18 |
| 19 | Glu(A14)Val(B16)Des(B30)-Insulin | Glu | Val | Phe | nd | 0.32 |
| 20 | Glu(A14)Glu(B3)Val(B16)Des(B30)-Insulin | Glu | Val | Phe | 0.4 | 0.28 |
| 21 | Glu(A14)His(B25)Des(B30)-Insulin | Glu | Tyr | His | nd | nd |
| 22 | Glu(A14)Ile(B25)Des(B30)-Insulin | Glu | Tyr | Ile | 0.01 | 0.04 |
| 23 | Glu(A14)Gly(A21)Trp(B25)Des(B30)-Insulin | Glu | Tyr | Trp | 0.56 | 0.37 |
| 24 | Glu(A14)Val(B25)Des(B30)-Insulin | Glu | Tyr | Val | 0.01 | 0.04 |
| 25 | Glu(A14)Gly(A21)Glu(B3)Val(B25)Des(B30)-Insulin | Glu | Tyr | Val | 0.02 | 0.03 |
| 26 | Glu(A14)Glu(B16)His(B25)Des(B30)-Insulin | Glu | Glu | His | 0.01 | 0.07 |
| 27 | Glu(A14)His(B16)Ala(B25)Des(B30)-Insulin | Glu | His | Ala | | 0.11 |
| 28 | Glu(A14)His(B16)His(B25)Des(B30)-Insulin | Glu | His | His | 0.12 | 0.11 |
| 29 | Glu(A14)Ile(B16)Ile(B25)Des(B30)-Insulin | Glu | Ile | Ile | | 0.01 |
| 30 | Glu(A14)Glu(B3)Ile(B16)Ile(B25)Des(B30)-Insulin | Glu | Ile | Ile | 0** | 0.01 |
| 31 | Glu(A14)Gly(A21)Glu(B3)Ile(B16)Trp(B25)Des(B30)-Insulin | Glu | Ile | Trp | 0.12 | 0.13 |
| 32 | Glu(A14)Ile(B16)Val(B25)Des(B30)-Insulin | Glu | Ile | Val | 0 | 0.04 |
| 33 | Glu(A14)Gly(A21)Glu(B3)Ile(B16)Val(B25)Des(B30)-Insulin | Glu | Ile | Val | 0.01 | 0.02 |
| 34 | Glu(A14)Leu(B16)Ala(B25)Des(B30)-Insulin | Glu | Leu | Ala | 0.01 | 0.04 |
| 35 | Glu(A14)Val(B16)Ile(B25)Des(B30)-Insulin | Glu | Val | Ile | 0 | 0.01 |
| 36 | Glu(A14)Gly(A21)Val(B16)Trp(B25)Des(B30)-Insulin | Glu | Val | Trp | 0.17 | 0.23 |
| 37 | Glu(A14)Gly(A21)Glu(B3)Val(B16)Trp(B25)Des(B30)-Insulin | Glu | Val | Trp | 0.21 | 0.19 |
| 38 | Glu(A14)Val(B16)Val(B25)Des(B30)-Insulin | Glu | Val | Val | 0 | 0.03 |
| 39 | Glu(A14)Glu(B3)Val(B16)Val(B25)Des(B30)-Insulin | Glu | Val | Val | 0 | 0.02 |
| 40 | Glu(A14)Gly(A21)Glu(B3)Val(B16)Val(B25)Des(B30)-Insulin | Glu | Val | Val | 0.01 | 0.01 |

*relative to human insulin, nd: not determined
** a value of 0 means that the binding affinity was below the delection limit C) Conclusions As can be derived from Table 5, various hydrophobic substitutions at positions B16 and/or B25 were tested (tryptophan, alanine, valine, leucine and isoleucine). Albeit to a different extent, all tested insulin analogs with hydrophobic substitutions at these positions showed a decrease of insulin receptor binding activity. As compared to tryptophan substitutions (see e.g. Analogs 4, 15 and 23), substitutions with aliphatic amino acids such as alanine, valine, leucine and isoleucine had a stronger impact on insulin receptor binding activity. The strongest effects were observed for valine, leucine and isoleucine, which are all branched-chain amino acids. Substitutions with isoleucine, valine and leucine resulted in a significant decrease of insulin receptor binding activity. Interestingly, insulin analogs with such substitutions at position B25 (such as valine, leucine or isoleucine substitution at B25, Analogs 11, 12, 22, 24, 25, 29, 30, 32, 33, 35 38, 39, 40) showed up to 6-fold enhancement in signal transduction than expected based on their IR-B binding affinities. Specifically, Leu(B25)Des(B30)-Insulin and Val(B25)Des(B30)-Insulin (Analogs 11 and 12, respectively) showed only 1% binding to insulin receptor B and 6% auto phosphorylation relative to human insulin. Similarly, a single leucine substitution at position B16 (Analog 3) also showed a similar enhancement in signal transduction albeit to a slightly lower extent. By comparison, with the exception of Analog 26, analogs bearing a histidine B25 substitution (Analogs 10, 13, 14, 21, 28) also showed reduced receptor binding, however a concomitant reduction in auto phosphorylation.

In some cases (Analogs 30, 32, 35, 38, 39), insulin receptor binding was 0% whilst still showing activity in the auto phosphorylation assay. All of these analogs have combinations of valine and/or isoleucine substitutions at positions B16 and B25 in common, suggesting that the combination is responsible for the further drop in insulin receptor binding. Insulins with no substitution at position B25 but with exchanges at position B16 exhibited slightly higher binding affinities in comparison to their autophosphorylation values (Analogs 3, 4, 16, 17, 18, 19, 20).

Alanine in position B25 shows similar effects as valine, leucine or isoleucine substitution (analogs 11, 12, 22), although to a lower extent. The receptor binding affinity and autophosphorylation activity of analogs with valine, leucine or isoleucine substitution is lower than analogs with an alanine substitution.

Example 9: Determination of In Vitro Stability in Different Recombinant Proteases and Gastric Simulated Fluid The insulin analogs generated were tested for proteolytic stability (α-chymotrypsin, cathepsin D, insulin degrading enzyme (IDE) and simulated gastric fluid).

A) Assay Conditions

| Protease | Final Protease concentration in the assay [pg/ml] | Used buffer system |
|---|---|---|
| Trypsin | 2 | 0.1M Ammonium bicarbonate, pH 8.3 |
| α-Chymotrypsin | 0.5 | 0.1M Ammonium bicarbonate, pH 8.3 |
| Carboxypeptidase A | 0.1 | Pre-activation (60 min) with Trypsin in TCNB-buffer, Assay Tris-Puffer 7.5 |
| Carboxypeptidase B | 0.1 | Pre-activation (30 min) with Trypsin in TCNB-buffer, Assay Tris-Buffer 7.5 |
| Cathepsin D | 2 | Acetate Buffer, pH 4.5 |
| IDE | 2 | Tris-Buffer pH 7.5 |

B) Preparation of Simulated Gastric Fluid

Two grams of sodium chloride and 3.2 g of purified pepsin (from porcine stomach mucosa, with an activity of 800 to 2500 units per mg of protein) were dissolved in 7.0 ml of hydrochloric acid. The volume was adjusted with water up to 1000 ml. The resulting solution was mixed and adjusted with either 0.2 N sodium hydroxide or 0.2 N hydrochloric acid to a pH of 1.2±0.1.

C) General Assay Procedure

The stability determination was done using appropriate time points (for SIF and SGF 15, 30, 60, 120 and 240 minutes, for proteases 15, 30, 60 and 120 minutes). The incubation was done at 37° C. and the % of remaining parent compound was calculated in reference to a T0 time point.

For the determination of the parent compound an appropriate bioanalytical LC-MS/MS or LC-HRMS method was used, using the supernatant, after protein precipitation with ethanol (1 eq. v/v) and a centrifugation step.

D) Preparation of Samples

Compounds were dissolved in diluted hydrochloric acid at a final concentration of 40 µM. The compound concentration in the assay was 2 µM. A 1:20 dilution of the working solution was done into the protease buffer and samples are then incubated at 37° C., under stirring. At the appropriate time point and aliquot was taken, the reaction was quenched ethanol (1 eq. v/v), than centrifuged. The supernatant was analyzed.

E) Conclusions

In particular, lipophilic amino acid substitutions such as valine and isoleucine at positions 16 and 25 in the B-chain were investigated. Of the tested Analogs (2, 7, 11, 12, 14, 16, 19, 22, 23, 24 and 38), only minor differences in stability were observed against the proteases trypsin, carboxypeptidase A and carboxypeptidase B relative to human insulin (data not shown). In general, all analogs bearing A14 and B25 (Analogs 22, 24, 38) substitution showed improved proteolytic stability against α-chymotrypsin, cathepsin D and insulin degrading enzyme (IDE). For example, in the case of α-chymotrypsin, human insulin was completely degraded within 2 hours whereas Analog 22 was almost completely resistant. Similarly, all B25-substituted analogs tested showed improved stability against cathepsin D, albeit with Analog 38 (a B16/B25 variant) showing superior stability compared to the other B25 variants.

One notable exception was observed in the case of IDE, in which Analog 19 with A14/B16 substitutions showed improved performance compared to the B25 variants. The data suggests however, that a substitution at A14, tested here with glutamic acid, is important for increased stability. Other substitutions were also shown to be beneficial for increased stability: such as substitutions at position B16 and at position B25. For example, Analog 7 with an amino acid exchange in position B25, lead to increased instability.

TABLE 6

Percent remaining insulin analog after incubation of different insulin analogs for 30 or 120 minutes with four different proteases (for the sequences of the tested analogs, see Table 4).

| Analog | Backbone | A14 | B16 | B25 | Gastric fluid (30 minutes) [%] | α-Chymotrypsin (120 minutes) [%] | Cathepsin D (30 minutes) [%] | Insulin degrading enzyme, IDE (30 minutes) [%] |
|---|---|---|---|---|---|---|---|---|
| WT | Insulin | Tyr | Tyr | Phe | 0 | 5 | 0 | 38 |
| 2 | Glu(A14)Des(B30)-Insulin | Glu | Tyr | Phe | 0 | 35 | 0 | 81 |
| 7 | Ala(B25)-Insulin | Tyr | Tyr | Ala | 30 | 58 | 52 | 2 |
| 11 | Leu(B25)Des(B30)-Insulin | Tyr | Tyr | Leu | nd | nd | nd | 12 |
| 12 | Val(B25)Des(B30)-Insulin | Tyr | Tyr | Val | 44 | 31 | 43 | 11 |
| 14 | Gly(A21)Trp(B16)His(B25)Des(B30)-Insulin | Tyr | Trp | His | nd | nd | nd | 41 |
| 16 | Glu(A14)His(B16)Des(B30)-Insulin | Glu | His | Phe | nd | nd | nd | 88 |
| 19 | Glu(A14)Val(B16)Des(B30)-Insulin | Glu | Val | Phe | 0 | 30 | 0 | 98 |

TABLE 6-continued

Percent remaining insulin analog after incubation of different insulin analogs for 30 or 120 minutes with four different proteases (for the sequences of the tested analogs, see Table 4).

| Analog | Backbone | A14 | B16 | B25 | Gastric fluid (30 minutes) [%] | α-Chymotrypsin (120 minutes) [%] | Cathepsin D (30 minutes) [%] | Insulin degrading enzyme, IDE (30 minutes) [%] |
|---|---|---|---|---|---|---|---|---|
| 22 | Glu(A14)Ile(B25)Des(B30)-Insulin | Glu | Tyr | Ile | 52 | 99 | 20 | 77 |
| 23 | Glu(A14)Gly(A21)Trp(B25)Des(B30)-Insulin | Glu | Tyr | Trp | nd | nd | nd | 80 |
| 24 | Glu(A14)Val(B25)Des(B30)-Insulin | Glu | Tyr | Val | 52 | 40 | 59 | 86 |
| 38 | Glu(A14)Val(B16)Val(B25)Des(B30)-Insulin | Glu | Val | Val | 36 | 34 | 62 | 86 | nd: not determined

Example 10: Generation of Further Conjugates—In Vivo Testing—Evaluation of Pharmacokinetic Effects Insulin conjugates 1 to 4 were prepared (as described in Example 3.4.1) and tested. As a control, insulin conjugate 5 was prepared, which has been described in WO2018109162A1.

The prepared insulin conjugates are summarized in the following table (Table 7). Further, insulin conjugates 1 to 4 are shown in FIG. 5 to 8.

TABLE 7

Overview on Conjugates 1 to 5

| Insulin conjugate | Insulin backbone* | Side Chain | Albumin binder |
|---|---|---|---|
| Conjugate 1 (see FIG. 5) | Glu(A14)Val(B25)Des(B30)-Insulin (Analog 24 in Table 4) | binder No. 5 in Table 1 | |
| Conjugate 2 (see FIG. 6) | Glu(A14)Val(B25)Des(B30)-Insulin (Analog 24 in Table 4) | binder No. 8 in Table 1 | |
| Conjugate 3 (see FIG. 7) | Glu(A14)Glu(B3)Val(B16)Val(B25)Des(B30)-Insulin (Analog 39 in Table 4) | binder No. 5 in Table 1 | |
| Conjugate 4 (see FIG. 8) | Glu(A14)Ile(B25)Des(B30)-Insulin (Analog 22 in Table 4) | binder No. 5 in Table 1 | |
| Conjugate 5 (described in WO2018109162A1) | Glu(A14)His(B16)His(B25)Des(B30)-Insulin Analog 28 in Table 4 | Eicosandioyl-gammaGlu-OEG$_2$ | Eicosandioyl-gammaGlu-OEG$_2$ |

*for the sequence, see Table 4 in Example 7

Healthy, normoglycemic Göttingen mini pigs were used to evaluate the pharmacodynamic and pharmacokinetic effects of very long-acting insulin conjugates in vivo (pigs between 0.5-6 years were used with body weight ranges, depending on age, between ~12-40 kg). The pigs were kept under standard laboratory animal housing conditions and were fed once daily with ad libitum access to tap water. After overnight fasting the pigs were treated with a single subcutaneous injection of a solution that contains either a placebo formulation or the respective insulin conjugate. The insulin conjugates 1-4 as well as insulin conjugate 5 (described in WO2018109162A1) were tested.

Blood collection was performed via pre-implanted central venous catheters for determination of blood glucose, pharmacokinetics and additional biomarkers from K-EDTA plasma. Blood sampling started before the administration of the test item (baseline) and was repeated 1-4 times per day until study end. During the study, the animals were fed after the last blood sampling of the day. All animals were handled regularly and clinical signs were recorded at least twice on the day of treatment and once daily for the remaining duration of the study. The animals were monitored carefully for any clinical signs of hypoglycemia, including behavior, coat, urine and fecal excretion, condition of body orifices and any signs of illness. In case of severe hypoglycemia the investigator was allowed to offer food or infuse glucose solution intravenously (i.v.) in case food intake was not possible. After the last blood sampling, the animals were transported back to the animal housing facility.

A) Effects on Fasting Blood Glucose

Figure 3:
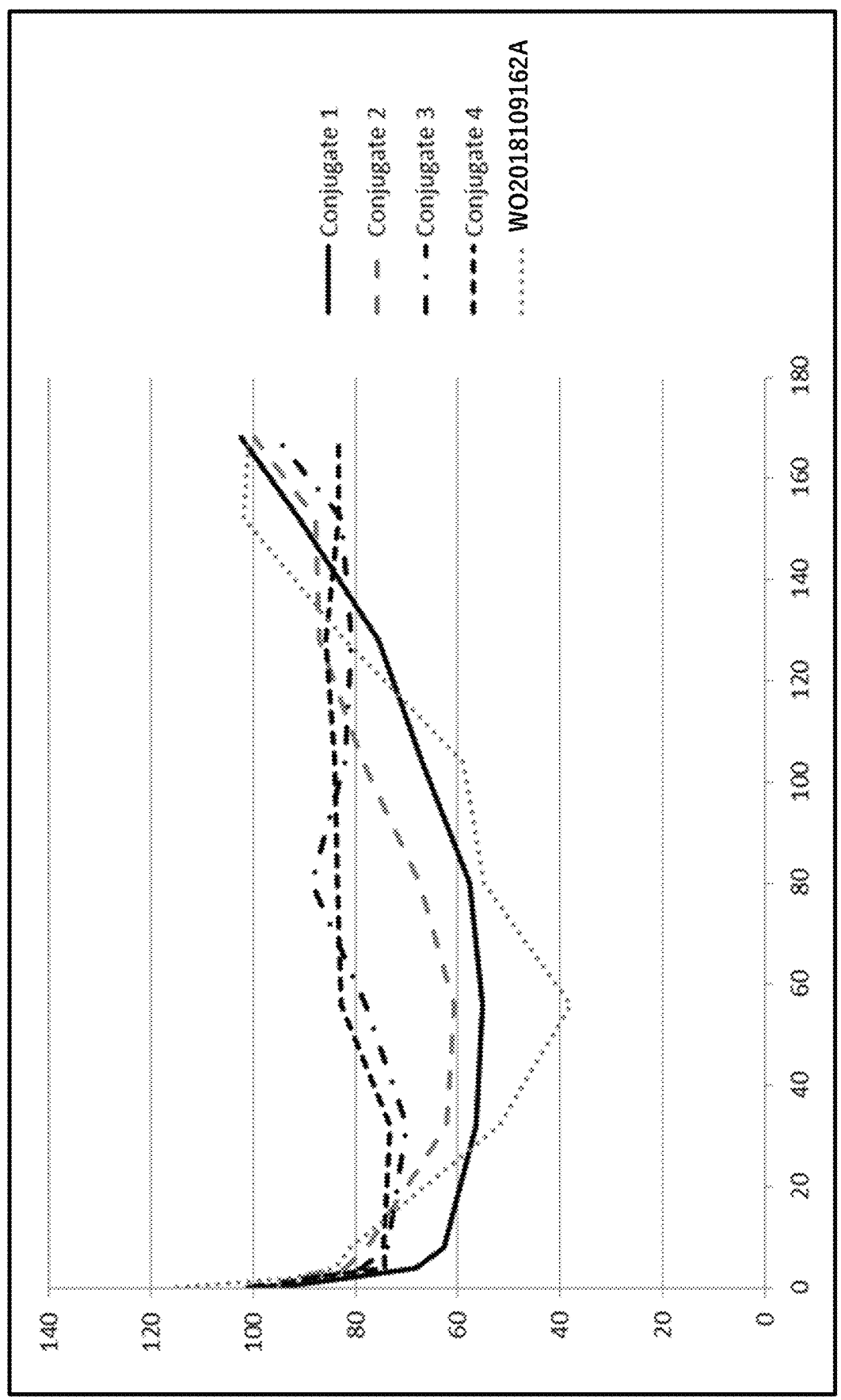
FIG. 3 shows blood glucose levels [% relative to placebo] after subcutaneous administration of insulin conjugates 1 to 5 (see Table 7 in Example 10).

Results are also shown in FIG. 3

TABLE 8

Effect on Blood Glucose

| Insulin conjugate | Insulin backbone | Side Chain | Dose [nM/kg] | FPG Duration of Glucose lowering >15% vs Placebo [h] | Maximal Glucose Lowering [%] |
|---|---|---|---|---|---|
| Conjugate 1 | Glu(A14)Val(B25)Des(B30)-Insulin (Analog 24 in Table 4) | binder No. 5 | 30 | >128 | 45 |
| Conjugate 2 | Glu(A14)Val(B25)Des(B30)-Insulin, (Analog 24 in Table 4) | binder No. 8 | 30 | >104 | 39 |
| Conjugate 3 | Glu(A14)Glu(B3)Val(B16)Val(B25)Des(B30)-Insulin (Analog 39 in Table 4) | binder No. 5 | 30 | >152 | 30 |
| Conjugate 4 | Glu(A14)Ile(B25)Des(B30)-Insulin (Analog 22 in Table 4) | binder No. 5 | 30 | >104 | 27 |
| Conjugate 5 | Glu(A14)His(B16)His(B25)Des(B30)-Insulin, Analog 28 in Table 4 | Eicosandioyl-Glu-OEG2 | 18 | >128 | 62 |

B) Measurements on Pharmacokinetic Parameters

Figure 4:
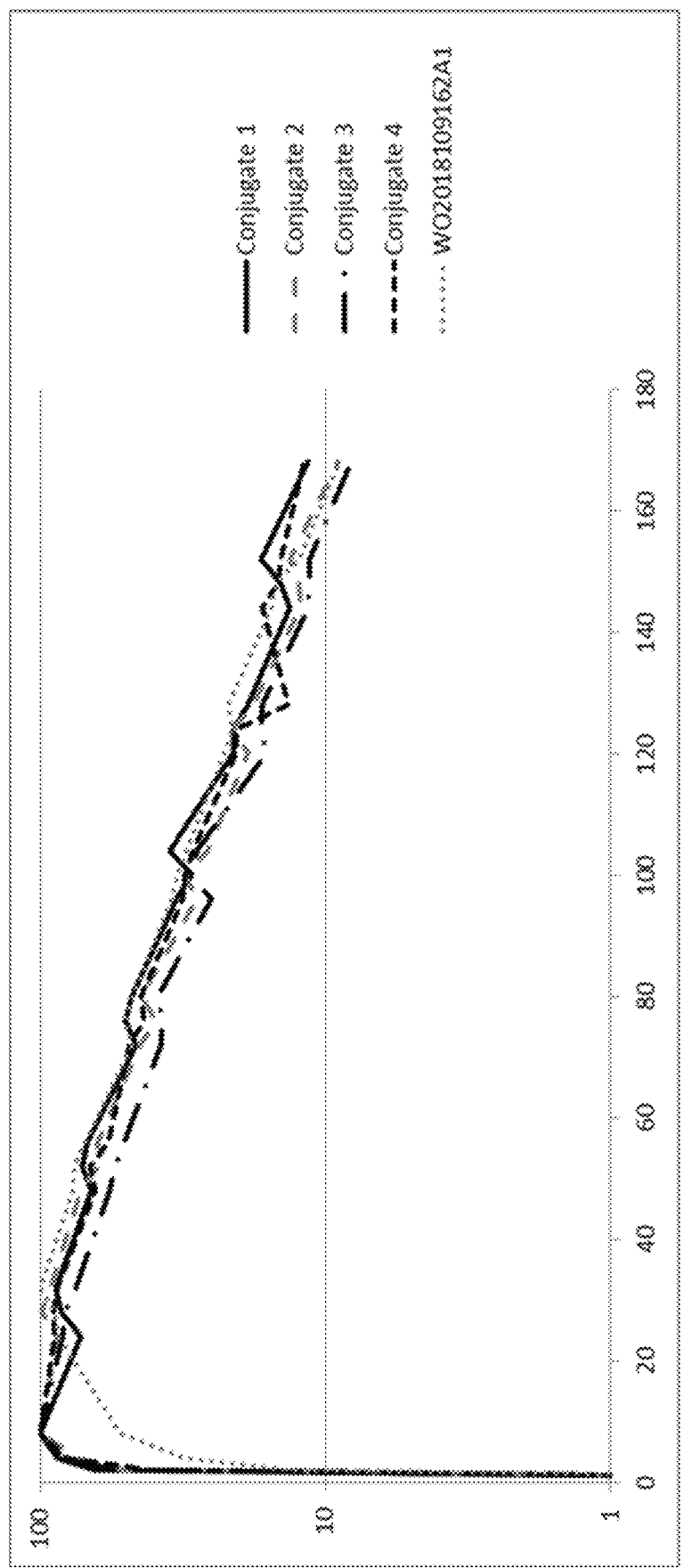
FIG. 4 shows normalized plasma concentration [ng/ml]-time [h] curves for insulin conjugates 1 to 5 (see Table 7 in Example 10).
Figure 5:
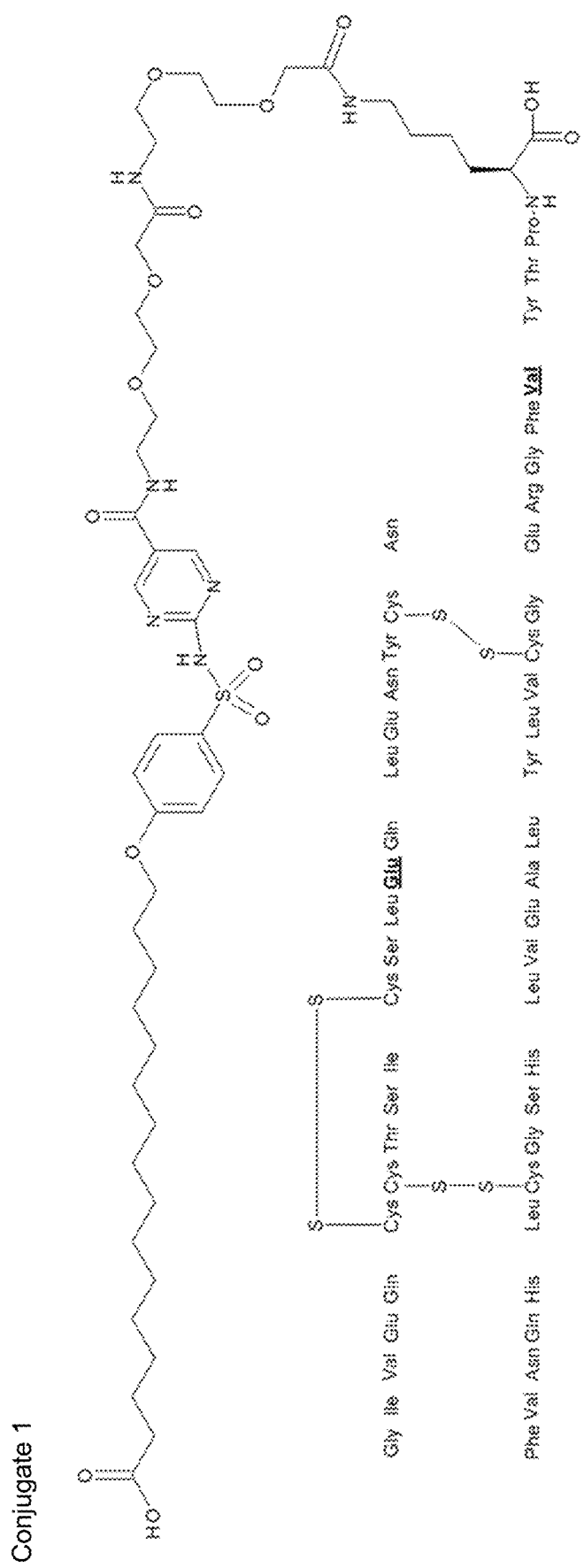
FIG. 5 shows insulin conjugate No. 1 (see Example 10 for more details). The sequences of the A chain (SEQ ID NO: 47) and the B chain (SEQ ID NO: 48) are indicated in three-letter-code, except for the last amino acid in the B chain (lysine at position B29). The structure of the lysine residue is shown. The Lysine residue is covalently bound to the binder (via the epsilon amino acid of the lysine residue).
Figure 6:
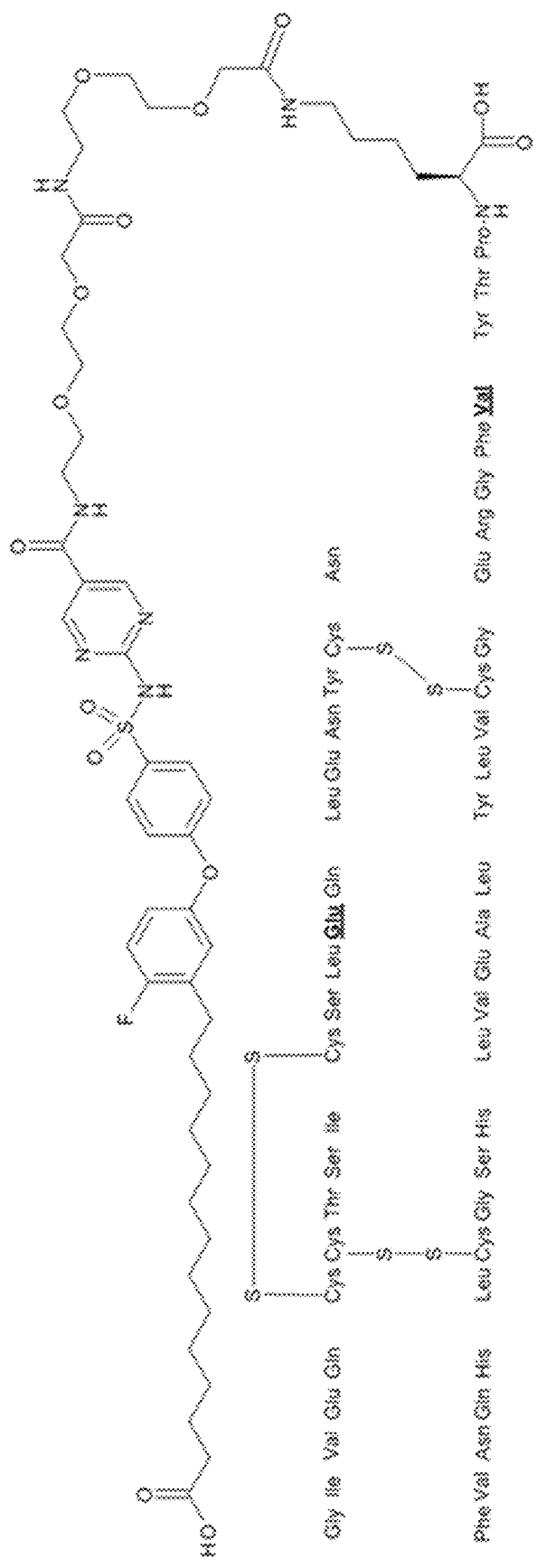
FIG. 6 shows insulin conjugate No. 2 (see Example 10 for more details). The sequences of the A chain (SEQ ID NO: 47) and the B chain (SEQ ID NO: 48) are indicated in three-letter-code, except for the last amino acid in the B chain (lysine at position B29). The structure of the lysine residue is shown. The lysine residue is covalently bound to the binder (via the epsilon amino acid of the lysine residue).
Figure 7:
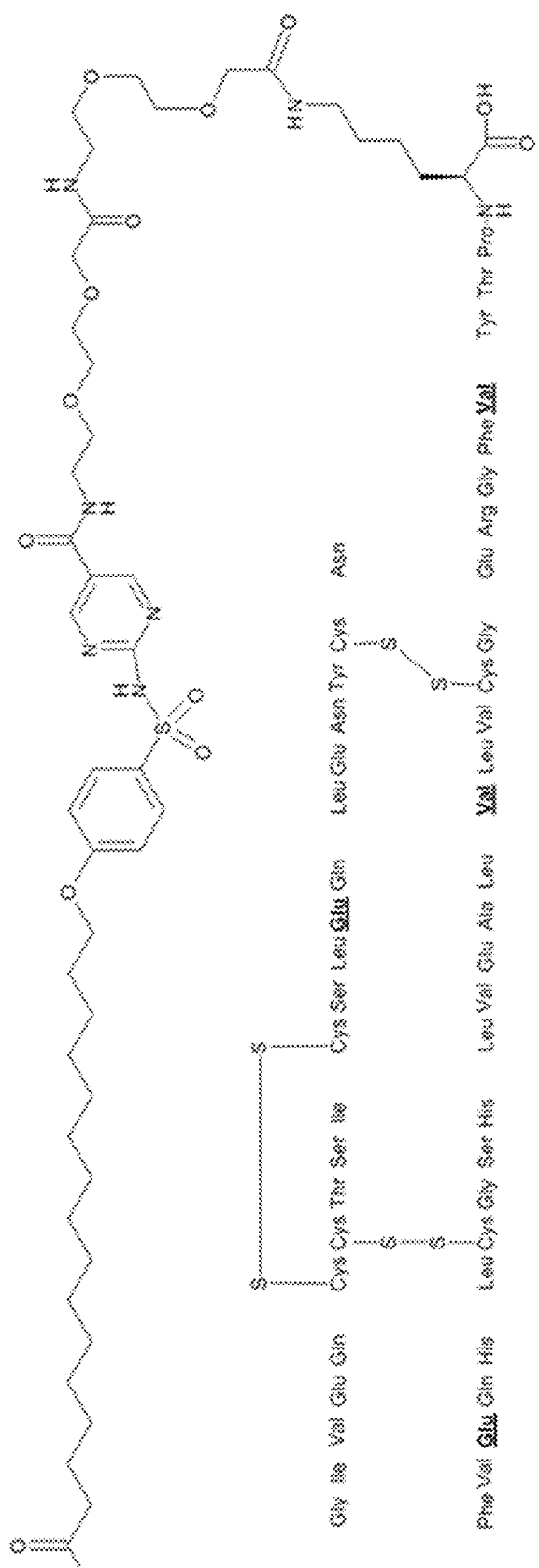
FIG. 7 shows insulin conjugate No. 3 (see Example 10 for more details). The sequences of the A chain (SEQ ID NO: 77) and the B chain (SEQ ID NO: 78) are indicated in three-letter-code, except for the last amino acid in the B chain (lysine at position B29). The structure of the lysine residue is shown. The lysine residue is covalently bound to the binder (via the epsilon amino acid of the lysine residue).
Figure 8:
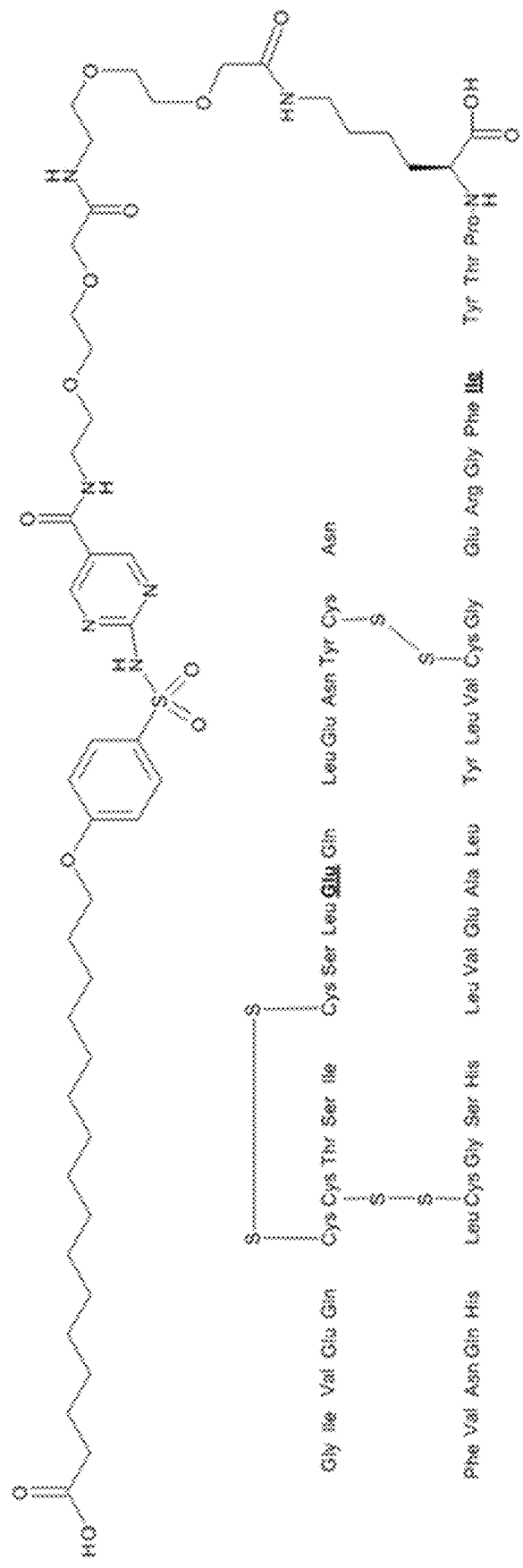
FIG. 8 shows insulin conjugate No. 4 (see Example 10 for more details). The sequences of the A chain (SEQ ID NO: 43) and the B chain (SEQ ID NO: 44) are indicated in three-letter-code, except for the last amino acid in the B chain (lysine at position B29). The structure of the lysine residue is shown. The lysine residue is covalently bound to the binder (via the epsilon amino acid of the lysine residue).

Results are also shown in FIG. 4

TABLE 9

Effect on Blood Glucose

| Conjugate | Sequence | Side Chain | Dose [nM/kg] | PK $t_{max}$ [h] | PK $t_{1/2}$ [h] |
|---|---|---|---|---|---|
| Conjugate 1 | Glu(A14)Val(B25)Des(B30)-Insulin | binder No. 5 | 30 | 8 | 45 |
| Conjugate 2 | Glu(A14)Val(B25)Des(B30)-Insulin | binder No. 8 | 30 | 20 | 38.9 |
| Conjugate 3 | Glu(A14)Glu(B3)Val(B16)Val(B25)Des(B30)-Insulin | binder No. 5 | 30 | 8 | 42.8 |
| Conjugate 4 | Glu(A14)Ile(B25)Des(B30)-Insulin | binder No. 5 | 30 | 14.7 | 45.2 |
| Conjugate 5 | Glu(A14)His(B16)His(B25)Des(B30)-Insulin | Eicosandioyl-Glu-OEG2 | 18 | 32 | 39 |

C) Conclusions

A single administration of insulin conjugate 4 (Ile(B25)), dosed at 30 nM/kg displayed a low to moderate glucose lowering effect with a flat profile up to 152 hours. Insulin conjugate 3, which contains mutations Val(B16) and Val(B25) displayed a flat profile of up to 152 hours with a moderate to medium glucose lowering effect. Furthermore, both insulin conjugates 1 and 2, containing the mutation Val(B25), lead to a stable glucose lowering effect without induction of hypoglycemia at a dose of 30 nM/kg. In contrast, insulin conjugate 5 (described in WO2018109162A1) was found to display a stronger glucose lowering effect with a less flat time-action profile compared to insulin conjugates 1-4 at a dose of only 18 nM/kg. Compound may have a higher risk for hypoglycemia.

Pharmacokinetic parameters show that insulin conjugates 1-4 display an earlier $T_{max}$ in the range of 8-20 hours in combination with a plateau at $C_{max}$ up to 50 hours. Because they display a terminal long $t_{1/2}$ in the range of 39-45 hours, a flat PK (pharmacokinetic) profile is achieved that is desired for once-weekly dosing due to the potentially reduced risk for hypoglycemic events.

CITED LITERATURE

Senshang Lin, Li-Lan H. Chen and Yie W. Chien, The journal of pharmacology and experimental therapeutics, 1998, 286, 959-966.

Clinical Pharmacokinetics Concepts and applications by Tozer and Rowland, 3rd edition (Publisher Lippincott Williams & Wilkins), 1995-Section II-6).

Hartmann et al., Effect of the long-acting insulin analogues glargine and degludec on cardiomyocyte cell signaling and function, Cardiovasc Diabetol. 2016; 15:96.

Sommerfeld et al., PLoS One. 2010; 5(3): e9540.

Handbook of Pharmaceutical Salts: Properties, Selection, and Use by Stahl and Wermuth (Wiley-VCH, 2002).

All patent applications, patents, and printed publications cited herein are incorporated herein by reference in the entireties, except for any definitions, subject matter disclaimers or disavowals, and except to the extent that the incorporated material is inconsistent with the express disclosure herein, in which case the language in this disclosure controls.

---

The invention claimed is:

1. An insulin comprising a chain A and a chain B, wherein the insulin comprises:
   (a) a mutation in chain A at position A14, or at positions A14 and A21, wherein position A14 is substituted with Glutamic Acid (Glu), Aspartic acid (Asp), or Histidine (His); and
   (b) at least one a mutation in the chain B at position B25, or at position B25 in combination with positions B3, B16 and/or B30 wherein position B16 and/or B25 is substituted with a branched-chain amino acid, wherein the insulin has two to six mutations relative to human insulin.

2. The insulin of claim 1, wherein the branched-chain amino acid of each mutation is independently selected from the group consisting of valine (Val), isoleucine (Ile), and leucine (Leu).

3. The insulin of claim 1, wherein the mutation at position A14 of the A chain is a substitution of A14 with glutamic acid (Glu).

4. The insulin of claim 1, wherein the mutation at position B30 of the B chain is a deletion of the amino acid at position B30 (Des (B30)-mutation).

5. The insulin of claim 1, wherein the mutation at position B3 of the B chain is a substitution at position B3 with glutamic acid (Glu).

6. The insulin of claim 1, wherein the mutation at position A21 of the A chain is a substitution at position A21 with glycine (Gly).

7. The insulin of claim 1, wherein the B chain comprises an amino acid sequence selected from the group consisting of:

```
                                             (SEQ ID NO: 22)
FVNQHLCGSHLVEALYLVCGERGELYTPK, (SEQ ID NO: 44)
FVNQHLCGSHLVEALYLVCGERGFIYTPK, (SEQ ID NO: 48)
FVNQHLCGSHLVEALYLVCGERGFVYTPK, (SEQ ID NO: 50)
FVEQHLCGSHLVEALYLVCGERGFVYTPK, (SEQ ID NO: 58)
FVNQHLCGSHLVEALILVCGERGFIYTPK, (SEQ ID NO: 60)
FVEQHLCGSHLVEALILVCGERGFIYTPK, (SEQ ID NO: 64)
FVNQHLCGSHLVEALILVCGERGFVYTPK, (SEQ ID NO: 66)
FVEQHLCGSHLVEALILVCGERGFVYTPK, (SEQ ID NO: 70)
FVNQHLCGSHLVEALVLVCGERGFIYTPK, (SEQ ID NO: 76)
FVNQHLCGSHLVEALVLVCGERGFVYTPK, (SEQ ID NO: 78)
FVEQHLCGSHLVEALVLVCGERGFVYTPK, (SEQ ID NO: 80)
FVEQHLCGSHLVEALVLVCGERGFVYTPK, (SEQ ID NO: 85)
FVNQHLCGSHLVEALYLVCGERGELYTPKT, (SEQ ID NO: 86)
FVNQHLCGSHLVEALYLVCGERGFVYTPKT, (SEQ ID NO: 87)
FVNQHLCGSHLVEALYLVCGERGFIYTPKT, (SEQ ID NO: 88)
FVNQHLCGSHLVEALYLVCGERGFVYTPKT, (SEQ ID NO: 89)
FVEQHLCGSHLVEALYLVCGERGFVYTPKT, (SEQ ID NO: 90)
FVNQHLCGSHLVEALILVCGERGFIYTPKT, (SEQ ID NO: 91)
FVEQHLCGSHLVEALILVCGERGFIYTPKT, (SEQ ID NO: 92)
FVNQHLCGSHLVEALILVCGERGFVYTPKT, (SEQ ID NO: 93)
FVEQHLCGSHLVEALILVCGERGFVYTPKT, (SEQ ID NO: 94)
FVNQHLCGSHLVEALVLVCGERGFIYTPKT, (SEQ ID NO: 95)
FVNQHLCGSHLVEALVLVCGERGFVYTPKT, (SEQ ID NO: 96)
FVEQHLCGSHLVEALVLVCGERGFVYTPKT,
and
                                             (SEQ ID NO: 97)
FVEQHLCGSHLVEALVLVCGERGFVYTPKT.
```

8. The insulin of claim 1, wherein the A chain has an amino acid sequence as shown in SEQ ID NO: 43 and the B chain has an amino acid sequence as shown in SEQ ID NO: 44.

9. The insulin of claim 1, wherein the A chain has an amino acid sequence as shown in SEQ ID NO: 47 and the B chain has an amino acid sequence as shown in SEQ ID NO: 48.

10. The insulin of claim 1, wherein the A chain has an amino acid sequence as shown in SEQ ID NO: 77 and the B chain has an amino acid sequence as shown in SEQ ID NO: 78.

11. The insulin of claim 1, wherein the mutation at position A21 of the A chain is a substitution at position A21 with Aspartic acid (Asp).

12. The insulin of claim 1, wherein the mutation at position A21 of the A chain is a substitution at position A21 with Histidine (His).

13. The insulin of claim 1, wherein the branched-chain amino acid of each mutation is valine (Val).

14. The insulin of claim 1, wherein the branched-chain amino acid of each mutation is isoleucine (Ile).

15. The insulin of claim 1, wherein the branched-chain amino acid of each mutation is leucine (Leu).

16. An insulin selected from the group consisting of:
Glu(A14)Leu(B16)Des(B30)-human insulin,
Glu(A14)Ile(B16)Des(B30)-human insulin,
Glu(A14)Val(B16)Des(B30)-human insulin,
Glu(A14)Leu(B16)-human insulin,
Glu(A14)Ile(B16)-human insulin,
Glu(A14)Val(B16)-human insulin,
Glu(A14)Leu(B25)Des(B30)-human insulin,
Glu(A14)Ile(B25)Des(B30)-human insulin,
Glu(A14)Val(B25)Des(B30)-human insulin,
Glu(A14)Leu(B25)-human insulin,
Glu(A14)Ile(B25)-human insulin, Glu(A14)Val(B25)-human insulin,
Glu(A14)Gly(A21)Glu(B3)Val(B25)Des(B30)-human insulin,
Glu(A14)Ile(B16)Ile(B25)Des(B30)-human insulin,
Glu(A14)Glu(B3)Ile(B16)Ile(B25)Des(B30)-human insulin,
Glu(A14)Ile(B16)Val(B25)Des(B30)-human insulin,
Glu(A14)Gly(A21)Glu(B3)Ile(B16)Val(B25)Des(B30)-human insulin,
Glu(A14)Val(B16)Ile(B25)Des(B30)-human insulin,
Glu(A14)Val(B16)Val(B25)Des(B30)-human insulin,
Glu(A14)Glu(B3)Val(B16)Val(B25)Des(B30)-human insulin,
Glu(A14)Gly(A21)Glu(B3)Val(B16)Val(B25)Des(B30)-human insulin,
Glu(A14)Gly(A21)Glu (B3)Val(B25)-human insulin,
Glu(A14)Ile(B16)Ile(B25)-human insulin,
Glu(A14)Glu(B3)Ile(B16)Ile(B25)-human insulin,
Glu(A14)Ile(B16)Val(B25)-human insulin,
Glu(A14)Gly(A21)Glu(B3)Ile(B16)Val(B25)-human insulin,
Glu(A14)Val(B16)Ile(B25)-human insulin,
Glu(A14)Val(B16)Val(B25)-human insulin,
Glu(A14)Glu(B3)Val(B16)Val(B25)-human insulin, and
Glu(A14)Gly(A21)Glu(B3)Val(B16)Val(B25)-human insulin.

17. An insulin comprising Glu(A14)Val(B25)Des(B30)-human insulin.

18. An insulin comprising Glu(A14)Ile(B25)Des(B30)-human insulin.

19. An insulin comprising Glu(A14)Val(B16) Val(B25) Des(B30)-human insulin.

20. The insulin of claim 1, wherein the insulin comprises two to five mutations in amino acid sequence.

21. The insulin of claim 1, wherein the insulin comprises two to four mutations in amino acid sequence.

* * * * *

UNITED STATES PATENT AND TRADEMARK OFFICE
CERTIFICATE OF CORRECTION

Page 1 of 1

PATENT NO. : 12,195,510 B2
APPLICATION NO. : 17/329558
DATED : January 14, 2025
INVENTOR(S) : Boehme et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 237 days.

Signed and Sealed this
Sixth Day of January, 2026

John A. Squires
*Director of the United States Patent and Trademark Office*